(12) United States Patent
Kandel et al.

(10) Patent No.: US 7,635,768 B2
(45) Date of Patent: Dec. 22, 2009

(54) METHODS AND REAGENTS FOR DENDRITIC LOCALIZATION OF POLYNUCLEOTIDES

(75) Inventors: Eric R. Kandel, Riverdale, NY (US); Mark Mayford, San Diego, CA (US)

(73) Assignee: The Trustees of Columbia University in the City of New York, New York, NY (US)

( * ) Notice: Subject to any disclaimer, the term of this patent is extended or adjusted under 35 U.S.C. 154(b) by 681 days.

(21) Appl. No.: 10/341,999

(22) Filed: Jan. 14, 2003

(65) Prior Publication Data

US 2004/0009497 A1   Jan. 15, 2004

Related U.S. Application Data

(63) Continuation of application No. 08/969,137, filed on Nov. 12, 1997, now Pat. No. 6,509,190.

(51) Int. Cl.
*C07H 21/04* (2006.01)
*C07H 21/02* (2006.01)

(52) U.S. Cl. ..................... 536/24.1; 536/23.1
(58) Field of Classification Search ............... 536/24.1, 536/23.1
See application file for complete search history.

(56) References Cited

U.S. PATENT DOCUMENTS

| | | | | |
|---|---|---|---|---|
| 5,814,500 | A | 9/1998 | Dietz | 435/172.3 |
| 6,509,190 | B2 | 1/2003 | Kandel et al. | 435/354 |

FOREIGN PATENT DOCUMENTS

| | | |
|---|---|---|
| WO | WO9746257 | 12/1997 |
| WO | WO9924457 | 5/1999 |
| WO | WO0009662 | 2/2000 |

OTHER PUBLICATIONS

Bej et al. (1991) Detection of coliform bacteria and *Escherichia coli* by multiplex polymerase chain reaction: Comparison with defined substrate and plating methods for water quality monitoring. Applied and Environmental Microbiology 57(8): 2429-2432.*
Abel, T., et al., (1997) Genetic demonstration of a role for PKA in the late phase of LTP and in hippocampus-based long-term memory. Cell 88: 625-626.
Bach, M., et al., (1995) Impairment of spatial but not contextual memory in CaMKII mutant mice with a selective loss of hippocampal LTP in the range of the ⊖ frequency. Cell 81: 905-915.
Chen, J. and Kelly P.T., (1996) Retinoic acid stimulates—CaMKII gene expression in PC12 cells at a distinct transcription initiation site. J. of Neuroscience 16(18): 5704-5714.
Kojima, N., et al., (1997) Rescuing impairment of long-term potentiation in fyn-deficient mice By introducing fyn transgene. Proc. Natl. Acad. Sci. 94: 4761-4765.
Mayford, M., et al., (1995) Transgenic approaches to cognition. Current Opin. Neurobiol. 5: 141-148.

Mayford, M., et al., (1995) CaMKII regulates the frequency-response function of hippocampal synapses for the production of both LTD and LTP. Cell 81: 891-904.
Mayford, M., et al., (1996) Control of memory formation through regulated expression of a CaMKII transgene. Science 274: 1678-1683.
Mayford, M., et al., (1996) CaMKII function in the nervous system explored from a genetic perspective. Cold Spring Harbor Lab. Press 59: 219-214.
Mayford, M., et al., (1996) The 3' -untranslated region of CaMKIIα is a cis-acting signal for the localization and translation of mRNA in dendrites. Proc. Natl. Acad. Sci. U. S. A. 93: 13250-13255.
Mayford, M. et al., (1997) Memory and behavior: a second generation of genetically modified mice. Current Biol. 7: R580-R589.
McHugh, T., et al., (1996) Impaired hippocampal representation of space in CA1-specific NMDAR1 knockout mice. Cell 87: 1339-1349.
Olson, N.J., et al., (1995) Functional identification of the promoter for the gene encoding the subunit of calcium/calmodulin-dependent protein kinase II. Proc. Natl. Acad. Sci. U.S.A. 92: 1659-1663.
Roush, W., (1997) New knockout mice point to molecular basis of memory. Science 275: 32-33.
Sunyer, et al, (1990) Sequence analysis and DNA-protein interactions within the 5' flanking region of the calcium ion alpha-subunit gene. Proc. Natl. Acad. Sci. U.S.A. 87:278-282.
Tsien, J., et al., (1996) Subregion- and cell type-restricted gene knockout in mouse brain. Cell 87: 1317-1326.
Winder et al., (1998) Genetic and Pharmacological evidence for a novel,intermediate phase of long-term potentiation suppressed by calcineurin. Cell 92:25-37.
European Search Report dated Apr. 3, 2002 issued in connection with PCT/US98/24157.
European Search Report (Partial) issued in connection with PCT/US99/18860 on Aug. 16, 2002.
European Search Report (Incomplete) issued in connection with PCT/US99/18860 on Jan. 24, 2003.
PCT International Search Report dated Feb. 24, 1999, issued in connection with International Application No. PCT/US98/24157.
PCT International Search Report dated Nov. 27, 2000, issued in connection with International Application No. PCT/US99/18860.
PCT Written Opinion dated Jun. 29, 2000, issued in connection with International Application No. PCT/US99/18860.
Alvarez, P. et al. (1994) "The animal model of human amnesia: Long-term memory impaired and short-term memory intact." Proc. Natl. Acad. Sci. USA. 51:5637-5641.

(Continued)

*Primary Examiner*—Anne-Marie Falk
(74) *Attorney, Agent, or Firm*—John P. White; Cooper & Dunham LLP

(57) ABSTRACT

A recombinant nucleic acid comprising nucleotides corresponding to a 3.2 kb 3' untranslated region present in mouse calcium calmodulin kinase II alpha subunit-encoding mRNA is provided. An isolated nucleic acid which hybridizes to the 3' untranslated region of mouse calcium calmodulin kinase II alpha subunit-encoding mRNA under conditions comprising two post-hybridization washes of 15 minutes each at 42° C. in 0.2× standard sodium citrate buffer is also provided.

5 Claims, 56 Drawing Sheets

OTHER PUBLICATIONS

Baier, G. et al. (1994) "Construction and characterization of lck- and fyn-specific tRNA: ribozyme chimeras." Mol. Immunol. 31(12):923-32.

Bartsch., D. et al. (1995) "Aplysia CREB2 represses long-term facilitation: relief of repression converts transient facilitation into long-term functional and structural change." Cell 83:979-992.

Bear, M.F., and Abraham, W.C. (1996) "Long-term depression in hippocampus." Ann. Rev. Neurosci. 19:437-462.

Bennett, P.C. et al. (1996) "Cyclosporin A, an inhibitor of calcineurin, impairs memory formation in day-old chicks." Brain Res. 730:107-117.

Bito, H. et al. (1996) "CREB phosphorylation and dephosphorylation: A calcium- and stimulus duration-dependent switch for hippocampal gene expression." Cell 87:1203-1214.

Blichenberg A. et al. (2001) "Identification of a cis-acting dendritic targeting element in the mRNA encoding the alpha subunit of Ca2+/calmodulin-dependent protein kinase II." Eur. J. Neurosci. (13):1881-8.

Bliss, T.V.P., and Collingridge, G. (1993) "A synaptic model of memory: long-term potentiation in the hippocampus." Nature 361:31-39.

Blitzer, R.D. et al. (1995) "Postsynaptic cAMP pathway gates early LTP in hippocampal CA1 region." Neuron 15:1403-1414.

Bolshakov V.Y. et al. "Recruitment of new sites of synaptic transmission during the cAMP-dependent late phase of LTP at CA3-CA1 synapses in the hippocampus." Neuron Sep. 1997;19(3):635-51.

Cummings, J.A. et al. (1996) "Calcium signaling requirements for long-term depression in the hippocampus." Neuron 16:825-833.

Figurov, A. et al. (1993) "Enhancement of AMPA-mediated synaptic transmission by the protein phosphatase inhibitor calyculin A in rat hippocampal slices." Eur. J. Neurosci. 5:1035-1041.

Good, P.D. et al. (1997) "Expression of small, therapeutic RNAs in human cell nuclei." Gene Ther. 4(1):45-54.

Gossen, M. et al. (1995) "Transcriptional activation by tetracyclines in mammalian cells." Science 268:1766-1769.

Huang, Y.Y. and Kandel, E. R. (1994) "Recruitment of long-lasting and protein kinase A-dependent long-term potentiation in the CA1 region of hippocampus requires repeated tetanization." Learn. Mem. 1:74-82.

Huang, Y.Y. et al. (1996) "Long-lasting forms of synaptic potentiation in the mammalian hippocampus." Learn. Mem. 3:74-85.

Ikegami S. et al. (1996) "A facilitatory effect on the induction of long-term potentiation in vivo by chronic administration of antisense oligodeoxynucleotides against catalytic subunits of calcineurin." Brain Res. Mol. Brain Res. Sep. 5;41(1-2):183-91.

Kindler S. and Monshausen M. (2002) "Candidate RNA-binding proteins regulating extrasomatic mRNA targeting and translation in mammalian neurons." Mol. Neurobiol. (2):149-65.

Krichevsky A.M., and Kosik K.S. (2001) "Neuronal RNA granules: a link between RNA localization and stimulation-dependent translation." Neuron 32(4):683-96.

Kuno, T. et al. (1992) "Distinct cellular expression of calcineurin Aα and Aβ in rat brain." J. Neurochem. 58:1643-1651.

Lisman, J. (1994) "The CaM kinase II hypothesis for the storage of synaptic memory." Trends Neurosci. 17:406-412.

Lu, Y. F. et al. (1996) "Calcineurin inhibitors, FK506 and cyclosporin A, suppress the NMDA receptor-mediated potentials and LTP, but not depotentiation in the rat hippocampus." Brain Res. 729:142-146.

Malenka, R.C., and Nicoll, R.A. (1993) "NMDA receptor-dependent synaptic plasticity: multiple forms and mechanisms." Trends Neurosci. 16:521-527.

Mansuy, I. et al. (1998) "Restricted and regulated overexpression reveals calcineurin as a key component in the transition from short-term to long-term memory." Cell 92:39-49.

Mansuy, I., et al., (1998) "Inducible and Reversible Gene Expression with the rtTA System for the Study of Memory." Neuron 21:257-265.

Marshall, E. (1995) "Gene therapy's growing pains." Science 269(5227):1050, 1052-5.

Martin, K.C. et al. (1997) "MAP kinase translocates into the nucleus of the presynaptic cell and is required for long-term facilitation in *Aplysia*." Neuron 18:899-912.

Miller, N. and Vile, R. (1995) "Targeted vectors for gene therapy." FASEB J. 9(2):190-9.

Mori Y. et al. (2000) "Two cis-acting elements in the 3' untranslated region of alpha-CaMKII regulate its dendritic targeting." Nat. Neurosci. 3(11):1079-84.

Morris, R.G.M. (1989) "Synaptic plasticity and learning: selective impairment of learning rats and blockade of long-term potentiation in vivo by the N-methyl-D-aspartate receptor antagonist AP5." J. Neurosci. 9:3040-3057.

Mulkey, R. M. (1994) "Involvement of a calcineurin/inhibitor-1 phosphatase cascade in hippocampal long-term depression." Nature 369:486-488.

Muller, D. et al. (1988) "Contributions of quisqualate and NMDA receptors to the induction and expression of LTP." Science 242:1694-1697.

Mulligan, R.C. (1993) "The basic science of gene therapy." Science 260:926-932.

O'Keefe, S.J. et al. (1992) "FK-506 and CsA-sensitive activation of the interleukin-2 promoter by calcineurin." Nature 357:692-694.

Osten, P. et al. (1996) "Protein synthesis-dependent formation of protein kinase M in long-term potentiation." J. Neurosci. 16:2444-2451.

Overton D.A. (1966) "State-dependent learning produced by depressant and atropine-like drugs." Psychopharmacologia 10(1):6-31.

Parsons J.N. et al. (1994) "Regulation of calcineurin phosphatase activity and interaction with the FK-506. FK-506 binding protein complex." J. Biol. Chem. 269(30):19610-6.

Paterson, J.M. et al. (1995) "Control of a novel adenylyl cyclase by calcineurin." Biochem. Biophys. Res. Comm. 214:1000-1008.

Perrino B.A., et al. (1995) "Calcium regulation of calcineurin phosphatase activity by its B subunit and calmodulin. Role of the autoinhibitory domain." J. Biol. Chem. 270(1):340-6.

Raman, I.M. et al. (1996) "β-adrenergic regulation of synaptic NMDA receptors by cAMP-dependent protein kinase." Neuron 16:415-412.

Roberson, E.D. et al. (1996) "A biochemist's view of long-term potentiation." Learn. Mem. 3:1-24.

Rook M.S. et al. (2000) "CaMKII alpha 3' untranslated region-directed mRNA translocation in living neurons: visualization by GFP linkage." J. Neurosci. 20(17):6385-93.

Schwaninger, M. et al. (1995) "Involvement of the calcium-dependent phosphatase calcineurin in gene transcription that is stimulated by cAMP through cAMP response elements." J. Biol. Chem. 270:8860-8866.

Shen K. et al. (1999) "Dynamic control of CaMKII translocation and localization in hippocampal neurons by NMDA receptor stimulation." Science 284(5411):162-6.

Shen K. and Teruel M.N. (1998) "CaMKII beta functions as an F-actin targeting module that localizes CaMKIIalpha/beta heterooligomers to dendritic spines." Neuron 21(3):593-606.

Shen K. et al. (2000) "Molecular memory by reversible translocation of calcium/calmodulin-dependent protein kinase II." Nat. Neurosci. 3(9):881-6.

Stanton, P.K. and Sarvey, J.M. (1984) "Blockade of long-term potentiation in rat hippocampal CA1 region by inhibitors of protein synthesis." J. Neurosci. 4:3080-3088.

Thomas, M.J. et al. (1996) "Activity-dependent (3-adrenergic modulation of low frequency stimulation induced LTP in the hippocampal CA1 region." Neuron 17:475-486.

Tong, G. et al. (1995) "Synaptic desensitization of NMDA receptors by calcineurin." Science 267:1510-1512.

Traynelis, S. F. and Wahl, P. (1997) "Control of rat GluR6 glutamate receptor open probability by protein kinase A and calcineurin." J. Physiol. 503:513-531.

Wang, J.H., and Kelly, P. T. (1996) "The balance between postsynaptic calcium-dependent protein kinase and phosphatase activities controlling synaptic strength." Learn. Mem. 3:170-181.

Wang, J.H., and Kelly, P. T. (1997) "Postsynaptic calcineurin activity downregulates synaptic transmission by weakening intracellular calcium signaling mechanisms in hippocampal CA1 neurons." J. Neurosci. 17:4600-4611.

Wang, J.H., and Stelzer, A. (1994) "Inhibition of phosphatase 2B prevents expression of hippocampal long-term potentiation." Neuroreport. 5:2377-2380.

Watanabe Y. et al. (1996) "Activation of calcineurin A subunit phosphatase activity by its calcium-binding B subunit." Biochemistry 35(2):562-6.

Yakel, J.L. (1997) "Calcineurin regulation of synaptic function: from ion channels to transmitter release and gene transcription." Trends Neurosci. 18:124-134.

Yin, J.C.P. et al. (1994) "Induction of a dominant negative CREB transgene specifically blocks long-term memory in *Drosophila*." Cell 79:49-58.

Yin, J.C.P. et al. (1995) "CREB as a memory modulator: induced expression of a dCREB2 activator isoform enhances long-term memory in *Drosophila*." Cell 81:107-115.

Zhao, W.Q. (1995) "The impairment of long-term memory formation by the phosphatase inhibitor okadaic acid" Brain Res. Bull. 36:557-561.

Zhao, W.Q. et al. (1994) "Effect of PKC inhibitors and activators on memory" Behav. Brain Res. 60:151-160; and.

Zhao, W.Q. et al. (1995) "Inhibitors of cAMP-dependent protein kinase impair long-term memory formation in day-old chicks." Neurobiol. Learn. Mem. 64:106-118.

Lehninger, Biochemistry (Worth Publishers Inc. New York, 2nd Edition) p. 717 (1995).

* cited by examiner

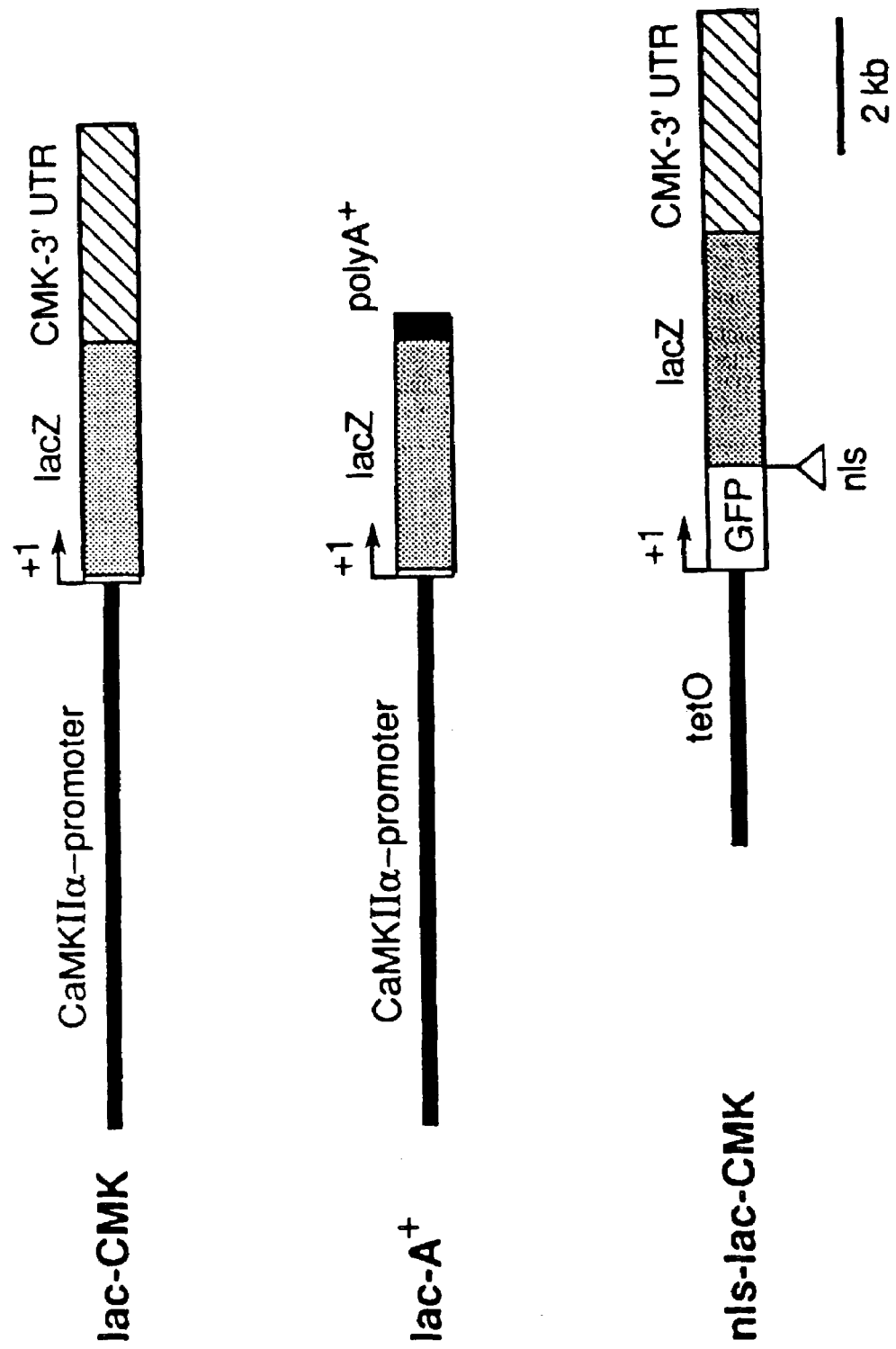

lac - A⁺ lac - CMK

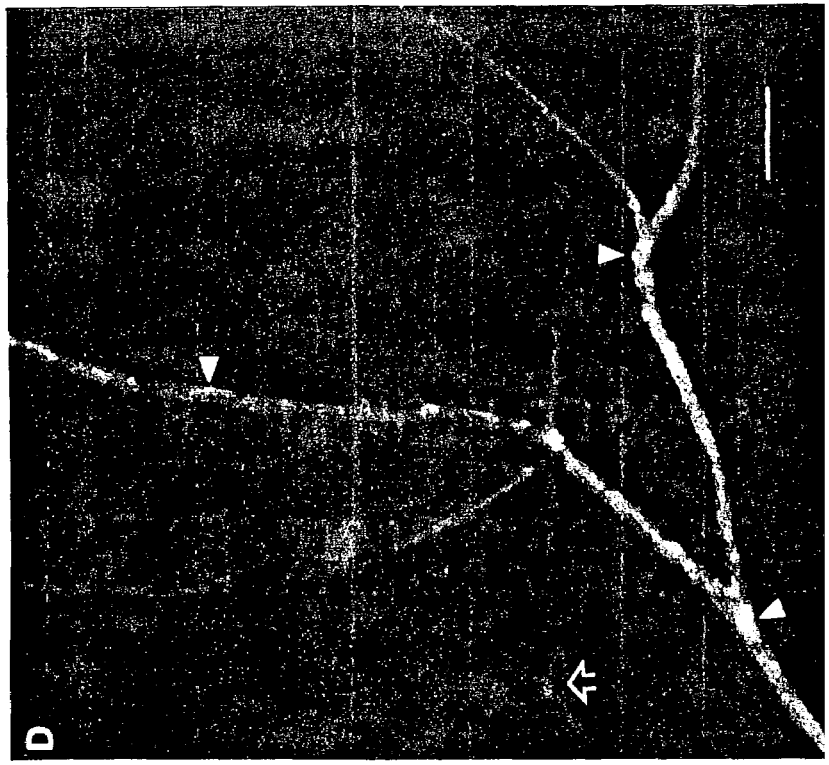
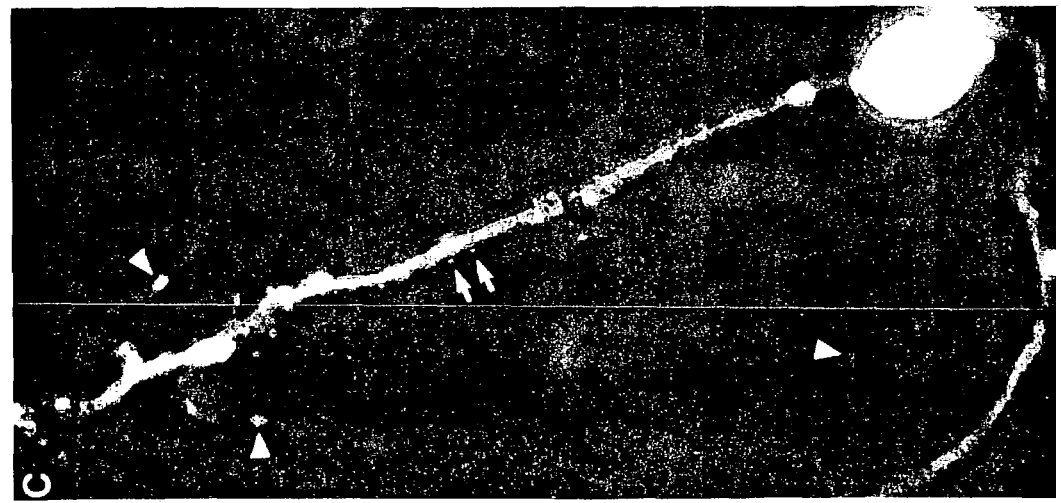

*FIGURE 6B*
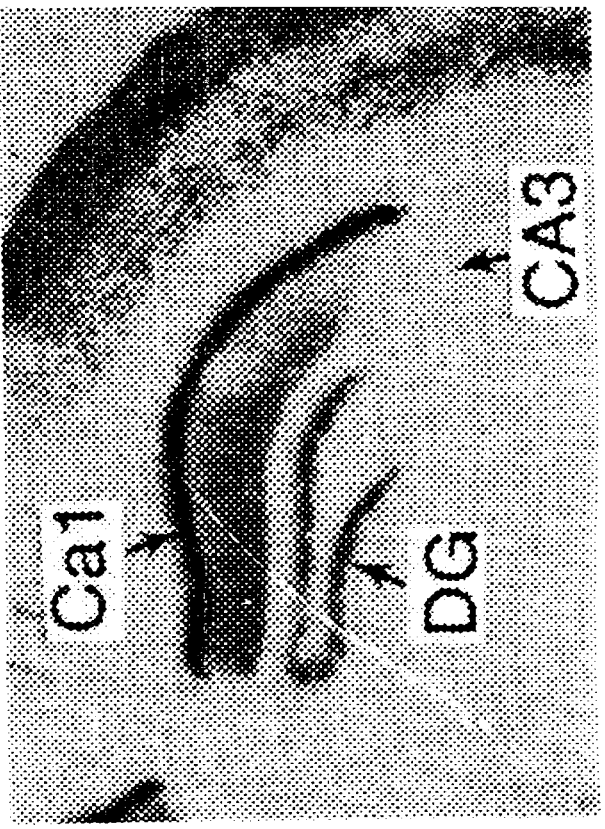
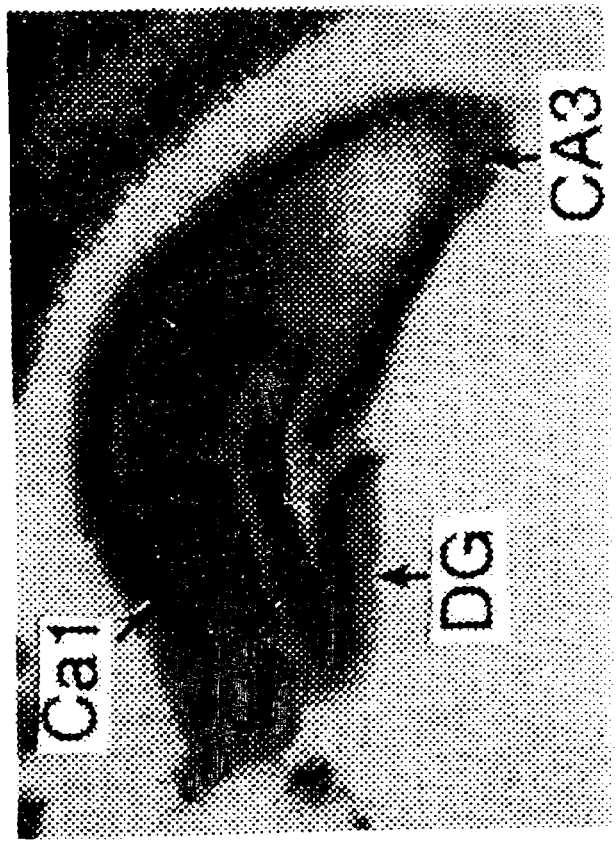

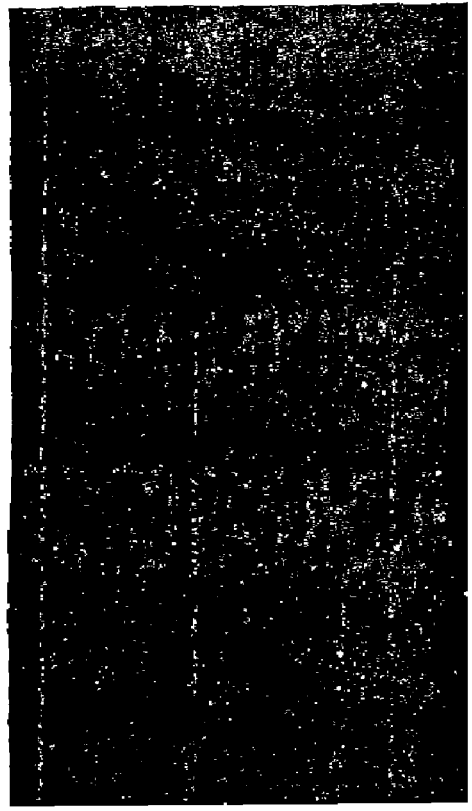
FIGURE 11D

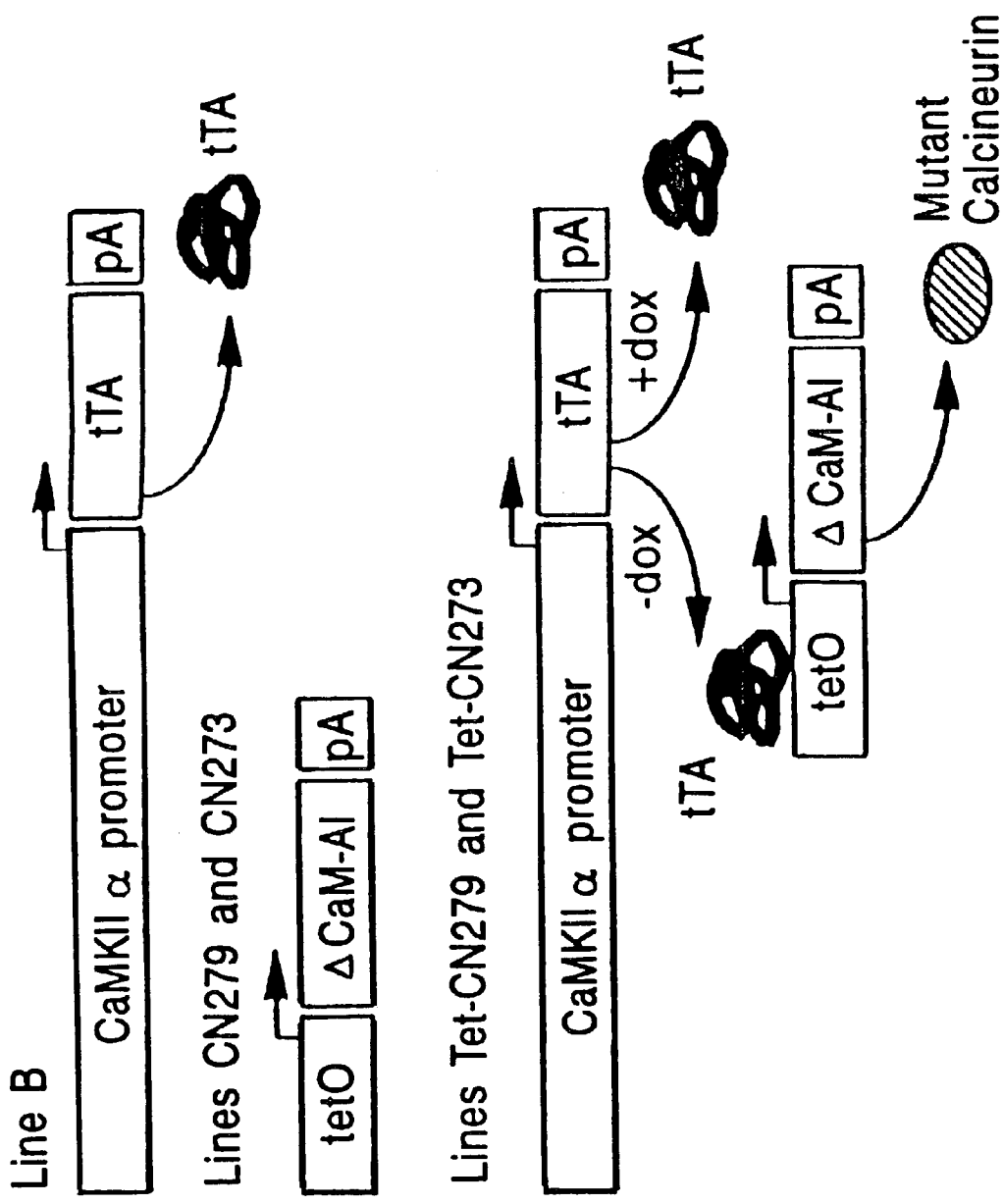

FIGURE 22B
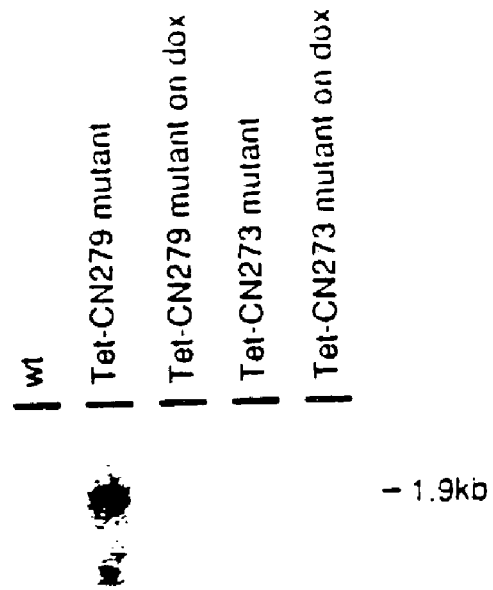
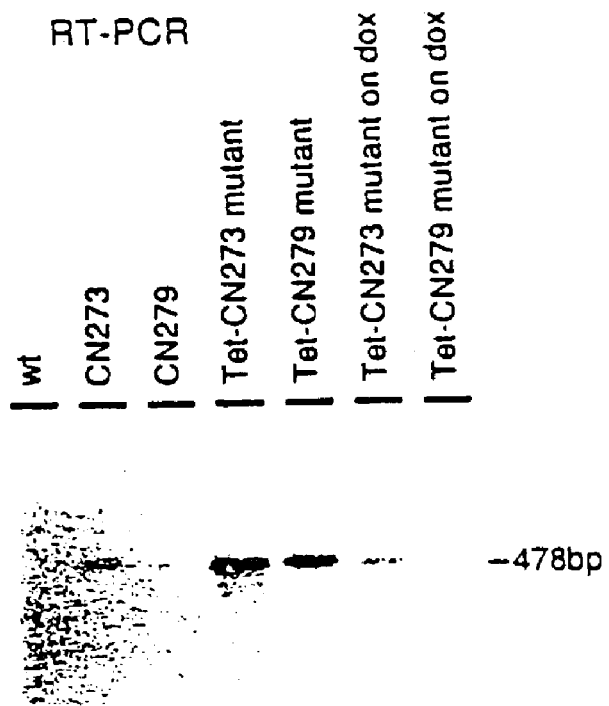

```
                         SEQUENCE LISTING

<160> NUMBER OF SEQ ID NOS: 8

<210> SEQ ID NO 1
<211> LENGTH: 25
<212> TYPE: PRT
<213> ORGANISM: SIMIAN VIRUS 40

<400> SEQUENCE: 1

Ser Ser Asp Asp Glu Ala Thr Ala Asp Ser Gln His Ser Thr Pro Pro
1               5                   10                  15

Lys Lys Lys Arg Lys Val Glu Asp Pro
            20                  25

<210> SEQ ID NO 2
<211> LENGTH: 35
<212> TYPE: DNA
<213> ORGANISM: ARTIFICIAL SEQUENCE
<220> FEATURE:
<223> OTHER INFORMATION: PROBE

<400> SEQUENCE: 2
gtgcatctgc cagtttgagg ggacgacgac agtat                              35

<210> SEQ ID NO 3
<211> LENGTH: 42
<212> TYPE: DNA
<213> ORGANISM: ARTIFICIAL SEQUENCE
<220> FEATURE:
<223> OTHER INFORMATION: PROBE
```

```
<400> SEQUENCE: 3
gccggaaacc aggcaaagcg ccattcgcca ttcaggctgc gc                          42

<210> SEQ ID NO 4
<211> LENGTH: 41
<212> TYPE: DNA
<213> ORGANISM: ARTIFICIAL SEQUENCE
<220> FEATURE:
<223> OTHER INFORMATION: PROBE

<400> SEQUENCE: 4
gtaaccgacc cagcgcccgt tgcaccacag atgaaacgcc g                           41

<210> SEQ ID NO 5
<211> LENGTH: 27
<212> TYPE: DNA
<213> ORGANISM: ARTIFICIAL SEQUENCE
<220> FEATURE:
<223> OTHER INFORMATION: PROBE

<400> SEQUENCE: 5
cttcaggcag tcgacgtcct gtctgtg                                           27

<210> SEQ ID NO 6
<211> LENGTH: 30
<212> TYPE: DNA
<213> ORGANISM: ARTIFICIAL SEQUENCE
<220> FEATURE:
<223> OTHER INFORMATION: PRIMER

<400> SEQUENCE: 6
gcaggatccg cttgggctgc agttggacct                                        30

<210> SEQ ID NO 7
<211> LENGTH: 24
<212> TYPE: DNA
<213> ORGANISM: ARTIFICIAL SEQUENCE
<220> FEATURE:
<223> OTHER INFORMATION: PRIMER

<400> SEQUENCE: 7
cctgcagcac aataatttgt tatc                                              24

<210> SEQ ID NO 8
<211> LENGTH: 24
<212> TYPE: DNA
<213> ORGANISM: ARTIFICIAL SEQUENCE
<220> FEATURE:
<223> OTHER INFORMATION: PROBE

<400> SEQUENCE: 8
taggtgacac tatagaatag ggcc                                              24
```

METHODS AND REAGENTS FOR DENDRITIC LOCALIZATION OF POLYNUCLEOTIDES

This application is a continuation of U.S. Ser. No. 08/969,137, filed Nov. 12, 1997, now U.S. Pat. No. 6,509,190 the content of which is hereby incorporated into this application by reference.

The invention disclosed herein was made with Government support under Grant No. 50733-03 from National Institutes of Mental Health. Accordingly, the U.S. Government has certain rights in this invention.

BACKGROUND OF THE INVENTION

Throughout this application, various publications are referenced by author and date. Full citations for these publications may be found listed alphabetically at the end of the specification immediately preceding the claims. The disclosures of these publications in their entireties are hereby incorporated by reference into this application in order to more fully describe the state of the art as known to those skilled therein as of the date of the invention described and claimed herein.

The insight that memory has time-dependent phases dates to 1890 when William James first proposed a distinction between a primary or short-term memory, a memory that has to be maintained continuously in consciousness, and secondary or long-term memory that can be dropped from consciousness and could be recalled at will at a later time (James, 1890). According to James view, short-term memory holds information for a few seconds whereas long-term memory holds information for long periods of time. Subsequent experimental work suggested that these two phases of memory are usually in series and that the transition from short- to long-term memory is facilitated by an increase in the saliency or the number of training trials (Ebbinghaus, 1885; Weiskrantz, 1970; Craik and Lockhart, 1972; Wickelgren, 1983; Mandel et al., 1989).

The distinction between these two major phases was placed on a firmer biochemical basis when long-term memory was found to require the synthesis of new proteins, whereas short-term memory does not (Davis and Squire, 1984). These Biochemical studies also revealed that short-term memory often lasted many minutes, and therefore was more enduring than the primary memory delineated y James. These studies therefore suggested that short-term memory may in turn have subdivisions, and that in addition to primary or working memory, there is a subsequent intermediate stage of, protein synthesis-independent, short-term memory. Further support for subcomponents of memory have also emerged from genetic studies in Drosophila and pharmacological studies in rodents and chicks (McGaugh, 1968; Cherkin, 1969; Gibbs and Ng, 1977; Frieder and Allweis, 1982; Rosenzweig et al., 1993; Tully et al., 1994; Zhao et al., 1995 a and b; Bennet et al., 1996).

In addition to being able to distinguish temporal phases in memory storage, studies in human and monkey also delineated two distinct neural systems for long-term memory based upon the types of information stored. Bilateral lesions of the medial temporal lobe revealed an impairment in declarative long-term memory, a memory for people, places and objects but these lesions spared non-declarative memory for perceptual and motor skill. Particularly, interesting was the finding that the lesions of the medial temporal lobe system, that interfere with declarative memory, only interfere with the long-term form of this memory and not with components of short-term memory, in particular not with working memory (Scoville and Milner, 1957; Mishkin, 1978; Zola-Morgan and Squire, 1985; Squire, 1987; Overman et al., 1990; Alvarez et al., 1994). These results indicate that structures in the medial temporal lobe, in particular the hippocampus, specifically subserve long-term memory but not some components of short-term memory.

SUMMARY OF THE INVENTION

The present invention provides for a recombinant nucleic acid molecule comprising a region of a calcium-calmodulin dependent kinase IIα promoter operatively linked to a gene of interest. The region of a calcium-calmodulin dependent kinase IIα promoter may comprise an 8.5 kilobase nucleic acid sequence which corresponds to the nucleic acid sequence of ATCC Accession No. 98532, designated pMM403. The present invention also provides a human cell line which has been stably transformed by a recombinant nucleic acid molecule comprising a gene of interest operatively linked to a nucleic acid encoding a calcium-calmodulin dependent kinase IIα promoter region which has a nucleotide sequence corresponding to the sequence of ATCC Accession No. 98582, designated pMM403. The present invention also provides for a transgenic nonhuman mammal whose germ or somatic cells contain a nucleic acid molecule which encodes a gene of interest under the control of a CaMKIIα promoter (ATCC Accession No. 98582), introduced into the mammal, or an ancestor thereof, at an embryonic stage. Another embodiment of the present invention is a method of evaluating whether a compound is effective in treating symptoms of a neurological disorder in a subject which comprises: (a) administering the compound to the transgenic nonhuman mammal whose germ or somatic cells contain a nucleic acid molecule which encodes a gene of interest under the control of CaMKIIα promoter, and (b) comparing the neurological function of the mammal in step (a) with the neurological function of the transgenic mammal in the absence of the compound, thereby determining whether the compound is effective in treating symptoms of the neurological disorder in a subject.

BRIEF DESCRIPTION OF THE FIGURES

FIGS. 1A-1B. Expression of lacZ mRNA in mouse forebrain. (FIG. 1A) schematic representation of the DNA constructs used for the generation of transgenic mice. lac-CMK: the 8.5-kbp CaMKIIα promoter region, as well as 84 nucleotides of the 5' non-coding exon, was fused to the *E.coli* lacZ gene. The entire 3'-UTR of the CaMKIIα mRNA was placed downstream of the lacZ coding region. lac-A: identical to lac-CMK except that the bovine growth hormone polyadenylation signal was substituted for the CaMKIIα 3'-UTR. nls-lac-CMK, the tet-O promoter (Craig et al., 1993) was linked to a modified lacZ gene with an in-phase fusion to the green fluorescent protein (GFP) and a nuclear localization sequence. (FIG. 1B) Northern blot analysis of poly (A)$^+$ RNA isolated from the forebrain of the lac-CMK and lac-A mice.

(FIG. 3A) In situ hybridization using a lacZ-specific oligonucleotide probe. SM (stratum molecular), dendritic layer of the dentate gyrus granule cells; SR (stratum radiatum), dendritic layer of the CA1 pyramidal cells. (FIG. 3B) X-gal staining of hippocampus from 20 μm horizontal sections as described in FIG. 2. (Bar=300 μm).

FIGS. 4A-4D. Differential expression of beta-gal within dendrites. (FIG. 4A) In situ hybridization against the nls-lac-CMK mouse using a lacZ specific probe. (FIG. 4B) Histochemical detection of β-gal in the nls-lac-CMK neuron in culture. The MAP2 antibody specifically labels microtubules along the dendritic shaft. MAP2 labeling is indicated in red. β-gal labeling is shown in green. Arrows denote β-gal in presumptive dendritic spines. Arrowheads indicate areas of punctate β-gal staining along the dendrite. (FIG. 4D) Expression of β-gal in a distal portion of the dendritic arbor. Arrowheads denote areas of punctate β-gal staining. Open arrow shows a dendrite arising from a neuron, which did not express the nls-lac-CMK transgene (Bar=10 μM)

(FIG. 5A) Strategy used to obtain forebrain-specific doxycycline-regulated transgene expression. Two independent lines of transgenic mice are obtained, and the two transgenes are introduced into a single mouse through mating. (FIG. 5B) Quantitation by RT-PCR Southern blot of CaMKII-Asp$^{286}$ expression from the tet-O promoter, RT-PCR was performed on total forebrain RNA and probed for expression of the CaMKII-Asp$^{286}$ mutant mRNA as described (7, 21). Tg1, mouse carrying only the CaMKII promoter-tTA transgene (line B). Tg2, mouse carrying only the tet-O-CaMKII-Asp$^{286}$ transgene (line 21) Tgq/Tg2, double transgenic mouse carrying both the CaMKII promoter-tTA transgene (line B) and tet-O-CaMKII-Asp$^{286}$ (line 21) transgenes. Tg1/Tg2+Dox, double transgenic mouse treated with doxycycline (2 mg/ml) plus 5% sucrose in the drinking water for four weeks.

FIGS. 6A-6B. Forebrain-specific activation of a tet-O-lacZ transgene. (FIG. 6A) Coronal section of double transgenic line B lac1 stained with X-Gal as described (Mayford et al., 1996). Ctx, cerebral cortex; Str, striatum; Hip, hippocampus; Amy, amygdala. (FIG. 6B) X-Gal-stained coronal section of the hippocampus from double transgenic lines B lac1 and B lac2. CA1, CA1 cell body layer; CA3, CA3 cell body layer; OG, dentate gyrus.

(FIG. 9A) The Barnes circular maze. (FIG. 9B) Percentage of B22 transgenic and wilt-type mice that met the learning criterion on the Barnes circular maze. On the Barnes circular maze (Bach et al., 1995) the mice (2.5 to 6 months of age) were tested once a day until they met the criterion (Five out of six sessions with three or fewer errors or until 40 days had elapsed). The order of holes searched was recorded by an observer who was blind to genotype and doxycycline condition, and from these data the number of errors was determined. Errors were defined as searches of any hole that did not have the tunnel beneath it. Searches included nose pokes and head deflections over the hole. At the end of each session the search strategy used was recorded by the observer. The spatial search strategy was operationally defined as reaching the escape tunnel with both error and distance scores≦3. Distance was calculated by counting the number of holes between the first hole searched within a session and the escape tunnel. A one-factor analysis of variance (ANOVA) (gender) revealed no significant effect of gender for either transgenic or wild-type mice, so the data were collapsed across this variable. For the error data, a three-factor ANOVA (genotype, doxycycline, and session block) with one repeated measure was used. For the spatial search strategy data, the two groups of B22 transgenic mice were compared with a two-way ANOVA (doxycycline and session block) with one repeated measure. A chi-square analysis revealed that the percentage of B22 transgenics acquiring the Barnes Maze (0%) was significantly different from B22 transgenics on doxycycline and both wild-type groups ($X^2$=53.05, P<0.0001). Four groups of mice were tested: B22 transgenics (n=6), B22 transgenics on doxycycline (1 mg/ml) for 4 weeks (n=6), wild types (n=8), and wild types on doxycycline (1 mg/ml) for 4 weeks (n=7) (FIG. 9C) Mean number of errors across session blocks composed of five sessions. Values represent group means±SEM. A three-way ANOVA revealed a main effect of genotype (F[1.23]=4.28, P=0.04). (FIG. 9D) The percentage of sessions in which the spatial search strategy was used across session blocks by B22 transgenic mice. Values represent group means±SEM. A two-way ANOVA revealed a significant main effect of doxycycline (F[1,10]= 7.313, P=0.02).

(FIG. 10C) Time line illustrating administration of doxycycline and behavioral training and testing. (FIG. 10D) Retention of context and cued conditioning. Percentage of time spent freezing to context and cue 6 weeks after training. Values represent group means±SEM. Post hoc analysis by the Scheffe test revealed that B21 transgenic mice that were switched to water froze significantly less to context than B21 transgenic mice on doxycycline (P=0.01) and wild types (P=0.008) and significantly less to cue than B21 transgenic mice on doxycycline (P=0.02) and wild types (P=0.0088). Three groups of mice were tested B21 transgenics on doxycycline for four weeks before training and 6 weeks after training (n=8), B21 transgenics on doxycycline for four weeks before training that were switched to water for the 6 weeks after training (n=8), and wild type mice (from both B22 and B21 lines, n=19). (FIG. 10E) The percentage of time spent freezing to an intruder during the first 120 s after the mouse was exposed to a rat. Values represent group means±SEM.

FIGS. 11A-D. Calcineurin transgene is expressed in the hippocampus of CN98 mutant mice forebrain.

FIG. 11A. Schematic representation of the calcineurin transgene construct used to generate the CN98 mice.

FIG. 11B. Northern blot analysis of total RNA from CN98 mice.

FIG. 11C. Enzyme activity determined in hippocampal extracts from CN98 mice. Dephosphorylation of $\alpha^{32}P$ substrate peptide was measured in the absence or presence of the $Ca^{2+}$ chelator EGTA. Values are mean±SEM. Wild-type: 4.63±0.44 nmol Pi/min/mg, n=6; CN98 mutant; 8.15±0.57 nmol Pi/min/mg, n=4, p<0.001; CN98 wild-type+EGTA: 0.427±0.16 nmol Pi/min/mg, n=6; CN98 mutant+EGTA: 0.32±0.14 nmol Pi/min/mg, n=4, p>0.05.

FIG. 11D. Regional distribution of calcineurin transgene in CN98 mice determined by in situ hybridization.

FIG. 12A. Input-output curve of fEPSP slope (mV/ms) versus stimulus intensity (V) at the Schaffer collateral-CA1 pyramidal cell synapse in CN98 mutant and wild-type mice. Data are presented as mean±SEM.

FIG. 12B. Plot of presynaptic fiber volley amplitude (PSFV, mV) versus fEPSP slope at the Schaffer collateral-CA1 pyramidal cell synapse from a random sample of slices from CN98 mutant and wild-type mice.

FIG. 12C. Input-output curve of fEPSP slope (mV/ms) versus intensity (V) at the Schaffer collateral-CA1 pyramidal cell synapse in CN98 mutant (13 slices, 4 mice) and wild-type (16 slices, 4 mice) mice in the presence of the non-NMDA glutamate receptor antagonist DNQX (10 μM) and reduced $MgSO_4$ (50 μM). Data are presented as mean±SEM. Inset shows representative NMDA receptor-mediated synaptic responses during a one second, 100 Hz tetanus in wild-type and mutant slices. Scale bar is 50 ms and 5 mV.

FIG. 12D. Comparision of PTP in CN98 mutant and wild-type mice. PTP was evoked by a single 100 Hz, one second train administered in the presence of 50 μM DL-AP5. Data are presented as mean±SEM of the nomalized fEPSP slope.

FIG. 12E. Comparison of PPF in CN98 mutant and wild-type mice with interstimulus intervals of 20, 50. 100 and 250 ms. Data are presented as the mean±SEM of the facilitation of the second response relative to the first response of 16 slices from 7 wild-type mice and 15 slices from 6 mutant mice.

FIG. 12F. Comparison of LTD induced by 15 minutes of 1 Hz stimulation in CN98 wild-type and mutant mice aged 3-4 weeks. Data are presented as mean±SEM of the normalized fEPSP slope.

Effect of overexpression of calcineurin on LTP in CN98 wild-type (●) and mutant (○) animals. LTP elicited by (A) a single 100 Hz train of one second duration, or (B) four 100 Hz trains spaced by five minute intervals. Each point in the time courses represents the mean fEPSP slope±SEM normalized to the average of the pretetanus fEPSP slope. Insets show representative fEPSP traces just before tetanus and FIG. 13A) 1 hour or FIG. 13B) 3 hours after.

Figure 13B:
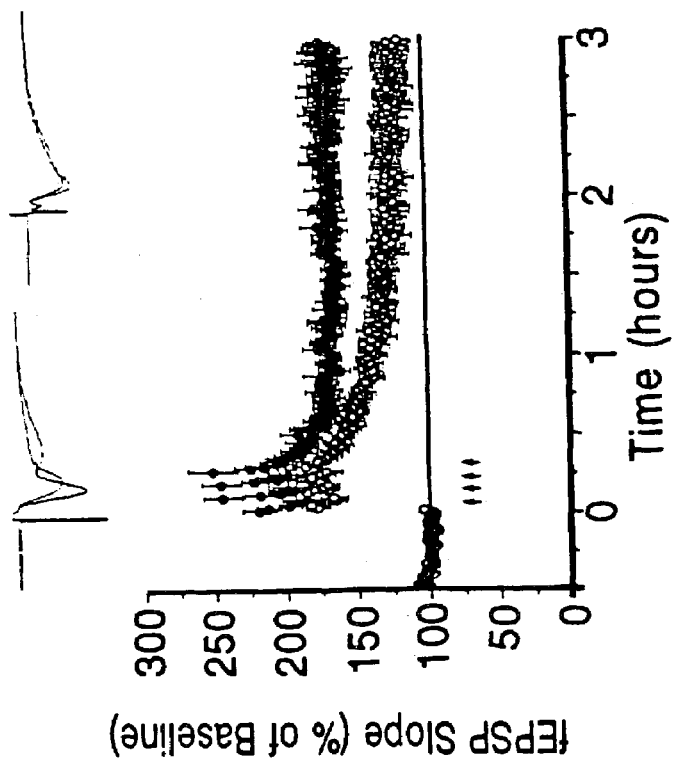
FIGS. 13A-13D. Overexpression of calcineurin inhibits L-LTP induced by four 100 Hz trains but not E-LTP induced by one 100 Hz train.
Figure 13A:
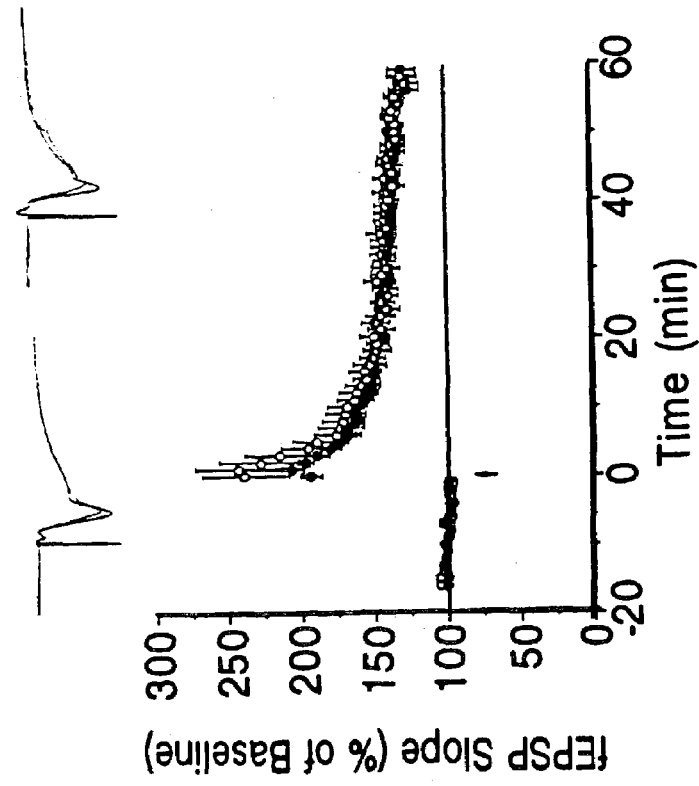
Figure 13D:
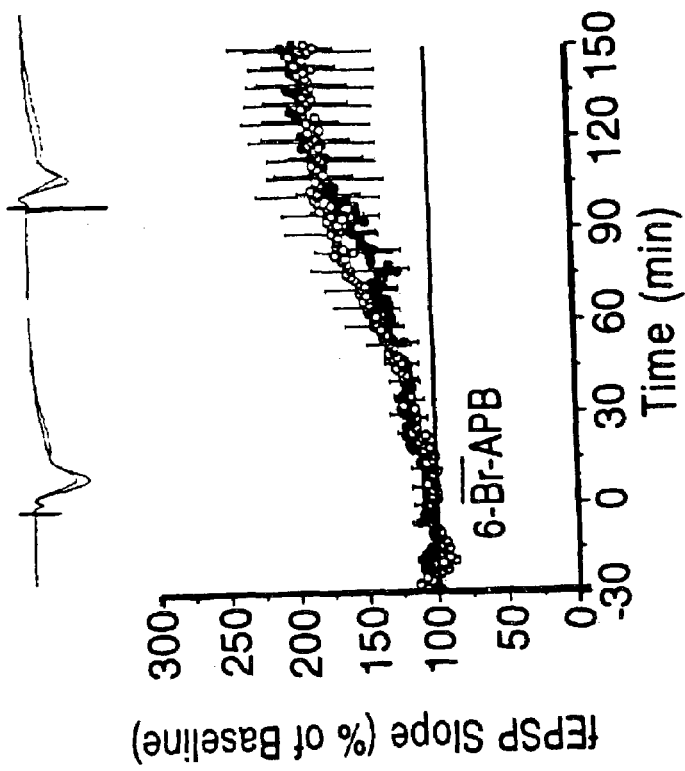
Figure 13C:
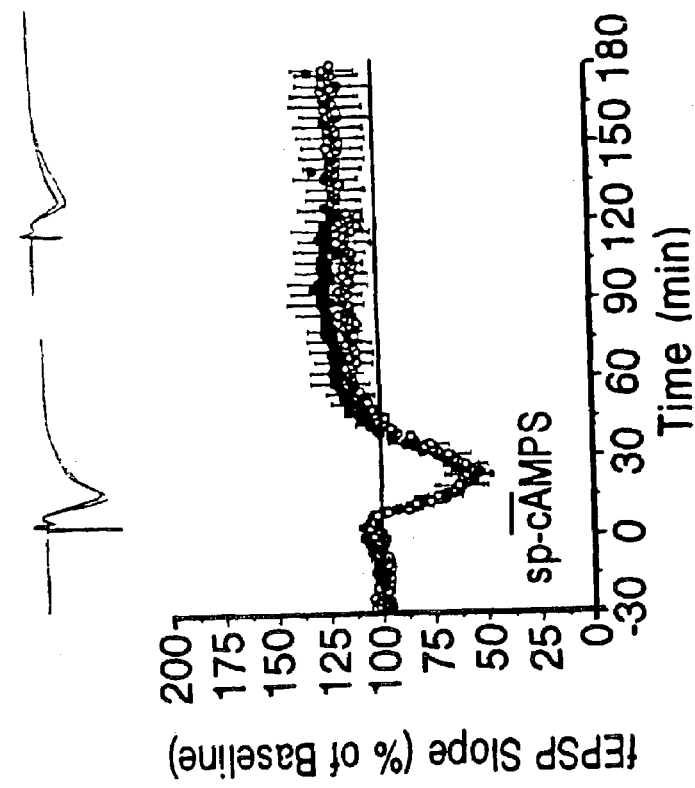

FIG. 13C) and FIG. 13D): Drug was added at the time indicated in both panels at a concentration of 100 μM. Each point in the time courses represents the mean fEPSP slope±SEM normalized to the average of the predrug fEPSP slope. Insets show representative fEPSP traces just before drug addition and 3 hours after. In (C), the decrease in the fEPSP slopes elicited towards the end of Sp-cAMPS application has been previously demonstrated to reflect a transient A1-adenosine receptor-mediated decrease in glutamate release (Frey et al., 1993).

FIGS. 14A-F. Effects of protein synthesis and PKA inhibitors on four train and two train LTP.

Figure 14A:
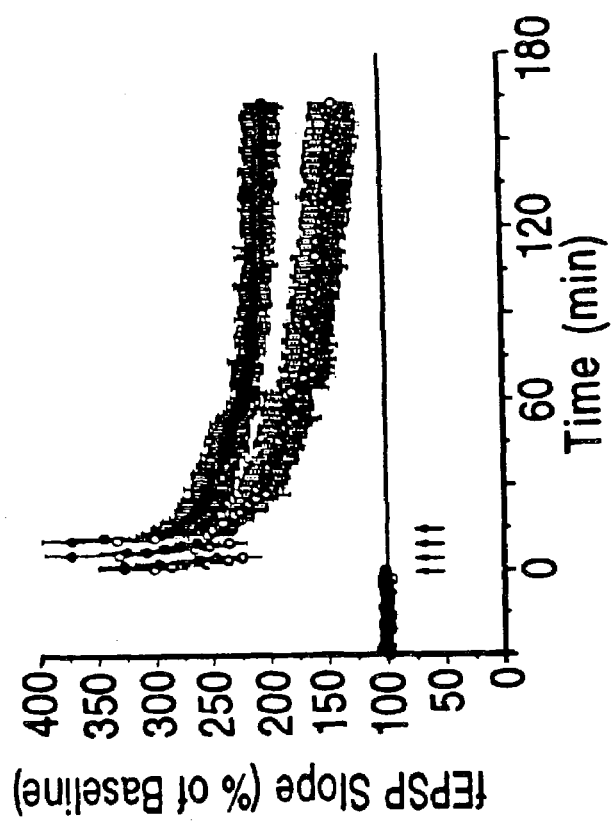

FIG. 14A. LTP induced by four 100 Hz trains, with a five minute intertetanus interval in the presence of anisomycin (□, 30 μM) or KT5720 (○, 1 μM) in wild-type mouse hippocampal slices. Drugs were added beginning 15 minutes prior to the first tetanus, and were washed out 15 minutes after the last tetanus. Each point in the time course represents the mean fEPSP slope±SEM normalized to the average of the pretetanus fEPSP slope.

Figure 14B:
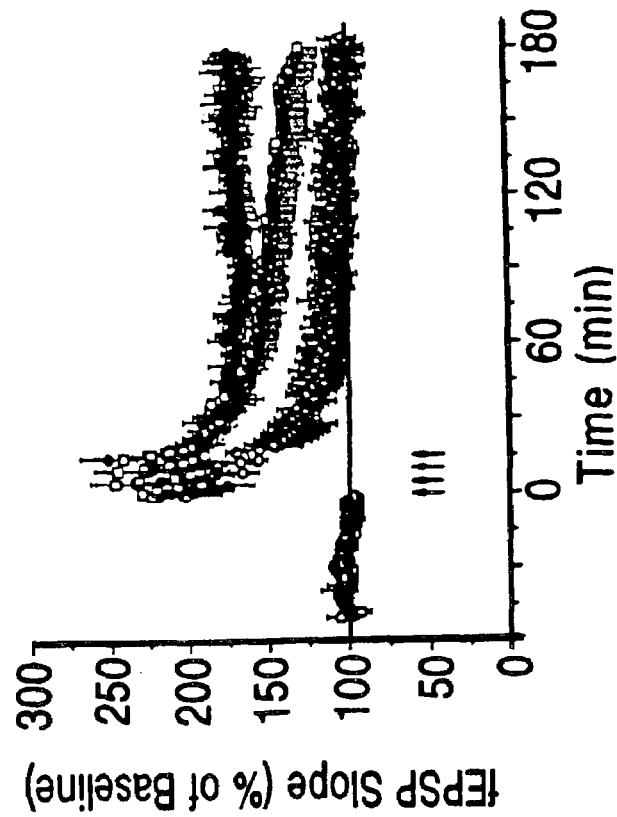

FIG. 14B. Effects of prolonged anisomycin pretreatment on LTP induced by four 100 Hz trains. Anisomycin (○, 30 μM) was added 60 minutes prior to the first tetanus, and was washed out 15 minutes after the last tetanus. Each point in the time course represents the mean fEPSP slope±SEM normalized to the average of the pretetanus fEPSP slope. No drug: 10 slices, 8 mice; Anisomycin 4 slices, 4 mice.

Figure 14D:
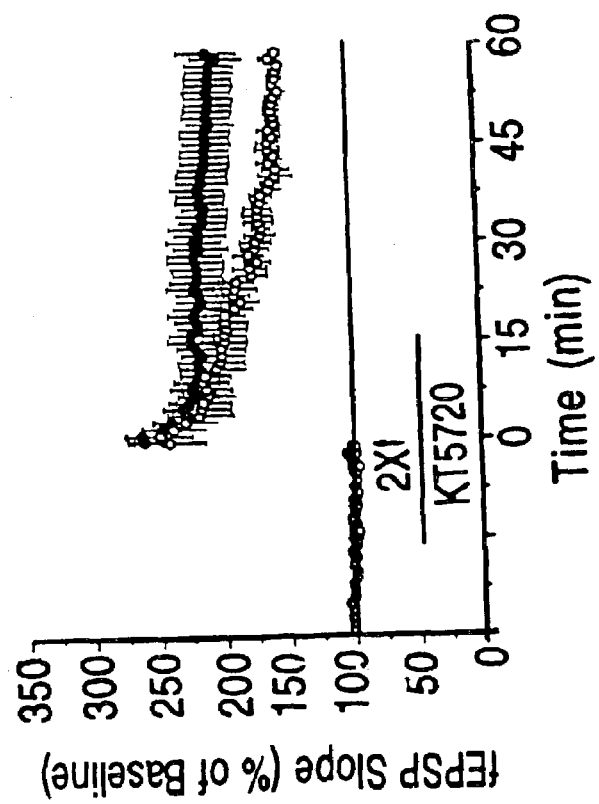
Figure 14C:
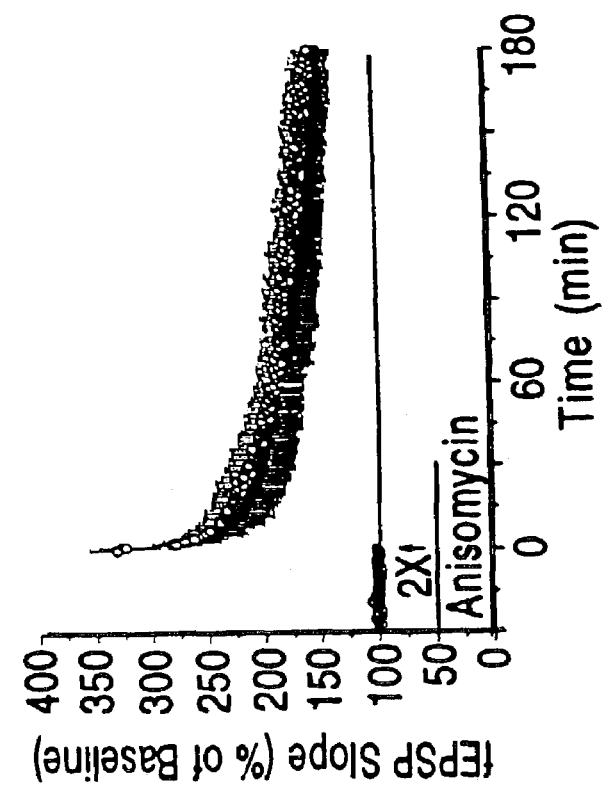

FIG. 14C. LTP introduced by two 100 Hz trains, with a 20 second interstimulus interval, in the presence or absence of anisomycin (○, 30 μM) in wild-type hippocampal slices. Each point in the time course represents the mean fEPSP slope±SEM normalized to the average of the pretetanus fEPSP slope. No drug: 8 slides, 5 mice; Anisomycin: 7 slices, 4 mice.

FIG. 14D. Effect of the PKA inhibitor KT5720 (○, 1 μM) on LTP induced by two 100 Hz trains in wild-type hippocampal slices. Each point in the time course represents the mean fEPSP slope±SEM normalized to the average of the pretetanus fEPSP slope.

Figure 14F:
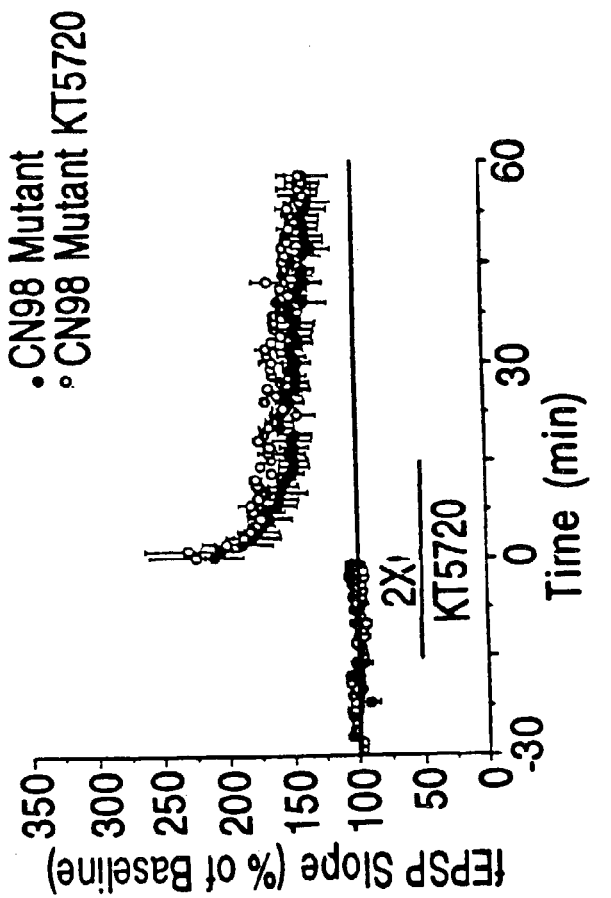
Figure 14E:
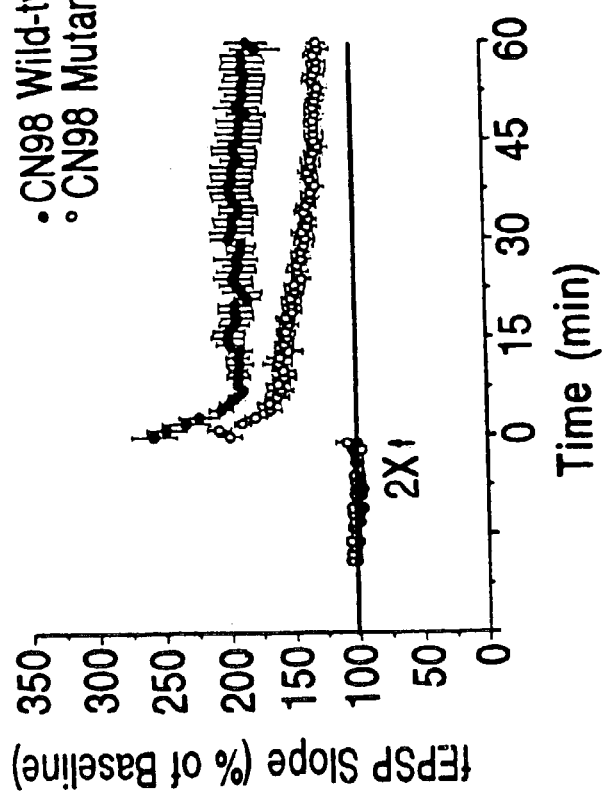

FIG. 14E. LTP induced by two 100 Hz trains in hippocampal slices from CN98 mutant (○) and wild-type (●) mice. Each point in the time course represents the mean fEPSP slope±SEM normalized to the average of the pretetanus fEPSP slope.

FIG. 14F. Effect of the PKA inhibitor KT5720 (○, 1 μM) on LTP induced by two 100 Hz trains hippocampal slices from CN98 mutant mice. Each point in the time course represents the mean fEPSP slope±SEM normalized to the average of the pretetanus fEPSP slope.

Figure 15A:
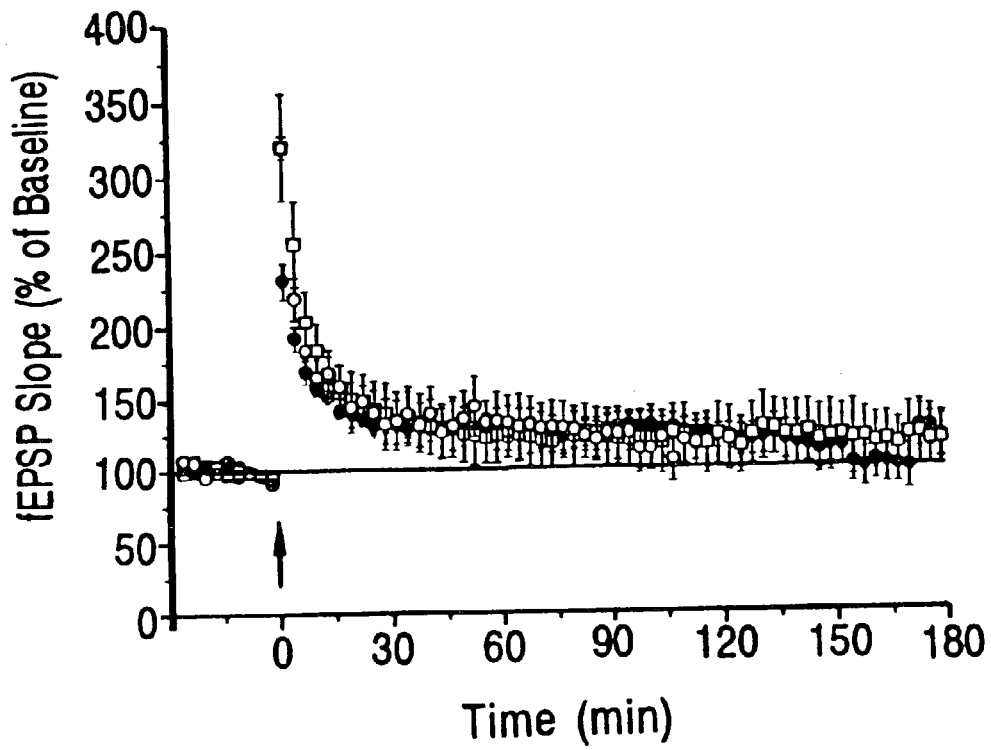
Figure 15B:
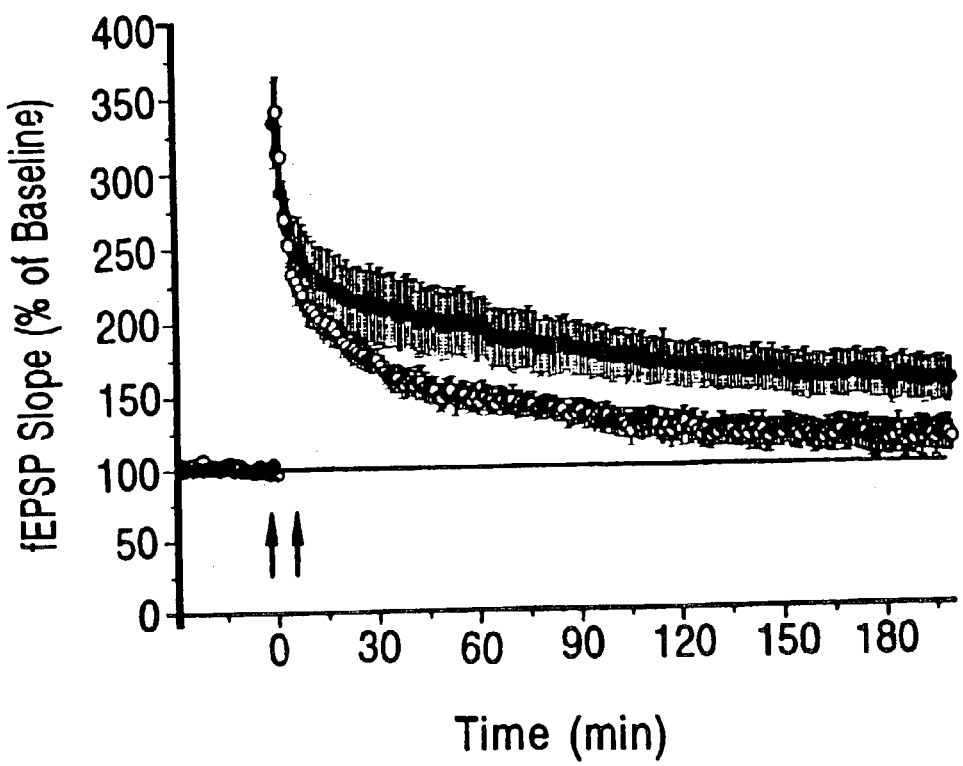
Figure 15C:
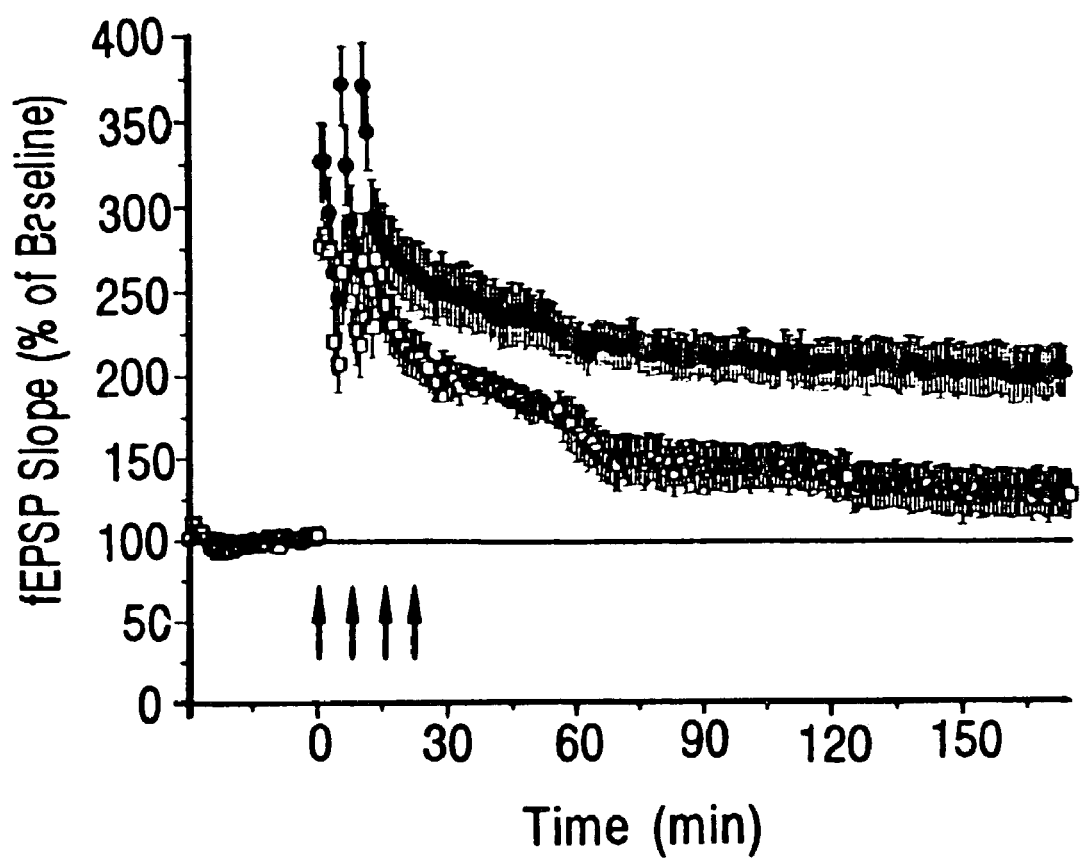

FIGS. 15A-C. LTP induced by two and four train (FIG. 15B and 15C), but not one train (FIG. 15A), protocols is reduced in wild-type mice (●) and mice overexpressing the calcineurin transgene with the tTA system (○). FIG. 14A. Wild-type (●): 14 slices, 9 mice, Tet-CN279 mutants (□): 6 slices, 3 mice; Tet-CN273 mutants (○): 4 slices, 3 mice; FIG. 15B. Wild-type (●): 7 slices, 4 mice; Tet-CN273 mutants (○): 6 slices, 3 mice. FIG. 15C. Wild-type (●): 10 slices, 8 mice; Tet-CN279 mutants (□)L 7 slices, 4 mice.

FIGS. 16A-D. Basal synaptic transmission and short term forms of synaptic plasticity are not altered by overexpression of calcineurin with the tTA system.

Figure 16A:
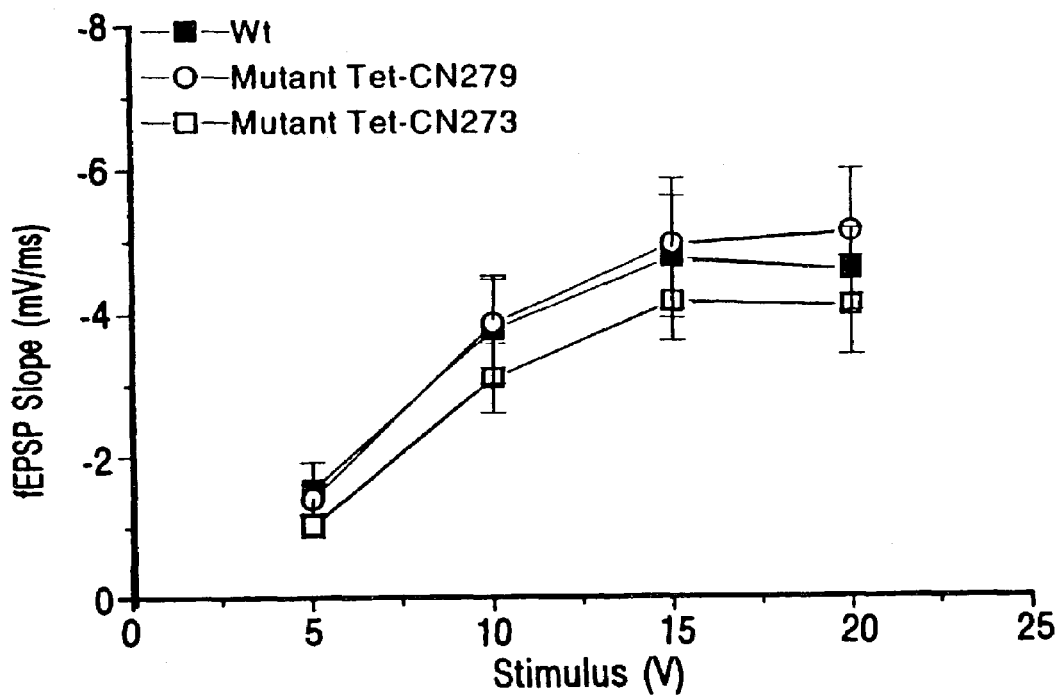

FIG. 16A. Input-output curve of fEPSP slope (mV/ms) versus stimulus intensity (V) at the Schaffer collateral-CA1 pyramidal cell synapse in Tet-CN279 (9 slices, 4 mice) and Tet-CN273 (20 slices, 7 mice) mutant and wild-type (21 slices, 9 mice) mice. Data are presented as mean±SEM.

Figure 16B:
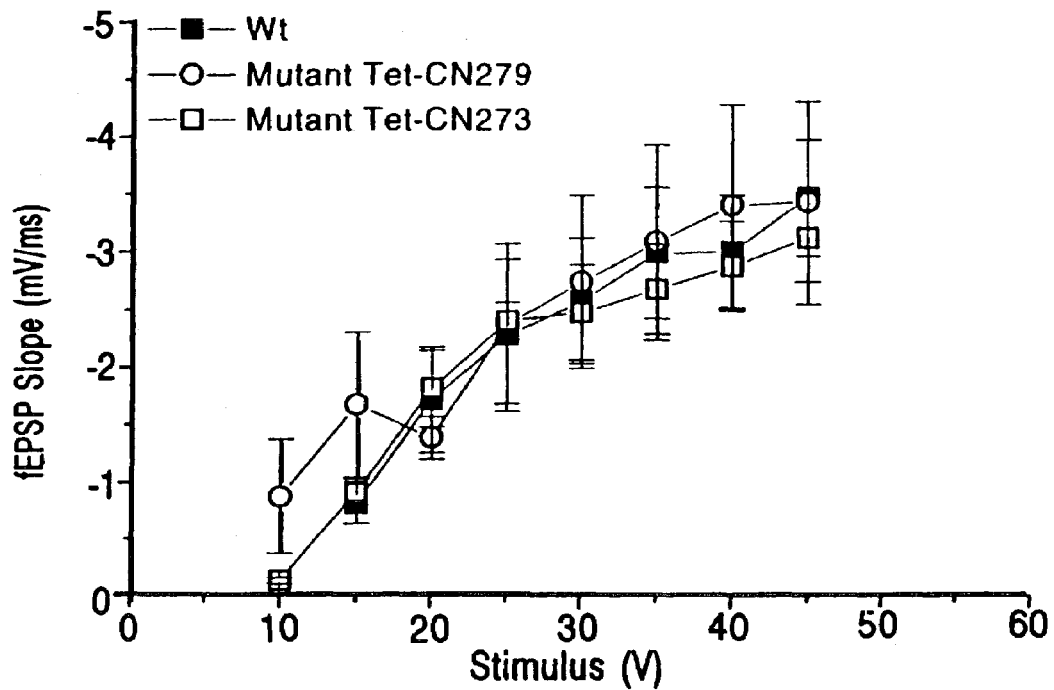

FIG. 16B. Input-output curve of fEPSP slope (mV/ms) versus intensity (V) at the Schaffer collateral-CA1 pyramidal cell syhapse in Tet-CN279 (8 slices, 4 mice) and Tet-CN273 (8 slices, 4 mice) mutant and wild-type (21 slices, 8 mice) mice in the presence of the non-NMDA glutamate receptor antagonist DNQX (10 µM) and reduced $MgSO_4$ (50 µM). Data are presented as mean±SEM.

Figure 16C:
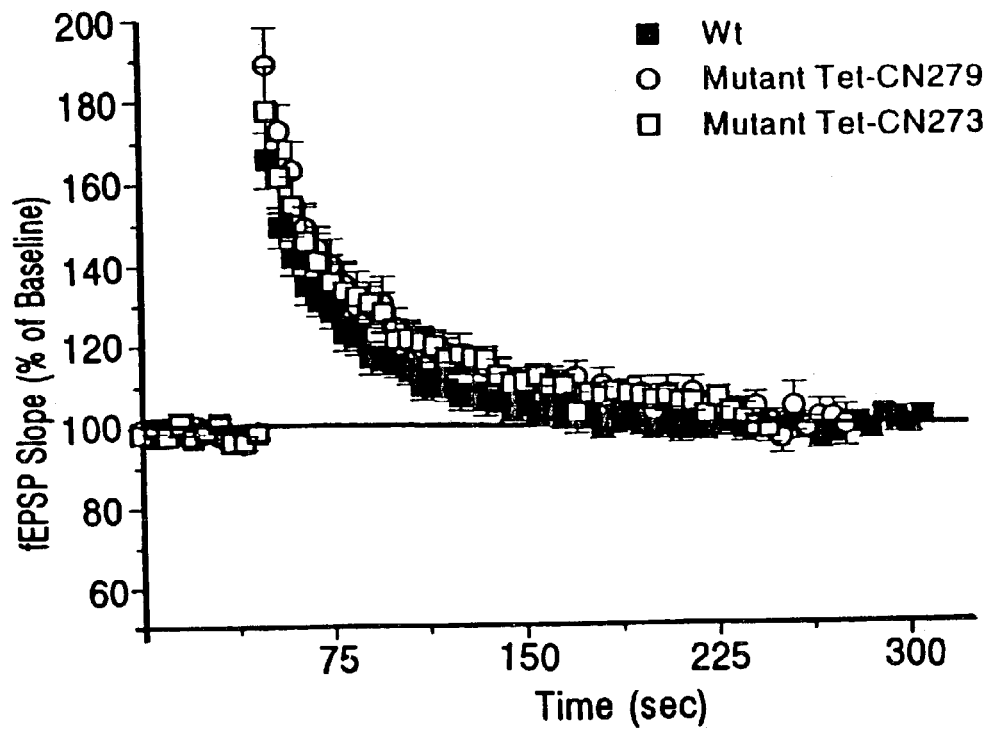

FIG. 16C. Comparison of PTP in Tet-CN278 (6 slices, 3 mice) and Tet-CN273 (8 slices, 4 mice) mutant and wild-types (15 slices, 8 mice) mice. PTP was evoked by a single 100 Hz, one second train administered in the presence of 50 µM DL-AP5. Data are presented as mean±SEM of the normalized fEPSP slope.

Figure 16D:
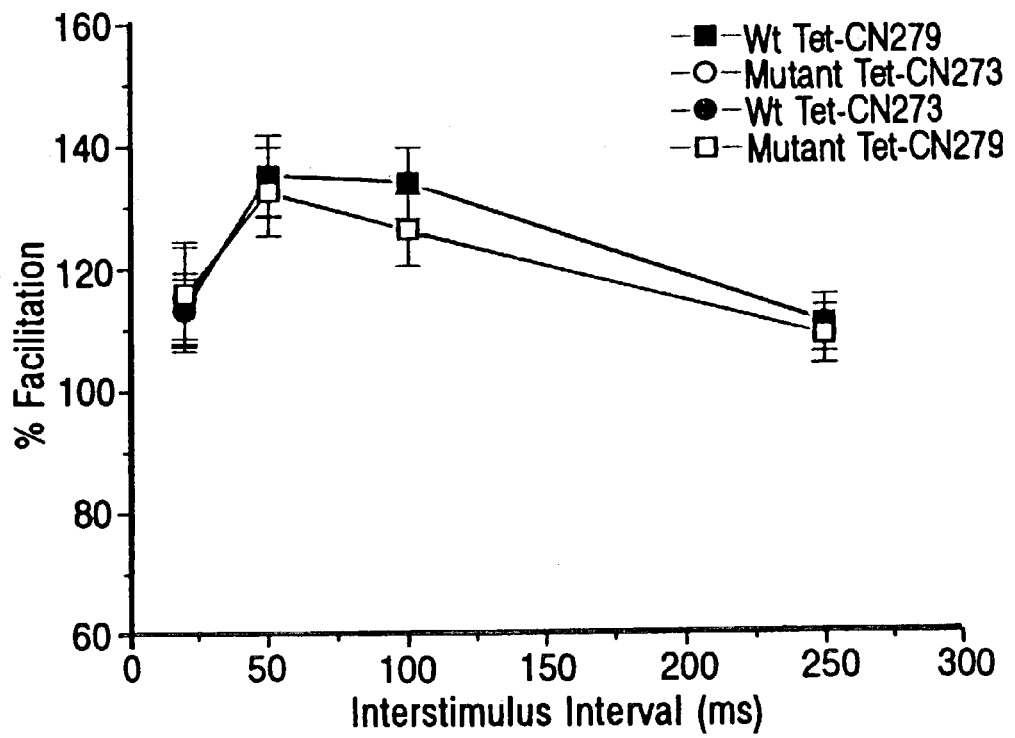

FIG. 16D. Comparison of PPF in Tet-CN273 (9 slices, 4 mice) and Tet-CN279 (13 slices, 4 mice) mutant and wild-type (27 slices, 10 mice) mice with interstimulus intervals of 20, 50, 100 and 250 ms. Data are presented as the mean±SEM of the facilitation of the second response relative to the first response.

Figure 17A:
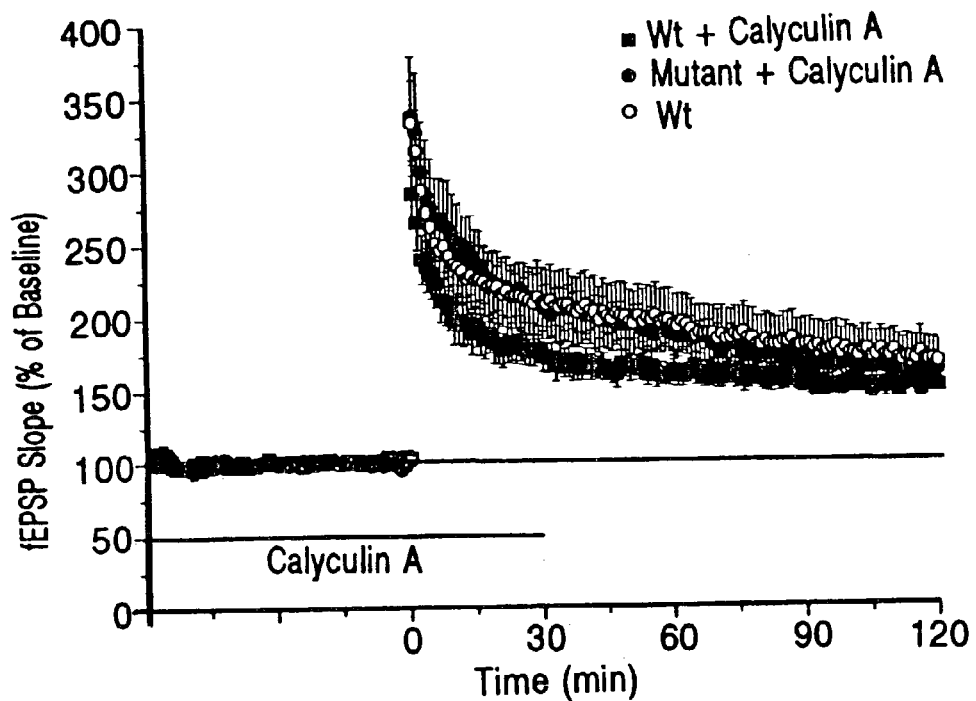
Figure 17B:
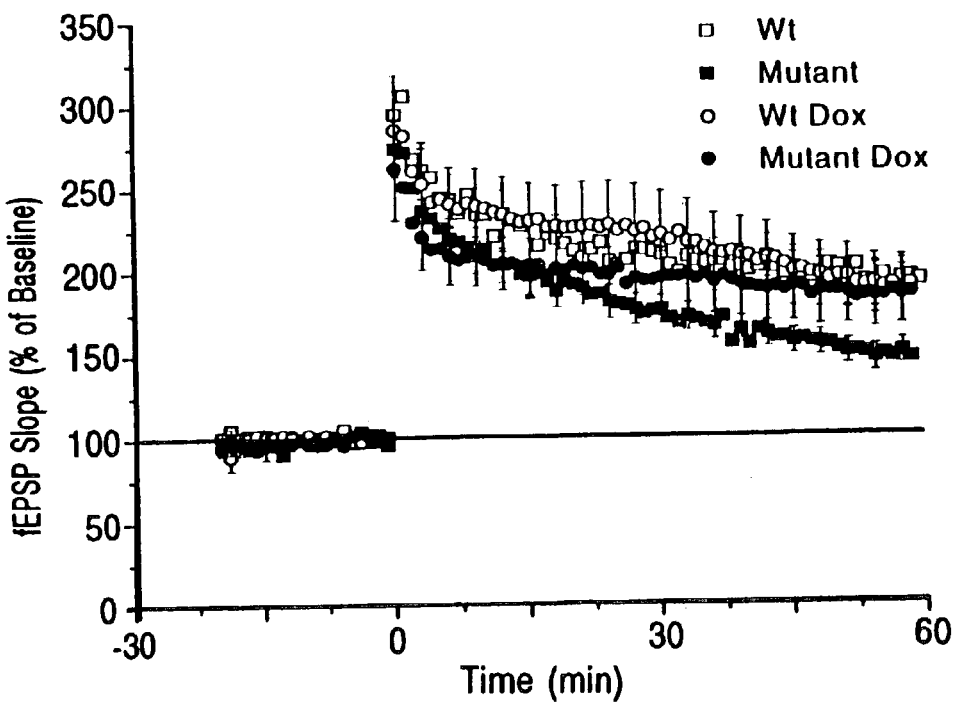

FIGS. 17A-B. FIG. 17A. Calyculin A (750 nM) rescues the deficit in LTP induced by two 100 Hz trains in Tet-CN279 mutant mice. Each point in the time course represents the mean fEPSP slope±SEM normalized to the average of the pretetanus slope. Wildtype (●), 7 slices, 4 mice), Mutant with calyculin A pretreatment (○), 6 slices, 3 mice), wildtdype with cayculin A pretreatment (■), 6 slices, 3 mice).

FIG. 17B. The LTP deficit seen in slices from Tet-CN279 mutants can be reversed be suppressing expression of the transgene with doxycycline. Each point in the time course represents the mean fEPSP slope±SEM normalized to the average of the pretetanus slope.

Figure 18A:
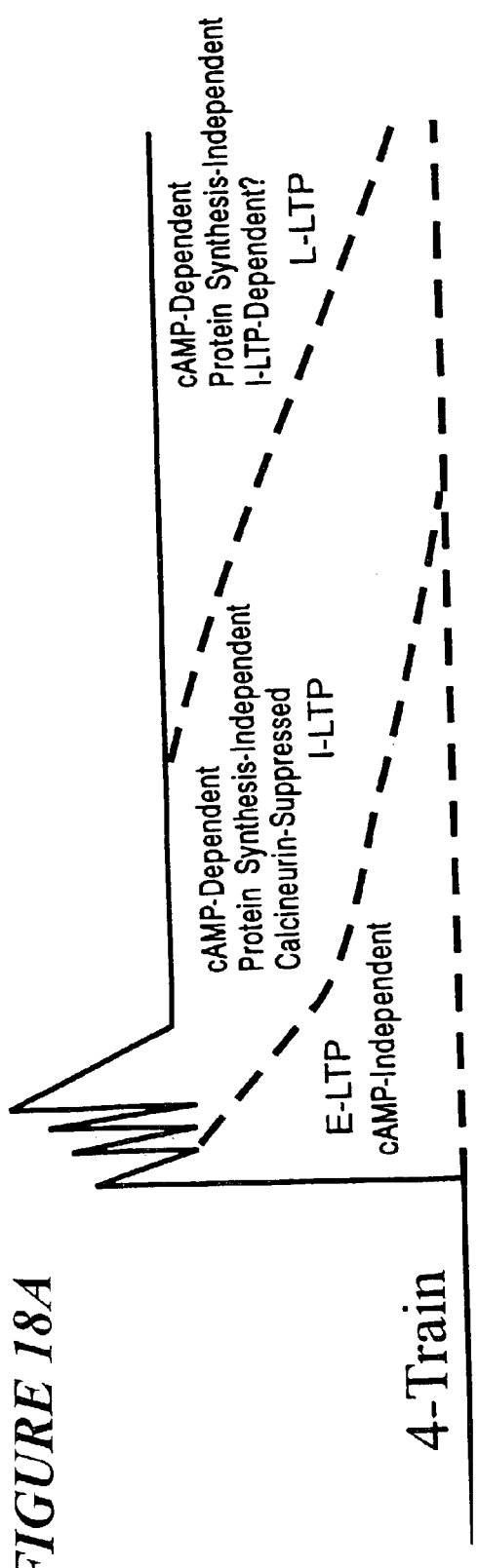
Figure 18B:
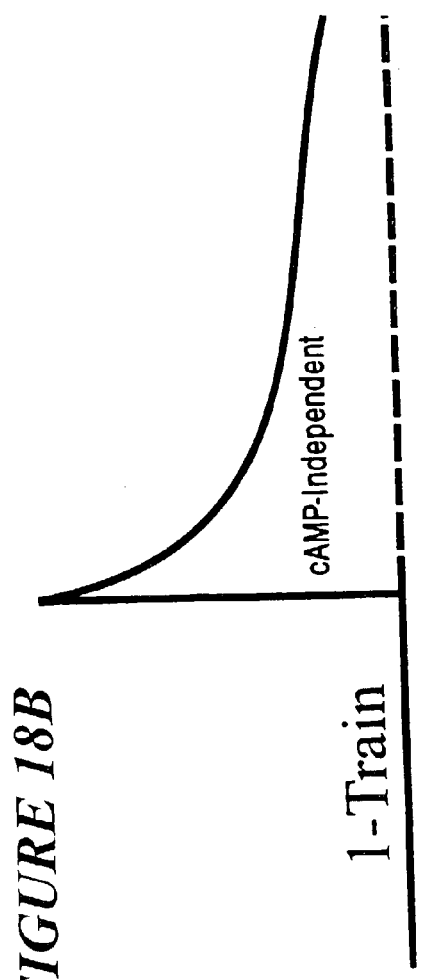

FIGS. 18A-B. A PKA-dependent, protein synthesis independent phase of LTP, I-LTP exists in mouse hippocampus.

FIGS. 18A-B. Schematic representation of the time course of potentiation induced by one train (lower panel, FIG. 18B) and four-train (upper panel, FIG. 18A) protocols.

Figure 19A:
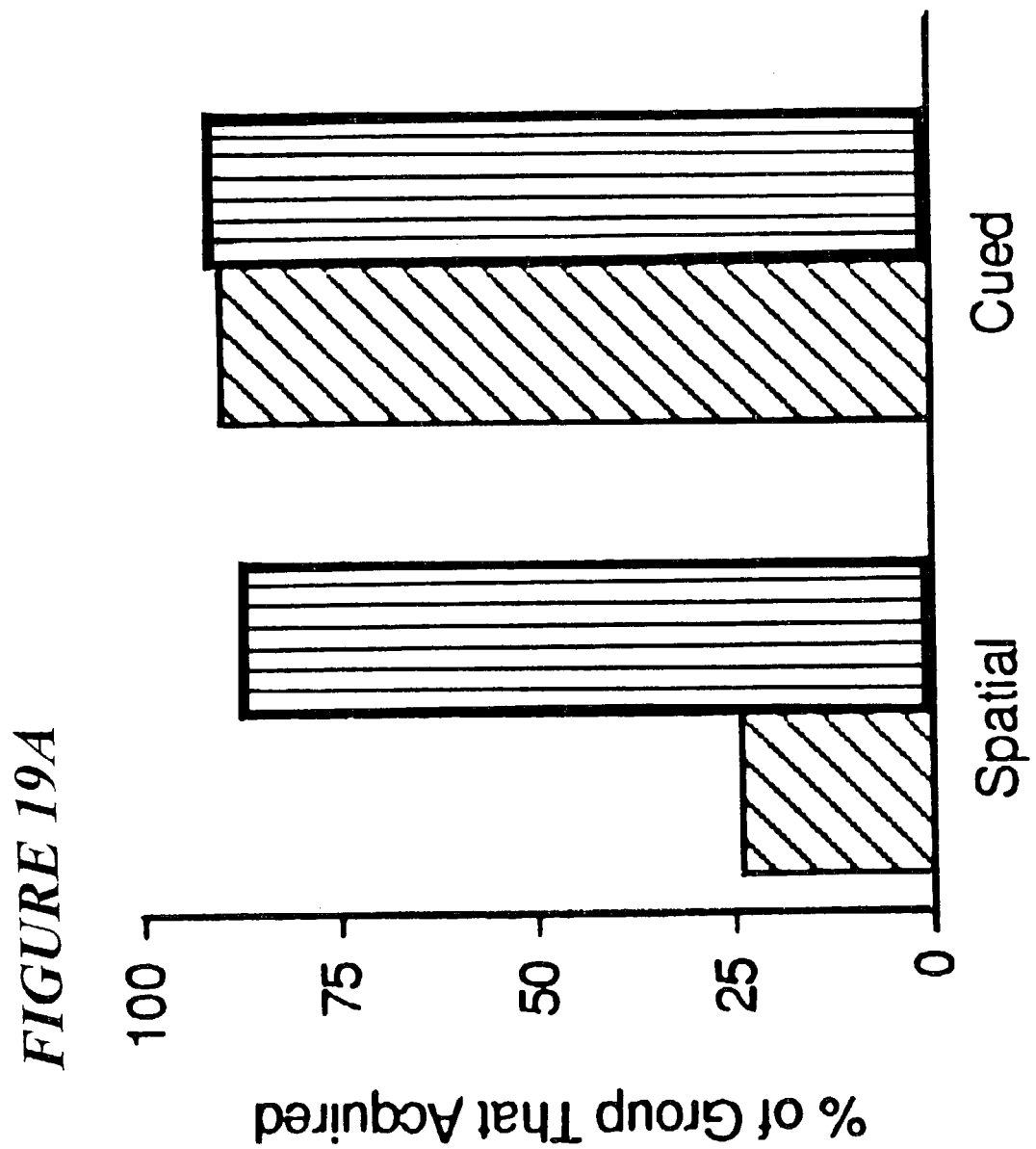
Figure 19B:
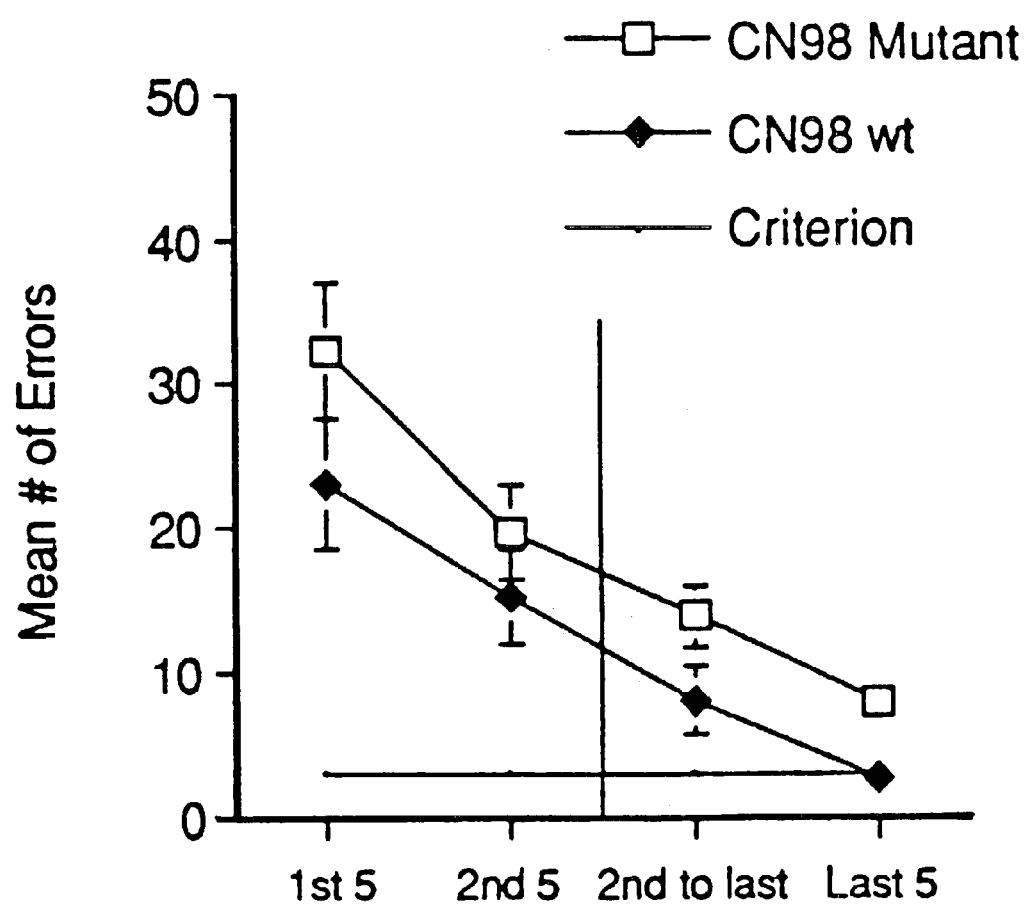
Figure 19C:
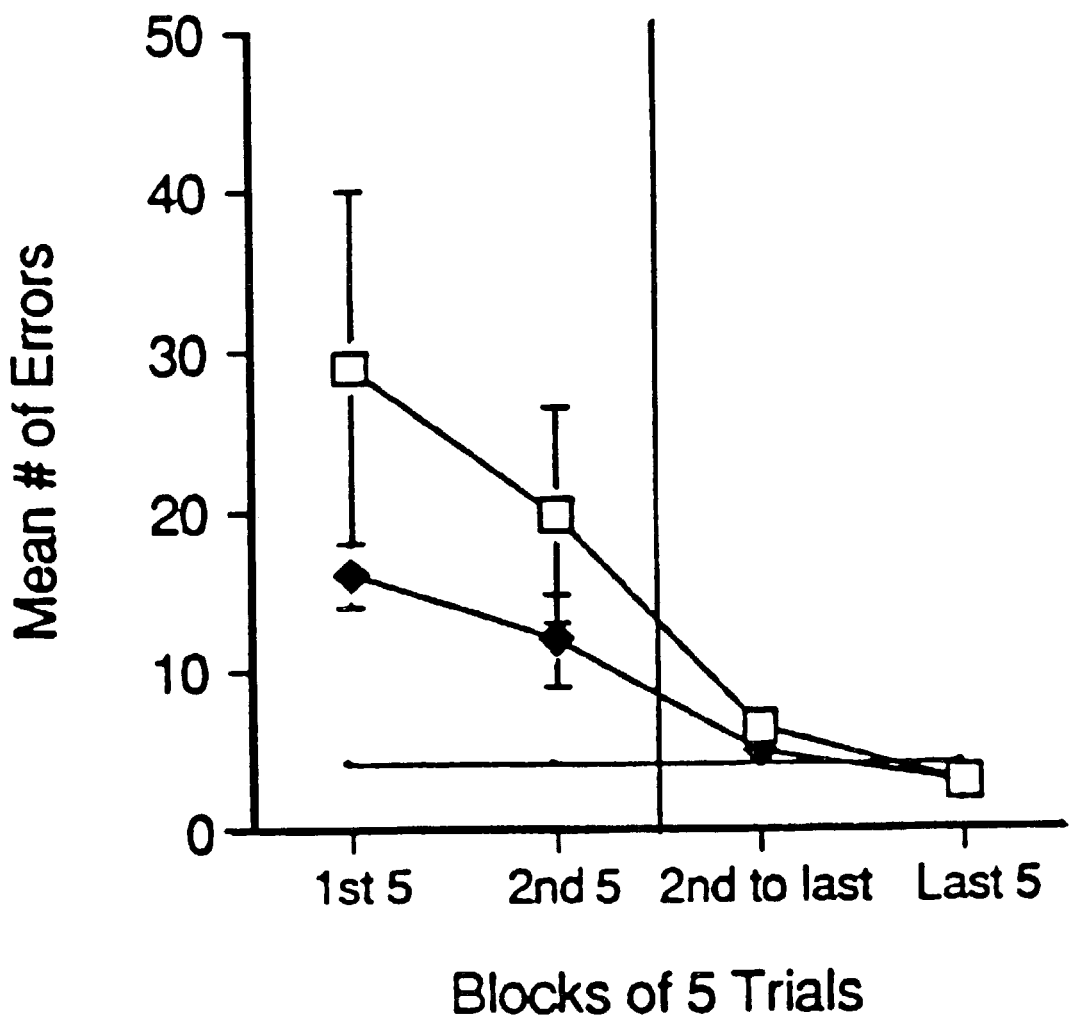

FIGS. 19A-C. CN98 mutant mice have impaired spatial memory on the Barnes maze when tested with one trial a day, but have normal memory on a cued version of the maze.

FIG. 19A. Percentage of CN98 mice that acquired the spatial and cued versions of the Barnes maze with 1 trial a day.

FIG. 19B. Mean number of errors made by CN98 mice on the spatial version of the Barnes maze with 1 trial a day.

FIG. 19C. Mean number of errors made by CN98 mice on the cued version of the Barnes maze with 1 trial a day.

Figure 20A:
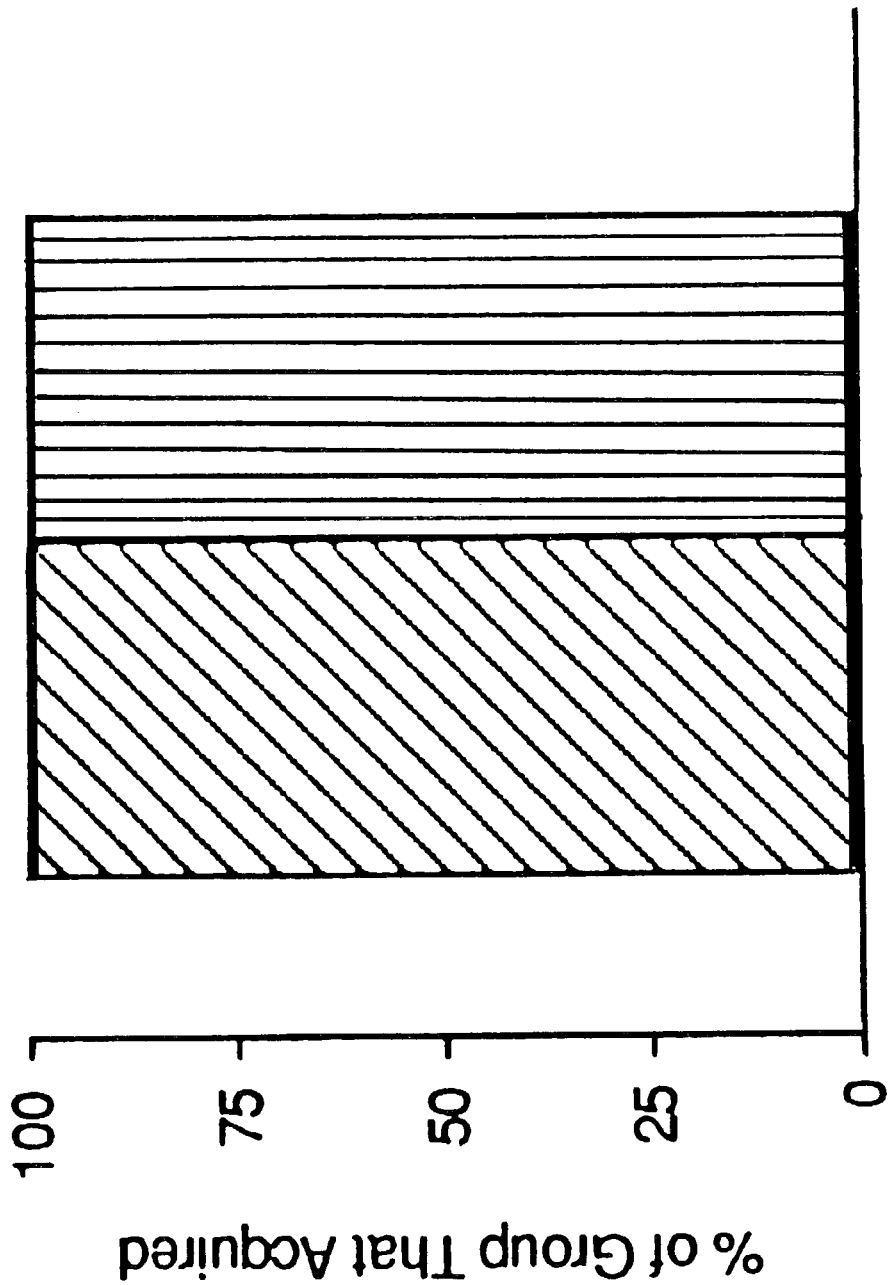
Figure 20B:
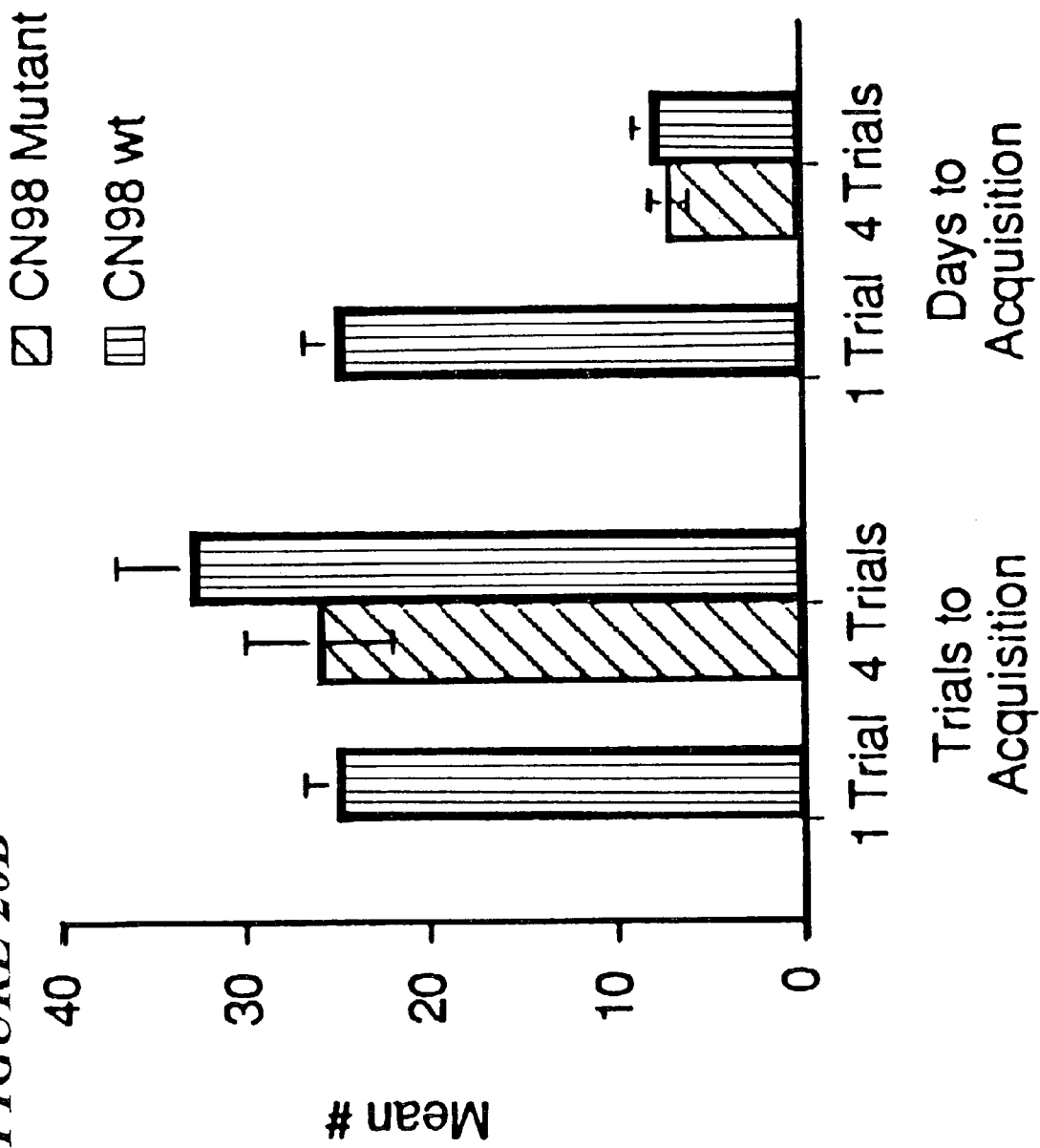
Figure 20C:
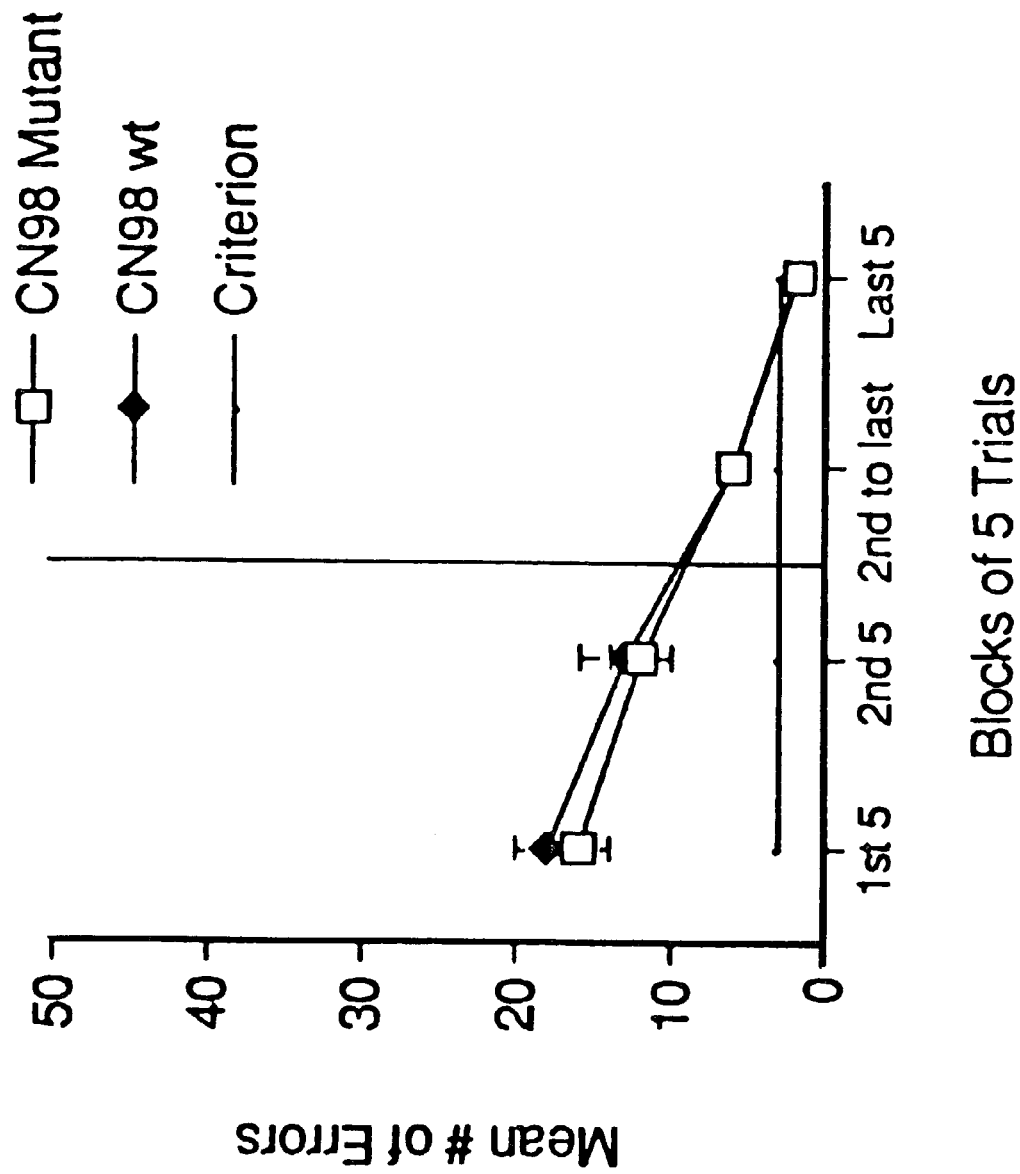

FIGS. 20A-C. CN98 mutant mice have a normal memory on the Barnes maze with four trials a day.

FIG. 20A. Percentage of CN98 mice that acquired the spatial version of the Barnes maze with four trials a day.

FIG. 20B. Mean number of trials and days to acquisition for CN98 mice on the spatial version of the Barnes maze with either one or four trials a day.

FIG. 20C. Mean number of errors made by CN98 mice on the spatial version of the Barnes maze with four trials a day.

Figure 21:
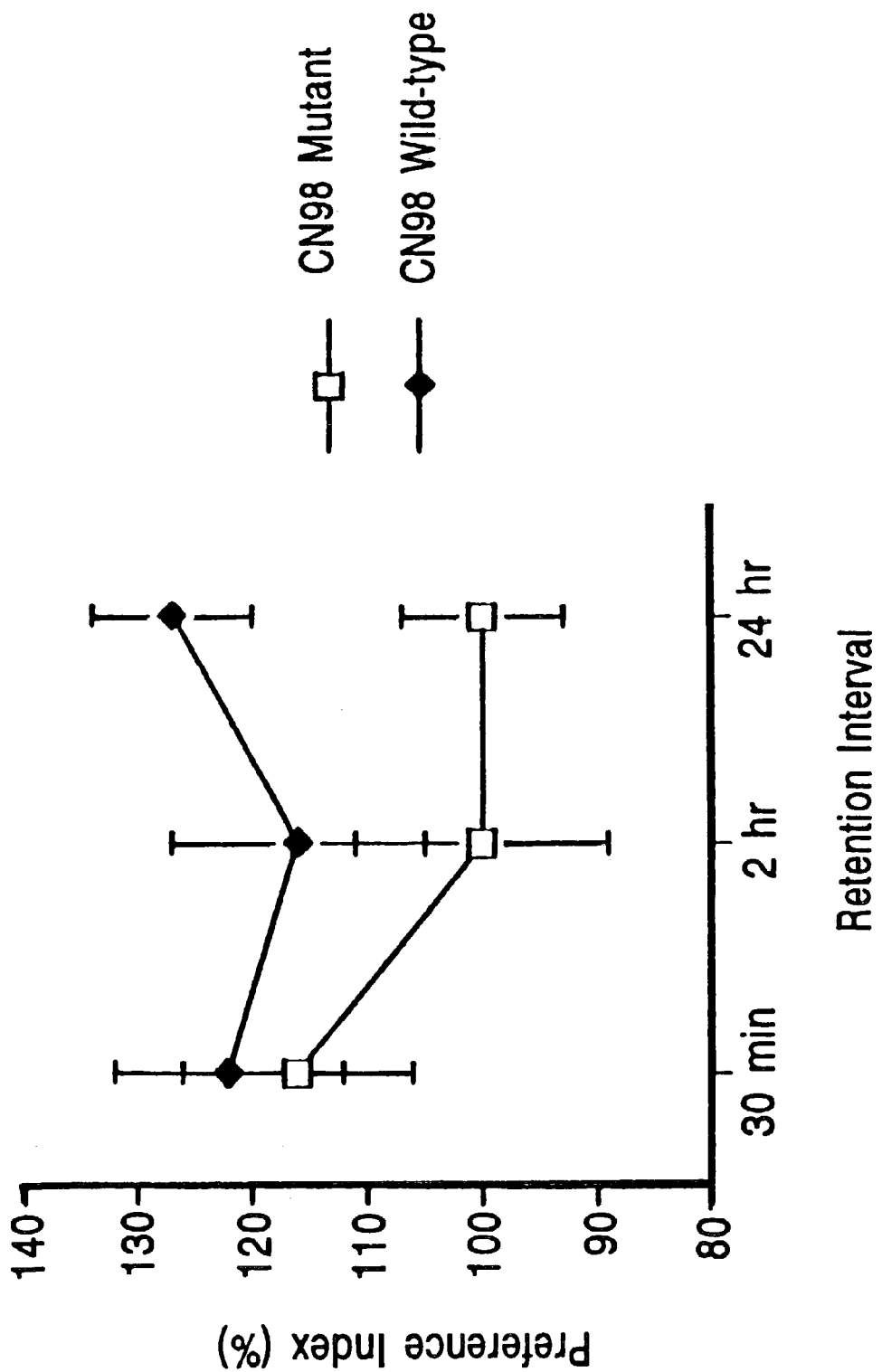

FIG. 21. CN98 mutant mice have normal short-term memory on the novel object recognition task. A preference index (PI) greater than 100 indicates preference for the novel object during testing. A PI equal to 100 indicates no preference whereas a PI inferior to 100 indicates a preference for the familiar object.

Figure 22C:
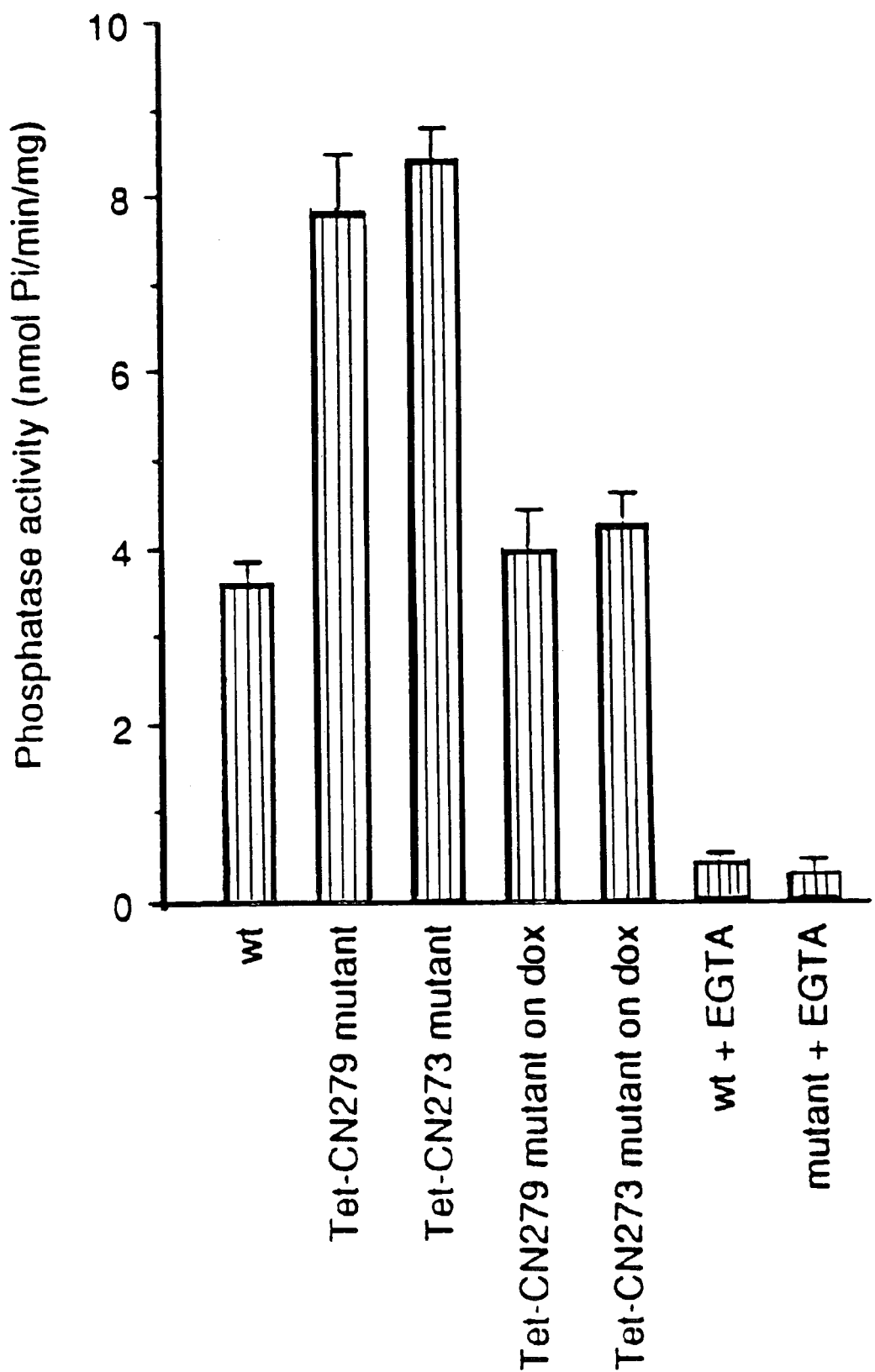
Figure 23B:
Figure 23D:
Figure 23A:
Figure 23C:

FIGS. 22A-C. Regulated expression of calcineurin transgene with the tTA system.

FIG. 22A. Strategy to obtain doxycycline-regulated expression of calcineurin transgene in mice. Mice from line B carry the CaMKIIα promoter-tTA transgene and mice from lines CN279 and CN273, the tetO promoter-ΔCaM-AI transgene. Both transgenes are introduced into the same mouse through mating to generate Tet-CN279 and Tet-CN273 mice. In Tet-CN279 and Tet-CN273 mice, expression of the calcineurin transgene is activated by tTA and can be repressed by doxycycline.

FIG. 22B. Northern blot analysis of total forebrain RNA from Tet-CN279 and Tet-CN273 wild-type and mutant mice on or off doxycycline and RT-PCR of total forebrain RNA from Tet-CN279 and Tet-CN273 wild-type, CN279 and CN273 mice, Tet-CN279 and Tet-CN273 mutant mice on or off doxycycline.

FIG. 22C. Enzyme activity determined in hippocampal extracts from Tet-CN279 and Tet-CN273 mice on or off doxycycline. Dephosphorylation of a radiolabeled peptide substrate was measured in absence or presence of the $Ca^{2+}$ chelator EGTA in Tet-CN279 and Tet-CN273 wild-type and mutant mice on or off doxycycline. Values are mean±SEM. Wild-type (Tet-CN279+Tet-CN273) : 3.58±0.26 nmol Pi/min/mg, n=6; Tet-CN279 mutant: 7078±0.70 nmol Pi/min/mg, n=4, $p>0.0001$; Tet-CN273 mutant: 8.39±0.39 nmol Pi/min/mg, n=3, $p>0.001$; Tet-CN279 mutant on dox.: 3.95±0.48 nmol Pi/min/mg, n=4, $p>0.05$; Tet-CN273 mutant on dox.: 4.23±0.36 nmol Pi/min/mg, n=3, $p>0.05$; wild-type (Tet-CN279+Tet-CN273)+EGTA: 0.432±0.11 nmol Pi/min/ng, n=7; mutant (Tet-CN279+Tet-CN273)+EGTA: 0.287±0.17 nmol Pi/min/mg, n=7, $p>0.05$.

FIGS. 23A-D. The expression of calcineurin transgene is primarily restricted to CA1 subfield in the hippocampus of Tet-CN279 and Tet-CN273 mutant mice and is repressed by doxycycline. Regional distribution of calcineurin transgene determined by in situ hybridization on mouse brain sagital sections from Tet-CN279 wild-type, Tet-CN279 and Tet-CN273 mutant on or off doxycycline.

FIGS. 24A-G. CN98 and Tet-CN279 mutant mice do not use the spatial search strategy.

Figure 24A:
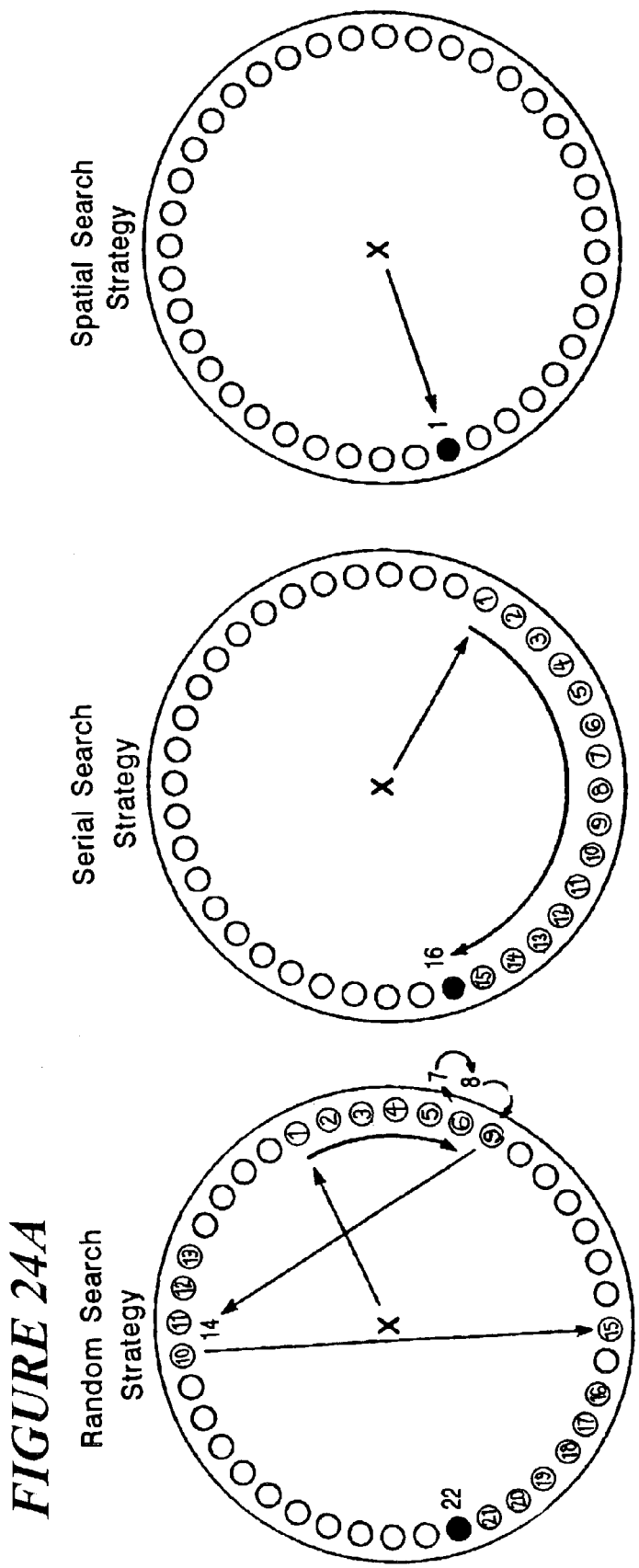
Figure 24C:
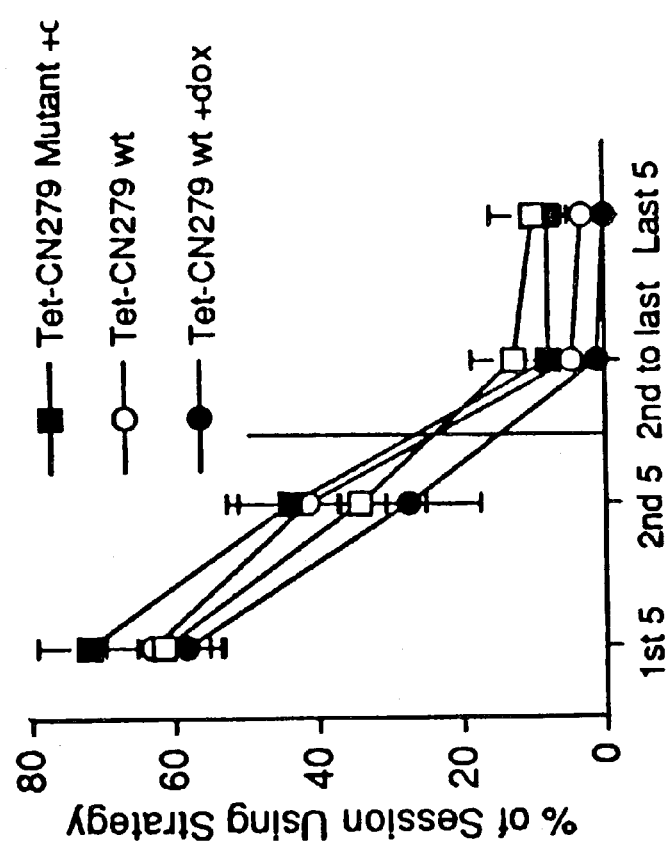
Figure 24B:
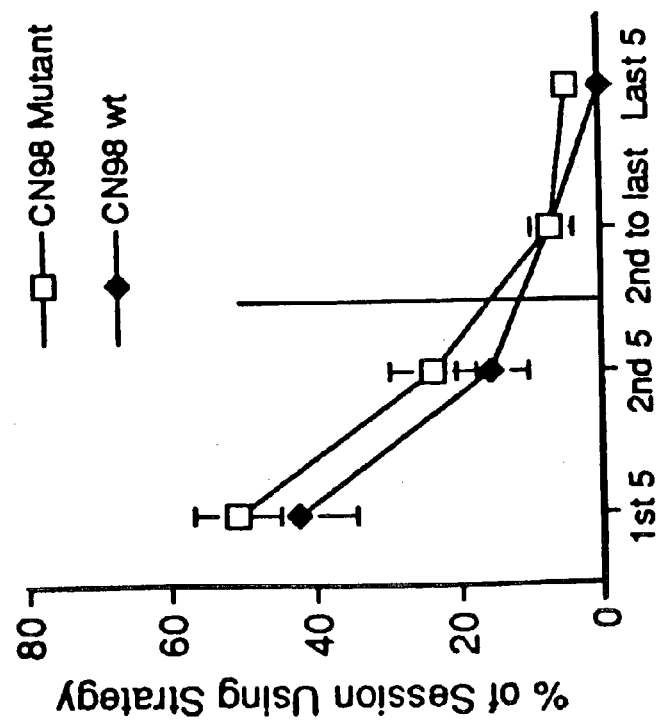
Figure 24E:
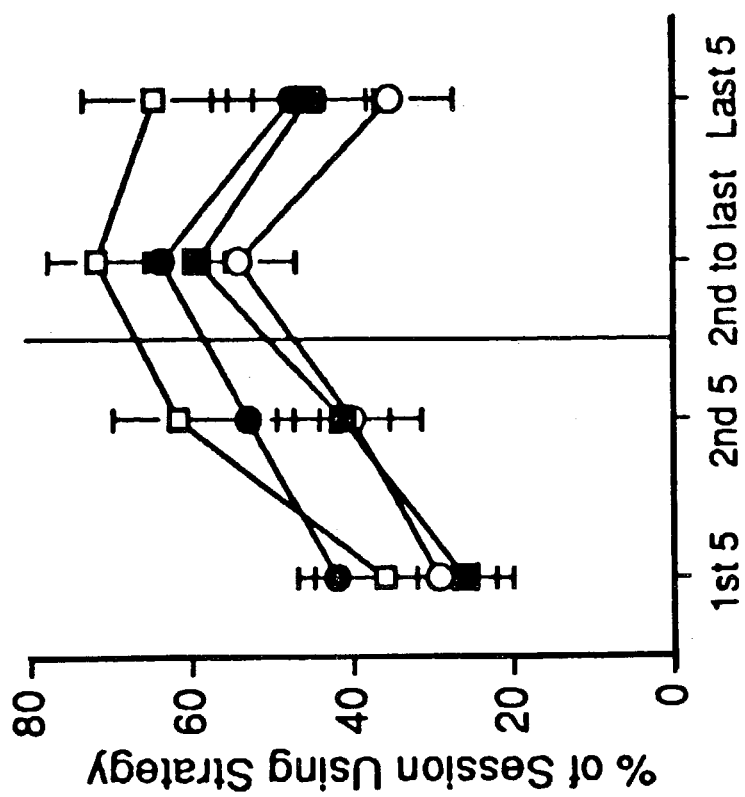
Figure 24D:
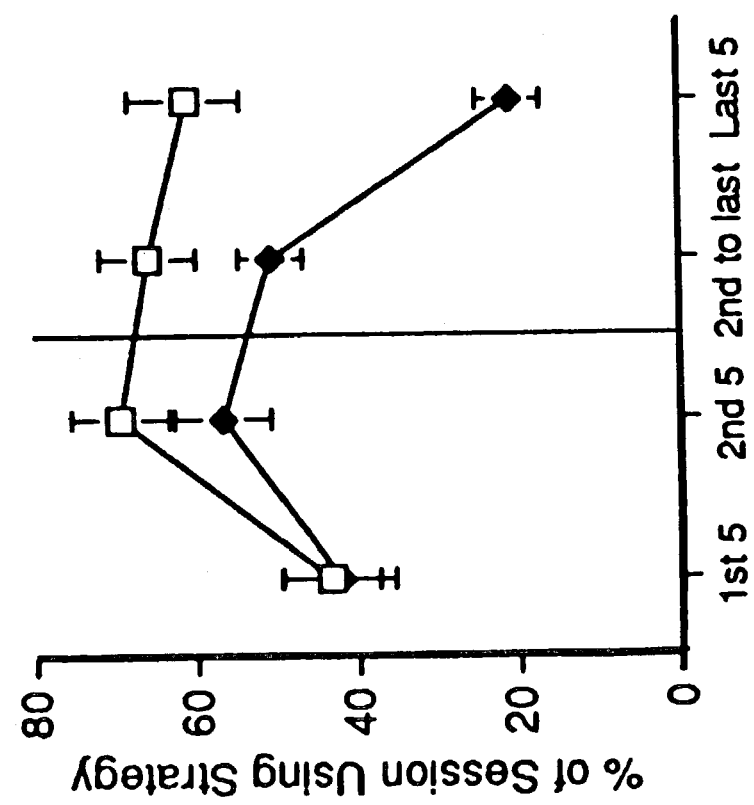
Figure 24G:
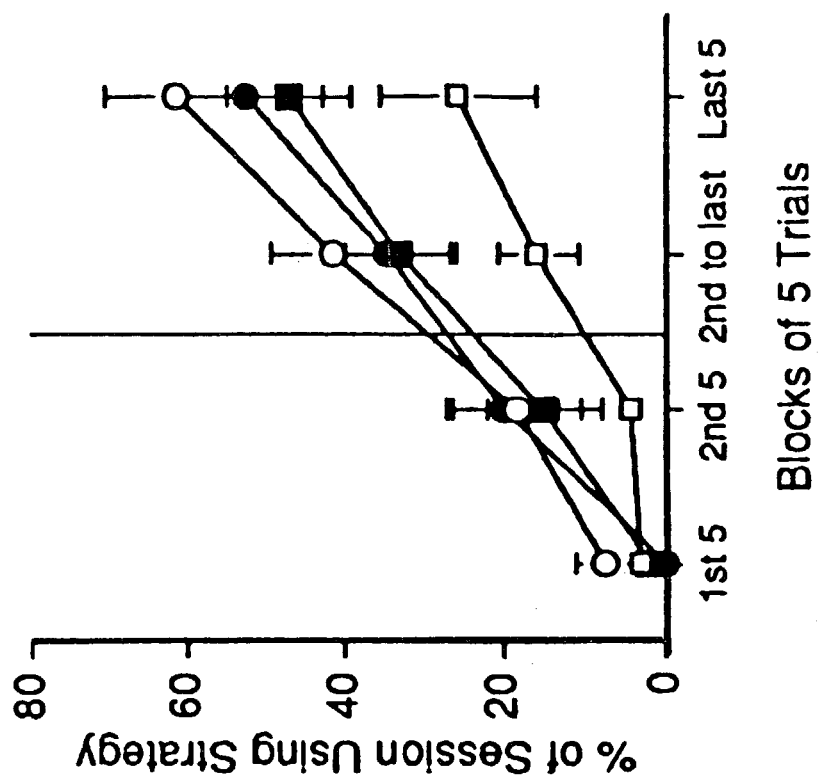
Figure 24F:
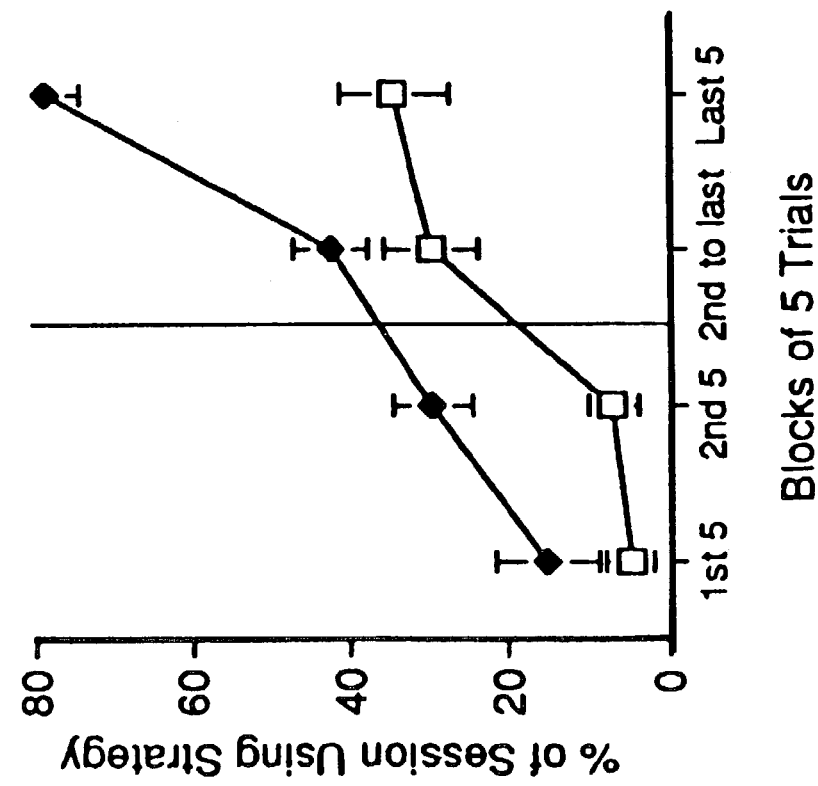

FIG. 24A. Representative examples of the search strategies employed on the spatial version of the Barnes circular maze task.

FIGS. 24B-G. Use of random search strategy by CN98 (B) and Tet-CN279 (C) mice, of serial search strategy by CN98 (D) and Tet-CN279 (E) mice and of spatial search strategy by CN98 (F) and Tet-CN279 (G) mice.

DETAILED DESCRIPTION OF THE INVENTION

The present invention provides for a recombinant nucleic acid molecule comprising a region of a calcium-calmodulin dependent kinase IIα promoter operatively linked to a gene of interest. The region of the calcium-calmodulin dependent kinase IIα promoter may comprise an 8.5 kilobase nucleic acid sequence which corresponds to the nucleic acid sequence of the insert of the plasmid designated pMM403, deposited with the American Type Culture Collection under Accession No. 98582 (see deposit details hereinbelow).

The gene of interest may comprise an acalcinurin gene, a gene involved in brain function, a growth factor gene, an ion channel gene, a kinase gene, a neurotransmitter gene, a neurotrophic factor gene, a phosphatase gene, a recombinase gene, a reporter gene, a receptor gene, a transactivator transcription factor gene, a transcription factor gene.

The neurotrophic factor may comprise ciliary neurotrophic factor; nerve growth factor; neurotrophic factor 4/5; brain-derived neurotrophic factor; or glial-derived neurotrophic factor.

One embodiment of the present invention is a human cell line which has been stably transformed by a recombinant nucleic acid molecule comprising a gene of interest operatively linked to a nucleic acid encoding a calcium-calmodulin dependent kinase IIα promoter region which has a nucleotide sequence corresponding to the sequence of the insert of the plasmid designated pMM403, deposited with the American Type Culture Collection under Accession No. 98582 (see deposit details hereinbelow). The gene of interest may be a calcineurin gene, a gene involved in brain function, a growth factor gene, a neurotrophic factor gene, a phosphatase gene, a recombinase gene, a reporter gene, a receptor gene, a trans-activator transcription factor gene or a transcription factor gene. The cell line may be a neuronal cell line.

The present invention also provides for a transgenic non-human mammal whose germ or somatic cells contain a nucleic acid molecule which encodes a gene of interest under the control of a CaMKIIα promoter (ATCC Accession No. 98582), introduced into the mammal, or an ancestor thereof, at an embryonic stage. The gene of interest may be an acalcinurin gene, a gene involved in brain function, a growth factor gene, an ion channel gene, a kinase gene, a neurotransmitter gene, a neurotrophic factor gene, a phosphatase gene, a recombinase gene, a reporter gene, a receptor gene, a trans-activator transcription factor gene, a transcription factor gene. The gene of interest may be any gene. The nucleic acid molecule which is the transgene of the transgenic nonhuman mammal may contain an appropriate piece of genomic clone DNA from the mammal designed for homologous recombination.

Another embodiment of the present invention is a method of treating a neurological disorder in a subject which comprises administering to the subject an effective amount of the recombinant nucleic acid comprising a region of a calcium-calmodulin dependent kinase IIα promoter operatively linked to a gene of interest so as to express the gene of interest in the subject and thereby treat the neurological disorder. The neurological disorder may be amnesia, Alzheimer's disease, amyotrophic lateral sclerosis, a brain injury, cerebral senility, chronic peripheral neuropathy, a cognitive disability, a degenerative disorder associated with learning, Down's Syndrome, dyslexia, electric shock induced amnesia or amnesia. Guillain-Barre syndrome, head trauma, Huntington's diseases a learning disability, a memory deficiency, memory loss, a mental illness, mental retardation, memory or cognitive dysfunction, multi-infarct dementia and senile dementia, myasthenia gravis, a neuromuscular disorder, Parkinson's disease, Pick's disease, a reduction in spatial memory retention, senility, or Turret's syndrome.

Another embodiment of the present invention is a method of evaluating, whether a compound is effective in treating symptoms of a neurological disorder in a subject which comprises: (a) administering the compound to the transgenic non-human mammal whose germ or somatic cells contain a nucleic acid molecule which encodes a gene of interest under the control of a CaMKIIα promoter, and (b) comparing the neurological function the mammal in step (a) with neurological function of the transgenic mammal in the absence of the compound, thereby determining whether the compound is effective in treating symptoms of the neurological disorder in a subject.

The neurological disorder may be amnesia, Alzheimer's disease, amyotrophic lateral sclerosis, a brain injury, cerebral senility, chronic peripheral neuropathy, a cognitive disability, a degenerative disorder associated with learning, Down's Syndrome, dyslexia, electric shock induced amnesia or amnesia. Guillain-Barre syndrome, head trauma, Huntington's disease, a learning disability, a memory deficiency, memory loss, a mental illness, mental retardation, memory or cognitive dysfunction, multi-infarct dementia and senile dementia, myasthenia gravis, a neuromuscular disorder, Parkinson's disease, Pick's disease, a reduction in spatial memory retention, senility, or Turret's syndrome.

The compound may be an organic compound, a nucleic acid, a small molecule, an inorganic compound, a lipid, or a synthetic compound. The mammal may be a mouse, a sheep, a bovine, a canine, a porcine, or a primate. The subject may be a human. The administration may comprise intralesional, intraperitoneal, intramuscular or intravenous injection; infusion; liposome-mediated delivery; gene bombardment; topical, nasal, oral, anal, ocular or otic delivery.

The present invention provides for a method of evaluating whether a compound is effective in treating symptoms of a neurological disorder in a subject which comprises: (a) contacting a human neuronal cell of the human neuronal cell line which has been stably transformed by a recombinant nucleic acid molecule comprising a gene of interest operatively linked to a nucleic acid encoding a calcium-calmodulin dependent kinase IIα promoter region with the compound, and (b) comparing the neuronal cell function of the neuronal cell in step (a) with neuronal cell function in the absence of the compound, thereby determining whether the compound is effective in treating symptoms of the neurological disorder.

The present invention also provides for a method for alleviating symptoms in a subject suffering from a neurological disorder which comprises administering to the subject an effective amount of the compound evaluated by the methods hereinabove in an amount effective to treat the symptoms in the subject suffering from a neurological disorder.

The neuronal cell population may be an aged neuronal cell population, an electrically stimulated neuronal cell population, or a cell population associated with a learning disability or a neurological disorder. The neuronal cell population may be from the CA1 or CA3 region of the hippocampus.

As used herein, the term "neuronal degradation" includes morphological and functional deterioration of neuronal cells characteristic of degeneration associated with age or characteristic of an association with a neurological disorder. "Neuronal degradation" also includes cognitive impairments which may be associated with aging, Alzheimer's disease, amyotrophic lateral sclerosis, chronic peripheral neuropathy, drug or alcohol use, electroshock treatment or trauma, Guillain-Barre syndrome, Huntington's disease, a learning disability, a memory deficiency, a mental illness, myasthenia gravis, Parkinson's disease and reduction in spatial memory retention.

As used herein, the term "learning disability" includes a hippocampal learning or memory deficit concurrent with an electrophysiological deficit.

As used herein, the term "stimulating a neuronal cell population" includes electrical stimulation to an evoke electrophysiological response from the neuronal cell population, treating the neuronal cell population with a compound or a drug to elicit a response, applying tetani to the neuronal cell population to elicit a electrophysiological response, treating a subject with a compound which compound is capable of stimulating the neuronal cell population of the subject or perfusing a solution containing a composition or compound over the neuronal cell population. The response may be late phase long term potentiation, early phase long term potentiation. The neuronal cell population may be in a hippocampal slice in vitro, in a subject in vivo, or in other neuronal tissue.

As used herein, the term "normal neuronal cell population" includes a neuronal cell population derived from a subject which does not appear to have neuronal degradation due to aging, a neurological disorder, a learning disability, exposure to trauma or electric shock.

As used herein, the term "cognitive disorder" includes a learning disability or a neurological disorder which may be Alzheimer's Disease, a degenerative disorder associated with learning, a learning disability, memory or cognitive dysfunction, cerebral senility, multi-infarct dementia and senile dementia, electric shock induced amnesia or amnesia.

Another embodiment of the subject invention is a method for treating a subject with a cognitive disorder of memory or a learning disability which comprises administering to the subject a therapeutically effective amount of a transgene capable of alleviating the symptoms of the cognitive disorder of memory or the learning disability in the subject thereby treating the cognitive disorder of memory or the learning disability in the subject, wherein the transgene is made from a CaMKIIα promoter-derived construct (ATCC Accession No. 98582, deposited on Nov. 11, 1997). The transgene may be associated with a suitable pharmaceutically acceptable carrier and administered intravenously or through the CSF for transient effects.

The subject may be a mammal or a human subject. The administration may be intralesional, intraperitoneal, intramuscular or intravenous injection; infusion; liposome-mediated delivery; gene bombardment; topical, nasal, oral, anal, ocular or otic delivery.

In the practice of any of the methods of the invention or preparation of any of the pharmaceutical compositions an "therapeutically effective amount" is an amount which is capable of alleviating the symptoms of the cognitive disorder of memory or learning in the subject. Accordingly, the effective amount will vary with the subject being treated, as well as the condition to be treated. For the purposes of this invention, the methods of administration are to include, but are not limited to, administration cutaneously, subcutaneously, intravenously, parenterally, orally, topically, or by aerosol.

As used herein, the term "suitable pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®.

Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

This invention also provides for pharmaceutical compositions including therapeutically effective amounts of protein compositions and compounds capable of alleviating the symptoms of the cognitive disorder of memory or learning in the subject of the invention together with suitable diluents, preservatives, solubilizers, emulsifiers, adjuvants and/or carriers useful in treatment of neuronal degradation due to aging, a learning disability, or a neurological disorder. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the compound, complexation with metal ions, or incorporation of the compound into or onto particulate preparations of polymeric compounds such as polylactic acid, polglycolic acid, hydrogels, etc, or onto liposomes, micro emulsions, micelles, unilamellar or multi lamellar vesicles, erythrocyte ghosts, or spheroplasts. Such compositions will influence the physical state, solubility, stability, rate of in vivo release, and rate of in vivo clearance of the compound or composition. The choice of compositions will depend on the physical and chemical properties of the compound capable of alleviating the symptoms of the cognitive disorder of memory or the learning disability in the subject.

Controlled or sustained release compositions include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

Portions of the compound of the invention may be "labeled" by association with a detectable marker substance (e.g., radiolabeled with 125I or biotinylated) to provide reagents useful in detection and quantification of compound or its receptor bearing cells or its derivatives in solid tissue and fluid samples such as blood, cerebral spinal fluid or urine.

When administered, compounds are often cleared rapidly from the circulation and may therefore elicit relatively short-lived pharmacological activity. Consequently, frequent injections of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently or in lower doses than with the unmodified compound.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The compound of the present invention capable of alleviating symptoms of a cognitive disorder of memory or learning may be delivered in a microencapsulation device so as to reduce or prevent an host immune response against the compound or against cells which may produce the compound. The compound of the present invention may also be delivered microencapsulated in a membrane, such as a liposome. Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

In one embodiment the compound of the present invention is associated with a pharmaceutical carrier which includes a pharmaceutical composition. The pharmaceutical carrier may be a liquid and the pharmaceutical composition would be in the form of a solution. In another embodiment, the pharmaceutically acceptable carrier is a solid and the composition is in the form of a powder or tablet. In a further embodiment, the pharmaceutical carrier is a gel and the composition is in the form of a suppository or cream. In a further embodiment the active ingredient may be formulated as a part of a pharmaceutically acceptable transdermal patch.

Transgenic Mice

The methods used for generating transgenic mice are well known to one of skill in the art. For example, one may use the manual entitled "Manipulating the Mouse Embryo" by Brigid Hogan et al. (Ed. Cold Spring Harbor Laboratory) 1986.

This invention further provides for a transgenic nonhuman mammal whose germ or somatic cells contain a nucleic acid molecule which comprises an 8.5 kb promoter region of the mouse CaMKIIα promoter, designated pMM403, which is operatively linked to a gene of interest, introduced into the mammal, or an ancestor thereof, at an embryonic stage.

Another embodiment of this invention is a 3' untranslated region of the mouse CaMKIIα gene, designated pMM281. Another embodiment of this invention is a 3' mouse intron designated pNN265.

The plasmids pMM403, pMM281 and pNN265 were deposited on Nov. 11, 1997, pursuant to the requirements of the Budapest Treaty on the International Recognition of the Deposit of Microorganisms for the Purposes of Patent Procedure with the American Type Culture Collection (ATCC), 10801 University Boulevard, Manassas, Va. 20110-2209, under ATCC Accession Nos. 98582, 98581 and 98583, respectively. During the pendency of the subject application, access to the deposit shall be afforded to the Commissioner upon request. All restrictions upon public access to this deposit shall be removed upon the grant of a patent on this application and the deposits shall be replaced if viable samples cannot be made by the depository named hereinabove.

The gene of interest will be expressed under the control of the CaMKIIα promoter region, therefore expression of the gene of interest will be specifcally localized to the hippocampal region of the brain of the mammal. This invention provides for a transgenic nonhuman mammal whose cells may be transfected with a suitable vector with an appropriate sequence designed to reduce expression levels of harmful genes in the hippocampus of the mammal. The transgenic nonhuman mammal may be transfected with a suitable vector which contains an appropriate piece of genomic clone designed for homologous recombination. Alternatively, the transgenic nonhuman mammal may be transfected with a suitable vector which encodes an appropriate ribozyme or antisense molecule. See for example, Leder and Stewart, U.S. Pat. No. 4,736,866 for methods for the production of a transgenic mouse.

Transgenic mice have been generated using a construct which is one embodiment of the present invention (a 8.5 kb region of the CaMKIIα promoter driving a gene of interest which may further comprise a 3' untranslated region). For example, the gene of interest may be a lacZ gene, a CRE recombinase gene, a tet-O tetracycline transactivator transcription factor gene, an acalcinurin gene, a phosphatase gene or any gene involved in brain function. The gene of interest can be any gene which is capable of being expressed as a heterologous gene driven by the CaMKIIα promoter.

The gene of interest may be a neurotrophic factor such as ciliary neurotrophic factor (see U.S. Pat. No. 4,997, 929); nerve growth factor (see U.S. Pat. No. 5,169,762); neurotrophic factor 4/5 (see PCT International Publication No. WO 92/05254); brain-derived neurotrophic factor (see U.S. Pat. No. 5,180,820); glial-derived neurotrophic factor (see PCT International Publication No. WO 93/06116) or any other neurotrophic factor (see European application EP 0 386 752 A1). The disclosures of these publications in their entireties are hereby incorporated by reference into this application in order to more fully describe the state of the art as known to those skilled therein as of the date of the invention described and claimed herein.

The gene of interest may be a neurotropic factor or a cytokine or a growth factor. Such factors may include transforming growth factor beta (TGF-β), ciliary neurotropic factor (CNTF), brain derived neurotropic factor (BDNF), NT-4, NT-5, NT-4/5, nerve growth factor (NGF), activins, agrin, cell differentiation factor (CDF), glial growth factor (GGF), and neu differentiation factor (NDF), ARIA, and heregulins. The gene of interest may be a gene encoding a pharmaceutically important protein, a transcription factor, an agonist, an antagonist, a kinase, a phosphatase, a nitric oxide synthase, CREB, a receptor, or a recombinase. The gene of interest may be any gene which encodes a protein which is functionally significant in brain functions, such as memory, cognitive functions and learning.

The gene of interest may be a gene encoding a neurotransmitter. The gene of interest may be a gene encoding a neurotransmitter receptor protein.

The CaMKIIα promoter construct (which includes a CaMKIIα promoter region and a gene of interest) may be used to treat any disease where levels of expression of genes in the hippocampus (forebrain) are changed or altered from that which would be present under normal conditions. For example, ion channel levels or activities are abnormal in some neurological disorders. Neurological disorders that affect the central nervous system, memory or cognitive functions may also be treated via the CaMKIIα promoter construct. Such disorders may be the result of the normal aging process or the result of damage to the nervous system by trauma, surgery, ischemia, infection or metabolic disease. The neurological disorder may be a neuromuscular disorder. Examples of neurological disorders include Alzheimer's disease, myasthenia gravis, Huntington's disease, Pick's disease, Parkinson's disease, and Turret's Syndrome. The gene of interest may be any gene which is identified or known to be involved in the development of a neurological disorder. For example, genes which may be involved in Alzheimer's Disease may be a gene of interest, see for example PCT Application No. PCT/EP93/03581, International Publication No. WO 94/13798.

This invention provides for a method of altering neuroreceptor expression. In this method, nucleic acid molecule comprising a CaMKIIα promoter driving expression of a gene of interest is administered to a subject which may result in a change in the expression of neuro-receptors.

This invention provides for improving the memory of a subject.

Another embodiment of this invention is wherein the gene of interest is a ribozyme which is capable of cleaving mRNA which is produced by a neuronal cell. See Cech, et al., U.S. Pat. No. 4,987,071; Altman et al., U.S. Pat. No. 5,168,053; Haseloff et al, U.S. Pat. No. 5,254,678 published European application No. Hampel et al., EP 360,257.

This invention also provides for a replicable vector which contains CaMKIIα promoter sequence and a host cell containing this vector. This expression vector may be a prokaryotic expression vector, a eukaryotic expression vector, a mammalian expression vector, a yeast expression vector, a baculovirus expression vector or an insect expression vector. Examples of these vectors include PKK233-2, pEUK-C1, pREP4, pBlueBacHisA, pYES2, PSE280 or pEBVHis. Methods for the utilization of these replicable vectors may be found in Sambrook, et al., 1989 or in Kriegler 1990. The host cell may be a eukaryotic cell, a somatic cell, a germ cell, a neuronal cell, a myocyte, a mammary carcinoma cell, a lung cell, a prokaryotic cell, a virus packaging cell, or a stem cell.

A "reporter molecule", as defined herein, is a molecule or atom which, by its chemical nature, provides an identifiable signal allowing detection of the circular oligonucleotide. A reporter molecule may be encoded by a reporter gene. Detection can be either qualitative or quantitative. The present invention contemplates using any commonly used reporter molecules including radionucleotides, enzymes, biotins, psoralens, fluorophores, chelated heavy metals, and luciferin. The most commonly used reporter molecules are either enzymes, fluorophores, or radionucleotides linked to the nucleotides which are used in circular oligonucleotide synthesis. Commonly used enzymes include horseradish peroxidase, alkaline phosphatase, glucose oxidase and α-galactosidase, among others. The substrates to be used with the specific enzymes are generally chosen because a detectably colored product is formed by the enzyme acting upon the substrate. For example, p-nitrophenyl phosphate is suitable for use with alkaline phosphatase conjugates; for horseradish peroxidase, 1.2-phenylenediamine, 5-aminosalicylic acid or toluidine are commonly used. The methods of using such hybridization probes are well known and some examples of such methodology are provided by Sambrook et al, 1989.

Gene Therapy

Several methods have been developed over the last decade for the transduction of genes into mammalian cells for potential use in gene therapy. In addition to direct use of plasmid DNA to transfer genes, retroviruses, adenoviruses, parvoviruses, and herpesviruses have been used (Anderson et al., 1995; Mulligan, 1993; The contents of whch are incorporated in their entirety into the subject application). For transfer of genes into cells ex vivo and subsequent reintroduction into a host, retroviruses have been the vectors of choice. Advantages are that infection of retroviruses is highly efficient and that the provirus generated after infection integrates stably into the host: DNA. A disadvantage however, is that stable integration requires cell division, and many of the earliest hematopoietic progenitor cells that would be the preferred targets of gene therapy, do not divide under conditions used for the infections and hence to not incorporate virus, or if they do they may not retain their potential to completely reconstitute a host. Notwithstanding this problem, it is possible that the long-term culture-initiating cells that can be transduced by retroviruses may be sufficient to repopulate some compartment with cells that are particularly long lived and stable.

Most current gene therapy protocols use murine retroviral vectors to deliver therapeutic genes into target cells; this process, which is called transduction, mimics the early events of retroviral infection. The crucial difference is that, unlike replication competent retroviruses, the vector genome packaged within the viral coat contains no genes for viral proteins and therefore is incapable of replication. For example, a vector would be designed to have 3' and 5' long terminal repeat sequences necessary only for the integration of the viral DNA intermediate into the target host cell chromosome and a packaging signal that allows packaging into viral structural proteins supplied by the packaging line in trans (Miller, 1992; Wilson et al., 1990; The contents of which are incorporated in their entirety into the subject application). Retroviral constructs are made in which the DNA of the gene of interest (that is, the gene which one wishes to have expressed under the control of the CaMKIIα 5' promoter, specifically localized expression to the forebrain, hippocampal regions) and is inserted downstream of the CaMKIIα promoter to generate a vector. Genomic integration is the terminal step for these defective retroviral vectors. They cannot make viral proteins in cells transduced with the packaged vector and therefore cannot produce progeny virus. The CaMKIIα promoter retroviral constructs are transfected into virus packaging cell lines to generate infectious, but non-replicating virus particles. Such virus packaging cell lines are known to those of skill in the art. Cloning procedures and retroviral infection of cell lines are well known to one skilled in the art and detailed protocols may be found in Kriegler, 1990. Producer lines with high virus titers are chosen for their ability to transduce the human neuronal cell lines resulting in expression of the gene of interest in that cell line.

There are several protocols for human gene therapy which have been approved for use by the Recombinant DNA Advisory Committee (RAC) which conform to a general protocol of target cell infection and administration of transfected cells (see for example, Blaese, R. M., et al., 1990; Anderson, W. F., 1992; Culver, K. W. et al., 1991). In addition, U.S. Pat. No. 5,399,346 (Anderson, W. F. et al., Mar. 21, 1995, U.S. Ser. No. 220,175) describes procedures for retroviral gene transfer. The contents of these support references are incorporated in their entirety into the subject application. It may be necessary to select for a particular subpopulation of originally harvested cells for use in the infection protocol. Then, a retroviral vector containing the gene(s) of interest would be mixed into the culture medium. The vector binds to the surface of the subject's cells, enters the cells and inserts the gene of interest randomly into a chromosome. The gene of interest is now stably integrated and will remain in place and be passed to all of the daughter cells as the cells grow in number. The cells may be expanded in culture for a total of 9-10 days before reinfusion (Culver et al., 1991). As the length of time the target cells are left in culture increases, the possibility of contamination also increases, therefore a shorter protocol would be more beneficial. In addition, the currently reported transduction efficiency of 10-15% is well below the ideal transduction efficiency of 90-100% which would allow the elimination of the selection and expansion parts of the currently used protocols and reduce the opportunity for target cell contamination.

This invention provides for the construction of retrovirus vectors containing the cDNA for the transactivating factor which is found 3' to the CaMKIIα gene. The efficiency of transduction of these vectors can be tested in cell culture systems.

In one embodiment of the method above the nucleic acid molecule is incorporated into a liposome to allow for administration to the subject. Methods of incorporation of nucleic acid molecules into liposomes are well known to those of ordinary skill in the art. In another embodiment of this method, the molecule may be delivered via transfection, injection, or viral infection. Other methods of delivery of nucleic acids and nucleic acid compositions as discussed herein include viral gene-mediated transfer, small particle bombardment, receptor-mediated endocytosis and intralesional, intraperitoneal or intramuscular injection. There are several protocols for human gene therapy which have been approved for use by the Recombinant DNA Advisory Committee (RAC) which conform to a general protocol of target cell infection and administration of transfected cells (see for example, Blaese, R. M., et al., 1990; Anderson, W. F., 1992; Culver, K. W. et al., 1991). In addition, U.S. Pat. No. 5,399, 346 (Anderson, W. F. et al., Mar. 21, 1995, U.S. Ser. No. 220,175) describes procedures for retroviral gene transfer. The contents of these support references are incorporated in their entirety into the subject application. Retroviral-mediated gene transfer requires target cells which are undergoing cell division in order to achieve stable integration hence, cells are collected from a subject often by removing blood or bone marrow.

Several methods have been developed over the last decade for the transduction of genes into mammalian cells for potential use in gene therapy. In addition to direct use of plasmid DNA to transfer genes, retroviruses, adenoviruses, parvoviruses, and herpesviruses have been used (Anderson et al., 1995; Mulligan, 1993; The contents of which are incorporated in their entirety into the subject application).

Another embodiment of this invention is a method for inducing neuronal regeneration which comprises administering to a subject an effective amount of the CaMKIIα promoter construct driving a gene of interest and a pharmaceutically acceptable carrier to induce the formation of a synaptic junction between a neuron and a target cell. The target cell may be a neuronal cell, an endocrine cell, a muscle cell or any cell capable of forming a neuro-muscular junction. Expression of the gene of interest may facilitate incorporation of implants into nervous tissue or to promote nerve regeneration following damage by trauma, infarction, infection or postoperatively. Alternatively, the transgenic nonhuman mammal may be transfected with a suitable vector which encodes an appropriate ribozyme or antisense molecule. See for example, Leder and Stewart, U.S. Pat. No. 4,736,866 for methods for the production of a transgenic mouse. Such antisense vector may be used as a gene therapy in humans to inhibit the expression of a gene in the forebrain.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

Example 1

The 3'-Untranslated Region of CaMKIIα is a cis-acting Signal for the Localization and Translation of mRNA in Dendrites Neuronal signaling requires that synaptic proteins be appropriately localized within the cell and regulated there. In mammalian neurons, polyribosomes are found not just in the cell body, but also in dendrites where they are concentrated within or beneath the dendritic spine. The α subunit of $Ca^{2+}$-calmodulin-dependent protein kinase II (CaMKIIα) is one of only five mRNAs known to be present within the dendrites, as well as in the soma of neurons. This targeted subcellular localization of the mRNA for CaMKIIα provides a possible cell biological mechanism both for controlling the distribution of the cognate protein and for regulating independently the level of protein expression in individual dendritic spines. To characterize the cis-acting elements involved in the localization of dendritic mRNA two lines of transgenic mice have been produced in which the CaMKIIα promoter is used to drive the expression of a lacZ transcript, which either contains or lacks the 3'-untranslated region of the CaMKIIα gene. Although both lines of mice show expression in forebrain neurons that parallels the expression of the endogenous CaMKIIα gene, only the lacZ transcripts bearing the 3'-untranslated region are localized to dendrites. The β-galactosidase protein shows a variable level of expression along the dendritic shaft and within dendritic spines, which suggests that neurons can control the local biochemistry of the dendrite either through differential localization of the mRNA or variations in the translational efficiency at different sites along the dendrite.

Polyribosomes are localized within neurons to the cell soma, the proximal part of the axon, and throughout the full extent of the dendritic authorization (Steward et al., 1982). Within dendrites the polyribosomes are not distributed randomly, but rather seem to be concentrated within or beneath the dendritic spines (Steward et al., Prog. Brain Res., 1983; Cold Spring Harbor Symp. Quant. Biol., 1983). Dendritic spines are elaborations of the dendrite on which excitatory synapses are formed. This concentration of the translational machinery at the site of synaptic input suggests the possibility that the local concentration of polyribosomes might function for the selective expression of certain gene products, which can be regulated in a synapse specific manner (Steward, 1992). Synapse specific gene expression might occur by the selective targeting of specific mRNAs to specific dendritic spines along with associated ribosomes. Alternatively, the mRNA for a given gene might be distributed uniformly to all dendritic spines in a neuron, but the translation of that mRNA might be differentially regulated at the individual spines.

Although the vast majority of neuronal mRNAs are restricted to the cell soma, a number of mRNAs have been found in the dendrite as well as the soma. These include the mRNAs for microtubule-associated protein 2 (MAP2), the $Ca^{2+}$-calmodulin dependent protein kinase IIα subunit, the IP3 receptor type II, and two genes of unknown function designated L7 and ARC (Burgin et al., 1990; Furuichi et al., 1993; Garner et al., 1988; Lyford et al., 1995; Link et al., 1995; Bian et al., 1996). The molecular mechanisms responsible for the localization of these mRNAs to dendrites are not known. However, dendritic mRNA appears to be associated with some component of the cytoskeleton (Davis et al., 1987; Bassell et al., 1994). The fact that only certain mRNAs are transported into dendrites suggests that a cis-acting signal, present only in those transcripts, mediates the targeting. That signal could be contained within the sequence or structure of the mRNA itself, or it could be carried within the nascent polypeptide chain. In the latter case, the entire complex consisting of polyribosome, mRNA, and nascent peptide would be transported into the dendrite.

The α subunit of $Ca^{2+}$-calmodulin-dependent protein kinase II (CaMKIIα) subunit gene is expressed specifically in neurons of the forebrain where its mRNA is found within the dendrites as well as the soma of the neuron. Cis-acting elements have been characterized in transgeneic mice, which elements mediate the forebrain specific expression as well as the dendritic localization of mRNA. A dendritically localized lacZ gene shows an uneven expression along the length of the dendrite. This suggests that the expression of dendritically localized mRNA is regulated either at the level of the mRNA distribution or at the level of local translation.

Materials and Methods

Transgerie constructs. The CAMKIIα promoter was isolated from a cosmid library prepared from C57BL6J mouse spleen using a 0.4-kb AvaI fragment comprising the transcription factor initiation region of the rat CAMKIIα gene (Sunyer et al., 1990). The full length CAMKIIα cDNA was isolated from a mouse brain (C57BL/6J) cDNA library using a rat CAMKIIα cDNA probe. Constructs were assembled using standard techniques. The lacZ gene was obtained from a 3.5 kb HindIII/DraI fragment of pNSE lac (Forss-Petter, et al., 1990). The bovine polyadenylation signal was from pRC/CMV (Invitrogen®). The GFP gene was from pGFP-C1 (CLONTECH®). The nuclear localization signal was from simian virus 40 large t antigen. It was inserted using synthetic oligonucleotides and consisted of the sequence SSDDEAT-ADSQHSTPPKKKRKVEDP (SEQ ID NO:1). Transgenic mice were produced by DNA injection into B6CBA $F_2$ or $B6/SJL_2F$ embryos using standard techniques. Northern blot analysis was performed using 4 µg of A+ RNA isolated from the forebrain of the lac-A and lac-CMK transgenic lines. The blot was hybridized with a lacZ-specific cDNA probe and washed for 40 min at 68° C. in 0.2X SSC/0.1% SDS and exposed for 5 hr.

β-Galactosidase (β-gal) Histochemistry. Brains were processed for histochemistry essentially as described (Forss-Petter et al., 1990). Animals were perfused with 2% paraformaldehyde/0.2% glutaraldehyde in PBS (pH 7.3) and cryoprotected in 30% sucrose. Fifty-micrometer horizontal sections were prepared and stained for β-gal activity for 4 hrs at 37° C. in 0.1 M sodium phosphate, pH 7.3/0.14 M NaCl/2 mM $MgCl_2$/3 mM $K_3Fe$ $(CN)_6$/3 mM $K_4Fe$ $(CN)_6$/1 mg/ml 5-bromo-4-chloro-3-indoyl β-D-galactosidase (X-gal).

In situ Hybridization. For in situ hybridization, 20-µm coronal sections were taken from fresh frozen mouse brains. The slices were fixed for 10 min in 4% paraformaldehyde and dehydrated. Slices were probed with a pool of three oligonucleotides specific for the LacZ gene, which had been labeled by tailing with $[\alpha^{35}S]$ dATP and terminal transferase to a specific activity of $>1 \times 10^9$ cpm/µg. Oligonucleotide sequence: lac 1, 5'-gtgcatctgccagtttgaggggacgacgacagtat-3' (SEQ ID NO:2); lac 2, 5'-gccggaaaccaggcaaagcgccattcgc-cattcaggctgcgc-3' (SEQ ID NO:3); lac 3, 5'-gtaaccgac-ccagcgcccgttgcaccacagatgaaacgccg-3' (SEQ ID NO:4). Hybridization was overnight at 42° C. in a solution containing 10% dextran sulfate, 50% formamide, 25 mM HEPES (pH 7.6), 600 mM NaCl, 100 mM DTT, 1 mM EDTA, 200 µg/ml denatured salmon sperm DNA, 200 µg/ml poly (A), 1X Denhardt's solution, $10^7$ cpm/ml probe. Slides were washed 2 times 10 min at reverse transcriptase with Kodak NTB2 emulsion, exposed for 3 weeks, developed, counterstained with toluidine blue, and photographed under darkfield illumination.

Neuronal Cultures. For neuronal cultures, hippocampi of P1-P3 mouse pups were dissected and treated for 30 min at 37° C. with 0.25% trypsin (Sigma®, type XI), and then gently titrated and the dissociated cells plated at a concentration of $2 \times 10^5$ per ml onto poly-D-lysine (Sigma®, 0.1 mg/ml) and laminin (Collaborative Research® 10 µg/ml) coated glass coverslips as described (Rayport, et al., 1992).

Cells were plated in minimal essential Eagle's medium (MEM) containing 10% heat inactivated fetal bovine serum (HyCLone®), 2 mM glutamine, and 0.76% glucose. On the following day, the medium was replaced with fresh SF1C medium, including B-27 supplements (GIBCO®). For immunocytochemistry, cells were labeled as described (Craig et al., 1993). Briefly, cells were fixed for 10 min at room temperature with 2% paraformaldehyde and incubated overnight at 4° C. with monoclonal antibody to MAP2 (Sigma®, 5 µg/ml) and rabbit polyclonal antibody to β-gal (Cappel®, 2 µg/ml) in PBS containing 10% goat serum. Cells were then stained with fluorescently conjugated secondary antibody (fluorescein isothiocyanate for β-gal detection and Cy3 for MAP2 detection). In several experiments a monoclonal antibody to β-gal (Promega®) was used. Images were obtained using an MRC-1000 laser confocal microscope (Bio-Rad®).

Results

Cis-acting elements of the CaMKIIα gene have been isolated: one, the promoter, which controls the forebrain-specific expression of the gene and the other, the 3'-untranslated region or 3' UTR, which controls the dendritic mRNA localization. Two DNA constructs (lac-CMK and lac-A, FIG. 1A) were prepared such that the lacZ reporter gene was placed downstream from an 8.5-kb fragment of CaMKIIα genomic DNA beginning 84 nucleotides following the transcription initiation site (Sunyer et al., 1990). In one construct, the entire 3' UTR of the CaMKIIα mRNA (3.2 kb) downstream from the lacZ coding region (lac-CMK) was included to determine whether the signal for dendritic RNA localization was contained in this region. As a control, the second construct contained a 3' polyadenylylation signal provided by bovine growth hormone (lac-A) . Transgenic mice were generated using the two DNA constructs. Of four founder animals obtained, two (one from each construct) expressed the lacZ gene and were analyzed in detail.

Figure 1B:
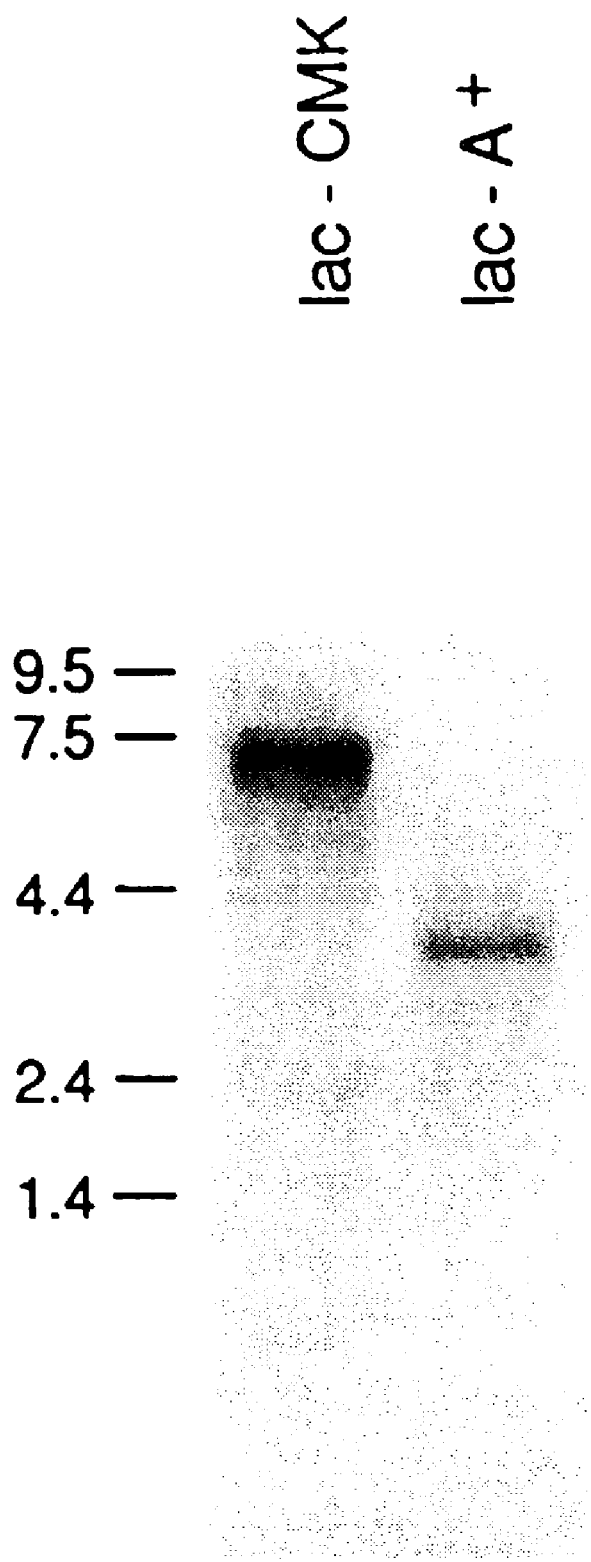

To determine whether the two different transgenic lines expressed mRNAs of the expected size, Northern blot analysis was performed of forebrain mRNA using a lacZ-specific probe. The lac-A and lac-CMK lines express lacZ-specific mRNAs of approximately 3.7 and 6.9 kb, respectively (FIG. 1B). In addition, the 6.9-kb transcript from the lac-CMK mice also hybridized to a probe specific for the CaMKII 3'-UTR.

Figure 2A:
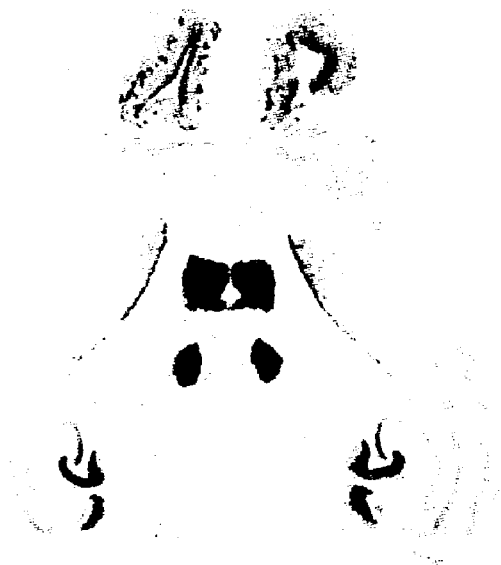
FIGS. 2A-2B. Beta-galactosidase histochemistry.
Figure 2B:

Histochemical detection of β-gal in brain sections revealed a similar pattern of expression in both lines (FIG. 2). With several exceptions, this expression was limited to those regions of the forebrain that normally express CaMKIIα. Notably, expression was absent in a medial layer of the cortex. Also, within the hippocampus, expression was much stronger in the dentate gyrus than in the CA3 and CA1 regions. Thus, the CaMKIIα promoter confers the expected cellular specificity on the expression of a heterologous transgene, with some variations in expression level.

Figure 3B:
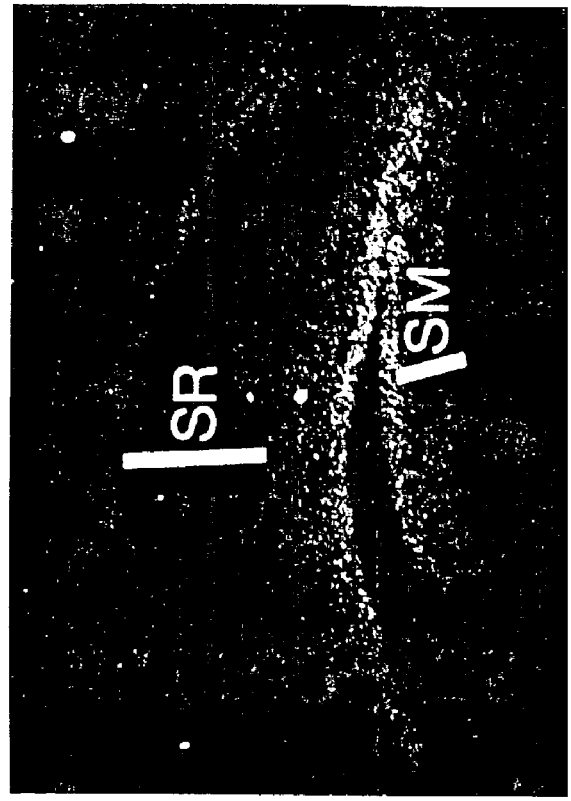
FIGS. 3A-3D. In situ localization of lacZ mRNA in hippocampus.
Figure 3A:
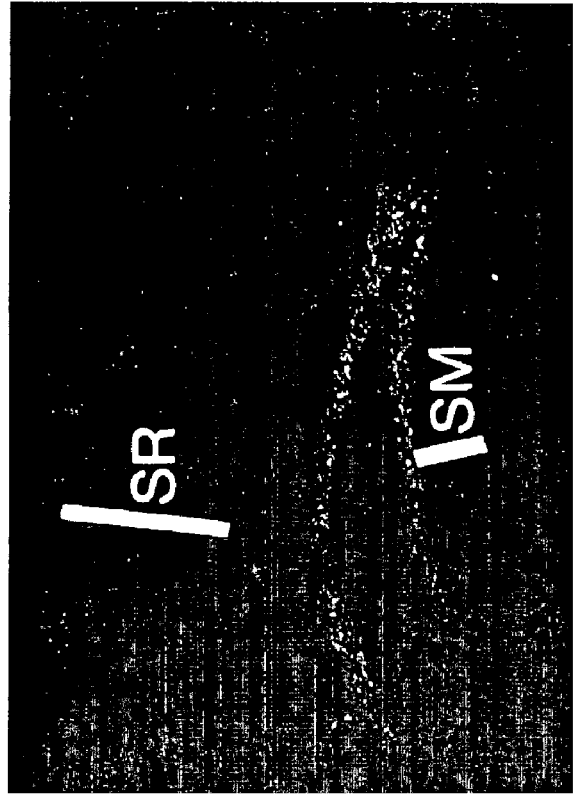
Figure 3D:
Figure 3C:
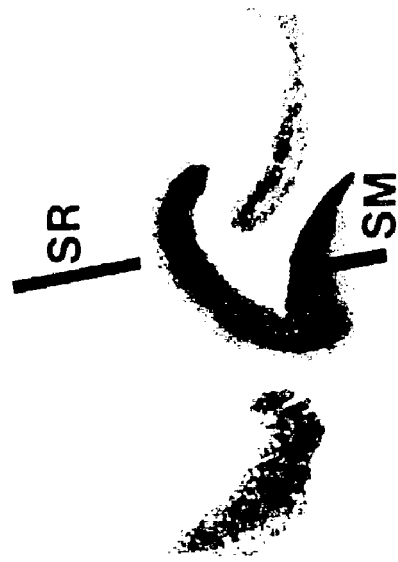

The 3'-UTR of CaMKII Targets mRNA to Dendrites. While the presence or absence of the CaMKIIα 3'-UTR seemed to have little effect on the regional distribution of transgene expression, in situ hybridization using a lacZ-specific oligonucleotide probe revealed a different subcellular localization of the lacZ mRNA between the two transgenic lines. (FIG. 3A). To examine this subcellular localization in greater detail, the hippocampus was examined where the neuronal and dendritic layers are well differentiated. In the lac-CMK mice the hybridization signal covers not only the cell body layers of the dentate gyrus and CA1 region, but also extends into the corresponding dendritic layers. By contrast, the lac-A mice show strong hybridization in the cell body layer of the dentate gyrus and a weaker signal in CA1 cell bodies but no signal in the corresponding dendritic layers. The hybridization signal in the lac-CMK mice appears to be uniform throughout the dendritic layer and to extend into the most distal regions of the dendrite. This parallels the subcellular distribution of the endogenous CaMKIIα mRNA and differs from that of MAP2, a dendritically-localized mRNA that is found only in the proximal portion of the dendrite (Garner et al., 1988). Thus, the presence of the CaMKIIα 3' UTR is sufficient to localize the lacZ mRNA to dendrites and to yield a distribution of the mRNA within the dendritic layers that is indistinguishable from that of the endogenous CaMKIIα gene.

In an attempt to identify a common sequence element, the nucleotide sequence of the other known dendritically localized mRNAs [MAP2, Arc, IP-3R1, BC1 (Furuichi et al., 1993; Garner et al., 1988; Lyford et al., 1995; Link et al., 1995; Tiedge et al., 1991)] was compared to that of the CaMKIIα 3'-UTR. No major sequence homology was found. However, the critical determinant of the cis-acting element may not be reflected in its primary sequence but in the three-dimensional structure of the folded mRNA. This appears to be the case for the RNA localization elements important in early embryonic development (Macdonald et al., 1988; Macdonald et al., 1993; Mowry et al., 1992). Alternately, the mechanism of localization for CaMKIIα may be different from that of the other dendritically localized RNAs. The difference in the extent of dendritic transport of the MAP2 and CaMKIIα mRNAs suggests some difference in the transport mechanism (Burgin et al., 1990; Garner et al., 1988).

Dendritically Localized mRNA Is Effectively Translated. Is this dendritically targeted mRNA effectively translated? Previous studies have yielded conflicting results regarding basal protein synthesis in dendrites (Torre et al., 1992; Gossen et al., 1992). In mice bearing the dendritically localized lacZ mRNA, the level of β-gal protein in the dendrites of the hippocampal pyramidal cells in increased relative to controls, in which the lacZ mRNA is restricted to the cell body (FIG. 3B). This suggests that the dendritic mRNA is translationally active in the intact animal under basal conditions. However, when expressed at high levels, β-gal can diffuse into neuronal processes. It therefore is possible that some of the protein found in dendrites actually arose from translation in the cell body.

To clearly distinguish between protein synthesized locally within the dendrites and that synthesized in the cell body and diffusing into the dendrites, transgenic mice were generated in which the lacZ gene carried a nuclear localization signal (nls) so that β-gal synthesized in the neuronal cell body would be sequestered in the nucleus, thereby preventing it from diffusing into the dendrite. Transgenic mice were generated using the nls-lac-CMK construct shown in FIG. 1A. In this case, the transgene of the tet-O-promoter was expressed using the tTA system (Craig et al., 1993; Mayford et al., 1995). Three lines of mice were obtained that expressed the nls-lac-CMK transgene in the hippocampus, one of which was examined in detail.

In situ hybridization revealed that the lacZ mRNA from the nls-lac-CMK line of mice was transported into dendrites (FIG. 4A). Histochemical detection of β-gal in this line revealed a pattern in which strong staining is found in the nucleus with little or no staining in the proximal dendrite and strong staining again in the more distal dendritic layer (FIG. 4B). Thus, the localization machinery is able to transport β-gal synthesized in the soma and proximal dendritic layer into the nucleus (compare FIG. 3B, lac-CMK, with FIG. 4B, nls-lac-CMK). Moreover, this expression. pattern suggests that the β-gal found in the distal dendrite arises from local translation of the lacZ mRNA in the distal dendrite.

β-Gal Is Unevenly Expressed Along the Dendrite. To assess whether the β-gal is expressed evenly along the whole length of the dendrite, hippocampal neurons were cultured from nls-lac-CMK mice and used double-immunofluorescent detection of β-gal and MAP2. The MAP2 antibody, which labels microtubules specifically along the shaft of the dendrites, gives a smooth staining pattern. By contrast, the β-gal immunoreactivity is surprisingly patchy in its distribution with localized hot spots of staining along the dendritic shaft and within some presumptive dendritic spines (FIGS. 4C and D). This pattern of β-gal staining was observed using two different antibodies and was not detected in cultures from wild-type mice. This patchy, differential expression of β-gal along the dendrite suggests that the neuron is able to regulate expression of the transgene locally within the dendrite. This local regulation might occur through regulated distribution of the lacZ mRNA within the dendrite or through local differences in the rate of its translation.

Discussion

Because neurons are highly polarized cells, a critical determinant of their function is the targeting of specific signaling molecules to their appropriate subcellular destination. In addition, neurons receive thousands of synaptic inputs and these can often be modulated independently in response to local differences in synaptic activity. For example, long-term potentiation or LTP is an activity-dependent form of synaptic plasticity that is synapse specific (Bliss et al., 1993). The potentiation of synaptic strength with LTP occurs only at those synapses that are stimulated and not at other synapses onto the same cell. Thus, the LTP inducing stimulus must produce a biochemical change specific to the activated synapse. One mechanism for controlling the local biochemistry of a synapse is by regulating the distribution and translation of specific mRNAs at that synapse.

The CaMKIIα gene is expressed specifically in forebrain neurons, plays an essential role in LTP, and is one of the few mRNAs that are known to be targeted to dendrites (Burgin et al., 1990; Silva et al., 1992; Mayford et al., 1995). Therefore, the signals controlling both the forebrain specific expression and the dendritic mRNA localization were investigated. It was discovered that an 8.5-kb fragment: of the CaMKIIα gene is able to confer forebrain specific expression on a heterologous lacZ transgene. Subsequently, this promoter element has been utilized to express a number of other transgenes and it has been found that in each case expression is limited to the forebrain neurons in a pattern similar to that shown in FIG. 2. The ability to direct transgene expression specifically to the forebrain neurons should prove useful in transgenic studies of neuronal function and its relation to behavior.

While the promoter targets CaMKIIα to the forebrain, the 3'-UTR of CaMKIIα localizes the heterologous lacZ mRNA to dendrites. The mapping of the dendritic targeting signal of the CaMKIIα mRNA to the 3'-UTR demonstrates that the localization process is independent of the protein translated similar to the regulation of mRNA localization in other systems (Bian et al., 1996; Sundell et al., 1990; Kleiman et al., 1993). The expression of a lacZ gene in which the mRNA was targeted to dendrites was examined, but the β-gal protein itself was targeted to the nucleus. Strong staining was found for the β-gal in the nucleus and distal dendrites with relatively little staining in the cytoplasm of the soma and proximal dendrite. These results suggest that the nuclear localization machinery may not function efficiently in the more distal regions of the dendrites. Within the dendrite, β-gal had an uneven distribution both along the shaft and in dendritic spines. This differential expression of the gene product provides a possible mechanism for the independent modulation of the biochemistry of individual synapses. The differential distribution could occur either through differential localization of the mRNA or differences in the translation of mRNA along the dendrite.

LTP is produced only at the appropriately stimulated synapses and its late phase is blocked by inhibitors of protein and mRNA synthesis (Bliss et al., 1993; Frey et al., 1988; Nguyen et al., 1994). The requirement for new gene expression in LTP, coupled with the synapse specificity of the process, implies that the new gene products are targeted to or functionally used only at those synapses where LTP is induced. One mechanism by which this might occur is for the LTP-inducing stimulus to convert the synapse from a translationally inactive to a translationally active state. This would lead to an immediate increase in the level of the gene product for those mRNA species localized to that synapse. In addition, newly transcribed mRNA species that were transported into dendrites would be expressed only at those translationally active synapses that received the LTP-inducing stimulation. Alternatively, an immediate increase in the translation of mRNA at the stimulated synapses might mark those synapses such that the newly induced gene products important for maintaining LTP would be targeted only to those marked synapses. Mislocalization of CaMKIIα mRNA, through deletion of the dendritic targeting signal, may interfere with the production or maintenance of a synapse-specific late phase for LTP.

Example 2

Control of Memory Formation Through Regulated Expression of CaMKII Transgene

Abstract

One of the major limitations in the use of genetically modified mice for studying cognitive functions is the lack of regional and temporal control of gene function. To overcome these limitations, a forebrain-specific promoter was combined with the tetracycline transactivator system to achieve both regional and temporal control of transgene expression. Expression of an activated calcium-independent form of calcium-calmodulin-dependent kinase II (CaMKII) resulted in a loss of hippocampal long-term potentiation in response to 10-hertz stimulation and a deficit in spatial memory, a form of explicit memory. Suppression of transgene expression reversed both the physiological and the memory deficit. When the transgene was expressed at high levels in the lateral amygdala and the striatum but not other forebrain structures, there was a deficit in fear conditioning, an implicit memory task, that also was reversible. Thus, the CaMKII signaling pathway is critical for both explicit and implicit memory storage, in a manner that is independent of its potential role in development.

Explicit memory—a memory for facts, places, and events—requires the hippocampus and related medial temporal lobe structures (Scoville et al., 1957; Squire et al., 1992), whereas implicit memory—a memory for perceptual and motor skills—involves a variety of anatomical systems (Schacter et al., 1994). For example, one form of implicit memory, that for conditioned fear, involves the amygdala (Blanchard et al., 1972; Davis, 1992).

Studies with genetically modified animals have sought to relate specific genes to specific forms of explicit or implicit memory storage (Grant et al., 1992; Silva et al., 1992; Mayford et al., 1995; Bach et al., 1995). However, current methodology does not allow one to distinguish between a direct effect on memory or its underlying synaptic mechanisms and an indirect effect of the development of the neuronal circuits in which the memory storage occurs (Grant et al., 1992; Mayford et al., 1995). In addition, the gene under study is typically over-expressed or ablated throughout the entire brain. As a result, the genetic modifications often affect, indiscriminately, both implicit and explicit memory as well as perceptual or motor performance. Thus, to analyze the molecular contribution of a given gene to a particular type of memory, it is essential not only to control the timing of expression but also to restrict expression to appropriate cell populations.

To address these issues and to achieve regulated transgene expression in restricted regions of the forebrain, a forebrain-specific promoter was used in combination with the tetracycline transactivator (tTA) developed by Bujard and his colleagues (Gossen et al., 1992; Furth et al., 1994). The role of CaMKII signalling in synaptic plasticity as well as in implicit and explicit memory storage was examined.

CaMKIIα is a serine-threonine protein kinase that is restricted to the forebrain (Miller et al., 1986; Burgin et al., 1990; Hanson et al., 1992). It is expressed in the neurons of the neocortex, the hippocampus, the amygdala, and the basal ganglia. After a brief exposure to $Ca^{2+}$, CaMKII can convert to a $Ca^{2+}$-independent state through an autophosphorylation at $Thr^{286}$ (Miller et al., 1986; Hanson et al., 1992; Fong et al., 1989, Thiel et al., 1988; Waldmann et al., 1990). This ability to become persistently active in response to a transient $Ca^{2+}$ stimulus led to the suggestion that CaMKII may be a molecular substrate of memory (Lisman, 1994). Targeted disruption of the CaMKIIα gene produces deficits in long-term potentiation (LTP) and severely impairs performance on hippocampal-dependent memory tasks (Silva et al., 1992; Silva et al., 1992, p. 201). Mutation of $Thr^{286}$ to Asp in CaMKIIα mimics the effect of autophosphorylation at $Thr^{286}$ and converts the enzyme to a $Ca^{2+}$-independent form (Fong et al., 1989; Walsmann et al., 1990). Transgenic expression of this dominant mutation of CaMKIIα (CaMKII-$Asp^{286}$) results in a systematic shift in response to low-frequency stimulation such that long-term depression (LTD) is favored in the transgenic mice (Mayford et al., 1995). Thus, although Schaffer collateral LTP in response to 100-Hz tetanus is not altered, LTP is eliminated in the range of 5 to 10 Hz, a frequency (the theta frequency) characteristic of the endogenous oscillation in neuronal activity seen in the hippocampus of animals during spatial exploration (Bland, 1986). Correlated with this selective deficit in LTP in the theta frequency range is a severe defect in spatial memory (Bach et al., 1995). These phenomena have been examined with regulated expression of the CaMKII-Asp$^{286}$ transgene.

Doxycycline regulation of transgene expression. The first type of mouse generated to achieve regulated expression of CaMKII-Asp$^{286}$ in forebrain neurons (FIG. 5A) expressed the tTA gene under the control of the CaMKIIα promoter (line B), which limits expression of the tTA transgene to neurons of the forebrain (Bland, et al., 1986). The CaMKIIα promoter consisted of 8.5 kb of genomic DNA upstream of the transcription initiation site of the mouse CaMKIIα gene, as well as 84 base pairs of the 5' noncoding exon. Genomic DNA was isolated from a C57 B16/J mouse spleen cosmid library with a rat genomic probe consisting of a 0.4-kb Ava I fragment comprising the transcription-initiation region of rat CaMKIIα (Sunyer et al., 1990). The tTA gene from plasmid pUHD 15-1 (Gossen et al., 1992) was flanked by an artificial intron and splice sites ats the 5' end (Choi et al., 1991) and by a polyadenylation signal from SV40 at the 3' end. The cDNA with intron and polyadenylation signal was placed downstream of the 8.5-kb CaMKII promoter fragment. The cDNAs for Escherichia coli lacZ and mouse CaMKIIα were similarly flanked by the hybrid intron and polyadenylation signal and placed downstream of the tet-O promoter element of plasmid pUHD 10-3 (Gossen et al., 1991). The CaMKIIα gene was a full-length cNDA (4.8 kb) isolated from a C57B16/J mouse brain cDNA library. The lacZ gene carried an SV40 large T antigen nuclear localization signal as well as the 3' untranslated region (UTR) of CaMKIIα, which targets the mRNA to dendrites (Mayford et al., 1996). In the second type of mouse, the tTA-responsive tet-O promoter is linked to the target gene of interest, in this case either lacZ or the CaMKII-Asp$^{286}$ gene. The tTA gene expresses a eukaryotic transcription activator that binds to and activates transcription from the tet-O promoter element; this transcription is blocked by the tetracycline analog doxycycline (Gossen et al., 1992). When both the tet-O and tTA transgenes were introduced into the same mouse, the tet-O-linked gene was activated, but only in those cells that express tTA.

The regulation of the CaMKII-Asp$^{286}$ transgene was assessed using a reverse transcriptase-polymerase chain reaction (RT-PCR) Southern (DNA) blot (RT-PCR was performed essentially as described in Mayford et al., 1995). Total forebrain RNA (100 ng) was used in each reaction with oligonucleotide primers to amplify a region of the transcript that includes the Thr$^{286}$→Asp mutation. Equal amounts of amplified cDNA (both wild-type and mutant sequences) were separated on a 3% agarose gel, transferred to nylon membranes, and hybridized with a $^{32}$P-labeled oligonucleotide probe specific for the ASP$^{286}$ mutation (oligonucleotide sequence 5'-ct-tcaggcagtcgacgtcctgtctgtg-3', SEQ ID NO:5). Blots were washed under conditions in which only the ASP$^{286}$ mutant cDNA was detected (2 times 15 min, 60° C., 0.2X standard saline citrate). A Northern (RNA) blot of total forebrain mRNA revealed expression of a shorter than expected CaMKII-Asp$^{286}$ transcript (~3.4 kb) As shown in FIGS. 7A-D, this shorter CaMKII-Asp$^{286}$ transcript did not localize to dendrites, presumably as a result of the loss of a sequence element in the 3' UTR that is necessary for mRNA targeting to dendrites (Mayford et al., 1996) to detect only the mutant transcripts (FIG. 5B). Mice carrying either one of the transgenes alone show little or no expression of CaMKII-Asp$^{286}$ mRNA. When both transgenes were introduced into the same mouse, there was a large activation of CaMKII-Asp$^{286}$ expression. The expression of this transgene was completely suppressed when the mice were given doxycycline (2 mg/ml) in the drinking water for 4 weeks.

Figure 6A:
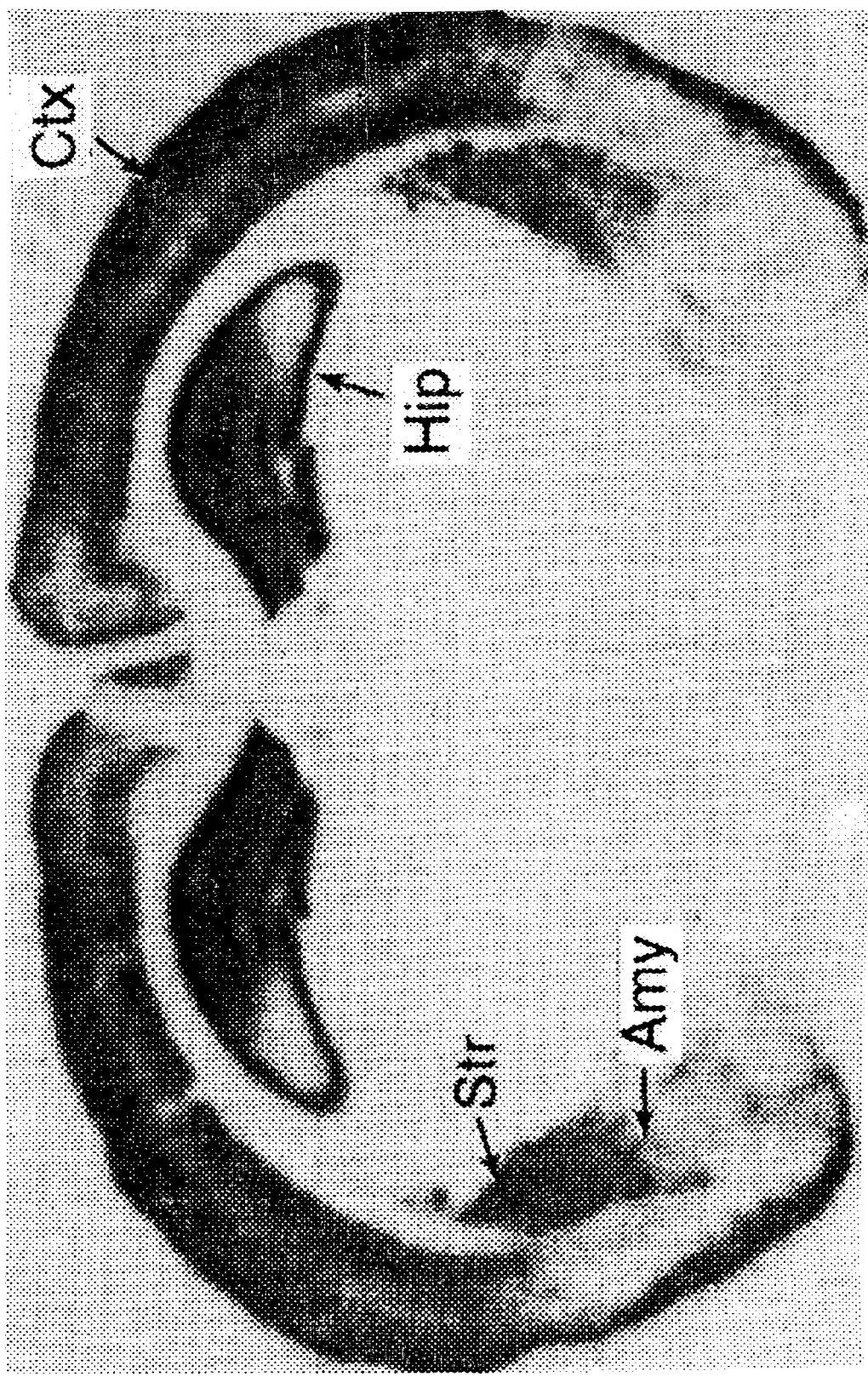
Figure 7A:
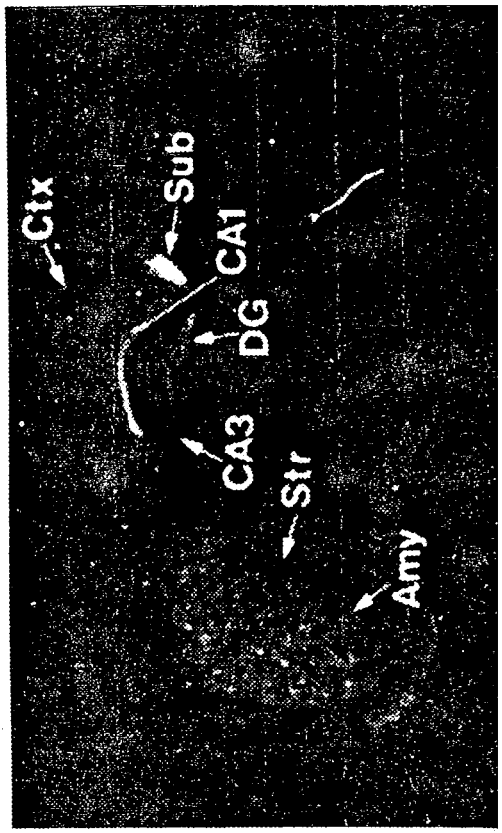
FIGS. 7A-7D. Regional distribution of the CaMKII-Asp$^{286}$ mRNA determined by in situ hybridization (Mayford et al., 1995). Medial sagittal sections of double transgenic lines B13, B21 and B22 showing CaMKII-Asp$^{286}$ transgene expression. B21/Amygdala shows a close-up view of a coronal section from the B21 double transgenic line of mouse.
Figure 7B:
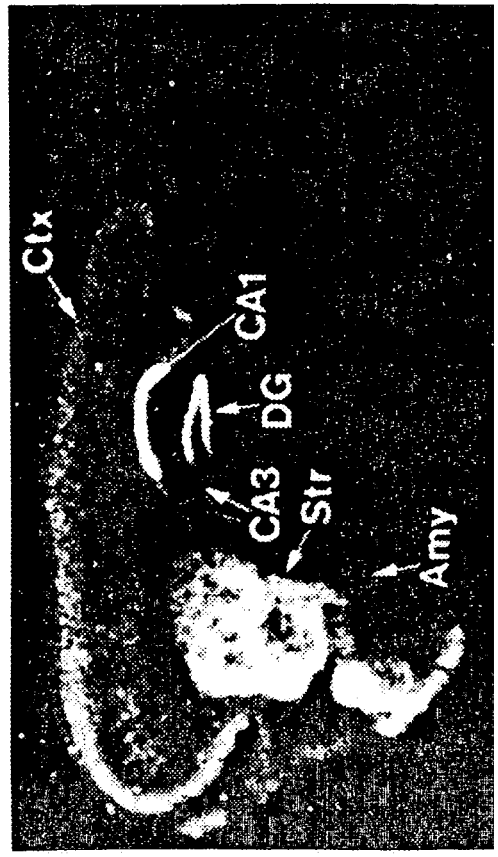
Figure 7C:
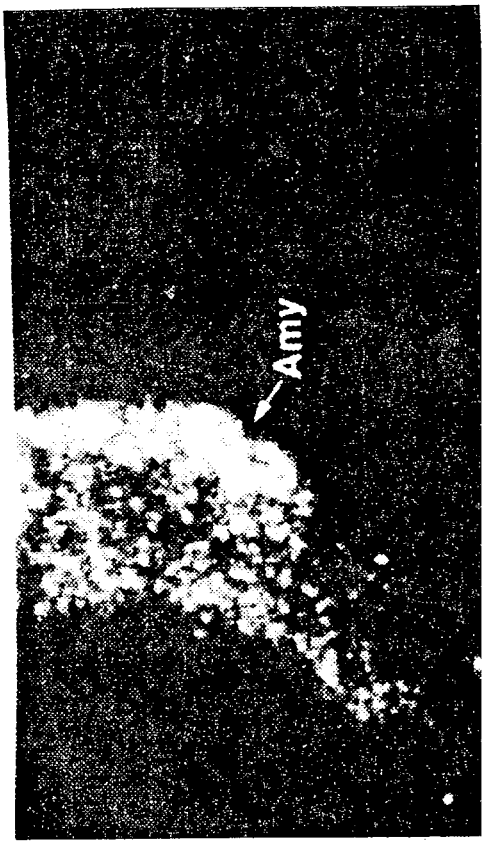
Figure 7D:
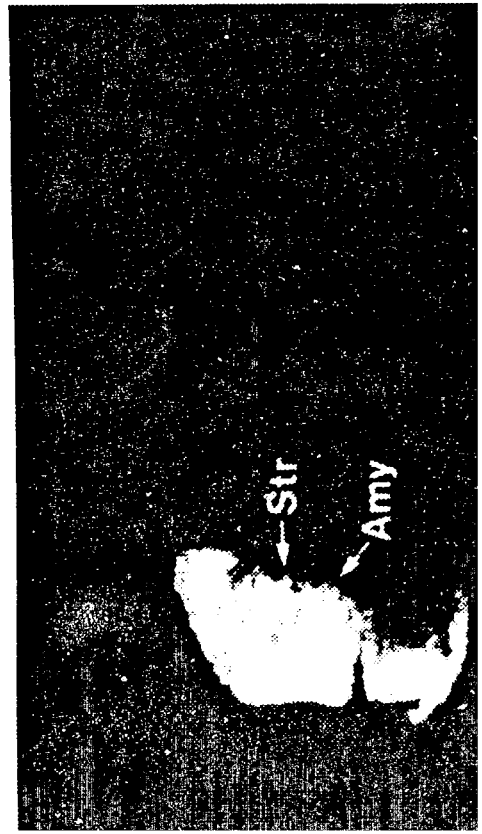

Restricted expression of the tet-O linked transgenes. The expression of β-galactosidase was examined in two tet-O lacZ reporter lines of mice that also carried that CaMKIIα promoter-tTA transgene (FIG. 6A). In the first line, expression was uniform throughout the forebrain, neocortex, hippocampus, amygdala, and striatum. This pattern mimics the expression of the endogenous CaMKIIα gene (Burgin et al., 1990). In the second lacZ line, expression was observed throughout the forebrain, but surprisingly, expression was absent in the CA# pyramidal cell body layer of the hippocampus (FIG. 6B).

Using in situ hybridization, the pattern of expression in three lines of double transgenic mice expressing tet-O-linked CaMKII-Asp$^{286}$ was examined (mouse lines B13, B21 and B22) (FIGS. 7A-7D). In the first line (B13), expression was evident throughout the forebrain. However, in the hippocampus, expression was strong in the dentate gyrus and CA2 region but was weak or absent in the CA3 region. In a second line of mice (B22), there was moderate expression in the hippocampus, subiculum, striatum, and amygdala, with little expression in neocortex. In the hippocampus, expression was again present in the CA1 region and absent in the CA3 region. In the third line (B21), there was little expression in the neocortex and hippocampus but strong expression in the striatum, in anterior and lateral amygdala nuclei, and in the underlying olfactory tubercle. Thus, whereas the CaMKII promoter can limit expression to forebrain neurons generally, expression of the tet-O-linked transgene is further limited to particular subsets of forebrain neurons, presumably due to integration site-dependent effects.

In double transgenic mice, a high level of expression of the CaMKII-Asp$^{286}$ mRNA was obtained (FIGS. 5B and 7A-D). To determine the effect of this expression on enzyme activity, CaMKII activity was measured in the striatum of the B21 line of mice (Table 1).

TABLE 1

Effect of CaMKII-Asp$^{286}$ mRNA expression on enzyme actibity Brains were removed and the striatum was dissected and immediately homogenized in 20 mN tris-HCl (pH 7.5), 0.5 mN EGTA, 0.5 mM EDTA, 2 mM leupeptin, 0.4 mM dithiothreitol, 0.1 mM phenylmethysulfonyl flouride, 0.4 mM molybdate, and 10 mM sodium pyrophosphate. CaMKII enzyme activity was determined as described (Mayford et al., 1995). B21 + Dox animals received doxycycline (1 mg/ml) plus 5% sucrose in the drinking water for 3 to 5 weeks. B21 + Dox withdrawal animals received doxycycline (1 mg/ml) for 3 to 5 weeks and were then switched to normal water for 6 weeks. The number of mice is given in parentheses.

CaMKII activity

| Mouse Line | Without Ca$^{2+}$ (pmol min$^{-1}$ μg$^{-1}$) | With Ca$^{2+}$ (pmol min$^{-1}$ μg$^{-1}$) | Ca$^{2+}$-independent (%) |
|---|---|---|---|
| Wild type | 0.13 ± 0.01 (5) | 10.4 + 1.2 | 1.33 + 0.21 |
| B21 | 0.90 ± 0.14 (5) | 20.9 + 2.9 | 4.62 + 1.02 |
| B21 + Dox | 0.16 ± 0.04 (5) | 12.9 + 1.5 | 1.22 + 0.03 |
| B21 + Dox withdrawal | 0.80 ± 0.03 (3) | 14.2 + 0.7 | 5.70 + 0.43 |

In these mice, Ca$^{2+}$-independent CaMKII activity was increased seven-fold relative to that of the wild type. However, when the mice were treated with doxycycline (1 mg/ml), CaMKII activity was suppressed to wild-type values. When the doxycycline treatment was discontinued, Ca$^{2+}$-independent CaMKII activity returned to those of the untreated transgenic mice. Thus, the CaMKII-Asp$^{286}$ transgene is functionally expressed and can be regulated with doxycycline.

Effects of LTP of CaMKII-Asp$^{286}$ expression in the hippocampus. Constitutive expression of the CaMKII-Asp$^{286}$ transgene in the mouse forebrain shifts the stimulation frequency required for the production of LTP and LTD in the Schaffer collateral pathway of the hippocampus (Mayford et al., 1995). In wild-type mice, stimulation at 1 Hz produced LTD, whereas stimulation at 5, 10 or 100 Hz produced LTP. However, stimulation in the 5- to 10-Hz range no longer produced LTP, but rather produced LTD or no change in synaptic strength.

Figure 8:
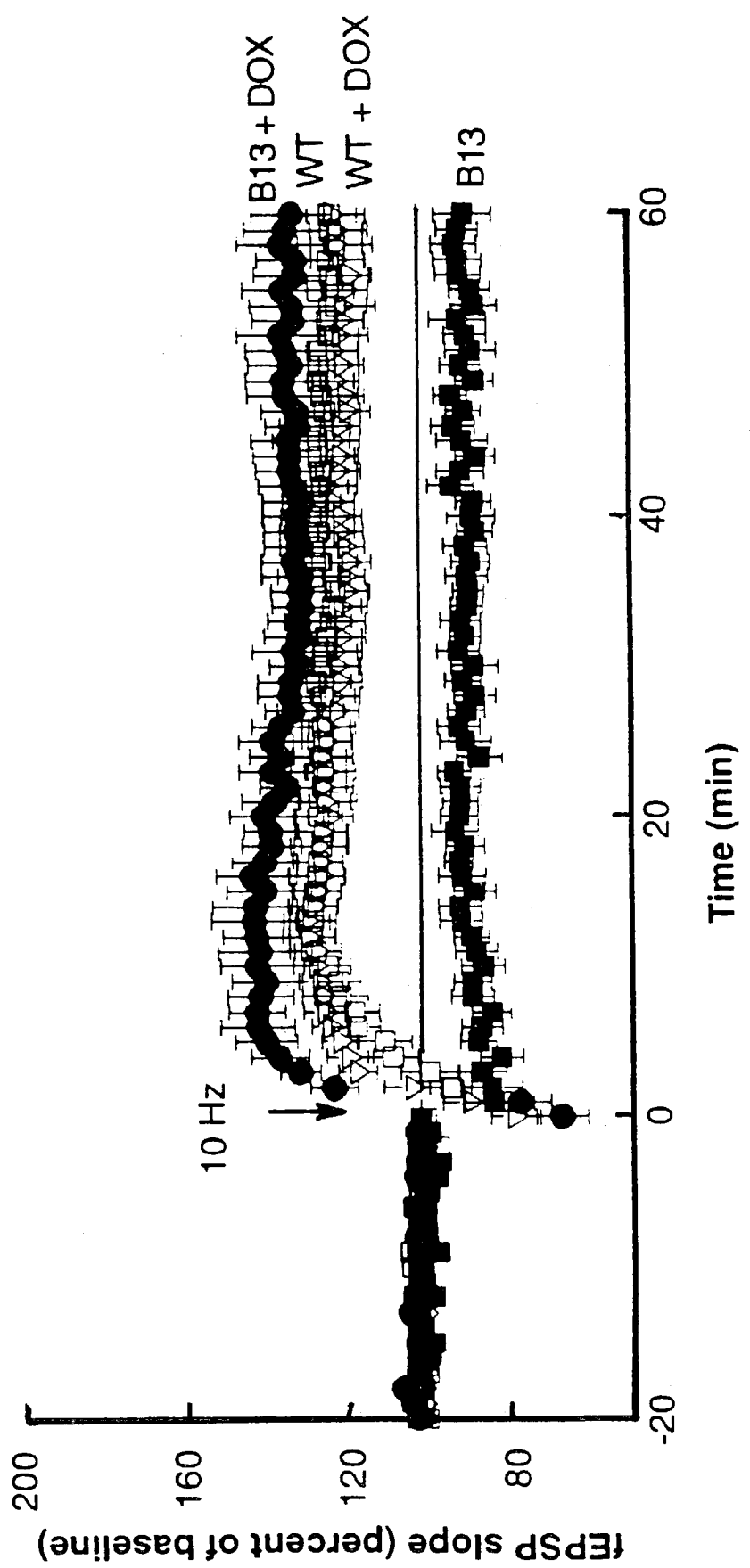
FIG. 8. Reversal of 10-Hz LTP deficit in CA1 of hippocampal slices. Field EPSP slopes before and after 1-Hz tetanic stimulation were recorded and expressed as the percentage of pre-tetanus baseline. Transverse slices (400 μm thick) of mouse hippocampus were prepared and placed in an interface slice chamber perfused with artificial cerebrospinal fluid as described (Mayford et al., 1995). Field excitatory postsynaptic potentials (EPSPs) were elicited once per minute with fine tungsten bipolar stimulation electrodes (0.05-ms pulse duration). Stainless steel recording electrodes were placed in striatum radiatum. The stimulation strength was set to produce 50% of the maximum obtainable EPSP in each slice. Baseline synaptic response was collected for 20 min. Before the tetanus. The 10-Hz tetanus was delivered for 1.5 min at the same intensity as used in the baseline recording. For doxycycline treatment, animals were administered doxycycline (1 mg/ml) plus 5% sucrose in the drinking water for 2 to 3 weeks, and the slices were then exposed to doxycycline (1 ng/ml) in the perfusate. All animals were 2.5 to 6 months of age at the time of recording. Stimulation at 10 Hz for 1.5 min induced a transient depression followed by potentiation in wild-type mice (123±9% at 60 min after tetanus; n=12 slices, 6 mice) (□). Tetanus (10 Hz) induced a slight depression in B13 double transgenic mice (89±6% at 60 min after tetanus; n=9 slices, 3 mice ) (■) Doxycycline treatment reversed the defect in B13 mice (132±10%; n=8 slices, 4 mice) (•) Doxycycline treatment had no effect on synaptic potentiation in wild-type mice (122±6%; n=16 slices, 6 mice) ∇.

Whether the transgene was acting presynaptically or postsynaptically was investigated by asking whether expression of the transgene specifically in the postsynaptic CA1 neurons would produce a shift in the frequency threshold for LTP and LTD. The B13 line of mice, which showed a uniformly high level of expression in the CA1 region, was examined with little or no expression in CA3 (Transverse slices (400 μg thick) of mouse hippocampus were prepared and placed in an interface slice chamber perfused with artificial cerebrospinal fluid as described (Mayford et al., 1995). Field excitatory postsynaptic potentials (EPSPs) were elicited once per minute with fine stungsten bipolar stimulation electrodes (0.05-ms pulse duration). Stainless steel recording electordes were placed in striatum radiatum. The stimulation strength was set to produce 50% of the maximum obtainable EPSP in each slice. Baseline synaptic response was collected for 20 minutes before the tetanus. The 10-Hz tetanus was delivered for 1.5 minutes at the same intensity as used in the baseline recording. For doxycycline treatment, animals were administered doxycycline (1 mg/ml) plus 5% sucrose in the drinking water for 2 to 3 weeks, and the slices were then exposed to doxycycline (1 ng/ml) in the perfusate. All animals were 2.5 to 6 months of age at the time of recording.). Thus, when Schaffer collateral LTP is measured in the B13 mice, the transgene will be expressed only in the postsynaptic neurons. Stimulation of slices from wild-type mice at 10 Hz resulted in a long-lasting potentiation of 123±9% (n=12 slices, 6 mice) (FIG. 8). By contrast, 10-Hz stimulation in B13 transgenic mice produced a slight depression to 89±6% of baseline (n=9 slices, 3 mice), which was significantly different from wild-type mice [t(19)=3.148; P<0.01, Student's t test].

To determine whether this effect was reversible, transgene expression was suppressed by administering doxycycline (1 mg/ml) for 2 to 3 weeks. Ten-hertz stimulation then produced potentiation similar to that in wild-type mice (132±10%, N=8 slices, 4 mice) (FIG. 8). Thus, suppression of transgene expression in adult mice reversed the electrophysiological phenotype [t(15)=3.675, P<0.005] These results suggest that the selective expression of the CaMKII-Asp$^{286}$ transgene in the postsynaptic CA1 neurons of the Schaffer collateral synapse is sufficient to alter the frequency threshold for LTP. Moreover, the shift in the frequency threshold is due to the acute expression of the transgene rather than to an irreversible developmental defect (It would also be useful to suppress transgene expression during development and then activate the gene only in the adult animal. However, it was found that treatment of wild-type mice with doxycycline (1 mg/ml) during development impaired adult spatial memory and memory for fear conditioning. The result suggests that doxycycline itself produces a defect in neuronal development. Transgene suppression was used only in the adult animal in which the doxycycline treatment did not affect memory. Given the activation of the transgene throughout development, it is possible that the LTP and memory phenotypes observed with the transgene active in the adult animal result from a synergistic interaction between development and adult expression rather than a direct acute effect of transgene expression in the adult animal.

Figure 9A:
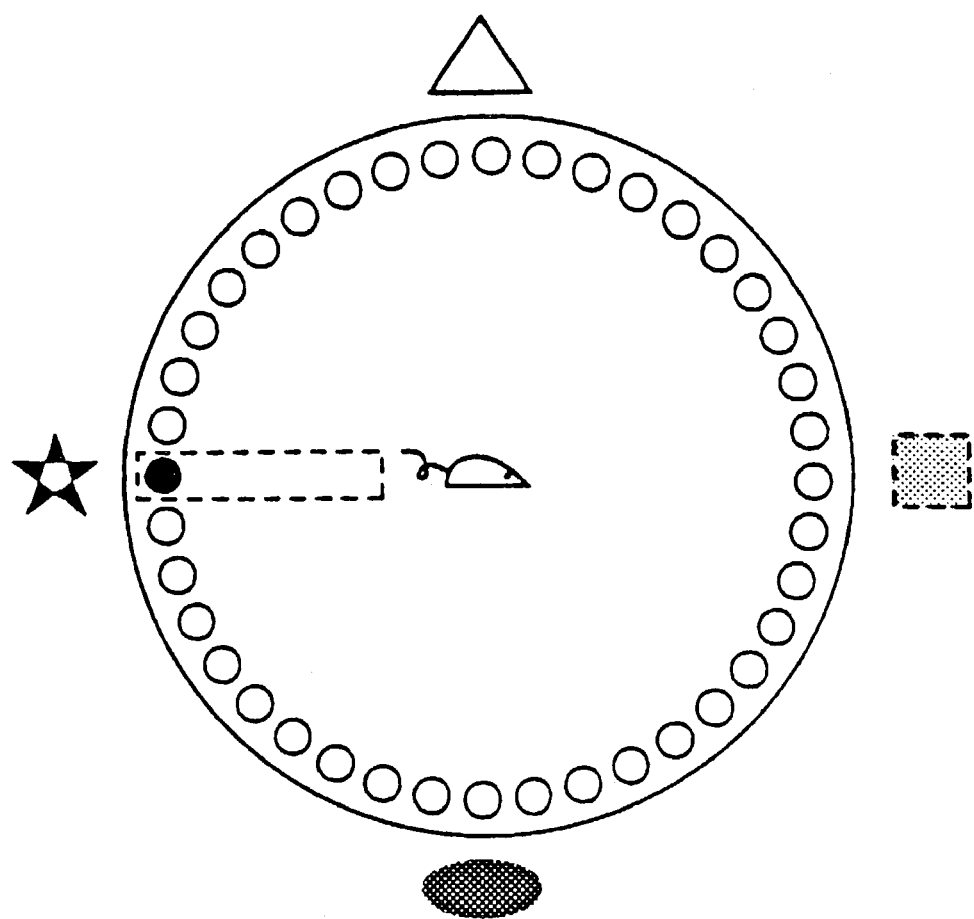
FIGS. 9A-9D. Reversible deficits in explicit learning and memory in mice expressing the CaMKIIα transgene.

Effect on explicit memory storage of CaMKII-Asp$^{286}$ expression in the hippocampus. Expression of the CaMKII-Asp$^{286}$ transgene in the forebrain interferes with spatial memory, a form of explicit memory, as measured in the Barnes circular maze (Bach et al., 1995). The Barnes circular maze is a brightly lit open disk with 40 holes in the perimeter (FIG. 9A). Mice have an aversion for brightly lit open areas and hence are motivated to escape form the maze. This can be achieved by finding the 1 hole in 40 that leads to a darkened escape tunnel. In the spatial version of this task, the mouse must use distal cues in the room to locate the hole that leads to the escape tunnel (On the Barnes circular maze (Bach et al., 1995), the mice (2.5 to 6 months of age) were tested once a day until they met the criterion (five out of six sessions with three or fewer errors, or until 40 days had elapsed). The order of holes searched was recorded by an observer who was blind to genotype and doxycycline condition, and from these data the number of errors was determined. Errors were defined as searches of any hole that did not have the tunnel beneath it. Searches included nose pokes and head deflections over the hole. At the end of each session the search strategy used was recorded by the observer. The spatial search strategy was operationally defined as reaching the escape tunnel with both error and distance scores≦3. Distance was calculated by counting the number of holes between the first hole searched within a session and the escape tunnel. A one-factor analysis of variance (ANOVA) (gender) revealed no significant effect of gender for either transgenic or wild-type mice, so the data were collapsed across this variable. For the error data, a three-factor ANOVA (genotype, doxycycline, and session block) with one repeated measure was used. For the spatial search strategy data, the two groups of B22 transgenic mice were compared with a two-way ANOVA (doxycycline and session block) with one repeated measure.).

Figure 9B:
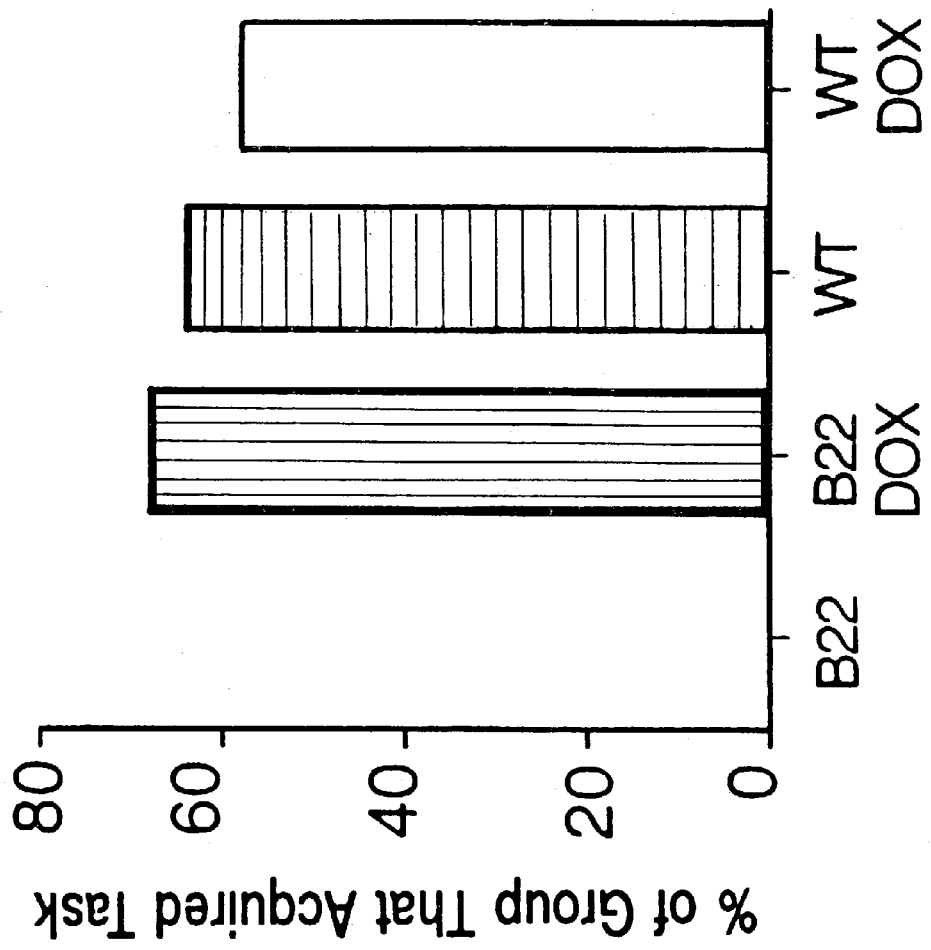
Figure 9C:
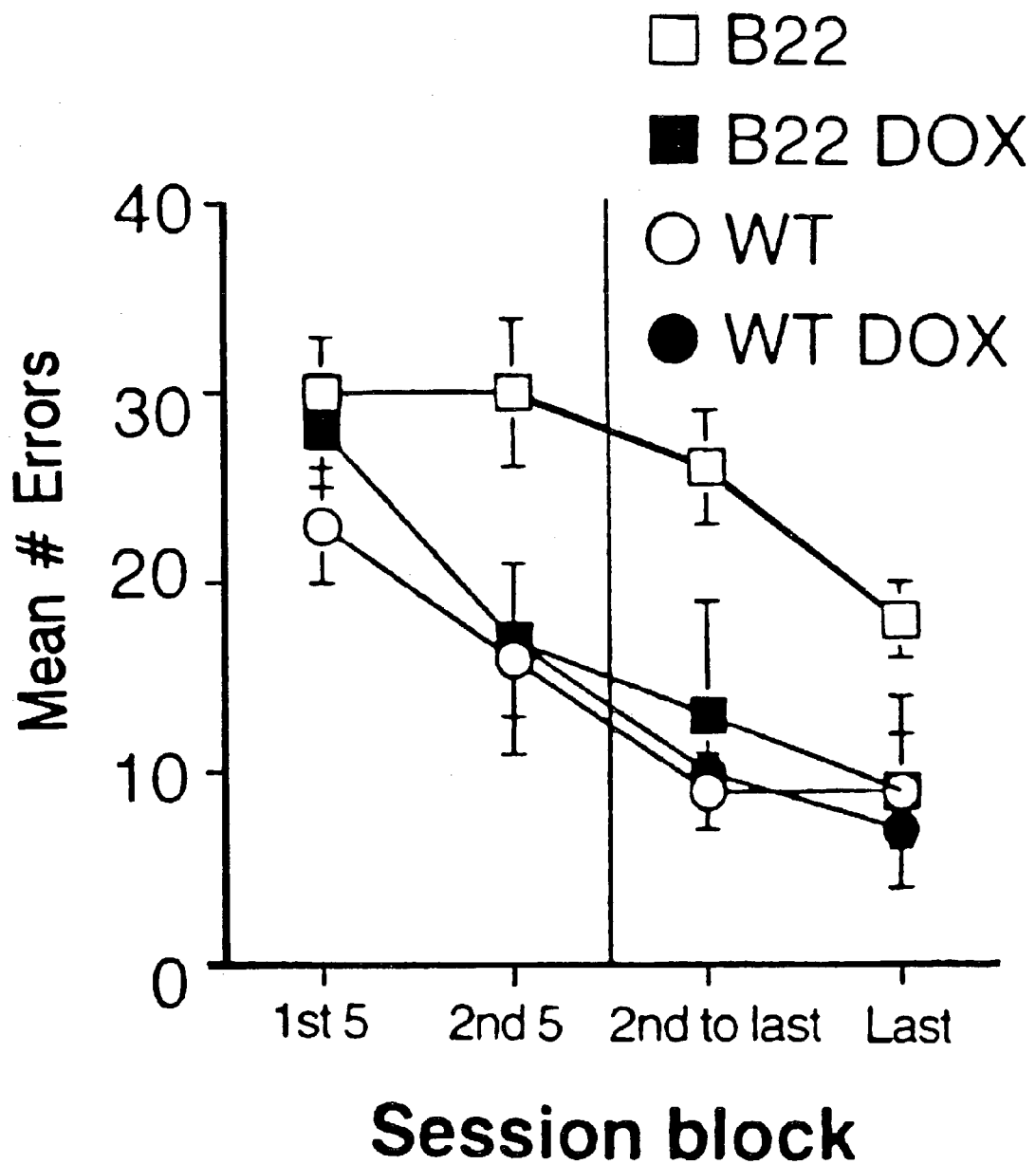
Figure 9D:
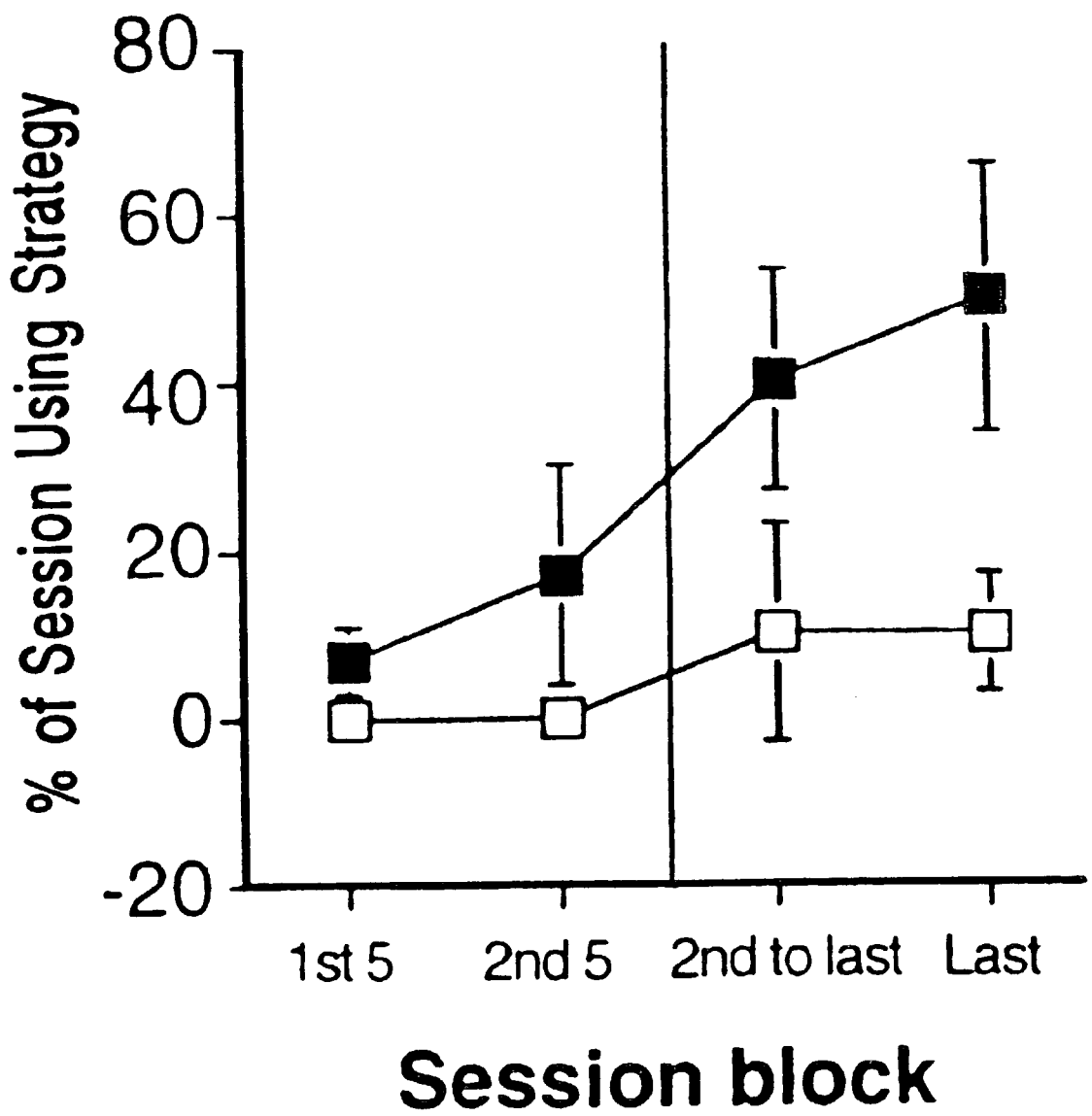

Expression of the CaMKII-Asp$^{286}$ transgene throughout the forebrain as seen in the B13 mice results in an impairment in the spatial but no the cued version of the Barnes maze task (Bach et al., 1995). To investigate those areas in the forebrain that are critical for this type of defect in spatial memory, the B22 transgenic mice were examined that show expression in the hippocampus, subiculum, striatum, and amygdala, but relatively little expression in the neocortex (FIGS. 7A-D). These mice exhibited significant impairment in spatial memory on the Barnes circular maze. None of the transgenic mice was able to acquire the task by using the spatial strategy, despite the fact that they were trained for 40 consecutive days (FIGS. 9B to 9D). Nevertheless, this profound memory impairment was reversed by suppression of transgene expression.

Figure 10A:
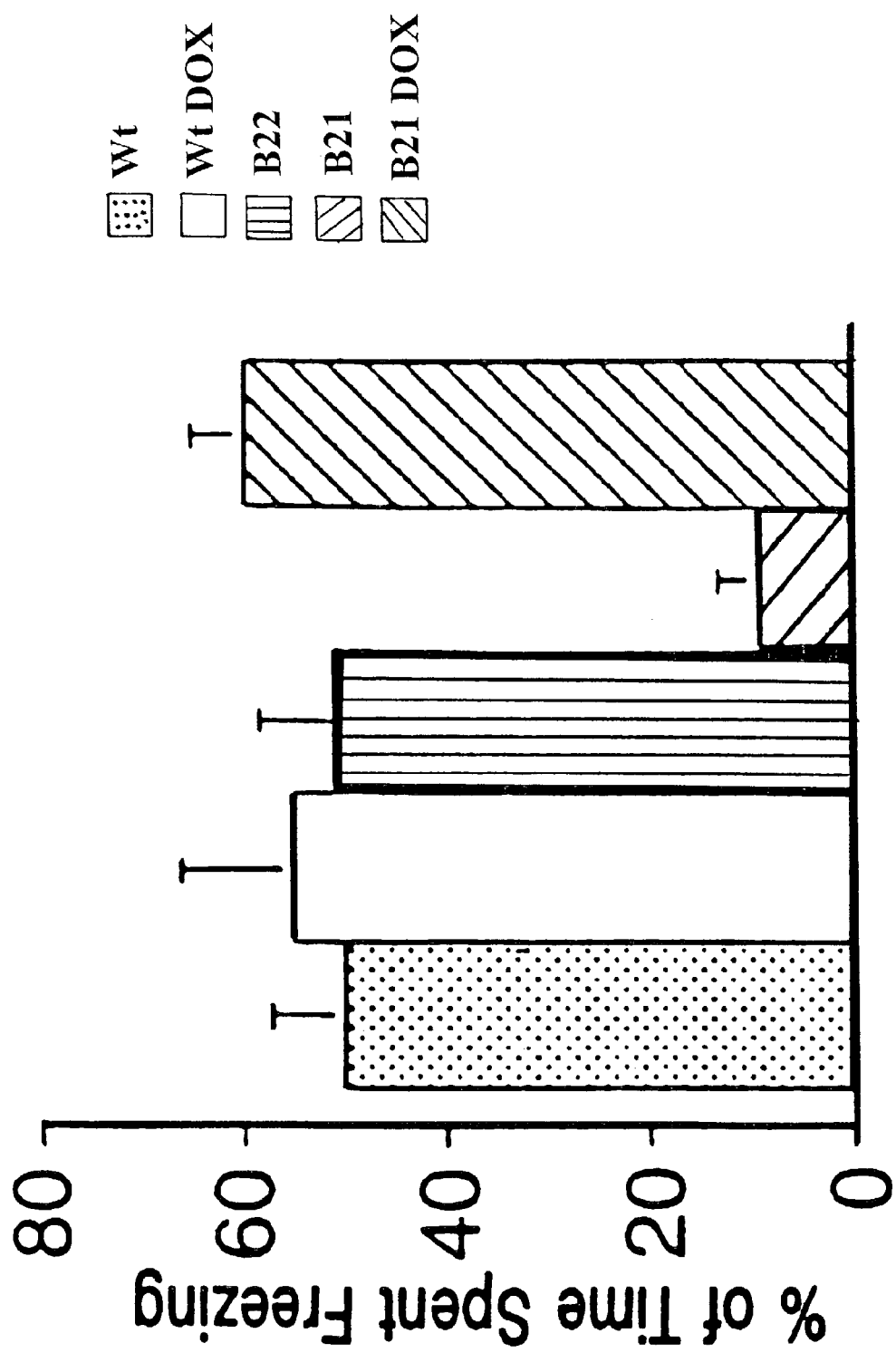
FIGS. 10A-10E. Reversible deficits in implicit learning and memory in mice expressing the CaMKIIα transgene. Percentage of time spent freezing to context (FIG. 10A) and to cue (FIG. 10B) 24 hours after training in the B22 and B21 lines. Values represent group means±SEM. A three-way ANOVA revealed a significant three-way interaction for context (genotype by line by doxycycline) (F[1,55]=9.177, P=0.0037) and a significant two-way interaction for cue (line by genotype) (F[1,55]=5.087 m P=0.0281) Six groups of mice were tested: B22 transgenics (n=6), B22 transgenics on doxycycline for four weeks (n=11), B21 transgenics on doxycycline for four weeks (n=19), wild types (from both B22 and B21 lines) (n=11), and wild types (from both B22 and B21 lines) on doxycycline for 4 weeks (n=8).
Figure 10B:
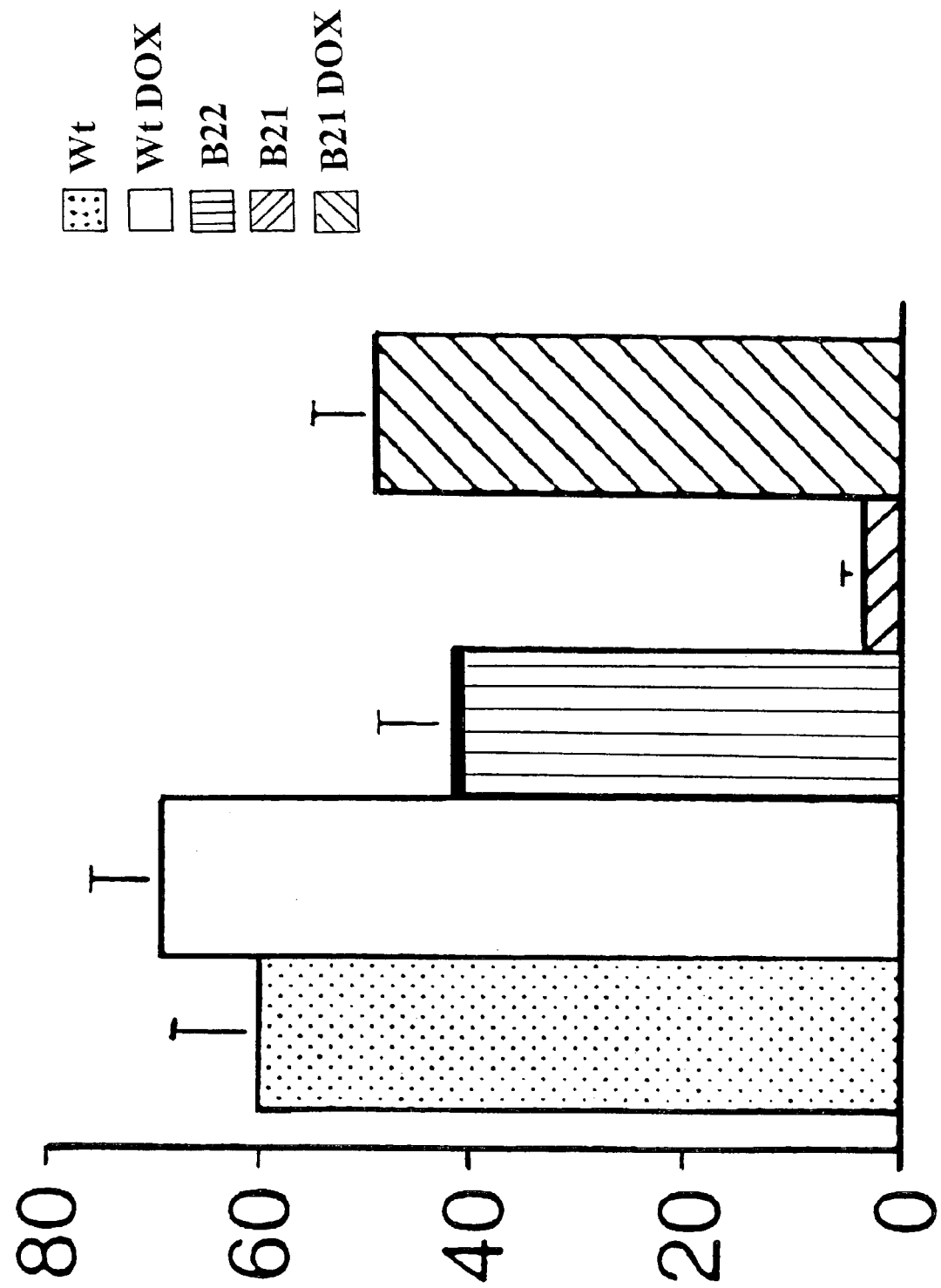

Effect on implicit memory of CaMKII-Asp$^{286}$ expression in the amygdala and striatum. Fear conditioning is a simple associative form of learning, in which both a novel environment and a tone are paired with a foot shock on the training day. In the conditioned fear task (Bach et al., 1995), freezing was defined as a total lack of movement with the exception of respiration and was measured by an experimenter who was blind to genotype and doxycycline condition. The percentage of time spent freezing to context and cue was calculated. No significant effect of gender was observed in the B22 or B21 transgenic mice or the wild-type mice, so the data were collapsed across this variable. Freezing to context and cue on testing day was analyzed by two three-factor ANOVAs (genotype, line, and doxycycline) that were used to compare the B22 and B21 transgenic and wild-type mice. Two one-way ANOVAs were used to compare the amount of freezing 6 weeks later to cue and context in B21 transgenics on doxycycline, B21 transgenics switched to water, and wild-type mice.). Memory is assessed 24 hours later by measurement of the amount of freezing (the fear response) elicited by either the novel environment (context conditioning) or the tone (cued conditioning). Fear conditioning shows components of both implicit and explicit forms of learning. The contextual version of the task is selectively impaired by lesions of the hippocampus (Kim et al., 1992) and thus can be viewed as an explicit form of learning, whereas both the cued and contextual versions of the task are impaired by lesion of the amygdala and are therefore viewed as implicit. In contrast to their spatial memory deficit, the B22 line of mice showed normal fear conditioning to both the cue and the context (FIGS. 10A and 10B). Thus, even though the B22 mice are impaired in spatial memory on the Barnes maze, they are not impaired in a second hippocampal-dependent task (contextual fear conditioning). This dissociation has been observed previously with constitutive expression of the CaMKII-Asp$^{286}$ transgene and may reflect the use of different synaptic mechanisms for the storage of memory in the two tasks (Mayford et al., 1995). In addition, these results demonstrate that the moderate level of transgene expression in the amygdala and striatum seen in the B22 mice (FIG. 3) is insufficient to interfere with the implicit component of fear conditioning.

Does a higher level of expression of the CaMKII-Asp$^{286}$ transgene in the striatum and amygdala affect implicit memory storage? To explore this question, the B21 mice were studied that showed strong expression in the lateral amygdala and striatum but little transgene expression in the hippocampus or neocortex (FIGS. 7A-7D). The B21 transgenic mice exhibited a severe impairment in both context and cued conditioning (FIGS. 10A and 10B). This learning impairment was again reversed by administration of doxycycline for 4 weeks before training.

This deficit in fear conditioning most likely arises from expression in the lateral amygdala, a structure that has been implicated in this form of learning by lesion studies (LeDoux et al., 1990). However, because there are many reciprocal connections between the striatum and the amygdala (Kita et al., 1990; Canteras et al., 1995), one cannot rule out the possibility that the deficit results from a functional disruption in the striatum that secondarily alters the amygdala.

Figure 10C:
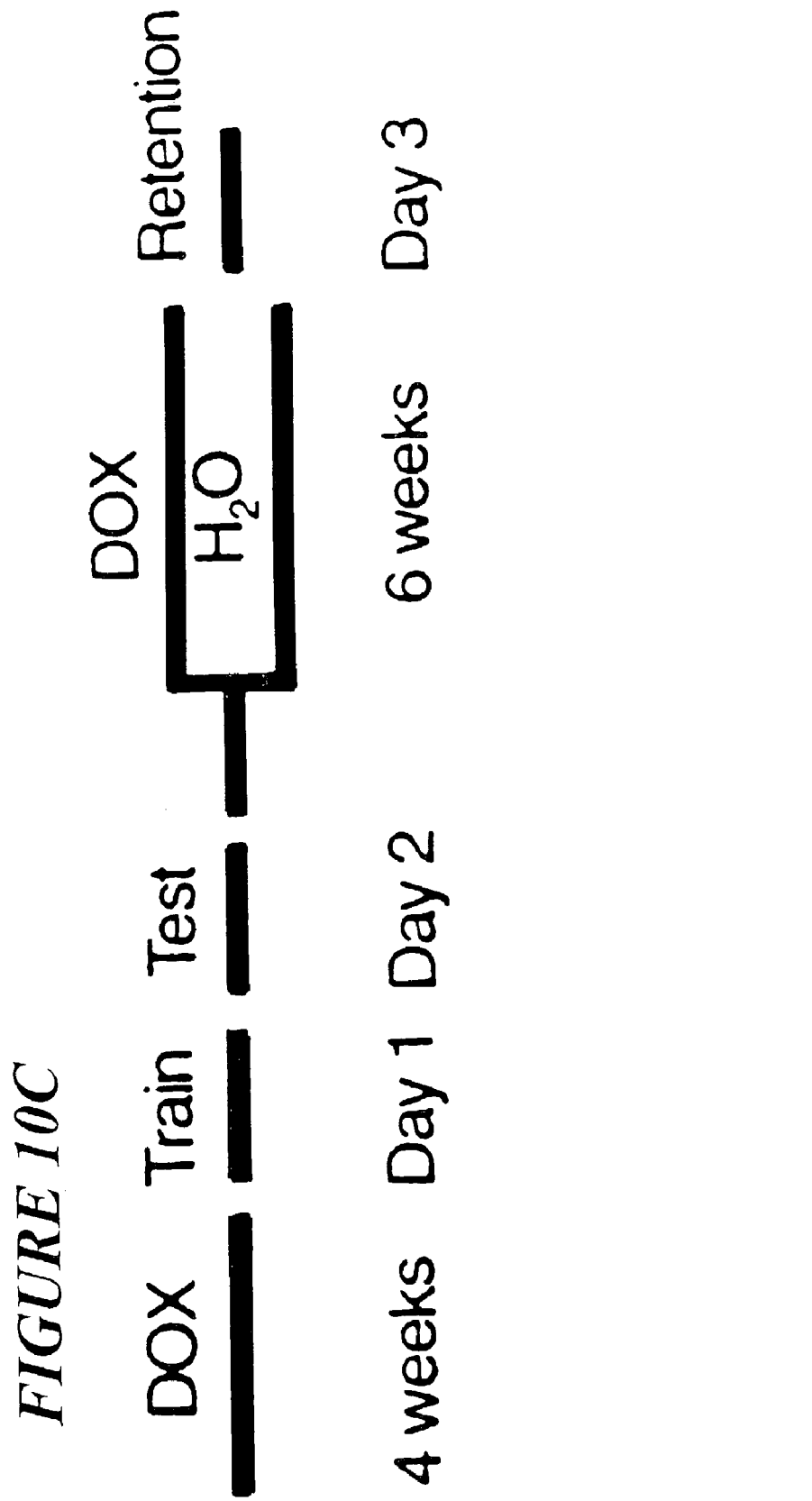
Figure 10D:
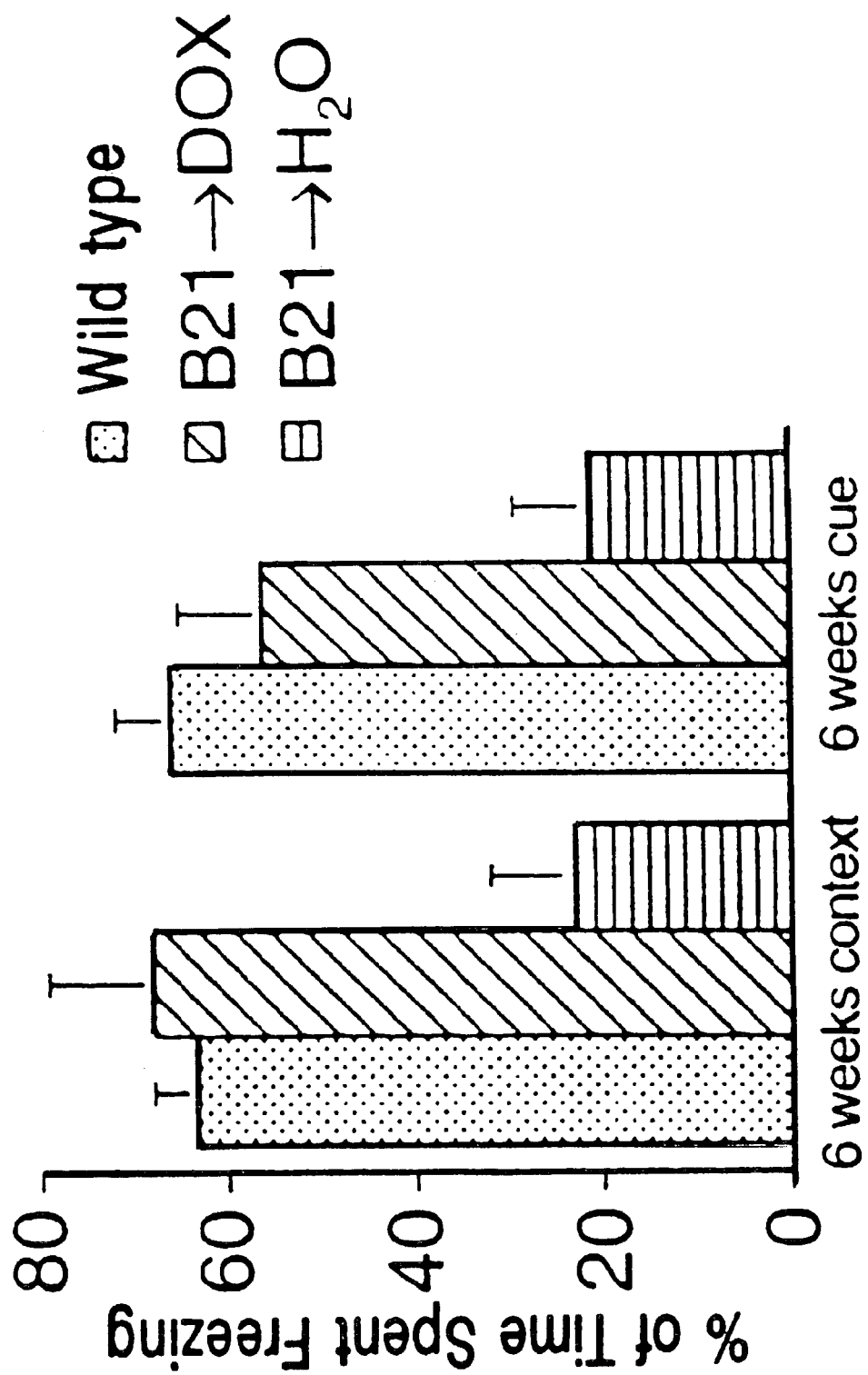

Effect on memory retrieval of CaMKII-Asp$^{286}$ Expression in the amygdala and striatum. Withdrawal of doxycycline after the initial period of transgene suppression resulted in a reactivation of gene expression (Table 1). Whether reexpression of the transgene, after normal learning has occurred, interferes with later stages of memory storage such as consolidation or retrieval was examined. B21 mice were trained with the transgene expression suppressed and observed robust fear conditioning. Once the animals had learned the task, transgene expression was reactivated by withdrawing doxycycline (FIG. 10C). After a 6-week period, the expression of the CaMKII-Asp$^{286}$ transgene returned to the same levels found in animals that had not received the drug (Table 1). These mice were then examined for retention of both context and cued conditioning and found a significant reduction in freezing compared to B21 mice in which suppression of the transgene was maintained (FIG. 10D).

Figure 10E:
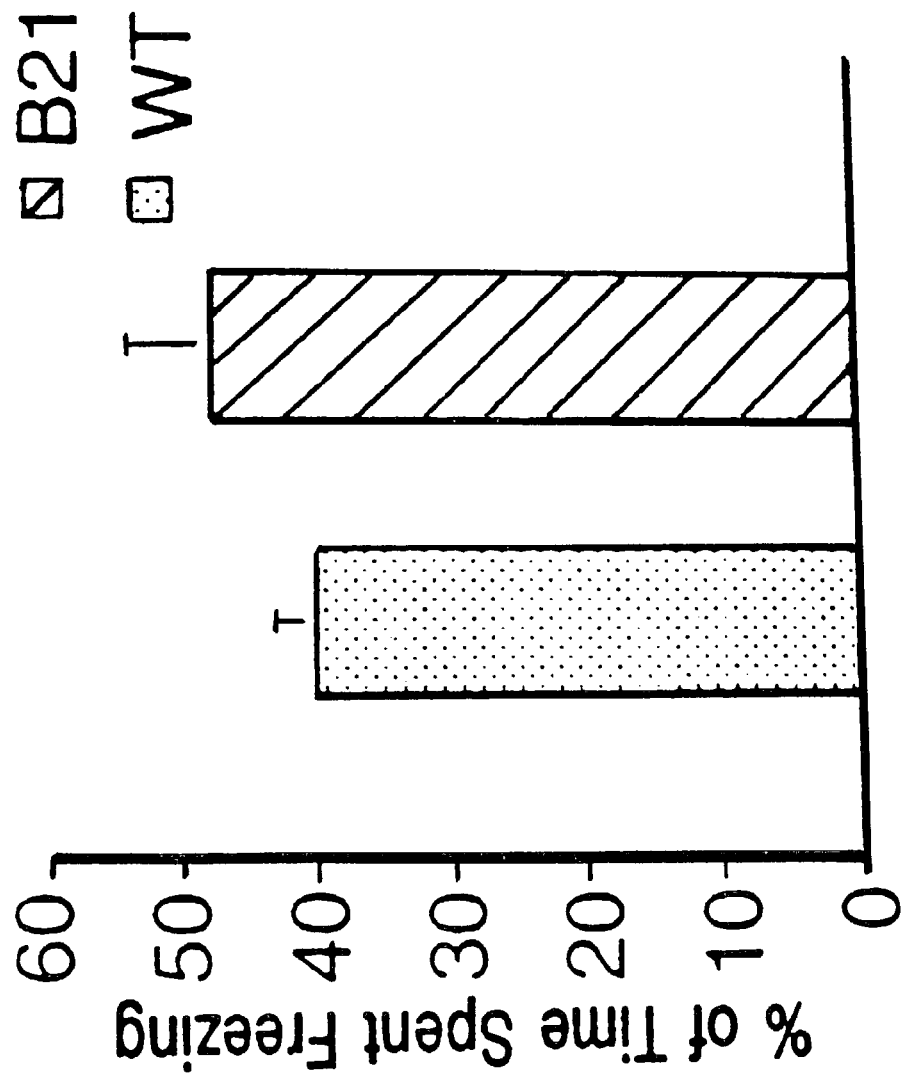

This reduction in freezing reflects either an impairment in memory consolidation or recall, or a deficit in performance. The evaluation of performance deficits is critical to the study of memory because one can only infer that memory storage is defective once all possible defects in perception, motor performance, and cognitive understanding of the task have been excluded. Although it is difficult to control for all consequences of a genetic manipulation on various components of performance, the two most likely classes of performance variables have been examined: (i) the ability to perceive the unconditioned stimulus, and (ii) the ability to attend to and freeze in response to fearful stimuli (the conditioned response). To rule out an impairment in perception of the unconditioned stimulus (foot shock), the sensitivity to shock was examined and found no difference between B21 transgenic and wild-type mice, suggesting that the observed fear-conditioning deficit did not result from a difference in the perception of the unconditioned stimulus (Plain sensitivity was measured in B21 transgenic (n=4) and wild-type mice (n=6)). The mice were placed individually in a mouse operant chamber with a metal grid floor and given 1-s foot shocks of increasing intensity (for example 1, 2, 3, mA . . . ). An experimenter who was blind to the genotype of the mice recorded the intensity of foot shock required to elicit each of the following three responses: startles, vocalizations, and jumps. A t test for each response revealed no significant effect of genotype. Next, the possibility of a defect in performance of the conditioned response (freezing) was examined by measuring unconditioned freezing in response to an intruder Unconditioned freezing in the presence of an intruder was measured in B21 transgenic (n=8) and wild-type mice (n=10) in a Nalgene plastic metabolism cage. The mice and intruder were placed in the upper and lower chambers, respectively. The chambers were separated by a metal grid floor. A seven-week-old male Sprague-Dawley rat served as the intruder and was placed in the lower chamber 10 minutes before introduction of the mouse. The amount of unconditioned freezing occurring during the first 120 s after the mouse was introduced was measured by an experimenter who was blind to genotype. A t test revealed no significant effect of genotype. No difference was found in the ability of B21 mice to freeze to an intruder (a rat) when the transgene was expressed (FIG. 10E). Thus, the B21 transgenic mice were able to attend to fearful stimuli and to express a normal freezing response. Although some occult defect in performance might have been present that was not detected, these control experiments argue that the transgene does not produce its effect on the perception of the unconditioned stimulus or on performance of the conditioned response. Rather, the results suggest that the CaMKII signaling pathway is important for some later aspects of memory storage such as the ability to consolidate or to recall the learned information.

Discussion. High levels of $Ca^{2+}$-independent CaMKII activity shifted the stimulation-frequency threshold for hippocampal LTP and LTD to favor LTD (Mayford et al., 1995). This shift in threshold is associated with an impairment in explicit, but not implicit, memory (Bach et al., 1995). To obtain regulated expression of this transgene in restricted regions of the forebrain so that one could study the underlying cellular and behavioral functions more effectively, the tTA system was used for regulated gene expression (Burgin et al., 1990; Hanson et al., 1992).

It was found that expression of the CaMKII-Asp$^{286}$ transgene altered adult synaptic plasticity and memory formation directly, and not by effects on neuronal development. In addition, expression of the transgene postsynaptically was sufficient to alter the frequency threshold for LTP induction, at least at 10 Hz. Finally, high-level activation of CaMKII in the striatum and lateral amygdala also interfered with implicit forms of memory.

How might an increase in $Ca^{2+}$-independent CaMKII activity alter the stimulation frequency required to produce LTP and LTD, and how might this in turn alter learning and memory storage? The results demonstrate that the effect of the CaMKII-Asp$^{286}$ transgene is likely mediated by changes in the postsynaptic CA1 neurons of the Schaffer collateral pathway. A simple mechanism for systematically shifting the frequency threshold for LTP and LTD to favor LTD would be to reduce the size of the postsynaptic Ca$^{2+}$ signal produced during the stimulation [(Cummings et al., 1996); however, see (Neveu et al., (1996)]. This could occur either through the increased phosphorylation of particular substrate proteins of CaMKII or by increased binding of Ca$^{2+}$-calmodulin by autophosphorylated CaMKII (Meyer et al., 1992). Independent of its detailed mechanisms, however, the data indicate that CaMKII activation alone may not be sufficient to produce the increase in synaptic strength associated with LTP, as has been suggested (Lisman, 1994; Petit et al., 1992). Rather, the level of CaMKII activation regulates the stimulation conditions under which LTP and LTD are produced.

In this study, synaptic physiology and behavior was not measured in the same group of animals. The expression of the CaMKII-Asp$^2$8 transgene in the CA1 region of the B22 mice was patchy; that is, some neurons expressed the transgene well, whereas in other neurons expression was absent. This patchy expression precluded an assessment of LTP in this line of mice by means of field recordings, which sample many synapses from different neurons in a region. However, it is assumed that in those neurons where the transgene was strongly expressed in these mice, a shift in the LTP/LTD frequency threshold would occur. Nevertheless, the effects of CaMKII activation on behavior are likely a consequence of its effect on the frequency threshold for LTP and LTD induction. That CaMKII activation interferes with synaptic plasticity in the 5- to 10-HZ range is particularly relevant for the explicit hippocampal-based spatial memory paradigm. Animals exploring the space of a novel environment show a rhythmic oscillation in hippocampal activity in the 5- to 10-HZ range (the theta rhythm) (Bland, 1986). Changes in synaptic strength can be produced by this endogenous activity and are thought to be necessary for storing information about space. Synaptic plasticity in the theta frequency range may regulate hippocampal place cells, the pyramidal neurons (in the CA3 and CA1 subfields) whose activity is correlated with the animals' location in the environment (O'Keefe et al., 1978).

Several lines of evidence implicate the lateral amygdala as the site of plasticity for fear conditioning. First, the lateral amygdala is the first site of convergence of somatosensory (unconditioned stimulus) and auditory (conditioned stimulus) information in the fear-conditioning pathway (Kim et al., 1992). Second, fear conditioning enhances the auditory-evoked responses of neurons in the lateral amygdala (Quirk et al., 1995). Third, these neurons exhibit robust LTP that can contribute to enhanced auditory-evoked responses (Rogan et al., 1995). Finally, lesions of the lateral amygdala block fear conditioning (Kim et al., 1992). How might the expression of CaMKII-Asp$^{286}$ affect fear conditioning? Expression of this transgene in the hippocampus increases the stimulation frequency required to produce LTP (FIG. 8). Were a similar increase in the frequency threshold to occur at excitatory synapses in the lateral amygdala, this increase in threshold could form the physiological basis for the observed impairment in implicit memory storage.

Expression of the transgene in striatum and amygdala also affected memory consolidation or recall. Models of learning generally invoke changes in synaptic strength only during the initial learning process (Churchland et al., 1992). Once formed, the changes in synaptic strength are thought to remain stable and to carry the actual memory trace. However, for some memories, such as hippocampal-based explicit memories, the anatomical locus of the memory changes with time during a several-week period after the initial learning (Kim et al., 1992). Moreover, the recall of memory typically is reconstructive—it requires a new recapitulation of the learned experience. Both transfer and reconstruction of memory might require an activity-dependent change in synaptic strength. If a similar process occurs for fear conditioning in the amygdala, the defect in retrieval observed in the transgenic mice could reflect a defect in synaptic plasticity caused by CaMKII-Asp$^{286}$ expression during this memory transfer or reconstruction phase.

The methods for regional and regulated transgene expression that are described here represent the development of an optimal technology for the genetic study of cognitive processes. To carry the molecular dissection of behavior further, it will be necessary to use promoters that are even more restricted in their pattern of expression and to adapt this technology to the regulation of targeted gene disruption. The methods described here should prove generally useful and should help in elucidating the cellular and molecular signaling pathways important for higher cognitive processes.

References

Bach, M. E. et al., ibid p. 905 (1995).
Bassell, G. J., Singer, R. H. & Kosik, K. S. (1994) Neuron 144: 565-572.
Bian, F., Chu, T., Schilling, K. & Oberdick, J. (1996) Mol. Cel. Neurosci. 7: 116-133.
Blanchard D. C. et al., J. Comp. Physiol. Psychol. 81: 281 (1972).
Bland, B. H. et al., Prog. Neurobiol. 26: 1 (1986).
Bliss, T. V. P. & Colingridge, G. L. (1993) Nature (London) 361:31-39.
Burgin, K. E. et al., J. Neurosci 10: 1788 (1990).
Canteras, R. B. et al., ibid 360: 213 (1995).
Choi, T. et al., Mol. Cell Biol. 11: 3070 (1991).
Churchland, P. S. et al., *The Computational Brain* Cambridge, Mass.: MIT Press, 1992.
Craig, A. M., Blackstone, C. D., Huganir, R. L. & Banker, G. (1993) Neuron 10: 1055-1068.
Cummings, J. A., et al., Neuron 16: 825 (1996).
Davis, M. *The Amygdala: Neurobiological Aspects of Emotion, Memory and Mental Dysfunction*. J. P. Appleton Ed. (Wiley-Liss, New York) 1992.
Davis, L., Banker, G. A. & Steward, O. (1987) Nature (London) 330: 477-572.
Feig, S. & Lipton, P. (1993) J. Neurosci 13: 1010-1021.
Fong, Y. L. et al., J. Bio. Chem. 264: 16759 (1989).
Forss-Petter, S., Danielson, P. E., Catsicas, S., Battenberg, E., Price, J., Nerenberg, M. & Sutcliffe, J. G. (1990) Neuron 5: 187-197.
Frey, U., Krug, M., Reymann, K. & Matthies, H. (1988) Brain Res. 452: 57-65.
Furth, P. A. et al., ibid, 91: 9302 (1994).
Furuichi, T., Simon-Chazottes, D., Fujino, I., Yamada, N., Hasegawa, M., Miyawaki, A., Yoshikawa, S., Gueenet, J. L., & Mikoshiba, K., (1993) Receptors Channels 1: 11-24.
Garner, C. C., Tucker, R. P., & Matus, A. (1988) Nature (London) 336: 674-677.
Grant, S. G. N. et al., Science 258: 1903 (1992).
Gossen, M. & Bujard, H. (1992) Proc. Natl. Acad. Sci. USA 89: 5547-5551.
Hanson, P. I. et al., Annu. Rev. Biochem., 61: 559 (1992).
Kim, J. J. et al., Science 256: 675 (1992).
Kita, H. Et al., J. Comp. Neurol. 298:40(1990).

Kleiman, R., Banker, G. & Steward, O. (1993) Proc. Natl. Acad. Sci. USA 90: 11192-11196.

LeDoux, J. E. et al., J. Neurosci. 10: 1062 (1990).

Link, W., Konietzko, U., Kauselmann, G. Krug, M., Schwanke, B., Frey, U. & Kuhl, D. (1995) Proc. Natl. Acad. Sci. USA 92: 5734-5738.

Lisman, J. Trends Neurosci. 17: 406 (1994).

Lledo, P. M. et al., Proc. Natl. Acad. Sci. USA. 92: 11175 (1995).

Lyford, G. L., Yamagata, K., Kaufmann, W. E., Barnes, C. A., Sanders, L. K., Copeland, N. G., Gilbert, D. J., Jenkins, N. A., Lanahan, A. A. & Worley, P. F. (1995) Neuron 14: 433-445.

Macdonald, P. M. & Struhl, G. (1988) Nature (London) 336: 595-598.

Macdonald, P. M., Kerr, K., Smith, J. L. & Leask, A. (1993) Development (Cambridge, U.K.) 118: 1233-1243.

Mayford, M. et al., Cell 81: 891 (1995).

Mayford, M. et al., Curr. Opin. Neurobiol. 5: 141 (1995).

Mayford, M. et al., Proc. Natl. Acad. Sci. USA 93: 13250 (1996).

Mayford, M., Wang, L., Podsypanina, K. & Kandel., E. R. (1995) Soc. Neuroscki. Abstr. 433.15.

Mayford, M. Wang, J. Kandel, E. R. & O'Dell, T. J. (1995) Cell 81: 891-904.

Meyer, T. Et al., Science 256: 1199(1992).

Miller, S. G. et al., Cell 44: 861 (1986).

Neveu, D. et al., ibid, p. 169 (1996).

Nguyen, P. V., Abel, T. & Kandel, E. R. (1994) Science 265: 1104-1107.

O'Keefe, J. et al., *The Hippocampus as a Cognitive Map* New York: Oxford University Press, 1978.

Petit, D. L. et al., ibid 266: 1881 (1994).

Quirk, G. J. et al. Neuron 15: 1029 (1995).

Rayport, S., Sulzer, D., Shi, W. X., Sawasdikosol, S., Monaco, J., Baston, D. & Rajendram, G., (1992) J. Neurosci. 12: 4264-4280.

Mowry, K. L. & Melton, D. A. 91992) Science 255: 991-994.

Rogan, M. T. et al., ibid., p. 127.

Scoville, W. B. et al., J. Neurol. Neurosurg. Psychiatry 20: 11(1957).

Silva, A. J., Stevens, C. F., Tonegawa, S. & Wang, Y. (1992) Science 257: 201-206.

Silva, A. J. et al., ibid 257: 200-201 (1992). Squire, L. R., Psychol. Rev. 99: 195 (1992).

Steward, O. & Levy, W. B. (1982) J. Neurosci. 2: 284-291.

Steward, O. & Fass, B. (1983) Prog. Brain Res. 58: 131-136.

Steward, O. (1983) Cold Spring Harbor Symp. Quant. Biol. 48: 745-759.

Steward, O. (1992) Trends Neurosci. 15: 180-186.

Sundell, C. L. & Singer, R. H. (1990) J. Cell Biol. 111: 2397-2403.

Sunyer, T. et al., Proc. Natl. Acad. Sci. USA. 87: 278 (1990).

Tiedge, H., Fremeau, R. T., Jr, Weinstock, P. H., Arancio, O. & Borsius, J. (1991) Proc. Natl. Acad. Sci. USA 88: 2093-2097.

Thiel, G. et al., Proc. Natl. Acad. Sci. USA 85: 6337 (1988).

Torre, E. R. & Steward, O. (1992) J. Neurosci. 12: 762-772.

Walsmann, P. Et al., Biochemistry 29: 1679 (1990).

Example 3

Genetic and Pharmacological Evidence for a Novel, Intermediate Phase of Long-Tem Potentiation (I-LTP) Suppressed by Calcineurin To begin to investigate the role of phosphates in synaptic plasticity using genetic approaches, we generated transgenic mice that over express a truncated form of calcineurin under the control of the CaMKIIα promoter. Mice expressing this transgene show increased calcium-dependent phosphate activity in hippocampus. Physiological studies of the calcineurin-overexpressing mice and parallel pharmacological experiments in wild-type mice reveal a novel, intermediate phase of LTP (I-LTP) in the CA1 region of hippocampus. This intermediate phase differs from E-LTP in requiring multiple trains for induction, and in being dependent on PKA. It differs from L-LTP in not requiring new protein synthesis. These data suggest that calcineurin acts as an inhibitory constraint on I-LTP that normally is relieved by PKA. This inhibitory constraint acts as a gate to regulate the synaptic induction of L-LTP.

Introduction

Long-Lasting modification of synaptic transmission are thought to play a role in a variety of brain functions ranging from memory storage to the fine tuning of synaptic connections during development. As a result, an intensive search has been carried out in both invertebrates and vertebrates to identify the molecular components of various forms of synaptic plasticity. In this search there has been a central focus on two types of synaptic enhancement: long-term facilitation in Aplysia and long-term potentiation (LTP) in the mammalian hippocampus. Both of these forms of synaptic plasticity last from minutes to days, depending on the strength and number of inducing stimulus. A major theme emerging from these studies is that protein kinases play key roles in long-term enhancement of synaptic transmission (for review, see Roberson et al., 1996). Thus, inhibitors of various kinases impair the induction or maintenance of both long-term facilitation in Aplysia and of LTP in the hippocampus (for review, see Roberson et al., 1996; Huang et al., 1996b; Martin et al., 1997). Further, genetically modified mice in which genes encoding specific kinases have been either overexpressed or deleted exhibit phenotypes which in most cases parallel those obtained with pharmacological inhibitors (Mayford et al., 1995a, 1997; Abel et al., 1997)

While much attention has been focused on protein kinases in synaptic plasticity, relatively little attention has been paid to protein phosphates. Yet, phosphates are likely to have signaling roles in synaptic plasticity that equal in importance those of kinases if only because of their inherently antagonistic relationship with protein kinases. Furthermore, most cellular models of learning postulate erasure mechanisms designed to counteract the long-lasting synaptic enhancement thought to be required for memory storage. Consistent with this idea, recent experiments have shown that whereas brief high frequency stimulation of the Schaffer collateral pathway in the hippocampus leads to LTP, prolonged low frequency stimulation of this same pathway results in a long-term depression (LTD) of synaptic transmission, and experiments with pharmacological inhibitors suggest an important role for phosphates in LTD (Mulkey et al., 1993, 1994; O'Dell and Kandel, 1994; for review see Bear and Abraham, 1996). Despite the potential importance of phosphatases for synaptic plasticity, however, the study of phosphates in hippocampus has been limited by the lack of specificity of the pharmacological inhibitors available (for example, see Helakar and Patrick, 1997) as well as by the long periods of preincubation often necessary for the inhibitors to produce alterations of synaptic function (Mulkey, et al. 1993; 1994). As a result, the role of phosphatases in LTP in not clear. While several experiments suggest that pharmacological inhibitors of phosphatases have no effect, or enhance LTP (Blitzer, et al., 1995, Mulkey et al, 1993; Muller, et al., 1995; Wang and Kelly, 1996), other studies report that these inhibitors block LTP (Wang and Stelzer, 1994; Lu et la., 1996a,b).

To overcome these limitations and to begin to examine more directly the precise role of specific phosphatases in synaptic plasticity, we have turned to a genetic approach. We have focused our initial efforts on calcineurin (PP2B), because this enzyme is thought to be the first step in a phosphatase cascade initiated by $Ca^{2+}$ signal through the NMDA receptor. Consistent with the idea that the $Ca^{2+}$ signal through the NMDA receptor is the initial event for both LTP and LTD in the hippocampus, pharmacological inhibitors of calcineurin block LTD (Mulkey et al, 1994), and have been reported by some to enhance LTP (Wang and Kelly, 1996; but see Wang and Stelzer, 1994; Wang and Kelley, 1997; Lu et al, 1996a,b).

Calcineurin is a calcium-sensitive serine/threonine phosphatase that is present at high levels in the hippocampus, is enriched at synapses, and is a heteromultimer that has both catalytic (calcineurin A, is a 60 kD protein that exists as three isoforms ($\alpha$, $\beta$, and $\gamma$), two of which, $\alpha$ and $\beta$, are present in brain (Kuno, et al., 1992). Once activated, calcineurin acts on two types of protein directly and thereby regulate specific cellular functions. Second, it can modulate an even larger variety of substrates indirectly by its ability to dephosphorylate inhibitor-1, a key of protein phosphatase-1, (PP1). Inhibitor-1 is a low molecular weight protein that, when phosphorylated, inhibits the function of PP1. Dephosphorylation of inhibitor-1 by calcineurin activities PP1 and leads to the dephosphorylation of a large and independent set of target proteins.

One interesting feature of the regulatory actions of calcineurin comes from its interactions with the cAMP-dependent protein kinase, PKA. Calcineurin dephosphorylates and inhibits the action of inhibitor-1 by dephosphorylating the site on inhibitor-1 that is phosphorylated by PKA (Hubbard and Klee, 1991). This dephosphorylation enhances the ability of RII$\beta$ to re-associate with and inhibit the function of the catalytic subunit of PKA (Rangel-Aldao and Rosen, 1976). Further, calcineurin and PKA antagonistically regulate NMDA and GluR6 glutamate receptor function (Tong, et al., 1995; Raman, et al, 1996; Traynelis and Wahl, 1997). Calcineurin also inhibits a novel isoform of adenylyl cyclase (Paterson et al., 1995). Finally, calcineurin can dephosphorylate the transcription factor CREB (Bito et al, 1996; Liu and Graybiel, 1996), another target of PKA, thereby regulating CRE-mediated transcription. This modulation of CREB phosphorylation by calcineurin is likely at least partially mediated by the inhibitor-1 cascade (Bito et al., 1996). While dephosphorylation of CREB Ser133 by calcineurin is though to reduce CRE-mediated transcription, calcineurin-mediated dephosphorylation of CREB at other regulatory site may result in enhancement of CRE-mediated transcription (Schwaninger, et al., 1995)

The interactions of PKA and calcineurin are of particular interest in the context of LTP. Based on the requirements for macromolecular synthesis, LTP can be divided into at least two components: an early component (E-LTP) and a late component (L-LTP). Delivery of a single 100 Hz train lasting one second to the Schaffer collateral-CA1 pyramidal cell synapse elicits E-LTP, a relatively short-lived and weak enhancement of synaptic transmission lasting 1-2 hr that does not require protein- and RNA-synthesis and is not dependent on PKA (for review, see Haung, et al., 1996b; Roberson et al, 1996). By contrast, administration of three or four trains of 100 Hz, elicit L-LTP, a more robust and stable form of LTP lasting many hours that is dependent on the synthesis of both RNA and protein (for review, see Haung, et al, 1996b; Roberson et al., 1996). Further, L-LTP is blocked by inhibitors of PKA (for review, see Huang et al., 1996b), and is dramatically impaired in mice expressing a dominant negative form of a regulatory subunit of PKA (Abel et al., 1997). Recent experiments with inhibitors of phosphatases suggest that one role of PKA in LTP in area CA1 may be to suppress the actions of either PP' or PP2A (Blitzer et al., 1995; Thomas et al., 1996). In particular, Blitzer et al., (1995) found that when LTP in area CA1 is induced by strong stimuli it can be blocked by inhibitors of PKA. However, his inhibition could be removed by preincubation of slices with PP1/PP2A inhibitors. This led Blitzer, et al, to suggest that under certain circumstances, PKA may "gate" LTP by suppressing a phosphatase cascade.

To examine further the role of phosphatases in synaptic plasticity and in memory storage, as well as to determine more precisely the interplay between PKA and phosphatases in the regulation of LTP, we have overexpressed in the mouse forebrain a truncated form of calcineurin A$\alpha$. Overexpression of this transgene results in an approximately 75% increase in phosphatase activity in hippocampus. Using these mice, we have addressed two questions: (1) What is the role of calcineurin in the expression of the various phases of LTP? (2) Does PKA modulate the action exerted by calcineurin on each of these phases?

Both generic and pharmacological evidence is provided which is consistent with the "gating" model for the actions of PKA in LTP (Blitzer, et al. 1995). In addition, date presented in this paper and its companion (Mansuy et al., submitted to Cell) extend this model by demonstrating that PKA "gate" has a distinct temporal component that represents an intermediate phase of LTP (I-LTP). This intermediate phase is induced by multiple trains and suppressed by calcineurin. It differs from E-LTP in requiring a much a stronger stimulus, the activation of PKA and the suppression' of calcineurin. The intermediate phase differs from L-LTP in not requiring protein synthesis. Our data further suggests that this constraint on I-LTP in not requiring protein synthesis. The data further suggest that this constraint on I-LTP imposed by calcineurin can be relieved by activation of PKA, and that this relief is required for the full expression of L-LTP. Thus, the over expression of calcineurin suppresses both I-LTP and L-LTP. The behavioral results detailed in the accompanying article (Mansuy, et al, submitted to Cell), suggest that the temporally distinct gating function, mediated by calcineurin, is important behaviorally and suppresses long-term memory formation.

Results

Generation of Transgenic Mice Overexpressing a Truncated Form of Calcineurin

To increase calcineurin-mediated phosphatase activity in the forebrain of transgenic mice, a deletion mutant of the catalytic subunit A$\alpha$ ($\Delta$CAM-AI) of murine calcineurin (O'Keefe et al., 1992) was expressed under the control of the CaMKII$\alpha$ promoter (Line CN 98, FIG. 1A; Mayford et al, 1996). The calcineurin mutant $\Delta$CAM-AI is a fragment of the catalytic A$\alpha$ subunit which lacks the autoinhibitory domain and a portion of the calmodulin binding domain, but retains the calcineurin B binding domain (O'Keefe et al., 1992; Parsons et al., 1994). This deletion weakens the calcium requirement for activation of calcineurin. Although this construct shows some Ca 2+independent activity when expressed in Jurkat cells (O'Keefe et al., 1992), we find that this mutant form of calcineurin requires calcium for activation in hippocampal neurons (FIG. 1C).

Figure 11A:
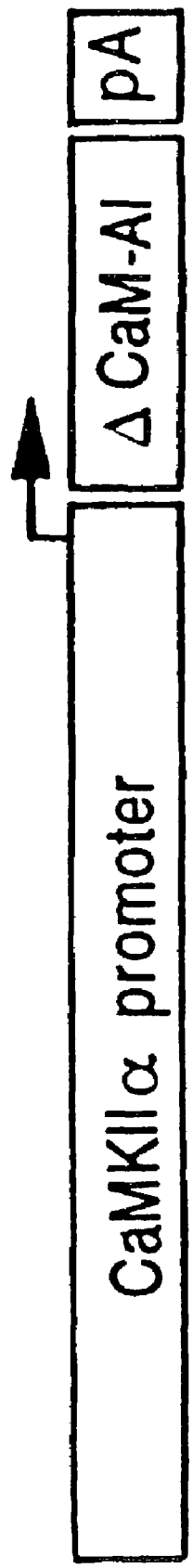
Figure 11B:
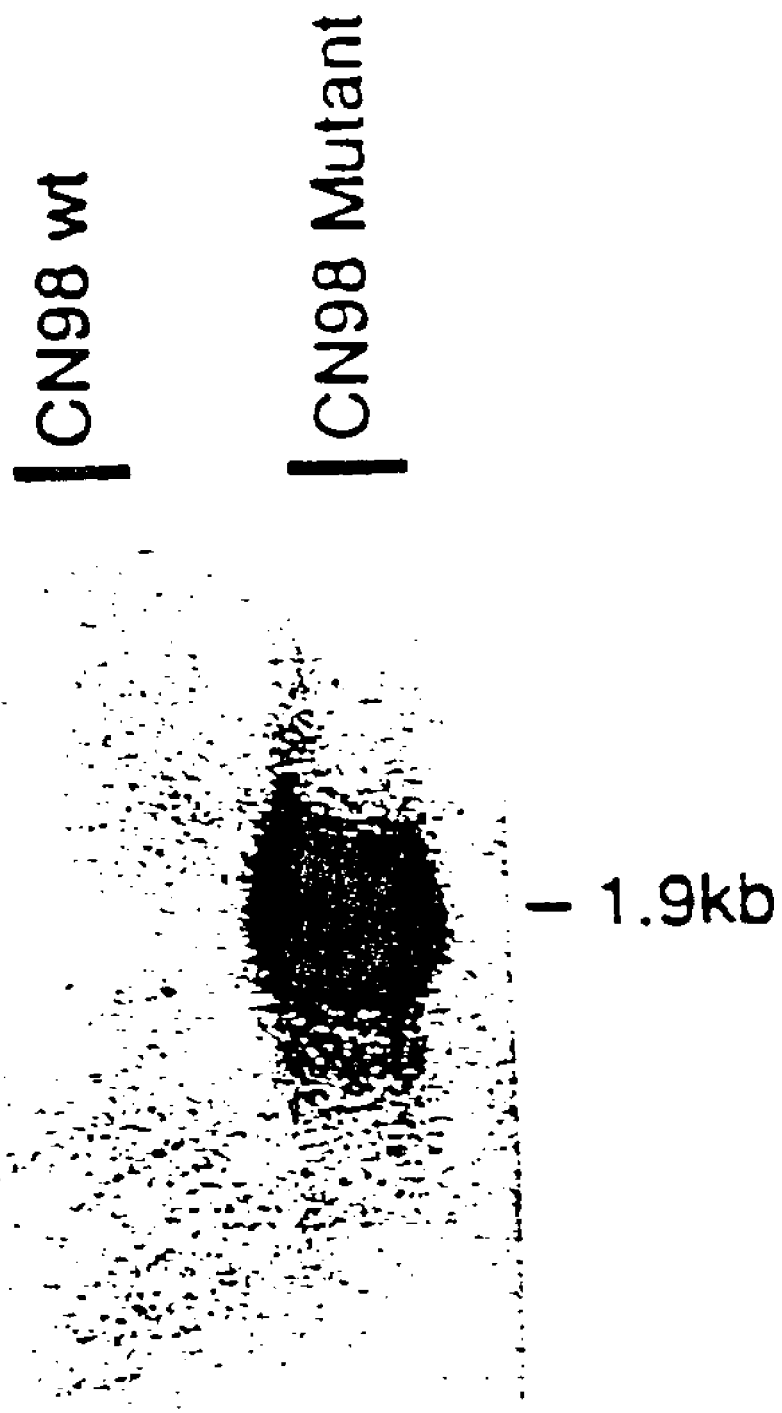

Calcineurin Overexpression is Primarily Restricted to the Hippocampus In CN 98 Mutant Mice The CaMKIIα promoter has the advantage of driving expression of transgenes postnatally to a restricted subset of neurons in the CNS; thus it was used to drive transgene expression selectively in neurons of forebrain structures including hippocampus, striatum, cortex and amygdala (Mayford, et al,. 1995a: Kojima et al 1997). Northern blot analyses performed on adult CN98 mutatn mouse forebrain revealed the expression of a 1.9 kb transcript corresponding to the mRNA of the transgene (FIG. 11B). The brain distribution of the mRNA was determined by in situ hyybridization using a radiolabled oligonucleotide specific for the transgene. The mRNA was detected in forebrain, primarily in the hippocampus in CA1, CA2, and CA3 regions as well as in dentate gyrus (FIG. 11D). No signal was detected in wild-type littermates (FIG. 11D).

Figure 11C:
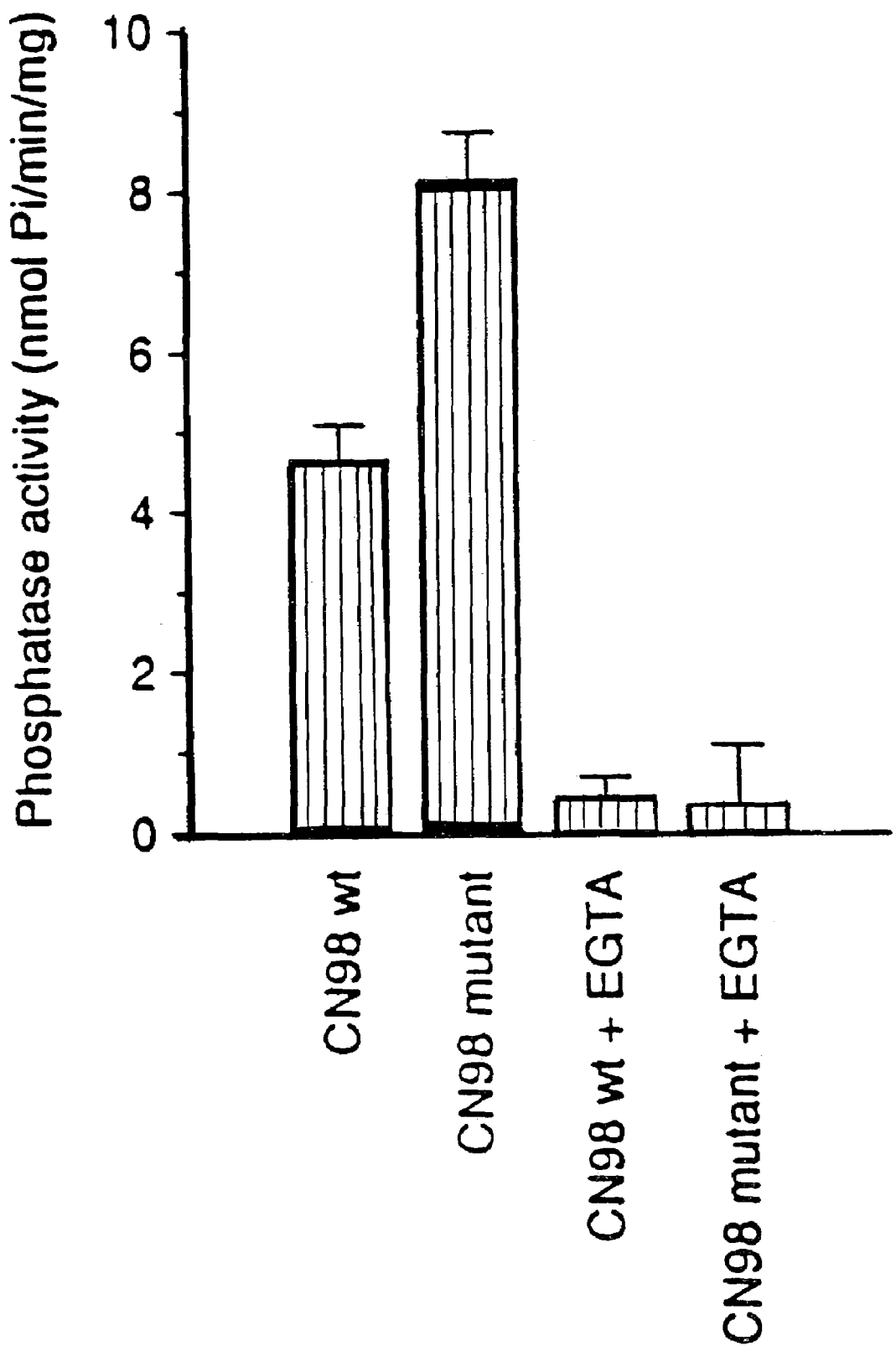

To determine if the determine if the transgene mRNA was properly translated into a functional protein, we measured phophatase activity in crude homogenates from the hippocampus in the presence of okadaic acid (FIG. 11C). In the extracts from transgenic hippocampi, there was an increase of 76%±12% in phosphatase activity compared to wild-type extracts. In the presence, of the calcium chelator EGTA, the phosphatase activity in both CN98 mutant and wild-type hippocampal extracts was virtually abolished, with no significant difference in phosphatase activity between CN98 wild-type and mutant extracts (FIG. 11C). Thus, CN98 mutant mice have significantly increased levels of calcium-stimulated phosphatase activity in hippocampus.

Basal Synaptic Transmission is not Altered in Mice Overexpressing Calcineurin

Figure 12A:
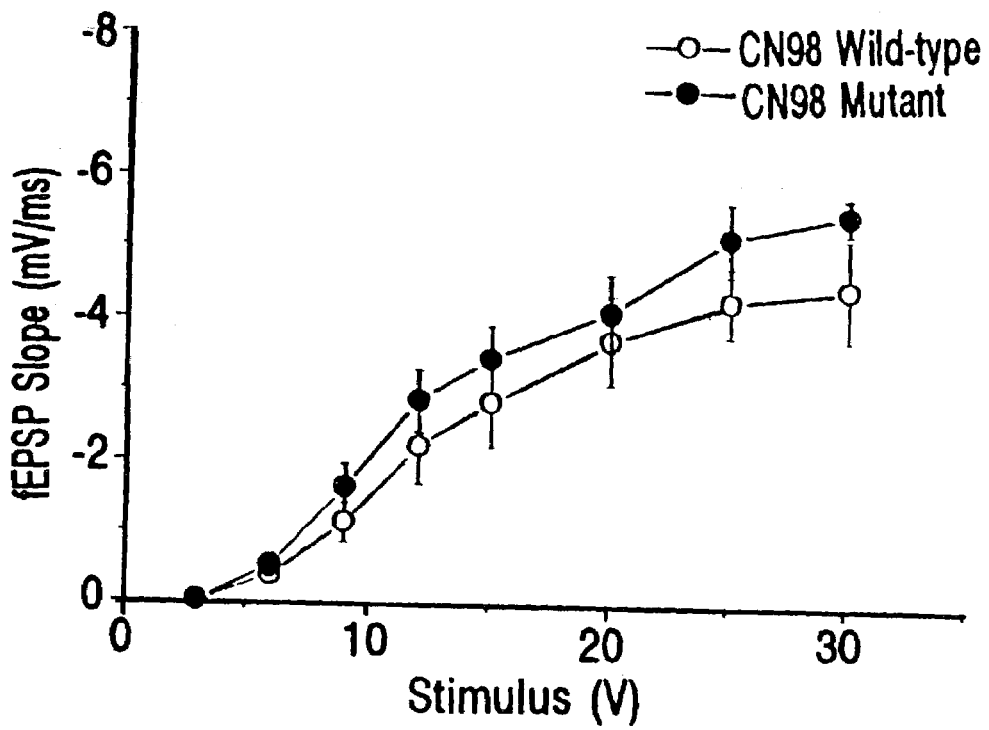
FIGS. 12A-12F. Basal synaptic transmission and short-term forms of synaptic plasticity are not dramatically altered by overexpression of calcineurin.
Figure 12B:
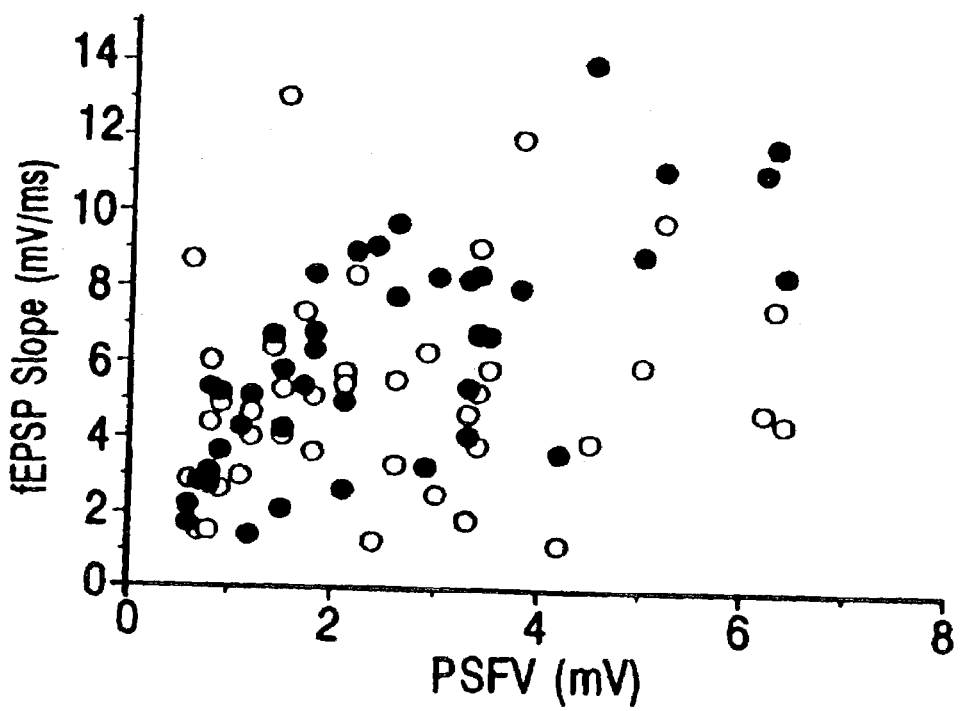

Studies with pharmacological inhibitors of phosphatases have suggested that endogenous phosphatase activity may regulate the basal level of synaptic transmission at the Schaffer collateral synapses (Firgurov et al., 1993, but see Mulkey et al., 1993; O'Dell and Kandel, 1994). In CN98 mice however, no difference in basal synaptic transmission were found. Stimulus-response curves obtained from CN 98 wild-type and mutant mice were not significantly different (FIG. 12A), and the slope of a fEPSP elicited by a given presynaptic fiber volley did not differ dramatically between wild-type and mutant mice (average ratio of fEPSP slope and presynaptic fiber volley amplitude expressed with standard deviation was 3.1±1.68 for CN98 wild-type and 2.9±1.3 for mutant; FIG. 12B).

Figure 12C:
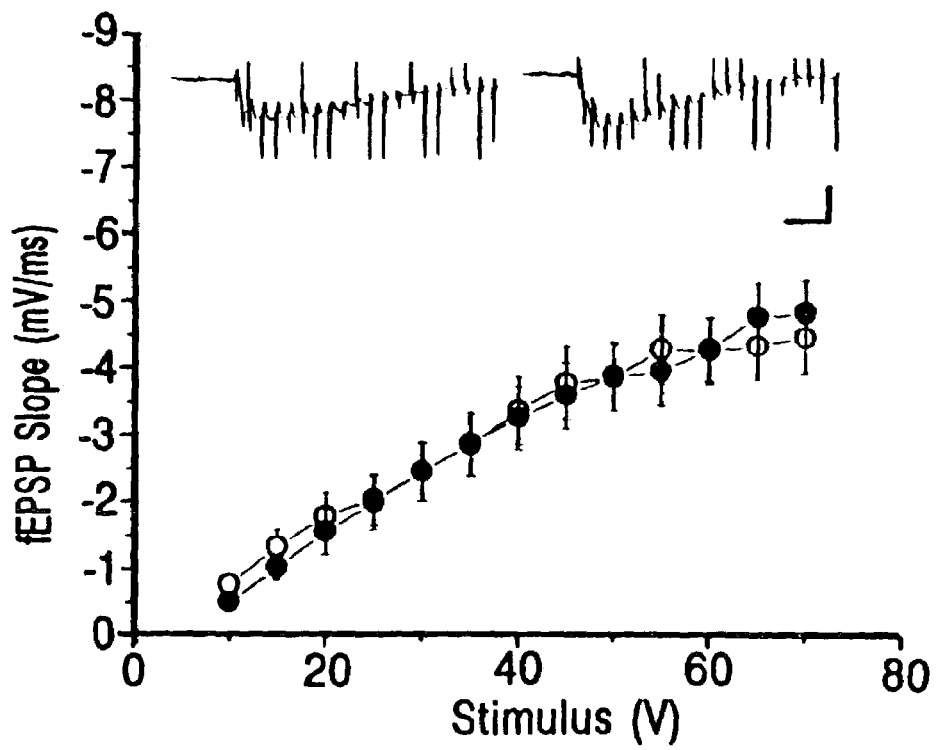

In addition to basal transmission mediated primarily by non-NMDA ionotropic glutamate receptors, previous studies have demonstrated that under certain circumstances calcineurin can subtly desensitize NMDA receptor-mediated synaptic currents (Tong et al., 1995; Raman et al., 1996). To determine whether overexpression of calcineurin altered NMDA-mediated synaptic transmission in CN98 mice, we measured NMDA-mediated synaptic potentials in the presence of 10 µM 6,7-dinitroquinozaline-2,3-dione (DNQX) and reduced $MG^{2+}$ (50 µM). Under these conditions, field potentials exhibited slower kinetics than in the absence of DNQX, and were completely antagonized by 50 µM DL-AP5, indicating that they were mediated by NMDA receptors. Stimulus-response curves generated for both CN98 mutant and wild-type animals under these conditions were not significantly different, suggesting that overexpression of calcineurin does not alter the function of the NMDA receptor (FIG. 12C). IN addition, under these conditions NMDA-mediated synaptic responses in mutant slices followed a 100 Hz, one second tetanus in a qualitatively similar manner to wild-types (FIG. 12C inset).

Figure 12D:
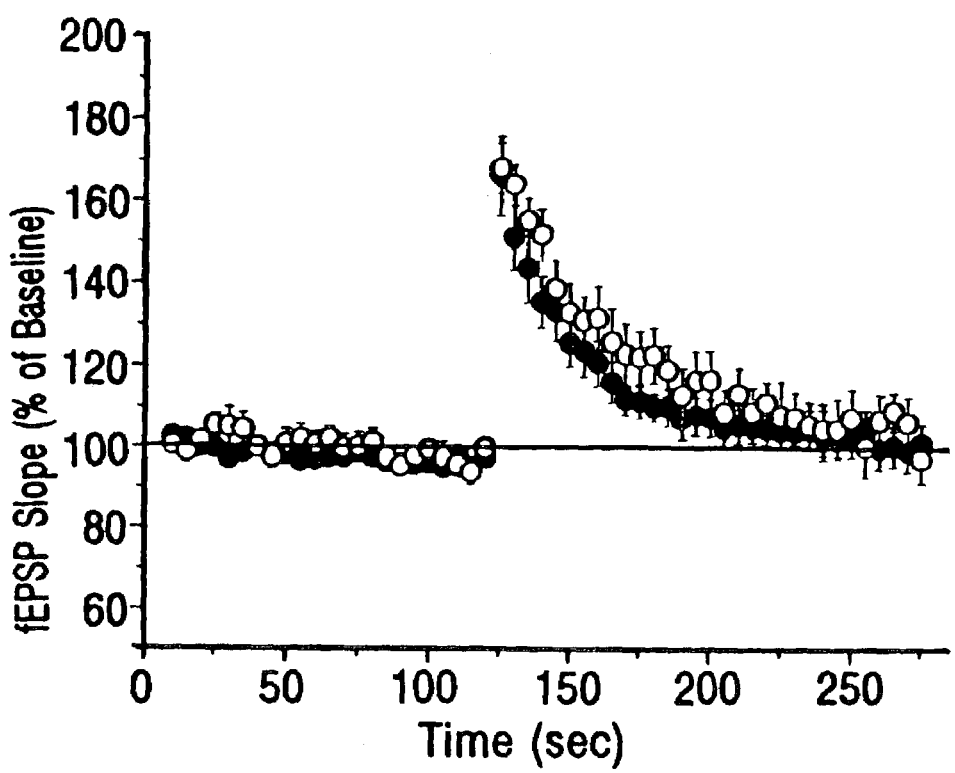

Because in the CN98 mutant mice the transgene is expressed in both CA1 and CA3 pyramidal cells, next an evaluation was done on presynaptic function in CN98 wild-type and mutant mice. It was begun by assessing post-tetanic potentiation (PTP, for review, see Zucker, 1989), a short-term form of presynaptic plasticity elicited by a high frequency tetanus (1 second, 100 Hz). In the presence of DL-AP5 (50 µM) to block NMDA-receptors, administration of a single 100 Hz tetanus resulted in a transient enhancement of transmission that rapidly decayed to baseline within 2-3 minutes as previously described (Huang et al., 1995; Abel et al., 1997). As evident in FIG. 12D, there was no difference in the peak PTP elicited between wild-type and mutant mice (160±5% peak potentiation in wild-type, 11 slices, 5 mice: 163±11% peak potentiation in CN98 mutant, 11 slices, 4 mice). These results suggest that overexpression of calcineurin does not markedly affect the ability of the Schaffer collateral-CA1 synapse to respond to controlled high frequency rates of simulation.

Figure 12E:
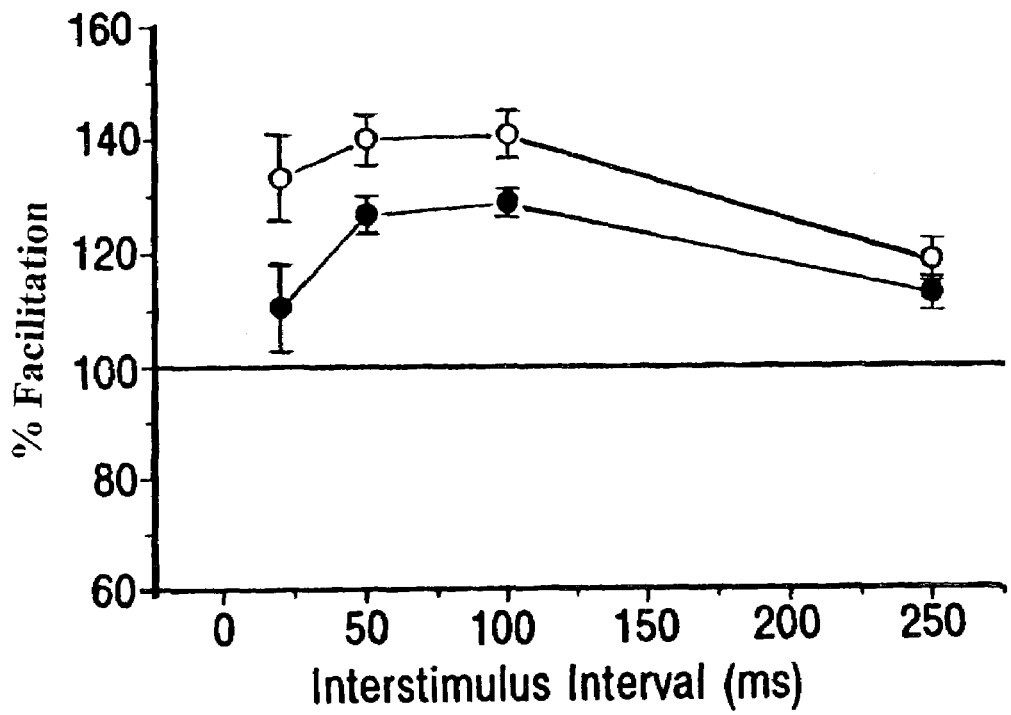

To obtain a second measure of presynaptic function, we examined paired-pulse facilitation (PPF). PPF is a transient form of presynaptic plasticity in which the second of two closely-spaced stimuli elicits enhanced transmitter release due to residual increases in calcium in the presynaptic terminal following the first stimulus (for review, see Zucker, 1989). Over an interval of 20-250 msec PPF was significantly reduced in CN98 mutant compared to wild-type mice (15 slices, 5 mice CN98 wild-type; 14 slices, 5 mice CN98 mutant; for 20 50, and 100 ms interstimulus intervals p<0.05 for CN98 wild-type versus mutant; FIG. 12E). Thus, data on PTP and PPF are consistent in showing that overexpressing calcineurin produces no gross deficits in synaptic transmission, it nevertheless does produce a clear alteration in one form of acute presynaptic plasticity.

Figure 12F:
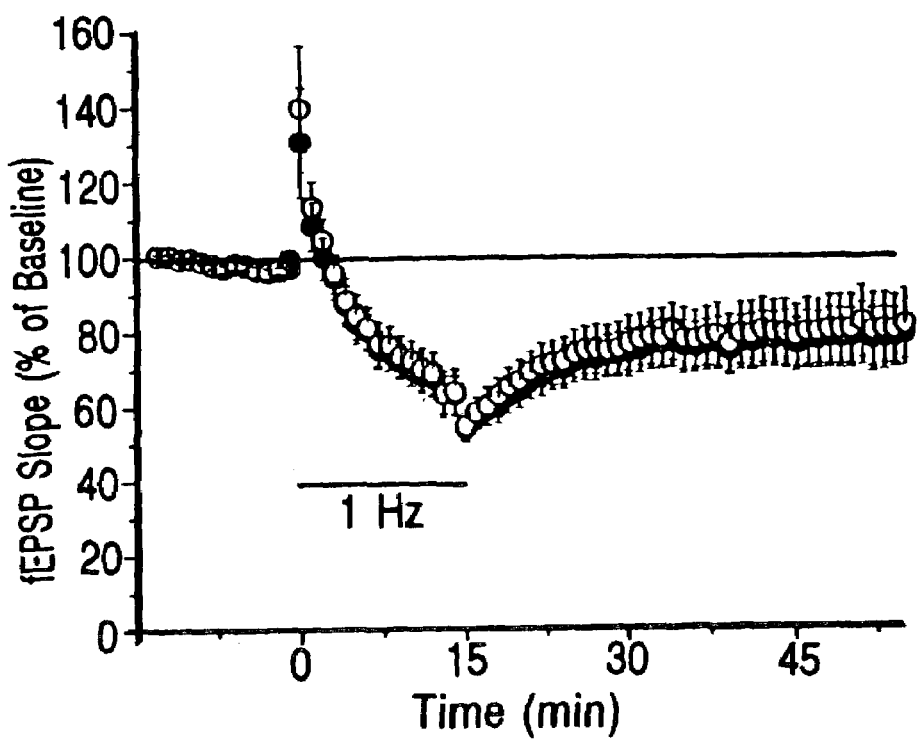

Overexpression of Calcineurin does not Affect the Expression of LTD at the Schaffer Collateral-CA1 Pyramidal Cell Synapse To begin to study the roles of calcineurin in synaptic plasticity, LTD induced by 15 minutes of 1 Hz stimulation at the Schaffer collateral-CA1 pyramidal cell synapse in adult animals from CN98 wild-types were compared to mutants. It was found that the response to 15 minutes of 1 Hz stimulation was virtually identical in CN98 wild-type and mutant animals (percent of baseline fEPSP slope 30 minutes after the end of 15 minutes of 1 Hz stimulation: CN98 wild-type 93±6%, 7 mice, 11 slices; CN98 mutant 95±7%, 4 mice, 14 slices) As has previously been reported (O'Dell and Kandel, 1994; Bear and Abraham, 1996), this stimulation protocol produced little if any LTD in hippocampal slices from adult animals. We therefore repeated these studies in slices from young mice (3-4 weeks old) where LTD is more robust (Bear and Abraham, 1996). As shown in FIG. 12F, although LTD was much more robust in these younger animals, there was still no difference detectable between CN98 wild-type and mutant animals (fEPSP slope percent of baseline 30 minutes after the end of 15 minutes of 1 Hz stimulation: CN98 wild-type 79±8%, 2 animals, 4 slices; CN98 mutant 76±7%, 4 animals, 7 slices). One possibility consistent with these data is that calcineurin may already be present at saturating concentrations, particularly since calcineurin is one of the most abundant proteins in brain (Yakel, 1997). If calcineurin were present in saturating concentrations, one would predict that further overexpression of calcineurin would not affect processes such as LTD that are likely mediated by activation of the phosphatase. However, overexpression might alter synaptic processes such as LTP where the suppression of phosphatase activity is thought to be required.

Overexpression of Calcineurin Diminishes LTP Induced by Multiple High-Frequency Trains but not a Single Train To begin to explore the roles of calcineurin in long-term synaptic enhancement, LTP induced by single or multiple one-second high frequency (100 Hz) trains was studied in wild-type and CN98 mutant mouse hippocampal slices. In slices from both CN98 wild-type and mutant mice, administration of a single, train at 100 Hz elicited a transient form of LTP that was comparable at one hour post-tetanus, even though immediately after the tetanus LTP was slightly reduced in CN98 mutants (CN98 mutant: 129±10% of baseline at 1 hr, 9 slices, 5 mice; CN98 wild-type: 130±6% of baseline at 1 hr. 7 slices, 4 mice; FIG. 13A). By contrast, administration of four 100 Hz trains separated by 5 minutes elicited robust, nondecremental LTP in wild-type hippocampal slices, but produced a greatly reduced LTP in mutant mice (CN98 wild-type: 169±8% of baseline at 1 hr after stimulus, 173±8% at 3 hr, 7 slices, 7 mice; CN98 mutant: 139±9% of baseline at 1 hr after stimulus, 118±10% at 3 hr, 8 slices, 7 mice; FIG. 13B). This defect in the CN98 mutant animals was visible immediately after the four tetani were administered ($p<0.05$ at 1 minute after the last tetanus).

Overexpression of Calcineurin Does not Affect Chemically-Induced L-LTP

The finding that LTP induced by four trains but not a single train is reduced in CN98 mutant mice suggests that overexpression of calcineurin may suppress the late phase of LTP. Is this reduction due to a direct effect on downstream components of L-LTP, or is it due to a failure to fully initiate L-LTP? To begin to explore this question we examined L-LTP evoked by pharmacological activation of the PKA pathway, which bypasses tetanic stimulation in area CA!. In addition to being evoked through multiple high frequency tetani to the Schaffer collaterals, L-LTP in area CA1 can be induced chemically through either application of D1/D5 dopamine receptor agonists or direct activators of adenylyl cyclase and PKA. In wild-type slices, application of agonists of D1/D5 dopamine receptors or the PKA agonist Sp-cAMPS, result in a slow-onset potentiation of synaptic transmission that is sensitive to protein and RNA-synthesis inhibitors, and mutually occlusive with L-LTP elicited by multiple high frequency trains (Huang and Kandel, 1994; Huang et al., 1994; Bolshakov et al., 1997). If overexpression of calcineurin directly affects the machinery necessary to produce the late phase, pharmacologically-induced L-LTP, that bypasses E- and I-LTP, would be impaired in CN98-mutant mice, as is the case with the late phase deficit in tPA-knockout mice (Huang et al., 1996a).

We tested the ability of both the D1/D5 receptor agonist 6-Br-APB (100 μM) and the PKA activator Sp-cAMPs (100 μM) to elicit slow-onset potentiation at the Schaffer collateral-CA1 synapse in CN98 mice. As shown in FIGS. 13C and 13D, application of 6-Br-APB and Sp-cAMPs elicited a slowly developing increase in synaptic transmission in CN98 mutant mice that was indistinguishable from that seen in wild-type mice (CN98 mutant: 181±41% of baseline at 3 hr after 6-Br-APB application, 5 slices, 5 mice; CN98 wild-type: 204±40% of baseline at 3 hr after Sp-cAMPS application, 6 slices, 6 mice; wild-type: 124±13% of baseline at 3 hr after Sp-cAMPS application, 7 slices, 6 mice).

Multiple Trains Elicit Two Distinct PKA Dependent Phases of LTP: One Dependent and the other Independent of Protein Synthesis In contrast to wild-type hippocampal slices where LTP induced by a single train is much weaker than that induced by four trains, in slices from CN98 mutants the magnitude of LTP that follows one train and four train protocols were similar. Indeed, the LTP following four trains in CN98 mutants is quite similar to that evident following four trains in wild-type hippocampal slices incubated with inhibitors of PKA (for review see Huang et al., 1996b), as well as to L-LTP in hippocampal slices from mice expression a dominant negative form of PKA (Abel et al., 1997). This would make it appear as if the PKA system is defective or reduced in its effectiveness in the mutant mice. Yet L-LTP induced by pharmacological activation of the cAMP cascade was not dramatically impaired in the mutant mice. How then do PKA and calcineurin interact?

One clue to the possible interaction of calcineurin with the PKA system in regulating LTP comes from the work of Blitzer et al. (1995) and Abel et al. (1997) showing that application of inhibitors of PP1 and PP2A removes the ability of PKA in LTP in area CA1 may be to inhibit the actions of phosphatases that are activated by tetanus. This would suggest that PKA may serve a double function. First, it can activate the late phase directly (FIG. 13C, 13D). Second, PKA has an earlier function in turning off an opposing phosphatase cascade. Consistent with this hypothesis, LTP generated by multiple 100 Hz trains in rat hippocampal slices (Huang et al., 1996b), as well as mouse hippocampal slices (FIG. 14A) decays more rapidly in the presence of PKA inhibitors such as Rp-cAMPS or KT5720 than in the presence of the protein synthesis inhibitor anisomycin, suggesting that in addition to mediating an action of the late phase of LTP that requires protein synthesis, PKA may mediate a second, perhaps earlier upstream, action that is independent of protein synthesis (Blitzer et al., 1995; Huang et al., 1996b).

To examine further the possibility that there are two independent phases both dependent on PKA, we reanalyzed the effects of anisomycin, an inhibitor of protein synthesis on LTP in mouse hippocampal slices, now increasing the preincubation time for anisomycin by 30 minutes. In earlier studies the concentrations of anisomycin used were sufficient to completely block protein synthesis in area CA1 of hippocampus (Stanton and Sarvey, 1984; Osten et al., 1996). Nonetheless, the difference in time course of inhibition by anisomycin and PKA inhibitors could be due to pharmacokinetic properties of these drugs. However, even in experiments where anisomycin (30 μM) was present in the bath for one full hour prior to tetanus (compared to the 20 minute pretreatment with the PKA inhibitor KT5720, 1 μM), the PKA inhibitor still elicited a much more rapid decay of LTP induced by four 100 Hz trains than anisomycin (FIG. 14A, 14B). This difference in time course between inhibitors of protein synthesis and PKA suggest that multiple trains that elicit L-LTP seem also to induce a novel intermediate phase of LTP that requires PKA but does no require protein synthesis.

A Novel PKA Dependent Intermediate Phase can also be Isolated Pharmacologically and by Varying the Number of Stimulus Trains In an attempt to isolate, in still another way, the novel intermediate phase in which PKA acts to suppress a phosphatase cascade we varied the number of tetanic trains of stimulation. One of the characteristics that distinguishes E-LTP from L-LTP is that weak stimuli such as a single 100 Hz train elicit E-LTP but not L-LTP. In contrast, to reliably induce L-LTP, 3-4 repeated 100 Hz trains are required. We therefore sought to determine if an intermediate phase of LTP could also be distinguished from these phases based on the strength of stimulus required. We elicited LTP with two 100 Hz trains spaced by 20 seconds. This protocol elicited LTP that was more robust than that elicited by one 100 Hz train, but less maintained than that elicited by four trains (FIG. 14C). In contrast to LTP elicited by a single 100 Hz train which is not affected by inhibitors of PKA (Huang et al., 1996), LTP elicited by two trains was partially sensitive to the PKA inhibitor KT5720 (no drug: 206±23% of baseline at 1 hr, 5 slices, 5 ice; 1 μM KT5720: 153±5% of baseline at 1 hr, 5 slices, 4 mice; p<0.05; FIG. 14D). However, unlike L-LTP, the LTP elicited by two trains was completely insensitive to preincubation with the protein synthesis inhibitor anisomycin, even at time points where LTP induced by four trains is reduced by anisomycin (FIG. 4C). These two types of experiments reveal a novel intermediate phase of LTP (I-LTP) exists that requires 1) a stronger stimulus than E-LTP, and 2) the activation of PKA. But unlike L-LTP, this intermediate phase does not require protein synthesis.

Genetic Evidence for an Interaction Between PKA and Phosphatases in Regulating a Novel Intermediate Phase of LTP (I-LTP)

To strengthen these pharmacological attempts to delineate an intermediate phase we turned to a genetic approach. Blitzer et al. (1995) and Thomas et al. (1996) suggested that the protein synthesis-independent role of PKA in LTP is to suppress the activity of PP1 or PP2A, perhaps through phosphorylation of inhibitor-1. Since the phosphorylation site of inhibitor-1 is dephosphorylated by calcineurin, one would predict that PKA and calcineurin would antagonistically regulate the function of PP1 and thereby regulate the level of synaptic output. If this were the case, we would predict that in mice overexpressing calcineurin the cAMP-dependent forms of LTP in area CA1 would be defective. Indeed, as we have seen, one train LTP, which is independent of PKA, was not decreased in CN98 mutant mice, while PKA-dependent four train LTP was. To examine this further, we compared CN98 wild-type and mutant mice by examining LTP induced by two trains, which we have shown recruits the intermediate phase without significantly recruiting the late phase. Consistent with the idea that the intermediate phase of LTP is antagonistically regulated by PKA and calcineurin, LTP elicited with two trains in mutant mice was markedly impaired (CN98 mutant: 127±7% of baseline at 1 hr, 12 slices, 7 mice; CN98 wild-type: 182±17% of baseline at 1 hr, 8 slices, 4 mice; p<0.05; FIG. 14E). Moreover, the LTP that remained in the mutant mice was insensitive to PKA inhibition, suggesting further that the function of PKA in the intermediate phase is to relieve the actions of calcineurin (FIG. 14F).

Overexpression of the Calcineurin Transgene Restricted to Postsynaptic CA1 Pyramidal Cells is Sufficient to Interfere with the Intermediate Phase of LTP The phenotype of CN98 mutant mice suggests that calcineurin suppresses an intermediate phase of LTP. However, because the calcineurin construct in these mice is expressed in both the presynaptic CA3 cells as well as the postsynaptic CA1 pyramidal cells, we cannot tell from these experiments alone where calcineurin is eliciting its action. In addition, it is conceivable that subtle alterations in presynaptic function, such as those observed in PPF and PTP in these mice could contribute to the phenotype. To investigate this possibility, as well as to verify that the deficit in I-LTP seen is not due to an insertion site effect, we analyzed two additional lines of mice which express the calcineurin transgene in a more spatially restricted manner in hippocampus. The two lines we tested, (Tet-CN279 and Tet-CN273), had the further advantage that the expression of the calcineurin transgene is regulated by the tetracycline-controlled transactivator (tTA) system (see accompanying article, Mansuy et al., submitted to Cell, for details of generation and characterization of these two lines). In contrast to line CN98, in which the transgene is strongly expressed both in CA3 and CA1 pyramidal cells, in lines Tet-CN279 and Tet-CN273 the transgene is expressed much more strongly in the CA1 postsynaptic pyramidal cells than in the CA3 pyramidal cells (Mansuy et al., submitted to Cell).

We first determined the effects of overexpression of the transgene in CA1 pyramidal cells on LTP by comparing slices from Tet-CN273 and Tet-CN279 on LTP elicited by one and two trains, and LTP induced by four 100 Hz trains in Tet-CN279 mice. Consistent with the results in the CN98 line, we found that overexpression of the calcineurin transgene under the Tet-system had no effect on LTP induced by a single train, but reduced LTP elicited by two and four trains (FIGS. 15A, B, C; FIG. 17B). It is interesting to note that, in contrast to the CN98 mice, where LTP was reduced immediately after two 100 Hz trains, both Tet-CN279 and Tet-CN273 mutant mice, which also exhibit a deficit in two train at 1 hour, showed little or no deficit immediately after the tetanus. Thus, the phenotype in these lines more closely parallels the defect observed after application of PKA inhibitors to wild-type slices than does the CN98 line, and supports the notion that delineation of the intermediate phase in these mutant mice is not an artifact of reduced presynaptic function. Further, these data imply that the site of action of the phosphate cascade is postsynaptic.

The Suppression of the Intermediate Phase of LTP by Overexpression of Calcineurin Can Be Rescued by Application of PP1 Inhibitors Similar to the results obtained in line CN98, we found no detectable differences in basal synaptic transmission, NMDA receptor-mediated synaptic potentials, and PTP in wild-type and mutant animals from lines Tet-CN279 and Tet-CN273 (FIGS. 16A, B, C). In contrast to the results in the CN98 line, however, we saw no deficits in PPF in line Tet-CN279 and Tet-CN273, consistent with weak or absent expression of the transgene presynaptically (FIG. 16D). As discussed above, Blitzer et al. (1995) reported that preincubation of hippocampal slices with PP1 inhibitors removed the ability of PKA inhibitors to block LTP elicited by a strong stimulus, suggesting that one role of PKA in LTP may be to suppress phosphatase activity in a "gate"-like manner. Because PKA regulates PP1 function through phosphorylation of inhibitor-1, a site that is dephosphorylated by calcineurin, it would be predicted that preincubation of hippocampal slices from mice overexpressing calcineurin should rescue LTP. To test this hypothesis, we pretreated slices from Tet-CN279 mutant and wild-type mice for 30 minutes with 750 nM calyculin A, after which LTP was induced with two 100 Hz trains. Consistent with the hypothesis that overexpressed calcineurin is suppressing LTP by regulating the activity of PP1, pretreatment of slices with calyculin A resulted in LTP in mutant mice that was indistinguishable from that seen in wild-type (FIG. 17A).

Regulated Overexpression of the Calcineurin Transgene Suggests that the Deficit in I-LTP Is Not Due to Developmental Effects of the Transgene in Hippocampus Since the tTA system allows for regulation of transgene expression, we next performed experiments to address whether the phenotype observed in mice overexpressing calcineurin reflected a consequence of the transgene on development of the nervous system or represented an acute effect of the transgene on synaptic plasticity. In the absence of the inhibitor, doxycycline, the transgene is expressed in the Tet-CN279 mice (Mansuy et al., submitted to Cell). However, when doxycycline (1 mg/ml) is administered in the animal's water supply, or in the ACSF (1 ng/ml) during electrophysiological experiments, the expression of the transgene is suppressed (Mansuy et al., submitted to Cell). We therefore compared LTP induced by two trains in Tet-CN279 mutant and wild-type mice on or off doxycycline. In wild-type mice either on or off doxycycline, stimulation with two trains resulted in robust LTP that was indistinguishable from that elicited in CN98 wild-type mice (Tet-CN279 Wt: 195±13% of baseline at 1 hr, 7 slices, 6 mice; Tet-CN279 mutant mice on doxycycline: 191±18% of baseline at 1 hr, 12 slices, 7 mice; FIG. 17B). In Tet-CN279 mutant mice off doxycycline, the response to two trains was significantly lower than that seen in wild-type one hour after the tetanus, and was completely reversed by doxycycline pretreatment (Tet-CN279 mutant: 147±8% of baseline at 1 hr, 15 slices, 9 -mice; Tet-CN279 on doxycycline: 184±18% of baseline at 1 hr, 8 slices, 5 mice; $p<0.01$ for Tet-CN279 mutant versus Tet-CN279 wild-type, FIG. 17B). These results clearly show that the calcineurin transgene produces its effect on the intermediate phase of LTP postsynaptically in the adult animal, and its effect is not attributable to a developmental consequence of the transgene.

Discussion

In an attempt to develop a genetic approach to study the role of phosphatases in synaptic plasticity, we have focused on calcineurin because it appears to function in the hippocampus as the first step in a calcium-dependent molecular signaling cascade of phosphatases. To both limit the expression of the transgene to forebrain, and reduce the likelihood that the phenotype produced is a result of the presence of the transgene during development, we have overexpressed calcineurin using the CaMKIIα promoter. To control further for a developmental role of the transgene, as well as to control for insertion-site dependent effects, we have also studied two other lines of mice (Tet-CN279, Tet-CN273) in which the phenotype exhibited by CN98 mice can be reproduced and reversed by suppression of the expression of the transgene using a regulatable transactivator (see Mansuy et al., submitted to Cell). With these lines we are able to show that the expression of calcineurin essentially limited to the CA1 neurons of the hippocampus selectively interferes with a novel phase of LTP that we isolated independently by pharmacological means and by using a two train stimulus protocol. Moreover this phenotype in mice overexpressing calcineurin is due to the expression of the transgene in the adult animal.

An Intermediate Component of LTP, I-LTP, Modulated by Calcineurin and PKA

These experiments have revealed several important features about the role of calcineurin and PKA in synaptic function at the Schaffer collateral-CA1 synapse. Converging lines of evidence, both from pharmacological studies in wild-type mice and genetic studies with calcineurin overexpressing mice suggest that an intermediate phase of LTP exists, and that this phase is suppressed by calcineurin. This suggestion, that a distinct intermediate phase of LTP exists, is based on two sets of findings (FIG. 18). First, E-LTP and I-LTP are distinguishable in three ways: 1) E-LTP is independent of PKA, whereas I-LTP is dependent on PKA. 2) I-LTP, but not E-LTP, is inhibited by overexpression of calcineurin. Finally, 3) I-LTP requires a stronger stimulus for initiation than E-LTP>

Second, I-LTP in turn also can be distinguished from L-LTP by two ways. First, whereas both I-LTP and L-LTP are dependent on PKA, only L-LTP is dependent on macromolecular synthesis. Second, while I-LTP could not be generated in mice overexpressing calcineurin, pharmacologically induced slow-onset potentiation, which is thought to utilize the same mechanisms as tetanically-induced L-LTP can still be generated.

Although the temporal features suggesting that PKA participates in a macromolecular synthesis-independent phase have not been clearly defined in earlier studies, it has been implicit in several of them. A number of groups have noted that an early, apparently protein synthesis-independent component of LTP, produced by multiple trains, requires PKA (Huang and Kandel, 1994; Blitzer et al., 1995). For example, Huang and Kandel (1994) have found that while LTP induced by multiple trains is rapidly inhibited by inhibitors of PKA, it was inhibited more slowly by inhibitors of protein synthesis. Consistent with this finding, Blitzer et al. (1995) found that LTP induced by three trains is partially blocked by inhibitors of PKA and that this blockade had a rapid time course. Further, Thomas et al. (1996) found that activation of β-adrenergic receptors by isoproterenol enables subthreshold stimuli to elicit robust enhancement of synaptic transmission at the Schaffer collateral synapse in a PKA-dependent manner. Both the effects delineated by Blitzer et al. and by Thomas et al. Were interpreted to reflect a PKA-mediated suppression of phosphatase activity. In each case the ability of PKA inhibitors to block LTP is reduced by phosphatase inhibitors such as calyculin A and okadaic acid.

While these earlier studies suggested that a role of PKA in LTP is to suppress phosphatase activity, these studies could not exclude an alternative explanation, that the phosphatase inhibitors enhanced the actions of residual, incompletely antagonized PKA. Moreover, although calcineurin was proposed to participate in suppressing LTP, calyculin A and okadaic acid are ineffective in inhibiting calcineurin at the concentrations used in these experiments, making it unclear whether calcineurin is important in regulating LTP. In fact, application of inhibitors of calcineurin to hippocampal slices has yielded contradictory results, with some studies reporting no effect (Mulkey et al., 1993; Muller et al., 1995) or enhancement (Wang and Kelly, 1996) of LTP, while other studies report blockade of LTP (Wang and Stelzer, 1994; Wang and Kelly, 1997; Lu et al., 1996a,b). Using genetic approaches, we have taken the opposite approach and demonstrated that PKA suppressed a phosphatase cascade by showing that overexpression of calcineurin removes the PKA-dependent component of LTP. Because this suppression is rescued by the PP1/PP2A inhibitor calyculin A, these data are also consistent with the proposed model that calcineurin and PKA interact at the level of inhibitor-1, a molecule that controls that activity of PP1.

The distinguishing features of I-LTP we report here extend these previous results on the roles of phosphatases and PKA in LTP by showing that overexpression of calcineurin removes the PKA-dependent components of LTP in area CA1. Thus our findings confirm the observation by Blitzer et al. (1995) that PKA plays an important gating role in LTP by suppressing phosphatase activity, and extends this idea by delineating that this role of PKA specifically involves a competition with calcineurin, that it represents a distinct temporal phase and that this phase has behavioral consequences (Mansuy et al., submitted to Cell).

We would emphasize that although I-LTP and E-LTP differ in several distinct ways, I-LTP very likely also shares a number of mechanisms in common with E-LTP. For example, the suppression of phosphatase activity by PKA during I-LTP, a suppression which requires a stronger stimulus than the one 100 Hz train necessary to produce E-LTP, may simply act to allow a more robust utilization of mechanisms recruited for E-LTP. In addition, while there is a temporal distinction between I-LTP, E-LTP and L-LTP in response to repeated high frequency trains, as well as a distinction in the strength of stimulus required to elicit these phases, these distinctions may become blurred under other circumstances, such as during periods in which neuromodulatory influences are recruited (Thomas et al., 1996). Indeed, the sensitivity of I-LTP to stimulus intensity explains why in a previous report overexpression of a dominant negative form of PKA had no effect on LTP elicited by two trains (Abel et al., 1997). When a stronger two train protocol was used that elicited LTP of a magnitude comparable to the present data, defective LTP in response to two trains was observed in R(AB) mutant mice (D. G. W. and Abel, T. Personal communication).

Our evidence suggests that the intermediate phase of LTP is inhibited by overexpression of calcineurin. Whether endogenous calcineurin performs the same function remains to be determined. However, pharmacological experiments suggest that this may be the case (Wang and Kelly, 1996). Thus, in future experiments it will be important to use other genetic manipulations, such as dominant negative constructs of calcineurin knockouts to investigate this intermediate phase further.

Interestingly, we find that several aspects of synaptic transmission thought to be mediated by calcineurin are not altered by overexpression of this enzyme. For example, overexpression of calcineurin failed to modulate LTD, basal synaptic transmission, or NMDA receptor-mediated synaptic potentials. While there are several possible explanations for these findings, one possibility is that a large excess of calcineurin exists in CA1 (a calcineurin reserve) Consistent with this idea, calcineurin is one of the most abundant proteins in brain (Yagel, 1997). If this hypothesis is correct, overexpression of calcineurin would only be expected to affect physiological actions that require the endogenous suppression of phosphatase activity, since overexpression would create a larger calcineurin reserve that might make it more difficult to completely inhibit phosphatase activity. Consistent with this idea, we find that overexpression of calcineurin places an inhibitory constraint on I-LTP.

PKA Is a Feed-forward Regulator of Calcium-Stimulated Kinase Activity

Calcineurin has a particularly high affinity for calcium/calmodulin. For example, it is at least an order of magnitude more sensitive to calcium/calmodulin than CaMKII. It was this feature of calcineurin which led Lisman (1989; 1994) to propose that low-level increases in calcium, induced by low frequency stimuli, would lead to synaptic depression through activation of calcineurin, while high frequency stimuli would lead to the large increases in calcium necessary to activate CaMKII and lead to LTP (Lisman, 1994). These aspects of Lisman's model have been supported by several studies (Malenka and Nicoll, 1993; Cummings et al., 1996).

Our studies provide support for a further prediction of the model. According to Lisman's model, robust LTP requires the inactivation of phosphatases. Consistent with this idea, we find that the phosphatases do indeed impose an inhibitory constraint on LTP, and suggest that PKA is required to suppress phosphatase activity sufficiently to fully elicit LTP. The calcium-sensitive adenylyl cyclases are ideally suited to increase cAMP levels and thereby inhibit the phosphatases only when large increases in intracellular calcium occurs (Lisman, 1994). Indeed, activation of NMDA receptors by robust tetanization that induces LTP increases cAMP levels in CA1 through a calmodulin-dependent process (Chetkovich et al., 1991; 1993). Therefore, while calcium directly regulates the balance of kinase and phosphatase activity, the generation of cAMP by NMDA-receptor-dependent activation of calcium-sensitive adenylyl cyclases can favor kinases further by inducing a PKA-dependent inactivation of the activation of PP1 by calcineurin through phosphorylation of inhibitor-1.

Thus our data extend Lisman's model in suggesting that there are four rather than two critical steps in the input-output relationship for hippocampal LTD and LTP. First, weak stimuli that elicit low-level increases in intracellular calcium result in LTD because of more complete activation of phosphatases than kinases. Second, moderated stimuli elicit larger intracellular calcium rises (such as one 100 Hz train), but elicit submaximal LTP (E-LTP) because, the kinases activated by the larger influx of calcium are opposed by phosphatases that are not suppressed. Third, strong stimuli (multiple 100 Hz trains for example) elicit robust LTP (I-LTP) because the calcium-dependent activation of kinases is now combined with a PKA-dependent suppression of phosphatases. Finally, if the stimulus is of sufficient strength (3-4 100 Hz trains), an additional role of PKA, that of establishing the macromolecular-synthesis dependent late phase of LTP would be activated. This model further explains why the slow-onset potentiation induced by Sp-cAMPS and D1/D5 dopamine receptor agonists is not affected by overexpression of calcineurin. These agents bypass synaptic tetanization to induced slow-onset potentiation, thereby avoiding activation of the calcium-dependent calcineurin phosphatase cascade, and therefore would not need to inhibit such an activated cascade.

Calcineurin May Act as a Shunt of Synaptically Evoked L-LTP

We find that L-LTP induced by four 100 Hz trains is defective in CN98 mutant mice. In an effort to determine whether the machinery required to induce L-LTP is intact in CN98 mice we determined whether or not we could pharmacologically elicit the late phase in a manner that bypasses tetanus. Thus, we found that application of activators of the PKA cascade induced a slow-onset potentiation of transmission that was normal in CN98 mutant slices. This slow-onset potentiation of transmission is thought to utilize the same machinery as four 100 Hz trains because they both are PKA and macromolecular synthesis dependent, and are mutually occlusive (Frey et al., 1993; Huang et al., 1996b). Indeed both tetanus-induced and pharmacologically induced L-LTP are impaired in cases in which molecules are ablated that are predicted to be downstream from macromolecular synthesis in the generation of L-LTP. For example, in $tPA^{-/-}$ mice which exhibit a defective tetanus-evoked L-LTP, the slow onset potentiation induced by D1/D5, agnonists and Sp-cAMPS is absent, consistent with the idea that $tPA^{-/-}$ mice lack the downstream machinery necessary for producing the late phase (Huang et al., 1996a).

As discussed above, this reduction of LTP in CN98 mutant mice overexpressing calcineurin is likely due to a shunting of the upstream kinases important for initiating L-LTP. Indeed, two recent reports are consistent with this possibility. First, Liu and Graybiel (1996) have shown that CREB phosphorylation and transcriptional activity in striosomes is negatively regulated by calcineurin. Further, Bito et al. (1996) have reported that CREB phosphorylation in hippocampal neurons in culture is also negatively regulated by calcineurin. Thus, regulation of transcription factors thought to be necessary for long-term synaptic modifications by calcineurin may prevent the formation of L-LTP in cases in which PKA is not activated sufficiently.

Multiple Inhibitory Constraints Must be Overcome to Evoke PKA-dependent Synaptic Plasticity Our data suggest that calcineurin acts as an inhibitory constraint on synaptic plasticity that opposes the formation of an intermediate and late phase of tetanus induced LTP. As we have indicated, PKA, which countervenes the actions of calcineurin, appears to act both as a disinhibitor of these phases and as a direct facilitator of the late phase.

Studies in the invertebrates Aplysia and Drosophila first revealed that the expression of learning-related synaptic plasticity is restricted by a number of inhibitory constraints that operate in different compartments within the cell, ranging from the cell membrane to the nucleus (Yin et al., 1994, 1995; Bartsch et al., 1995). For example, Bartsch et al. (1995) found that an isoform of the transcription factor CREB (CREB-2) normally suppresses the formation of long-term facilitation by a single pulse of serotonin. However, removal of this constraint by injection of antibodies or antisense oligonucleotides directed against this transcription factor allows one pulse of serotonin, which normally only elicits short-term facilitation to elicit long-term facilitation. These studies imply that to induce long-lasting enhancement of synaptic transmission, different types of inhibitory constraints are also acting on plasticity in the mammalian brain. In the accompanying article (Mansuy et al., 1997), we show that excessive activation of this inhibitory constraint interferes with memory storage.

Materials/Methods

Plasmid Construction

A cDNA encoding a truncated form of the murine calcineurin subunit Aα, ΔCaM-AI (provided by S. J. O'Keefe) was used to construct the expression vector for the generation of CN98 mice. ΔCaM-AI lacks the autoinhibitory domain and a portion of the calmodulin-binding domain of calcineurin Aα and was shown to be active in Jurkat T-cells (O'Keefe et al., 1992). A 1.27 kb EcoRI fragment of ΔCaM-AI cDNA was made blunt-ended and subcloned into the EcoRV site of pNN265 vector (provided by N. Nakanishi). The plasmid pNN265 carries upstream from the EcoRV site, a 230 bp hybrid intron that contains an adenovirus splice donor and an immunoglobulin G splice acceptor (Choi et al., 1991) and has a SV40 polyadenylation signal downstream from the EcoRV site. The ΔCaM-AI cDNA flanked by the hybrid intron in 5' and the poly(A) signal was 3' was excised from pNN265 with NotI and the resulting 2.7 kb fragment was placed downstream of the 8.5 kb mouse CaMKIIα promoter including the transcriptional initiation site (Mayford et al., 1996) to generate the CN98 mice (FIG. 11A) was excised from the vector by digestion with SfiI. Prior to microinjection, all cloning junctions were checked by DNA sequencing.

Generation and Maintenance of CN98 Transgenic Mice

The transgenic mice CN98 were generated by microinjection of the linear constructs into fertilized eggs collected from BL6/CBA F1/J superovulated females mated with BL6/CBA-F1 males (Jackson Laboratories; Hogan et al., 1991). Before microinjection, the DNA fragment was gel purified then put through Elutip (Schleicher and Schuell) for further purification. Microinjected eggs were kept overnight at 37° C. in 5% $CO^2$ and one day later, the two-cell embryos were transferred into pseudopregnant BL6/CBA F1/J females. Analysis of founder mice for integration of the transgene, was performed by Southern blotting and PCR. The founder mouse was backcrossed to C57BL6 F1/J mice to generate the transgenic line CN98. The genotype of the offspring was checked by Southern blotting or PCR. Transgenic mice were maintained in the animal colony according to standard protocol.

Northern Blot Analysis

Forebrains from adult CN98 mice were collected and total RNA was isolated by the guanidinium thiocyanate method (Chomczynski and Sacchi, 1987). Ten micrograms of RNA were denatured in 1 M formaldehyde, 50% formamide, 40 mM triethanolamine, 2 mM EDTA (pH 8), electorphoresed on a 1% agarose gel and transferred to a nylon membrane (GenScreen Plus, NEN) in 0.4 N NaOH. The membrane was hybridized to a 1.1 kb [$\alpha^{32}$P]dCTP-labeled EcoRV-NotI fragment from pNN265. The hybridization was performed overnight at 42° C. in 50% formamide, 2×SSC, 1% SDS, 10% dextran sulfate, 0.5 mg/ml denatured salmon sperm DNA. The membrane was washed 10 min at room temperature in 2×SSC, 1% SDS then twice 15 min at 42° C. in 0.2×SSC, 1% SDS and exposed to film for three days.

In Situ Hybridization

Brains from adult mice were dissected out and rapidly embedded into Tissue-Tek™ medium on dry ice (Miles, Inc.). Fifteen millimeter cryostat sections were placed onto gelatin-coated glass slides, dried 15 mm at 55° C. then fixed 10 min in freshly prepared 4% paraformaldehyde, rinsed two times in PBS (pH 7.2) and dehydrated through a gradient of ethanol. The sections were rehydrated, permeabilized into 0.1 M triethanolamine pH 8, 0.25% acetic anhydride, washed two times in 2× SSC, rinsed in 70% ethanol then dried. The sections were hybridized overnight at 37° C. to an OPC purified oligonucleotide (5'-gcaggatccgcttgggctgcagttggacct-3', SEQ ID NO:6) derived from pNN265. The oligonucleotide was labeled by 3' poly(A) tailing using [$\alpha^{35}$S] dATP (NEN) and terminal transferase (Boehringer Mannheim) and the hybridization was performed in a humidified chamber in 50% formamide, 10% dextran sulfate, 35 mM HEPES (pH 7) , 1 mM EDTA (ph8), 100 mM DTT, 400 μg/ml denatured salmon sperm DNA, 400 μg/ml poly (dA), 1 X Denhart's, 600 mM NaCl and $10^7$ cpm oligonucleotide/ml hybridization solution. After hybridization, slides were washed twice for 10 min in 2× SSC at room temperature, twice for 60 min in 0.2X SSC at 65° C. then once 10 min in 2× SSC at room temperature. Slides were dehydrated in 70% ethanol, dried and exposed to Kodak Biomax MR film for 2-3 weeks.

Phosphatase Assay

Phosphatase assays were performed according to Hubbard and Klee (1991). Briefly, mice were injected with 5 ml/kg of pentobarbital and decapitated. Hippocampi were dissected out, homogenized in 2 mM EDTA (pH 8), 250 mM sucrose, 0.1% β-mercaptoethanol and centrifuged. Supernatants were diluted in 40 mM Tris-HCl (pH 8), 0.1 M NaCl, 0.04 mg/ml bovine serum albumin, 1 mM DTT, 0.45 mM okadaic acid (Buffer 1) and incubated at 30° C. for 1 min in Buffer 1 containing 1 mM of the peptide [$\gamma^{32}$P]-RII subunit of cyclic AMP-dependent protein kinase (PKA) and either 0.1 mM calmodulin (Sigma) and 0.66 mM $Ca^{2+}$ or 0.33 mM EGTA (pH 7.5). The peptide $^{97}$[Ala]-RII (Peninsula Labs) was labeled with 0.3 mM [$\gamma^{32}$P]ATP (NEN) using 4 mg catalytic subunit of PKA (Fluka). The reaction was stopped with 5% TCA in 0.1 M $KH_2PO_4$ and the enzyme activity was calculated as previously described (Klee et al., 1983) and is expressed in nmol Pi release/min/mg protein. The protein concentration was determined using the bicinchroninic acid protein assay kit (Sigma). All samples were performed in triplicate.

Electrophysiology

Transverse hippocampal slices were prepared as previously described (Huang and Kandel, 1994). Mice of either sex, aged 7-18 weeks were used. In all appropriate cases, the experimenter was blinded to animal genotype. Hippocampi was rapidly unilaterally dissected out on ice, and 400 mm slices were cut on a McIlwain tissue chopper and placed in oxygenated ACSF (NaCl, 124 mM; KCl, 4,4 mM; $CaCl_2$, 2.5 mM; $MgSO_4$, 1.3 mM; $NaH_2PO_4$, 1 mM; glucose, 10 mM; and $NaHCO_3$ 26 mM). The slices were then transferred to an interface chamber where they were subfused with oxygenated ACSF (1-2 ml/min) and allowed to equilibrate for 60-90 min at 28° C.

For extracellular recordings, ACSF-filled glass electrodes (1-3 MΩ) were positioned in the stratum radiatum of area CA1. A bipolar nichrome stimulating electrode was also placed in stratum radiatum for stimulation of Schaffer collateral afferents (0.05 ms duration). Unless otherwise mentioned, test stimuli were applied at a frequency of 1 per minute (0.017 Hz), and at a stimulus intensity that elicits a fEPSP slope that was 35% of the maximum. Experiments in which a significant change in the fiber volley amplitude occurred, were discarded. Drugs were applied through the perfusion medium. DL-AP5, calyculin A, KT5720 and R(+)-6-Bromo-7,8-dihydroxy-3-allyl-1-phenyl-2,3,4-tetrahydro-1H-3-benzazepine (6-Br-APB) were purchased from Research Biochemicals International, Natick, Mass. DL-AP5 was dissolved directly into ACSF prior to use. Calyculin A, KT5720 and 6-Br-APB were dissolved as 100× stocks in DMSO and diluted into ACSF just before use. Sp-cAMPS (Biolog, La Jolla, Calif.) was dissolved directly in ACSF.

References for Example 3

Abel, T et al., (1997). "Genetic demonstration of a role for PKA in the late phase of LTP and in hippocampal-based long-term memory," Cell 88: 1-11;

Bartsch, D et al., (1995). "Aplysia CREB2 represses long-term facilitation: relief of repression converts transient facilitation into long-term functional and structural change," Cell 83: 979-992;

Bear, M F et al., (1996). "Long-term depression in hippocampus," Ann. Rev. Neurosci. 19: 437-462;

Bito, H et al., (1996). "CREB phosphorylation and dephosphorylation: A $Ca^{2+}$-and stimulus duration-dependent switch for hippocampal gene expression," Cell 87: 1203-1214;

Blitzer, R D et al., (1996) "Postsynaptic cAMP pathway gates early LTP in hippocampal CA1 region," Neuron 15: 1403-1414;

Bolshakov, V Y et al. (1997). "Recruitment of new sites of synaptic transmission during the cAMP-dependent late phase of LTP at CA3-CA1 synapses in the hippocampus," Neuron 19: 635-651;

Chetkovich, D M et al., (1991). "N-Methyl-D-aspartate receptor activation increases cAMP levels and voltage-gated Ca2+ channel activity in area CA1 of hippocampus," Proc. Natl. Acad. Sci. USA 88: 6467-6471;

Chetkovich, D M et al., (1993). "NMDA receptor activation increases cyclic AMP in area CA1 of the hippocampus via calcium/calmodulin stimulation of adenylyl cyclase," J. Neurochem. 61: 1933-1942;

Choi, T et al., (1991). "A generic intron increases gene expression in transgenic mice," Mol. Cell. Biol. 11: 3070-3074;

Chomczynski, P et al., (1987). "Single-step method of RNA isolation by acid gnanidinium thiocyanate-phenol-chloroform extratction," Anal. Biochem. 162: 156-159;

Cummings, J A et al., (1996). "Ca2+ signaling requirements for long-term depression in the hippocampus," Neuron 16: 825-833;

Figurov, A et al., (1993). "Enhancement of AMPA-mediated synaptic transmission by the protein phosphatase inhibitor calyculin A in rat hippocampal slices," Eur. J. Neurosci 5: 1035-1041;

Frey, U et al., (1993). "Effects of cAMP stimulate a late stage of LTP in hippocampal CA1 neurons," Science 260: 1661-1664;

Helekar, S A et al., (1997) Peptidyl prolyl cis-trans isomerase activity of cyclophillin A in functional homo-oligomeric receptor expression," Proc. Natl. Acad. Sci. USA 94: 5432-5437;

Hogan, B et al., (1994). *Manipulating the mouse embryo, 2nd Edition*. (Cold Spring Harbor Press: Cold Spring Harbor, N.Y.);

Huang, Y Y et al., (1994). "Recruitment of long-lasting and protein kinase A-dependent long-term potentiation in the CA1 region of hippocampus requires repeated tetanization," Learn. Mem. 1: 74-82;

Huang, Y Y et al., (1995). "D1/D5 receptor agonists induce a protein synthesis-dependent potentiation in the CA1 region of the hippocampus," Proc. Natl. Acad. Sci. USA 92: 2446-2450;

Huang, Y Y et al., (1996a). "Mice lacking the gene encoding tissue-type plasminogen activator show a selective interference with late-phase long-term potentiation in both Schaffer collateral and mossy fiber pathways," Proc. Natl. Acad. Sci. USA 93: 8699-8704;

Huang, Y Y et al., (1996). "Long-lasting forms of synaptic potentiation in the mammalian hippocampus," Learn. Mem. 3: 74-85;

Hubbard, M J et al., (1991). "Exogenous kinases and phosphatases as probes of intracellular modulation," Molecular Neurobiology, A Practical Approach (Chad, J. and Wheal, J., Oxford) 135-157;

Klee, C B et al., (1983). "Isolation and characterization of bovine brain calcineurin: a calmodulin-stimulated protein phosphatase," Methods Enzymol. 102: 227-244;

Klee, C B et al., (1991). "Concentrated regulation of protein phosphorylation and dephosphorylation by calmodulin," Neurochem. Res. 16: 1059-1065;

Kojima, J et al., (1997). "Rescuing impairment of long-term potentiation in fyn-deficient mice by introducing fyn transgene," Proc. Natl. Acad. Sci. USA 94: 4761-4765;

Kuno, T et al., (1992). "Distinct cellular expression of calcineurin Aα and Aβ in rat brain," J. Neurochem. 58: 1643-1651;

Lisman, J (1989). "A mechanism for the Hebb and anti-Hebb processes underlying learning and memory," Proc. Natl. Acad. Sci. USA, 86: 9574-9578;

Lisman, J. (1994). "The CaM kinase II hypothesis for the storage of synaptic memory," Trends Neurosci 17: 406-412;

Liu, F C et al.,: (1996). "Spatiotemporal dynamics of CREB phosphorylation: transient versus sustained phosphorylation in the develoopine striatum," Neuron 17: 1133-1144;

Lu, Y F et al., (1996a). "FK506, a Ca$^{2+}$/calmodulin-dependent phosphatase inhibitor, inhibits the induction of long-term potentiation in the rat hippocampus," Neurosci. Lett. 205: 103-106;

Lu, U F et al., (1996b). "Calcineurin inhibitors, FK506 and cyclosporin A, suppress the NMDA receptor-mediated potentials and LTP, but not depotentiation in the rat hippocampus," Brain Res. 729: 142-146;

Malenka, R C et al., (1993). "NMDA receptor-dependent synaptic plasticity: multiple forms and mechanisms," Trends Neurosci., 16: 521-527;

Martin, K C et al., (1997). "MAP kinase translocates into the nucleus of the presynaptic cell and is required for long-term facilitation in Aplysia," Neuron 18: 899-912;

Mayford, M et al., (1995a). "Transgenic approaches to cognition," Curr. Opin. Neurobio. 5: 141-148;

Mayford, M et al., (1995) "CaMKII regulates the frequency-response function of hippocampal synapses for the production of both LTD and LTP," Cell 81: 891-904;

Mayford, M et al., (1996). "Genetic control of Ca$^{2+}$/calmodulin-dependent protein kinase activity in hippocampus and amygdala: Regulated disruption of explicit and implicit memory storage," Science 274: 1678-1683;

Mulkey, R M et al., (1993). "An essential role for protein phosphatases in hippocampal long-term depression," Science 261: 1051-1055;

Mulkey, R M et al., (1994). "Involvement of a calcineurin/inhibitor-1 phosphotase cascade in hippocampal long-term depression," Nature 369: 486-488;

Muller D et al., (1995). "Heterosynaptic interactions between LTP and LTD in CA1 hippocampal slices," Neuron 14: 599-605;

Muller, D et al., (1988). "Contributions of quisqualate and NMDA receptors to the induction and expression of LTP," Science 242: 1694-1697;

O'Dell, T J et al., (1994). "Low-frequency stimulation erases LTP through an NMDA receptor-mediated activation of protein phosphatases," Learn and Mem. 1: 129-139;

O'Keefe, S J et al., (1992). FK-506 and CsA-sensitive activation of the interleukin-2 promoter by calcineurin," Nature 357: 692-694;

Osten, P et al., (1996). "Protein synthesis-dependent formation of protein kinase Mζ in long-term potentiation," J. Neurosci. 16: 2444-2451;

Parsons, J N et al., (1994). "Regulation of calcineurin phosphatase activity and interaction with the FK-506-FK-506 binding protein complex," J. Biol. Chem. 269: 19610-19616;

Paterson, J M et al., (1995). "Control of a novel adenylyl cyclase by calcineurin," Biochem. Biophys. Res. Comm. 214: 1000-1008;

Raman, I M et al., (1996). "β-adrenergic regulation of synaptic NMDA receptors by cAMP-dependent protein kinase," Neuron 16: 415-421;

Rangel-Alsao, R et al., (1976). "Dissociation and reassociation of the phosphorylated and nonphosphorylated forms of adenosine 3':5'-monophosphate-dependent protein kinase from bovine cardiac muscle," J. Biol. Chem. 251: 3375-3380;

Roberson, E D et al., (1996). "A biochemist's view of long-term potentiation," Learn. and Mem. 3: 1-24;

Schwaninger, M et al., (1995). "Involvement of the Ca$^{2+}$-dependent phosphatase calcineurin in gene transcription that is stimulated by cAMP through cAMP response elements," J. Biol. Chem. 270: 8860-8866;

Stanton, P K et al., (1984). "Blockade of long-term potentiation in rat hippocampal CA1 region by inhibitors of protein synthesis," J. Neurosci. 4: 3080-3088;

Thomas, M J et al., (1996). "Activity-dependent β-adrenergic modulation of low frequency stimulation induced LTP in the hippocampal CA1 region," Neuron 17: 475-482;

Tong, G et al., (1995). "Synaptic desensitization of NMDA receptors by calcineurin," Science 267: 1510-1512;

Traynelis, S. F. et al., (1997). "Control of rat GlyR6 glutamate receptor open probability by protein kinase A and calcineurin," J. Physiol. 503: 513-531;

Wang, J H et al., (1996). "The balance between postsynaptic Ca$^{2+}$-dependent protein kinase and phosphatase activities controlling synaptic strength," Learn. And Mem. 3: 170-181;

Wang, J H et al., (1994). "Inhibition of phosphatase 2B prevents expression of hippocampal long-term potentiation," Neuroreport 5: 2377-2380;

Yakel, J L et al., (1994). "Calcineurin regulation of sunaptic function: from ion channels to transmitter release and gene transcription," Trends Neurosci. 18: 124-134;

Yin; J C P et al., (1994). "Induction of a dominant negative CREB transgene specifically blocks long-term memory in Drosophila," Cell 79: 49-58;

Yin, J C P et al., (1995). "CREB as a memory modulator: induced expression of a dCREB2 activator isoform enhances long-term memory in Drosophila," Cell 81: 107-115;

Zucker, R S (1989). "Short-term synaptic plasticity," Annu. Rev. Neurosci. 12: 13-31.

Example 4

Restricted and Regulated Overexpression Reveals Calcineurin as A Kay Component in the Transition From Short-Term to Long-Term Memory To investigate whether phosphates play a role in memory storage, hippocampal-dependent memory was assessed in transgenic mice by expression, primarily in the hippocampus, a truncated form of calcineurin. These mice have normal short-term memory but have a defect in long-term memory that is evident on both a spatial task (the spatial version of the Barnes maze) and on a visual recognition task, thus providing genetic evidence for the role of the rodent hippocampus in spatial as well as non-spatial memory storage. Further on the Barnes maze, the defect in long-term memory could be fully rescued by increasing the number of training trials. These results suggest that the transgenic mice overexpressing calcineurin have the capacity for long-term memory which prevents the storage of long-term memory. Using the tTA system, transgenic mice overexpressing calcineurin in a regulated manner were analyzed and found that the memory defect observed is reversible and therefore is most likely due to the transgene and not to a developmental abnormality. Together with our electrophysiological findings that mice overexpressing calcineurin have a defect in an intermediate phase of long-term potentiation (I-LTP), behavioral results suggest that calcineurin has a role in the transition from short- to long-term memory and that there is a correlation between this transition in memory storage and a novel intermediate phase of LTP.

Introduction

Mice that overexpress a truncated form of the phosphatase calcineurin in the hippocampus is described (lines CN98, Tet-CN98m Tet-CN279 and Tet-CN 273). These mice exhibit a specific defect in an intermediate phase of long-term potentiation (I-LTP). There is now increasing evidence that LTP can contribute to the storage of declarative forms of memory (Bliss and Collingridge, 1993; Eichenbaum, 1995; Mayford et al., 1996; Tsien et al., 1996). Like the temporal phases of memory, LTP also is not unitary but has at least two major phases: an early phase (E-LTP) elicited by a weak stimulus (1 train of Is 100 Hz) and that is PKA- and protein synthesis-independent, and a late phase (L-LTP) induced by strong stimuli (4 trains of is 100 Hz) that requires PKA and protein synthesis (Huang and Kandel, 1994; Huang et al., 1996).

In addition to its role in the late phase of LTP, PKA is thought to be a component of a gate that regulates the initiation of LTP by opposing the actions of the phosphatases PP1 and PP2A (Blitzer et al., 1995; Thomas et al., 1996). The electrophysiological results with mice expressing a truncated form of calcineurin are consistent with this idea and suggest (that this gate has a distinct temporal component and forms a novel intermediate phase of LTP (I-LTP) that can be suppressed by calcineurin and that has three defining features: (1) it requires strong stimulation (a minimum of 2 train of 1 s 100 Hz) (2) it depends on PKA (3) it does not require protein synthesis.

In the present study the hippocampal-dependent memory was assessed in mice that express a truncated form of calcineurin. It was found that mutant mice have normal short-term memory but exhibit a profound and specific defect in long-term memory on both the spatial version of the Barnes maze and on a task requiring the visual recognition of a novel object. To determine whether mutant mice have the capacity for long-term memory, the training protocol was intensified on the spatial version of the Barnes Maze by increasing the number of daily training trials and found that the memory defect was fully reversed, indicating that these mice are capable of forming long-term memory. This rescue experiment suggests that mice overexpressing calcineurin have impaired long-term memory possibly due to a specific defect in the transition between short-term and long-term memory that may reflect a weakening of an intermediate component of memory.

Finally, it is shown that the memory defect observed was not the result of a developmental abnormality due to the genetic. manipulation. In mice in which the expression of calcineurin transgene is regulated by the tetracycline-controlled transactivator (tTA) system, the spatial memory defect was reversed when the expression of the transgene was repressed by doxycycline.

Results

Mice Overexpressing Calcineurin are Deficient on the Spatial Version of the Barnes Maze with One Trial a Day A physiological analysis is described of transgenic mice overexpressing calcineurin primarily in the hippocampus (line CN98). This analysis revealed that CN98 mutant mice lacked an intermediate phase of LTP between the early, protein synthesis- and PKA-independent phase and the late, protein synthesis- and PKA-dependent phase. As a first step in analyzing the memory capability of these mice, the mice were tested on a hippocampal-dependent memory task: the spatial version of the Barnes maze (Barnes. 1979; Bach et al., 1995).

The Barnes maze is a circular maze that has 40 holes in the perimeter and a hidden escape tunnel placed under one of the holes. The mouse is placed in the center of the maze and is motivated to find the tunnel to escape the open brightly lit maze and an aversive buzzer. To locate the tunnel the mouse needs to remember and use the relationships among the distal cues in the environment. To achieve the learning criterion on this task the mouse must make three errors or less across five out of six consecutive trials. Errors were defined as searching any hole that did not have the tunnel beneath it. Previous research has established that performance on this task depends on the hippocampus (Barnes et al., 1979).

CN98 mice were tested on the Barnes maze once each day (1 trial per day, 24 h intertrial interval) until they met the learning criterion or until 40 consecutive days elapsed. Despite the fact that they were tested for 40 consecutive days, only 25% of the CN98 mutant mice met the learning criterion compared to 88% of the wild-type littermates (FIG. 19A). An analysis of the mean number of errors made across 4 blocks of 5 trials by mutant and wild-type mice revealed that the mutant mice made significantly more errors than wild-type mice across the last 2 trial blocks (Main effect genotype F [1,30]= 4.63 m p, 0.05 m FIG. 19B).

The impairment on the spatial version of the maze observed in the CN98 mutant mice could be due to a deficit in spatial memory or to a performance deficit such as a gross motor, visual or motivational impairment. To exclude a performance deficit, another group of CN98 mice were tested on a cued version of the Barnes maze, a task which does not require the hippocampus. The cured version has similar contingencies and response requirements as the spatial version except that the position of the escape tunnel is made visible to the mice by putting a cue behind the hole where it is placed. Thus to locate the escape tunnel, the mice simply need to associate the cue with the tunnel. CM98 mutant mice acquired the task in a manner similar to that of their wild-type littermates (FIG. 19A) and made a similar number of errors across all trial blocks (Main effect genotype F[1,18]=2.44, p<0.05; FIG. 19C). These data indicate that CN98 mutant mice exhibit normal motivation and do not have any gross motor, motivational or visual impairments.

The Spatial Memory Deficit can be fully Rescued by Repeated Training Trials

The results from the behavioral experiments on the spatial version of the Barnes maze which is a hippocampal-dependent task, indicate that CN98 mutant mice have a defect in spatial long-term memory. Have the mutant mice totally lost their ability to form long-term memory? Or do these mice have a block in the transition from short-term to long-term memory? Can the mice store long-term memory when trained with a more intensive protocol?

Our electrophysiological experiments indicated that L-LTP was reduced in CN98 mutant mice (Winder et al., 1997). Nevertheless, a potentiation similar to L-LTP could be induced by pharmacological agents that activate the PKA pathway. These results suggested that the machinery for the expression of L-LTP is intact in CN98 mutant mice and that the impairment seems to reside in an intermediate phase, between the early and the late phase, that is necessary for the production of the late phase (Winder et al., 1997). Since L-LTP is thought to parallel long-term memory (Abel et al., 1997), these results suggest that CN98 mutant mice may indeed have the ability to form long-term memory but may be deficient in an earlier phase of memory essential for the storage of long-term memory.

To test whether CN98 mutant mice have the capacity for long-term memory, the Barnes maze protocol was modified by increasing the number of daily trials from one to four per day. The trials were separated by a 1.5 min. intertrial interval. When trained with four trials per day, 100% of CN98 mutant mice were able to learn the spatial version of the Barnes maze as were 100% of wild-type mice (FIG. 20A). A comparison of the mean number of trials and days to criterion across the single versus repeated trials protocols revealed that a similar number of trials was required for the wild-type mice to learn the task whether a single or repeated trial was given each day (FIG. 20B) However, the number of days necessary for the acquisition of the task was much lower with four trials per day than with only one trail a day (FIG. 20B). An analysis of the mean number of errors revealed that mutant mice were similar to wild-type mice across all trial blocks (Main effect genotype $F[1,8]=0.5191$, $p>0.05$)(FIG. 20C).

These results demonstrate that CN98 mutant mice have impaired long-term memory on the spatial version of the Barnes maze when tested with one trial per day (24 h intertrial interval) but have normal long-term memory when tested with four trials per day (1.5 min intertrial interval) suggesting that CN98 mutant mice have the capacity for long term memory but have a deficiency in storing long-term memory.

Short-Term Memory is Normal in Mice Overexpressing Calcineurin

The demonstration that CN98 mutant mice have the capacity for hippocampal-dependent long-term memory when trained with repeated trials raised the question: Why do mutant mice have defective spatial memory when trained with one trial per day? Is short-term memory impaired? If so, can the defect in long-term memory be explained by a defect in short-term memory? Since spatial tasks such as the spatial version of the Barnes do not readily lend themselves to exploring short-term memory, the CN98 mutant mice were assessed for short-term memory using a recognition task for novel objects. Spontaneous exploratory activity in rodents can be used as a measure of memory and in particular, it can be assessed to determine the recognition of a novel versus a familiar object in an object recognition task (Aggleton, 1985; Ennaceur and Delacour, 1988). In humans, the hippocampal region has been shown to play a role in the detection of novel visual stimuli (Tulving et al., 1996). Patients with hippocampal lesions exhibit impaired responses to novel stimuli (Knight et al., 1996; Reed and Squire, 1997). Monkeys and rodents with hippocampal lesions are similarly defective on a task requiring the recognition of novel objects (Myhrer, 1988a,b; Phillips et al., 1988; Mumby et al., 1995).

In the recognition task for novel objects, the mice were trained by being placed in a novel environment that, contained two novel objects and were allowed to explore the objects for 15 min. During the testing phase, following different retention intervals, the mice were placed back in the environment but one of the two familiar objects was replaced with a third novel object. Mice with normal object recognition memory show an increase in exploration of the third novel object. This increase in exploration indicates that information regarding the familiar object was stored during training and further exploration of this object is no longer needed.

Exploration was assessed during the training phase by examining the amount of time spent exploring both novel objects and did not observe any difference between mutant and wild-type mice (main effect of genotype $F[1,67]=1.48$, $p=0.228$). Then, exploration of the novel object was assessed following different retention intervals: short-term (30 min), intermediate-term (2 hr), and long-tern (24 hr). For this analysis, a preference index (PI) was determined by calculating the ratio between the amount of time spent exploring the novel object and the amount of time spent exploring both the novel and familiar objects during the first 5 min of the testing phase (the preference index was normalized and expressed as a percentage with PI=100% indicating no preference and PI greater than 100% indicating preference for the novel object). A significant difference in exploration of the novel object between mutant and wild-type mice was observed (Main effect genotype $F[1,67]=4.03$, $p=0.049$). Post hoc analysis using a Student t test was performed for each retention interval and revealed that mutant mice exhibited and increase in exploration towards the novel object comparable to wild-type at 30 min ($t=0.449$, $p>0.05$) (FIG. 21). This indicates that the early components of short-term memory are intact in mutant mice. When mutant mice were tested at the 2 hr retention interval, they exhibit a slight memory defect compared to wild-type, although this difference was not significant ($t=1.114$, $p>0.05$) (FIG. 21). However, when tested at the 24 hr retention interval, mutant mice showed a long-term memory deficit that was statistically significant. Whereas wild-type mice exhibited a significant preference for the novel object, mutant mice explored both objects equally ($t=2.061$, $p<0.05$) (FIG. 21).

These results provide independent evidence for a deficit in long-term memory in CN98 mutant mice and suggest that the early components of short-term memory or intact. These results support the findings from the single versus repeated trial protocol in the Barnes maze in showing that mice overexpressing calcineurin have normal short-term memory and the capacity for long-term memory that is strengthened with repetition (four trials protocol) and allows long-term memory to be stored.

Calcineurin Overexpression can be Regulated by the tTA System

To verify that the memory impairment observed in CN98 mutant mice is not due to a developmental defect caused by the increase in calcineurin activity during postnatal development or to an effect of the insertion site of the transgene, spatial memory was assessed in mice expressing the calcineurin transgene in a regulated manner under the control of the tTA system (lines Tet-CN279 and Tet-CN273, FIG. 22A). To obtain regulated expression of the calcineurin transgene, mice were crossed that express the tTA gene under the control of the CaMKIIα promoter (line B, Mayford et al., 1996) with mice carrying the tTA-responsive promoter tetO fused to a cDNA encoding the truncated form of calcineurin ΔCaM-AI (lines CN279 and CN273) (FIG. 22A).

Northern blot analysis revealed a 1.9 kb transcript corresponding to the transgene mRNA in Tet-CN279 and Tet-CN 273 mutant mice (FIG. 22B). Further, a RT-PCR revealed expression of transgene mRNA in Tet-CN 279 and Tet-CN 273 mutant mice that was dramatically reduced when mutant mice were administered doxycycline for at least one week (FIG. 22B). Phosphatase assays revealed a 112% ±9% and 114% ±5% increase in Ca2+-dependent calcineurin activity respectively in Tet-CN279 and Tet-CN273 mutant compared to wild-type mice (FIG. 22C). This increase in phophatase activity in Tet-CN279 and Tet-CN273 mutant mice was slightly higher than that detected in Cn98 mutant mice (76% ±12%, see Winder et al., 1997). In Tet-CN279 and Tet-CN273 mutant mice, phosphatase activity was suppressed to wild-type levels upon administration of doxycycline for at least one week (FIG. 22C).

The spatial distribution of the transgene transcript was examined by in situ hybridization on adult brain in Tet-CN279 and Tet-CN273 mice. The transgene mRNA was detected mainly in the hippocampus and striatum, almost no expression was detected in neocortex. In the hippocampus, it was found primarily in area CA1 and dentate gyrus with relatively little expression in area CA3 (FIG. 23). In contrast, no signal was detected in mutant mice administered 1 mg/ml doxycycline for at least one week or in wild-type mice (FIG. 23).

The memory defect can be reversed by repression of the calcineurin transgene by doxycycline To assess whether the memory defect could be reversed by repression of calcineurin transgene with doxycycline in-adult mice, Tet-CN279 and Tet-CN273 mice were tested on the spatial version of the Barnes maze. When performing the spatial version of the Barnes maze, mice normally progress through three search strategies: random, serial and spatial (Barnes, 1979; Bach et al., 1995) (FIG. 24A). The random search strategy is operationally defined as a random localized search of holes separated by center crossings which results in a large number of errors. The serial search strategy is defined operationally as a systematic search of consecutive holes in a clockwise or counter-clockwise fashion and use of the strategy results in less errors than for the random-search strategy (FIG. 24A). The spatial search strategy, the most efficient strategy of the three and the only one that requires that hippocampus, is defined operationally as navigating directly to the tunnel with three or fewer errors (FIG. 24A). During the first 5 trials, CN98 and Tet-CN279 mutant mice and their respective wild-type mice either on or off doxycycline (FIGS. 24B and 24C) primarily used the random strategy and both exhibited a similar decrease in use across the remaining trial blocks (CN98: Main effect genotype by time $F[3.28]=0.5$, $p>0.05$; Tet-CN279: Main effect genotype $F[1,54]=1.63$, $p>0.05$). The decrease in the use of the random strategy is paralleled by an increase in the use of the serial search strategy in CN98m Tet-CN279 mutant and wild-type mice. The serial strategy was employed significantly more often by CN98 and Tet-CN279 mutant mice during the last 2 trial blocked (FIGS. 24D and 24E) (CN98: Main effect genotype by time $F[3,28]=5.22$, $p<0.01$; Tet-CN279: Main effect genotype by doxycycline $F[1,54]=6.12$, $p<0.05$). By contrast, during the last 2 trial blocks, CN98 wild-type mice, Tet-CN279 mutant mice on doxycycline and wild-type mice employed primarily the spatial search strategy (FIGS. 24F and 24G) CN98: Main effect genotype by time $F[3,28]=5.4$, $p<0.005$; Tet-CN279: Main effect genotype $F[1, 54]=4.64$, $p<0.05$).

These results show that CN98 and Tet-CN279 mutant mice have similar defect in spatial memory in that they do not employ the spatial search strategy. When the expression of the calcineurin transgene was repressed by doxycycline in Tet-CN279 mutant mice, this defect was reversed. The ability to reverse the memory loss suggests that the defect observed is probably not developmental but most likely due to expression of the calcineurin transgene and the resulting increase in calcineurin and its interference with memory storage in the adult brain.

Discussion

Calcineurin Plays a Role in Hippocampal-Dependent Memory: Transition from Short-Term to Long-Term Memory Mice expressing a truncated form of calcineurin exhibit a specific memory defect on the spatial version of the Barnes maze, a hippocampal-dependent task. No defect was observed on the cued version of the task, which is hippocampal-independent, indicating that the defect observed on the Barnes maze was in spatial memory and was not a motivational or sensory-motor defect. Further, the defect in spatial memory was reversible in adult mice overexpressing calcineurin in a regulated manner with the tTA system. These results provide the first genetic evidence that a phosphatase, and specifically calcineurin, has a role in the hippocampus-based memory storage.

Although our data do not allow us to determine whether a specific phase of memory is impaired by the overexpression of calcineurin transgene, they allow us to being to delineate the components of memory that are affected and to identify components of memory that are not impaired. Our results indicate that by increasing the number of daily trials on the spatial version of the Barnes maze, the long-term memory defect observed in the CN98 mutant mice was fully rescued. This shows that although they exhibit an apparent defect in spatial long-term memory, mutant mice indeed still have the capacity to store long-term memory. The finding that the memory deficit observed with one trial a day can be rescued with repeated training suggest that mutant mice have a defect in some upstream processes required for the storage of long-term memory. These results therefore suggest that the short-term memory trace generated by a single daily trial disintegrates before the transition into long-term memory is complete. When the training is intensified so that the defective short-term trace is strengthened, long-term memory can be achieved.

Genetic Evidence Support the Notion that the Hippocampus Stores some Aspects of Short-Term as well as Long-Term Memory for Spatial and Non-Spatial Tasks Our results from the Barnes maze support those obtained on the novel object recognition task. On this task, the mutant mice have normal short-term memory at 30 min but have a significant defect in long-term memory at 24 hr. The combined results on the spatial version of the Barnes maze and the novel object recognition task further strengthen the hypothesis that the defect that leads to the impairment in long-term memory storage is a defect in the process or stages whereby short-term memory is converted into long-term memory. Since the calcineurin transgene is primarily expressed in the hippocampus, this defect in the transition very likely resides in the hippocampus. Whereas additional genetic manipulations would be required to establish this idea more firmly, the present results strengthen the important idea, well documented in humans and in primates (Scoville and Milner, 1957; Mishkin, 1978; Zola-Morgan and Squire, 1985; Overman et al., 1990), that the hippocampus is involved not only in the storage of long-term memory, but also in some aspects of the storing of short-term memory downstream from working memory. As a corollary, our experiments provide independent evidence that the rodent hippocampus is concerned with storing information other than space. In addition to showing a defect in spatial memory, genetic interference with I-LTP that is restricted to the hippocampus, also interfered with the recognition of novel object. These findings support the idea (Squire et al., 1992) that the rodent hippocampus is similar to that of humans in supporting a variety of memories that require the complex association of clues in all sensory modalities.

The Defect in the Transition from Short-Term to Long-Term Memory Correlates with a Defect in I-LTP Our behavioral and electrophysiological results suggest that an increase in calcineurin activity in the hippocampus leads to a defect in a transition phase of spatial memory between short-term and long-term memory-as well as to a defect in a novel intermediate phase of LTP between early and late phase (Winder et al., 1997). Since short-term memory and E-LTP on one hand, long-term memory and L-LTP on the other have common properties in that short-term memory and E-LTP do not require protein synthesis whereas long-term memory and L-LTP depend on PKA and the synthesis of new proteins, our results showing a similarity in the behavioral and electrophysiological phenotypes suggest a correlation between the transition from short- to long-term memory and the novel intermediate phase of LTP. Our data also suggest a possible correlation between short-term memory and E-LTP since both are intact in our mice. Finally, our results extend further the correlation suggested between long-term memory storage and L-LTP (Abel et al., 1997). First, both long-term memory and L-LTP are impaired in our mice. Second, both long-term memory and L-LTP defects were rescued when the electrophysiological and behavioral protocols were systematically manipulated.

The Behavioral Rescue of Long-Term Memory Defect by Repeated Training is not seen in CREB and CaMKII-Asp$^{286}$ Mutant Mice Repeated training experiments similar to those carried out here, have been performed in other genetically modified mice. In CREB knockout mice, the deficit in spatial long-term memory observed on the Morris water maze task was attenuated but not fully rescued by increasing the number of daily trials from 1 to 12 with 1 min intertrial interval, or from 1 to 2 with 10 min intertrial interval (Bourtchouladze et al., 1994; Kogan et al., 1996). However, when the interval between daily trials (2 trials per day) was increased to 60 min, performance in mutant mice was improved (Kogan et al., 1996). Further, mice overexpressing a constitutively active form of CaMKII (CaMKII-Asp$^{286}$) were shown to have a spatial memory defect on the Barnes maze with one trial a day. In these mice, no improvement in spatial memory was observed when the number of trials was increased to 10 trials per day with 1 min intertrial interval and further, no improvement in performance was observed within a day across the 10 trials (Mayford et al., 1995; Bach, M, unpublished results). These results suggest that CREB knockout and CaMKII-Asp$^{286}$ mutant mice may have spatial memory defects distinct from the defect observed in mice overexpressing calcineurin (a comparison of performance on the Barnes and Morris water maze is possible since both tasks involve similar cognitive processes). Specifically, CREB mutant mice have a defect in long-term memory although CaMKII-Asp$^{286}$ mutant mice may have a defect in the formation of the short-term memory trace.

In turn, the behavioral deficits observed in mice overexpressing calcineurin and in CREB knockout mice provide an interesting comparison with mice expressing a dominant negative form of the regulatory subunit of PKA, R(AB) (Abel et al., 1997). In both mice overexpressing calcineurin and in R(AB) mutant mice, the PKA pathway is modified. In mice overexpressing calcineurin, the PKA pathway is affected indirectly through an increase in calcineurin activity which is suggested to suppress the PKA pathway (Winder et al., 1997) whereas in R(AB) mice, the PKA pathway is directly affected by the genetic manipulation since the activity of PKA itself is decreased. In CREB knockout mice, the defect appears to be further downstream from PKA since CREB has been implicated in the activation of gene transcription (Brindle and Monminy, 1992; Lee and Masson, 1993). Consistent with these three genetic manipulations acting on complementary sites, all three types of mice have a similar phenotype: short-term memory and E-LTP are normal but L-LTP and long-term memory are impaired.

Experimental Procedures

Barnes Circular Maze

Barnes maze experiments were performed as previously described with animals singly housed for at least three days before the first day of experiment (Bach et al., 1995) Thirty four CN98 mice (mutant: n=17, wild-type: n=17), 58 Tet-CN279 (mutant: n=14, on doxycycline n=20, wild-type: b=13, on doxycycline n=11) were tested on the spatial version of the Barnes maze. Thirteen Cn98 mice (mutant: n=7, wild-type: n=6) were tested on the cued version of the maze. Briefly, the Barnes maze is a circular platform with forty holes at the periphery with an escape tunnel placed under one of the holes. On the first day of testing, each mouse was placed in the tunnel and left there for 1 min. The first session started 1 min after the training trial. At the beginning of each session, each mouse was put in a starting chamber in the center of the maze for 10 s and a buzzer was turned on. The start chamber was then lifted and the mouse was allowed to explore the maze. The session ended when the mouse entered the tunnel or after 5 min elapsed. The buzzer was then turned off and the mouse was allowed to stay in the tunnel for 1 min. In the spatial version of the maze, the tunnel was always located under the same hole which was randomly determined for each mouse. When tested with 4 trials per day, after being removed from the escape tunnel, the mouse was placed into the start chamber on the maze for 30 sec. Thus, each trial was separated by an intertrial interval of 90 sec (60 sec in the escape tunnel and 30 sec in the start chamber). In the cued version of the maze, the mice were tested once a day until they met the criterion of three errors or less on 5 out of 6 consecutive days or until 40 days elapsed. An error was defined as searching a hole that did not have the tunnel beneath it. The order of holes searched and the search strategy employed were manually recorded by an experimenter blind to genotype.

For both the spatial, cued and repeated trials versions, within the CN98 line, a two factor ANOVA (genotype and one repeated measure) was employed. For the Tet-CN279 line a three factor ANOVA (genotype, doxycycline, an one repeated measure) was employed.

Novel Object Recognition Task

Seventy-three mice from the CN98 line (mutant: 30 min n=9, 2 hr n=12, 24 hr n=15; wild type: 30 min n=9; 2 hr n=11; 24 hr n=17) were individually assessed on the novel object recognition task. Three mutant and three wild-type mice were excluded because they displayed a strong preference (Preference index<60) towards the familiar object during both training and testing. During the training trial, mice were placed in a square novel environment (20" long by 8" high) constructed from plywood and painted white with epoxy paint. Two (of three possible) plastic toys (between 2.5 and 3 inches) that varied in color, shape and texture were placed in specific locations in the environment 14 inches away from each other. Two different combinations of object pairs were counterbalanced across genotype and retention intervals. The mice were able to freely explore the environment and objects for 15 min and then were placed back into their individual home cages. Following various retention intervals (30 min, 2 hr or 24 hr), mice were placed back into the environment with two objects in the same locations but now one of the familiar objects was replaced with a third novel object. The mice were then again allowed to freely explore both objects for 15 min. The objects were throughly cleaned with a mild detergent (Roccal, diluted 1:50 in water) before each experiment to avoid instinctive odor avoidance due to mouse's odor from the familiar object. During both training and testing phases, an experimenter blind to genotype recorded the number of seconds spent exploring each individual object for each minute across 15 min. A mouse was considered exploring the object when its head was facing the object at a distance of 1 inch or less or when any part of its body except the tail was touching the object. For the purpose of data analysis we added the total number of seconds spent exploring each object for the first 5 min during the testing phase and calculated a preference index (PI). The amount of time spent exploring the novel object was divided by the amount of time exploring both the novel and familiar objects. The resulting value was divided by 0.5 which represents no preference for either object and that result was then multiplied by 100. A PI greater than 100 indicates preference for the novel object during testing. A PI equal to 100 indicates no preference whereas a PI inferior to 100 indicates a preference for the familiar object. A two factor ANOVA (genotype and one repeated measure) and individual Student t tests for each retention interval were employed to assess the effect of genotype on the PI at the different retention intervals.

Plasmid Construction

Construction of the plasmid used to generate the CN98 mice is described in Winder et al., 1997. For the generation of Tet-CN279 and Tet-CN273 mice, a plasmid was constructed with a cDNA encoding a truncated and active form of the murine calcineurin catalytic subunit Aµ, ΔCaM-AI (provided by S. J. O'Keefe). ΔCaM-AI lacks the autoinhibitory domain and a portion of the calmodulin-binding domain of calcineurin Aα and was shown to be constitutively active in Jurkat T-cells (O'Keefe et al., 1992). A 1.27 kb EcoRI fragment of ΔCaM-AI cDNA was made blunt-ended and subcloned into the EcoRV site of pNN265 vector (provided by N. Nakanishi). The plasmid pNN265 carries upstream from the EcoRV site, a 230 bp hybrid intron that contains an adenovirus splice donor and an immunoglobulin G splice acceptor (Choi et al., 1991) and has a SV40 polyadenylation signal downstream from the EcoRV site. The ΔCAM-AI cDNA flanked by the hybrid intron in 5' and the poly(A) signal in 3' was excised from pNN265 with NotI and the resulting 2.7 kb fragment was placed downstream of tetO promoter from plasmid pUHD10-3 (Gossen and Bujard, 1992) to generate CN279 and CN273 mice (FIG. 22A). The final 3.1 kb tetO-ΔCaM-AI (FIG. 22A) fragment was excised from the vector by NotI digestion. Prior to microinjection, all cloning junctions were checked by DNA sequencing.

Generation and Maintenance of Tet-CN279 and Tet-CN273 Transgenic Mice

The transgenic mice Tet-CN279 and Tet-CN273 were generated by microinjection of the linear construct as previously described (Hogan et al., 1994; Windor et al., 1997). Analysis of founder mice for integration of the transgene was performed by Southern blotting and PCR. The founder mice were backcrossed to C57BL6 F1/J mice to generate the transgenic lines Tet-CN279 and Tet-CN273. To generate Tet-CN279 and Tet-CN273 mice, CN279 and CN273 F1 mice were crossed with CaMKIIα promoter-tTA mice (line B, Mayford et al., 1996) (FIG. 22A). The offspring was checked by Southern blotting or PCT. Transgenic mice were maintained in the animal colony according to standard protocol. Tet-CN279 and Tet-CN273 mice were administered either water or 1 mg/ml doxycycline (in 5% sucrose) in the drinking water at least one week before being used.

Northern Blot

Northern blot analysis was performed as described in. Winder et al., 1997. Briefly, forebrains from adult Tet-CN279 and Tet-CN273 mice administered water or doxycycline were collected and total RNA was isolated by the guanidinium thiocyanate method (Chomzxynski and Sacchi, 1987). Ten micrograms of RNA were denatured, electrophoresed on a 1% agarose gel and transferred to a nylon membrane in 0.4 N NaOH. The membrane was hybridized overnight at 42° C. to a radiolabeled 1.1 kb EcoRV-NotI fragment from pNN265, washed and exposed to film for three days.

RT-PCR

For RT-PCR, total RNA from forebrain was amplified according to the manufacturer's protocol (Gibco BRL). Briefly, cDNA was synthesized from 3 µg of total RNA with the Superscript™ II RT in a 20 µl reaction. Amplification was performed with Taq™ Polymerase (Boehringer Mannheim) for 25 cycles as follows: 94° C. for 30s, 50° C. for 30s and 72° C. for 1 min. The following oligonucleotides were used as primers: 5'-CCTGCAGCACAATAATTTGTTATC-3' (SEQ ID NO: 7) and 5'-AGGTGACACTATAGAATAGGGCC0-3' (SEQ ID NO:8). They produced a 478 bp fragment containing 406 bp of ΔCAM-AI cDNA and 72 bp of pNN265 sequences. Samples were run on a 2% agarose gel then transferred onto Nylon membrane. The membrane was hybridized to $[\alpha^{32}P]$ dCTP-labeled probe specific for pNN265 sequences in the PCR product. Hybridization was performed overnight at 42° C. in 50% formamide, 2× SSC, 1 SDS, 10% dextran sulfate, 0.5 mg/ml denatured salmon sperm DNA. The membrane was washed 10 min at room temperature in 2×SSC, 1% SDS, twice 15 min at 42° C. in 2×SSC, 1% SDS, 0.2× SSC and exposed to film.

In situ Hybridization

In situ hybridization were performed as described in Winder et al., 1997. Briefly, brains from adult Tet-CN279 and Tet-CN273 mice either on or off doxycycline were dissected out and sectioned. Sections were fixed 10 min in 4% paraformaldehyde, rinsed in PBS and dehydrated. Sections were rehydrated, permeabilized, washed and rinsed before being hybridized overnight at 37° C. to a transgene-specific $[\alpha^{35}S]$ATP-labeled oligonucleotide consisting of the sequence 5'-GCAGGATCCGCTTGGGCTGCAGTTG-GACCT-3' (SEQ ID NO: 6). After hybridization, slides were washed, dehydrated then exposed to Kodak Biomax MR film for 2 to 3 weeks.

Phosphatase Assay

Phosphatase assays were performed as described in Winder et al., 1997. Briefly, mice were injected with 5 ml/kg of pentobarbital and decapitated. Hippocampi were dissected out, homogenized in 2 mM EDTA (pH 8), 250 mM sucrose, 0.1% β-mercaptoethanol. Supernatants were incubated at 30° C. for 1 min in presence of the $[\alpha^{32}P]$-labeled [Ala97]-RII peptide and either 0.1 mM calmodulin and 0.66 mM $Ca^{2+}$ or 0.33 mM EGTA. The reaction was stopped and the enzyme activity calculated previously as described (Klee et al., 1983; 1987). The activity was expressed in nmol Pi released/min/mg protein. The protein concentration was determined using the bicinchroninic acid protein assay kit (Sigma). All samples were performed in triplicate.

References for Example 4

Abel, T et al., (1997). "Genetic demonstration of a role for PKA in the late phase of LTP and in hippocampus-based long-term memory," Cell 88: 615-626;

Aggleton, J. P. (1985). "One-trial object recognition by rats," Quart. J. Exp. Psychol. 37: 279-294;

Alvarez, P et al., (1994). "The animal model of human amnesia: Long-term memort impaired and short-term memory intact," Proc. Natl. Acad. Sci. USA 91: 5637-5641;

Bach, M E et al., (1995). "Impairment of spatial but not contextual memory in CaMKII mutant mice with a selective loss of hippocampal LTP in the range of theta frequency," Cell 81: 905-915;

Barnes, C (1979). "Memory deficits associated with senescence: A neurophysiological and behavioral study in the rat," J. Comp. Physiol. 93: 74-104;

Bennett, P C et al., (1996). "Cyclosporin A, an inhibitor of calcineurin, impairs memory formation in day-old chicks," Brain Res. 730: 107-117;

Bliss, T V P et al., (1993). "A synaptic model of memory: long-term potentialtion in the hippocampus," Nature 361: 31-39;

Blitzer, R D et al., (1995). "Postsynaptic CAMP pathway gates early LTP in hippocampal CA1 region," Neuron 15: 1403-1414;

Bourtchouladze, R et al., (1994). "Deficient long-term memory in mice with a targeted mutation of the cAMP-responsive element-binding protein," Cell 79: 59-68;

Brindle, P K et al., (1992). "The CREB family of transcription activators," Curr Opin. Genet. Dev. 2: 199-204;

Cherkin, A, 1969). "Kinetics of memory consolidation: role of amnesic treatment parameters," Proc. Natl. Acad. Sci. USA 63: 1094-1101;

Choi, T et al., (1991). "A generic intron increases gene expression in transgenic mice," Mol. Cell. Biol. 11: 3070-3074;

Chomczynski, P et al., (1987). "Single-step method of RNA isolation by acid gnanidinium thiocyanate-phenol-chloroform extraction," Anal. Biochem. 162: 156-159;

Craik, F I M et al., (1972). "Levels of processing: a framework for memory research," J. Verb. Learn. Verb. Behav. 11: 671-684;

Davis, H P et al., (1984). "Protein synthesis and memory: a review," Psychol. Bull. 96: 518-559;

Ebbinghaus, H. (1885). *Memory: A Contribution to Experimental Psychology*. (Dover, New York);

Eichenbaum, H (1995). "The LTP-memory connection," Nature 378: 131-132;

Ennaceur, A et al., (1988). "A new one-trial test for neurobiological studies of memory in rats. I: Behavioral data," Behav. Brain Res. 31: 47-59;

Frieder, B et al., (1982). "Memory consolidation: further evidence for the four-phase model from the time courses of diethylthiocarbamate and ethacrinic acid anmesias," Physiol. Behav. 29: 1071-1075;

Gibbs, M E et al., (1977). "Psychobiology of memory: towards a model of memory formation," Biobehav. Rev. 1: 113-136;

Gossen, M et al., (1992). "Tight control of gene expression in mammalian cells by tetracycline-responsive promoters," Proc. Natl. Acad. Sci. USA 89: 5547-5551;

Hogan, B et al., (1994). *Manipulating the mouse embryo, 2nd Edition. (Cold Spring Harbor Press: Cold Spring Harbor, N.Y.);*

Huang, Y Y et al., (1994). "Recruitment of long-lasting and protein kinase A-dependent long-term potentiation in the CA1 region of hippocampus requires repeated tetanization," Learn. Mem. 1: 74-82;

Huang, Y Y et al., (1996). "Long-lasting forms of synaptic potentiation in the mammalian hippocampus," Learn. Mem. 3: 74-85;

James, W (1890). *The Principles of Psychology* (New York: Holt);

Klee, C B et al., (1983). "Isolation and characterization of bovine brain calcineurin: a calmodulin-stimulated protein phosphatase," Methods Enzymol. 102: 227-244;

Knight, R. T. (1996). "Contribution of human hippocampal region to novelty detection," Nature 383: 256-259;

Kogan, J H et al., (1996). "Spaced training induces normal long-term memory in CREB mutant mice," Curr. Biol. 7: 1-11;

Lee, K A et al., (1993). "Transcriptional regulation by CREB and its relatives," Biochem. Biophys. Acta. 1174: 221-233;

Mandel, R. J. et al., (1989) "Enhanced detection of nucleus basalis nagnocellularis lesion-induced spatial learning deficit in rats by modification of training regimen," Behav. Brain Res. 31: 221-229;

Mayford, M et al., (1995) "CaMKII regulates the frequency-response function of hippocampal synapses for the production of both LTD and LTP," Cell 81: 891-904;

Mayford, M et al., (1996). "Genetic control of $Ca^{2+}$/calmodulin-dependent protein kinase activity in hippocampus and amygdala: Regulated disruption of explicit and implicit memory storage," Science 274: 1678-1683;

McGaugh, J L et al., (1968) "A multi-trace view of memory storage. Recent advances in learning and memory," (Roma Accademia Nazionale dei Lincei: Rome);

Mishkin, M (1978). "Memory in monkeys severely impaired by combined but not by separate removal of amygdala and hippocampus," Nature 273: 297-298;

Mumby, D G et al., (1995). "Memory deficits following lesions of hippocampus or amygdala in rat: Assessment by an object-memory test battery," Psychobiology 23: 26-36;

Myhrer, T (1988a). "Exploratory behavior and reaction to novelty in rats with hippocampal perforant path system disrupted," Behav. Neurosci. 102: 356-362;

Myhrer, T. (1988b). "The role of medial and lateral hippocampal perforant path lesions and object distinctiveness in rats reaction to novelty," Physiol. Behav. 42: 3711-3717;

O'Keefe, S J et al., (1992). FK-506 and CsA-sensitive activation of the interleukin-2 promoter by calcineurin," Nature 357: 692-694;

Overman, W H et al., (1990). "Picture recognition versus picture descrimination learning in monkeys with medial temporal removal," Exp. Brain Res. 79: 18-24;

Phillips, R R et al., (1988). "Dissociation of the effects of inferior temporal and limbic lesions on object discrimination learning with 24-h intertrial intervals," Behav. Brain Res. 27: 99-107;

Reed, J M et al., (1997). "Impaired recognition memory in patients with lesions limited to the hippocampal formation," Behav. Neurosci. 111: 1-9;

Rosenzweig, M R et al., (1993). "Short-term, intermediate-term and long-term memories," Behav. Brain Res. 57: 193-198;

Scoville, W B et al., (1957). "Loss of recent memory after bilateral hippocampal lesions," J. Neurol. Neurosurg. Psychiatry 20: 11-21;

Squire, L (1987). Memory and Brain (New York: Oxford University Press);

Squire, L (1992). "Memory and the hippocampus: A synthesis from findings with rats, monkeys and humans," Psychol. Rev. 99: 195-231;

Thomas, M J et al., (1996). "Activity-dependent β-adrenergic modulation of low frequency stimulation induced LTP in the hippocampal CA1 region," Neuron 17: 475-482;

Tsien, J Z et al. (1996). "The essential role of hippocampal CA1 NMDA receptor-dependent synaptic plasticity in spatial memory," Cell 87: 1327-1338;

Tully, T et al., (1996). "Genetic dissection of consolidated memory in Drosophila," Cell 79: 35-47;

Tulving, E et al., (1996). "Novelty nad familiarity activations in PET studies of memory encoding and retrieval," Cereb. Cortex 1: 71-79;

Weiskrantz, L (1970). *A long-term view of short-term memory in Psychology. Short-term changes in neural activity and behavior*. (Cambridge University Press: England);

Wickelgren, W A (1973). "The long and the short of memory," Psychol. Bull. 80: 425-432;

Zhao, W Q et al., (1994). "Effect of PKC inhibitors and activators on memory," Behav. Brain Res. 60: 151-160;

Zhao, W Q et al., (1995a). "The impairment of long-term memory formation by the phosphatase inhibitor okadaic acid," Brain Res. Bull. 36: 557-561;

Zhao, W Q et al., (1995b). "Inhibitors of cAMP-dependent protein kinase impair long-term memory formation in day-old chicks," Neurobiol. Learning Memory 64: 106-118;

Zola-Morgan, S et al., (1985). "Medial temporal lesions in monkeys impair memory on a variety of tasks sensitive to human amnesia," Behav. Neurosci. 99: 22-34.

Example 5

Memory and Behavior: a Second Generation of Genetically Modified Mice

[The Figures corresponding to the figure legends at the end of this example may be found in Mayford et al., Current Biology 1997; R580-R589.]

Introduction

One of the insights of modern cognitive neural science is that memory is not unitary but has at least two forms; implicit (or nondeclarative) and explicit (or declarative) (Squire et al., 1996). Explicit memory refers to the conscious recollection of information about facts and events involving places, people objects. Implicit memory refers to the unconscious use of information relating to various habits and perceptual and motor strategies, and to the memories for simple forms of learning in Aplysia and Drosophila has provided some initial understanding of the molecular mechanics that contribute to implicit memory storage (Carew, 1996; Martin et al., 1996; Tully et al., 1996). By contrasts, although is now has been four decades since Scoville and Milner (Scoville et al., 1957) first established that explicit forms of memory require the medical temporal lobe system of the brain, much less is known of the mechanisms that contribute to these forms of memory storage.

Studies of the medical temporal lobe system have been hindered by its complexity (FIGS. 1, 2). In humans, this system consists of several interconnected cortical structure—including multimodal association areas in the neocortex, the perirhinal and entorhinal cortices, the dentate gyrus, the hippocampus and entorhinal cortices, the dentate gyrus, the hippocampus and the subicular complex—each of which is thought to be important for aspects of explicit memory storage. To study the function of these individual regions in human would required many patients with very specifics brain lesions. Fortunately, recent anatomical and behavioral studies indicate that, even though there are some differences in the detail there is a striking similarity between the organization of the medial temporal lobe system in human, non-human primates, and simpler mammals such as rats and mice (FIG. 1) [Burwell et al., 1996]. Moreover, even simple mammals such as the mouse require the medial temporal system for the storage of memory about places and objects, and this type of memory has several of the characteristics, the integration not simply of one but of a multiplicity of distal cues. Studying a form of explicit memory in mice has the advantage that it makes this cognitive process accessible to a genetic approach.

Of the several structures of the medical temporal lobe in the mouse, the hippocampus as proven to be most suitable, and the most accessible, target for a rigorous genetic analysis of aspects of explicit memory storage. Each of the three major synaptic pathways within the hippocampus (FIGS. 2) is well define anatomically and is capable of undergoing long-term potentiation (LTP), an activity-dependent from of plasticity thought to be important for memory storage (Bliss et al., 1973; Bliss et al., 1993). Lesions of the hippocampus interfere with the formation of the new spatial memories—memory for places—which is particularly well studied in rodents (Morris et al., 1982). In the freely behaving animal, the pyramidal cells of the hippocampus—the cells that give rise to LTP—encode spatial locations in their action potential firing patterns. Pyramidal cells are therefore 'place cells' that fire only when an animal occupies a particular location in its environment (O'Keefe et al., 1971). These findings raise a serial of questions that have been central to studies of spatial memory during the past few years. What are the molecular mechanism of LTP? Is LTP important for spatial memory storage? If so, how does LTP moderate the properties of place cell to give rise to spatial memory storage? Does it do so by acting during the initial formation or subsequent stabilization of place fields?

In the review, we limit ourselves to two areas. First, we look at how new techniques for producing temporally regulated and anatomically restricted generic modification in the mouse have been used to examine the mechanisms of LTP and the role it plays in spatial memory. Second, we consider a complementary set of studies in genetically modified mice that use single-unit recording of place cell in the hippocampus. Here, the attempt is to examine the relationship of LTP to the cognitive map of space in the hippocampus. In this section of the review we will ask whatever LTP is required for the information of place fields and for their stability over time. If so, how do these properties of place cells relate to the acquisition and maintenance of spatial memory?

A First Generation of Genetically Modified Mice

With the development of genetically modified mice, it became possible to ask how the perturbation of a single gene affects LTP, on the one hand, and whole animal behavior, on the other. The initial studies of spatial memory in genetically modified animals (Silva et al., 1992, p. 201, 206; Grant et al., 1992) took as their starting point several important and well documented finding from earlier pharmacological studies about the sequence of steps involved in the induction of LTP (Bliss et al., 1993). These studies focused on one of the key pathways in the hippocampus, the Schaffer collateral pathway between the axons of the pyramidal cells of the CA3 region and the postsynaptic target cells in the CA1 region. Earlier research had shown that, in this pathway, the initiating step for L.P. involves the release of glutamate from the presynaptic terminals of the CA3 neurons. This leads to the activation of N-methyl-D-aspartate (NMDA) receptors on the postsynaptic CA1 pyramidal cells, resulting in an influx of $Ca^{2+}$ into the postsynaptic neuron. The $Ca^{2+}$ signal, in turn, activates a number of second messengers kinase, including $Ca^{2+}$/calmodulin-dependent protein kinase II (CaMKII), protein C, protein kinase A and one or more tyrosine kinase.

Building upon these pharmacological findings, homologous recombination in embryonic stem cells was used to delate in mice the genes encoding the α subunit of CaMKII (CaMKIIα) and the tyrosine Fyn (Silva et al., 1992, p. 201, 206; Grant et al., 1992). In each case, deletion of the target gene led to a defect in L.P. and to an impairment in explicit spatial memory. Thus, the initial genetic studies not only supported the earlier pharmacological work in showing that both CaMKIIα and Fyn seem to be involved in the signal transduction pathway important for L.P., but also showed that interfering with L.P. affects memory.

A Second Generation Approach

Although these results illustrated the potential usefulness of genetic approaches for analyzing synaptic plasticity and for relating it to explicit memory, it also was clear that there were limitations that needed to be overcome. For example, to understand the role in memory storage of L.P. within a given component of the medial temporal lobe system, such as the hippocampus, the generic change must be restricted to that specific anatomical component. The genetic change also needs to be regulated in a temporal manner, to exclude possible developmental defects and to ensure that the physiological or behavior phenotype reflects a change in the functioning of the adult brain. To understand the effects of the genetically induced alterations in L.P. on memory, the changes in L.P. in the mutant mice must be related to changes in neuroma activity in freely behaving animals. Within the last year, substantial progress has been made in each of these three areas.

The CaMKIIα Promoter

Genetically modified mice come in two major varieties, termed 'knockouts' and 'transgenics'. In knockout mice, the endogenous gene of interest is specifically deleted by homologous recombination in embryonic stem cells. The gene of interest is therefore deleted in al cells of the body and is absent for the entire life of the animal. Thus, conventional knockouts lack both anatomical restrictions and temporal regulation. In transgenic mice, an additional gene—the transgene—is added to the mouse genome by the microinjection of DNA into the oocyte. The transgene ma by the wild-type version of a gene—in which case the gene product is overexpressed—or it may be a mutant version of the gene, designed to enhance or suppress function. The transgene carries with it an appropriate promoter element that directs the anatomical and temporal pattern of its expression. By selecting the appropriate promoter, the anatomical and temporal expression of the genetic change can be controlled, at least partially. As many molecules are likely to be used during development and learning (Martin et al., 1996), the promoter should drive transgene expression in the critical medial temporal lobe structures, with the onset of expression occurring late in brain development. Otherwise, one cannot be certain that one is examining learning and memory specifically without interfering with development.

As first step in this directions, we isolated the promoter of CaMKIIα gene (Mayford et al., 1996), which drives expression of a transgene specifically in forebrain structures, especially the hippocampus. The promoter is active only in neurons and not in glial cells (FIGS. 3a), and the onset of expression occurs at a relatively late developmental stage, usually the first to second postnatal week (Kojima et al., 1997). As discussed below, the anatomical sites at which gene expression occurs are restricted further when the CaMKIIα promoter is combined with other regulatory elements such as the Crerecombinase or the tetracycline transactivator (tTA) (Mayford et al., 1996; Tsien et al., 1996). These features of the CaMKIIα promoter have been crucial in developing the second generation of genetic approaches to behavior in mice and illustrate, as we discuss below, that the future efforts will require the isolation of other promoters that are specific for each of the components of the medial temporal lobe.

Regional Restriction: the CaMKIIα Promoter and Cre Recombinase

The most dramatic evidence for anatomical restriction of the CaMKIIα promoter emerged from collaborative experiments with Susumu Tonegawa and his colleagues in which we applied to the brain the Cre-loxP system, a system developed by Klaus Rajewski's group for B-Cell-specific gene deletion (Gu et al., 1994; Lakso et al., 1992). This system uses the Cre recombinase, a site-specific recombinase derived from P1 bacteriophage that catalyzes recombination between 34 base-pair loxP recognition sequence sequences (Abremski et al., 1984; Sauer et al., 1988). When two appropriately oriented loxP sites flank a piece of DNA, Cre-mediated recombination leads to the deletion of DNA between the loxP sites.

Two different types of mice are required to obtain Cre-loxP-mediated gene deletion. The first is transgenic mouse in which a promoter—in this case the CaMKIIα promoter—is used to drive expression of the Cre recombinase in a specific subset of neurons in the brain (with no effect, as loxP target sites are absent from the genome). In the second type of mouse. LoxP sites are introduced by homologous recombination into the endogenous gene of interest (the gene to be "knocked out") such that they flank an exon critical for the gene's function. The loxP sites are placed in intros so that they do not alter the normal function of the gene and do not produce a phenotype in the absence of Cre recombinase. When, through mating, the Cre recombinase transgene and the loxP-flanked endogenous gene are introduced into the same mouse, the portion of the endogenous gene between the loxP sites will be deleted by the Cre recombinase. This deletion will lead to a knockout of the loxP-flanked gene only in neurons that express the Cre recombinase. In cells that do not express Cre recombinase, the loop-flanked gene remains intact and functional (FIG. 4a).

Surprisingly, when expression of the Cre recombinase was driven by the CaMKIIα promoter (Tsien et al., 1996), the Cre-mediated deletion was restricted to just CA1 neurons of the hippocampus in three of the first five lines (FIGS. 4b,c). The molecular basis for the CA1 restriction of Cre-mediated recombination is still unclear. Forebrain neurons outside of CA1 also expressed cre recombinase, albeit at a lower level, but this expression did not lead to effective gene deletion Tsien et al., 1996. This suggest that a high level of Cre expression is required to achieve recombination, and in many line s of mice this high threshold level of expression is achieved only in the CA1 neurons.

The CaMKIIα-Cre-loxP system was then used by the Tonegawa laboratory to knock-out the NMDA receptor 1 ($R_1$) gene in a CA1-restricted manner Tsien et al., 1996, p. 1327). The mutant mice had a complete loss of LTD in Ca1 as well as a profound defect in spatial memory, showing that NMDA receptor-mediated transmission in the CA1 neurons of the hippocampus is critical for explicit memory formation and strengthening the idea that L.P. in the Schaffer collateral pathway is important from memory formation. These results are complementary to earlier findings that selective interference with mossy fiber L.P. between the granule cells and the CA3 neurons has no effect on spatial memory (Huang et al., 1995).

The CaMKIIα-Cre-loop approach solves one of anatomical restrictions—but there is still the possibility that the impairment is spatial memory observed in these mice results from some development abnormality caused by prolonged absence of the NMDA $R_1$ gene. Although this is unlikely, given the late onset of expression of the CaMKIIα promoter, we turned to a technology for obtaining temporal regulation of transgene expression.

Temporal Restriction: the CaMKIIα Promoter and tTA

In a parallel series of experiments designed to obtain temporal as well as anatomical control over the expression of a transgene, we used the tetracycline-regulatable tTA system developed by Herman Bujard's group (Gossen et al., 1992; Furth et al., 1994). The tetracycline repressor (tetR) is a protein from the *Escherichia coli* Tn10 tetracycline resistance operon that recognizes and binds tetO, a specific DNA sequence in the operon. The interaction of tetR with its tetO DNA target is disrupted by low levels of the antibiotic tetracycline and its derivatives. By fusing the tetR protein to the transcription activation domain of VP16, a herpes simplex virus protein, Bujard produced a regulatable eukaryotic transcription factor termed the tetracycline transactivator (tTA). When tetO sequences, along with a minimal eukaryotic promoter element, are placed next to the target gene of interest, the tTA transcription factor can activate the expression of the tetO-linked gene in eukaryotic cells. When exposed to low levels of the tetracycline analog doxycycline, however, the binding of tTA to tetO is prevented and transcription of the tetO-linked gene is turned off.

Figure 5A:
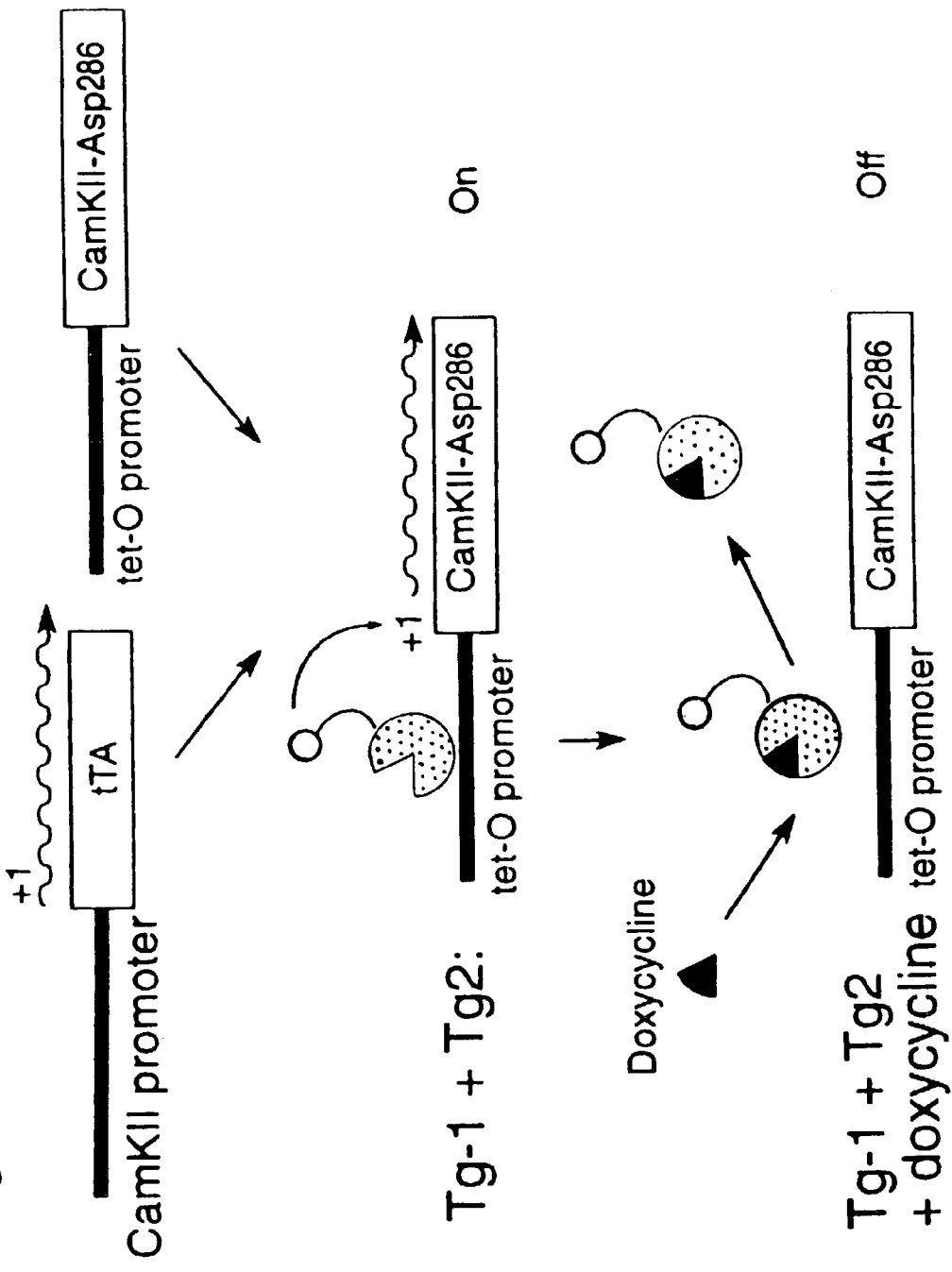
FIGS. 5A-5B. Regulation of the CaMKII-Asp286 transgene with the tTA system.
Figure 5B:
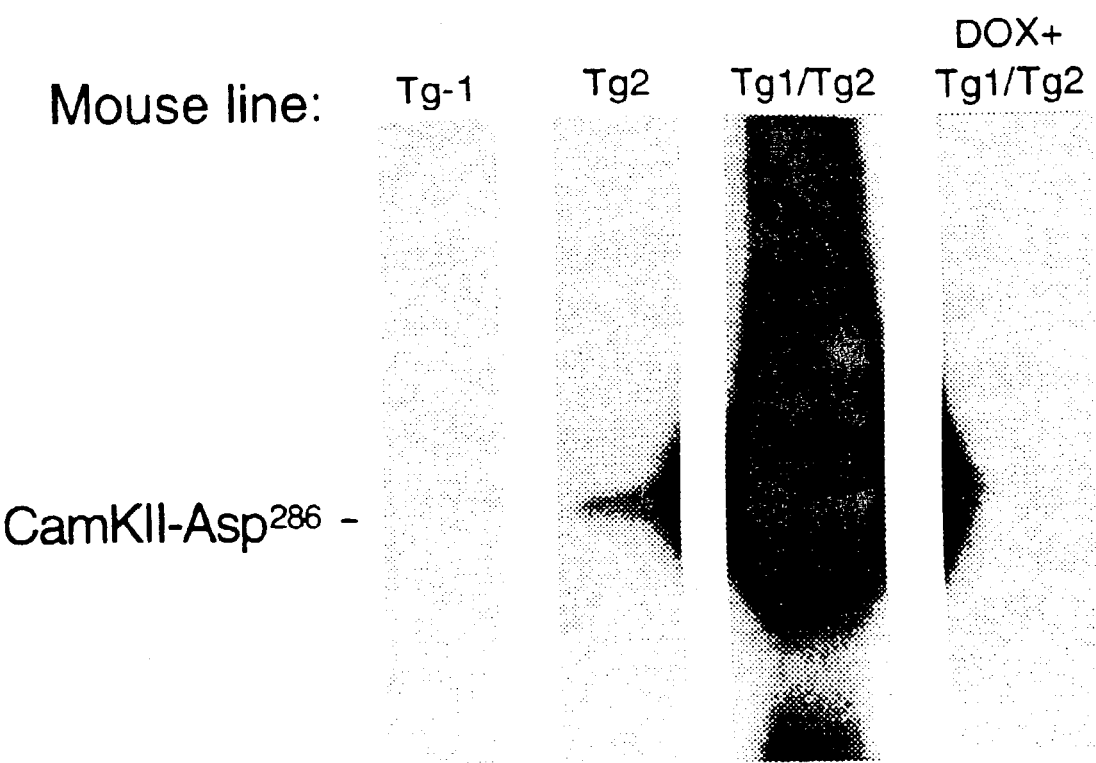

To obtain doxycycline regulatable transgene expression, two different types of transgenic mice are required (FIG. 5a). In the first line of mouse, the CaMKIIα promoter is used to drive expression of the tTA gene in forebrain neurons (with no effect, as there are no endogenous tetO sites). The second line of transgenic mouse carries a tetO site linked to the particular gene of interest, in this case a constitutively active form of CaMKIIα (CaMKII-Asp286), whose properties we consider below (Mayford et al., 1996). When both transgenes are introduced into a single mouse through mating, the CaMKII-Asp286 transgene is expressed only in the forebrain neurons that express tTA. The strong expression of the CaMKII-Asp286 gene can now be suppressed by administering doxycycline to the mice in their drinking water.

We selected CaMKII-Asp 286 as a transgene for study because, as discussed above, the initial pharmacological and genetic studies pinpointed CaMKII as a key molecular mediator of synaptic plasticity and memory formation. Pharmacological blockade of CaMKII prevents LTP (Malinow et al., 1989; Miller et al., 1988), and deletion of the CaMKIIα gene in mice led to a loss of LTP and spatial memory (Silva et al., 1992, p. 201; Silva et al., 1992, p. 206). Moreover, earlier biochemical studies revealed several interesting features of this kinase (Miller et al., 1986). In the absence of $Ca^{2+}$/calmodulin, CaMKII shows little or no enzymatic activity. After a brief pulse of $Ca^{2+}$/calmodulin, full enzymatic activity is induced. When $Ca^{2+}$ levels fall, however, rather than returning to the low basal level of activity as seen before the $Ca^{2+}$ pulse, the enzyme remains substantially active even in the complete absence of $Ca^{2+}$.

This persistent switch from a $Ca^{2+}$-dependent to a $^{2+}Ca$-independent state represents a form of biochemical memory for the $Ca^{2+}$ signal. Because LTP is, in essence, a long-lasting biochemical alteration resulting from a brief $Ca^{2+}$ signal, Lisman (1994) suggested that the switch of CaMKII from the $Ca^{2+}$-dependent to the $Ca^{2+}$-independent state represents the biochemical mechanism of LTP.

To test Lisman's model, it became important to ask whether turning on CaMKII was sufficient, by itself, to produce LTP. The conversion of CaMKII from the $Ca^{2+}$-dependent to the $Ca^{2+}$-independent state requires the phosphorylation of a single amino acid residue, threonine 286 (Schworer et al., 1988; Miller et al., 1988; Thiel et al., 1988). Mutation of this residue to aspartate mimics the effects of autbphosphorylation and produces a $Ca^{2+}$-independent enzyme (Fong et al., 1989; Waldmann et al., 1990). The mutant CaMKII-Asp286 kinase now provides a molecular genetic means for increasing the baseline activity of CaMKIIα.

In initial studies, we used the CaMKIIα promoter to express CaMKII-Asp286 and examined the effect on LTP and memory (Mayford et al., 1995; Bach et al., 1995). We found that the activation of CaMKIIα alone was not sufficient to switch on LTP; rather, CaMKIIα seems to act as a regulator of the frequency of synaptic activity at which LTP or long-term depression (LTD) will be produced. When the levels of $Ca^{2+}$-independent CaMKIIα were elevated in CaMKII-Asp286 transgenic mice to levels greater than that produced during LTP, the stimulation frequencies necessary to produce LTP or LTD were altered. In wild-type animals, 1 Hz stimulation produces LTD, whereas 5 Hz or 10 Hz produce a modest amount of LTP and 100 Hz produces maximal LTP. In the CaMKII-Asp286 transgenic mice, 100 Hz LTP is normal, while in the 5-10 Hz range of stimulation LTD is favored over LTP.

The shift from LTP in the wild-type to LTD in the mutant in the 5-10 Hz frequency range is particularly interesting because there is an endogenous 5-10 Hz oscillation in neuronal activity (the "theta-rhythm") in the hippocampus of rodents. It has been suggested that patterned neuronal activity in the theta-frequency range represents the endogenous mechanism for inducing LTP in the hippocampus during spatial learning (Staubli et al., 1987; Huerta et al., 1995). If this idea is correct, then mice that lack LTP in the theta frequency might show impaired spatial memory. Consistent with this idea, analysis of the CaMKII-Asp286 transgenic mice showed that they did not have a severe deficit in spatial memory function.

These experiments did suffer, however, from both of the problems discussed earlier: possible developmental abnormalities and lack of precise anatomically restricted expression. To address the developmental problems, we used the tTA system to express CaMKII-Asp286 (Mayford et al., 1996). When the transgene expression was suppressed by doxycycline, the memory impairment, evident in the spatial memory task described in FIG. 5b, was completely reversed—the transgenic mice performed as well as wild-type mice. In parallel, the suppression of transgene expression also reversed the deficit in theta-frequency LTP observed in the hippocampus. These experiments with regulated gene expression therefore showed that both the behavioral and electrophysiological effects of the CaMKII-Asp286 transgene are the direct consequence of the acute elevation in CaMKIIα activity, and are not the effect of an anomaly in neuronal circuitry caused by expression of the transgene during development.

Combining Temporal and Regional Restriction

In the course of this work, we found that, in one line of mice in which the CaMKIIα promoter was combined with tTA, there was little or no expression of the CaMKII-Asp286 transgene in the neocortex (FIG. 3a). The expression was limited to certain deep structures of the forebrain—the subiculum, striatum, amygdala and hippocampus. Within the hippocampus, expression of the transgene was strong in the CA1 region, which contains the postsynaptic cells of the Schaffer collateral pathway, but was not expressed in the CA3 region, which contains the presynaptic neurons of this pathway (FIG. 3b).

This line of mice could therefore be used to ask whether the CaMKII-Asp286 transgene had to be expressed in the presynaptic CA3 neurons to produce the deficit in 5-10 Hz LTP, or whether it was sufficient to restrict expression to the postsynaptic CA1 neurons. As the transgene expression was temporally regulatable, we could also ask whether its expression in the CA1 neurons impaired LTP and memory by interfering directly with normal plasticity in the adult brain, or whether it did so through a disruption of neuronal development. We found that reversible expression of the CaMKII-Asp286 transgene—limited to the CA1 neurons—was sufficient to reversibly impair LTP in the 5-10 Hz theta frequency. Moreover, we found that expression of the transgene in the deep structures of the forebrain was sufficient to impair spatial memory reversibly.

Although the regional restriction achieved by combining the CaMKIIα promoter with tTA is not as limited as that achieved by combining the CaMKIIα promoter with Cre, the former is nevertheless informative, especially in physiological terms where we have been able to examine the relative contribution of the pre- and post-synaptic element of a monosynaptic connection. Moreover, this restriction, albeit limited, carries with it the great benefit of also being regulatable, assuring that the phenotype is due to direct effects in the adult brain and is not due to developmental abnormalities.

Spatial Memory in the Adult Mouse: the Role of-LTP and Place Fields

The study of neuronal mechanisms of explicit memory requires not only the production of highly defined molecular lesions in the brain, but also an analysis of the physiological and plastic properties of neurons in freely behaving animals when they are challenged to learn and recall new information. Do the modifications of connection strength induced by LTP occur naturally in an intact animal doing a spatial memory test? If so, haw are these modifications reflected in the firing properties of neurons within the network that controls the behavior under study?

As first shown by O'Keefe and Dostrovsky (1971), the pyramidal cells of the hippocampus that are stimulated artificially during LTP experiments are, in the freely behaving rat, "place cells" that encode spatial location in their action potential firing patterns. A given place cell will fire only when an animal occupies a particular location in its environment. When the animal moves to a different location in the same environment, other place cells fire. If the animal enters a new environment, the selection of place cells from among the pyramidal cells changes. These new place cells form within a matter of minutes and remain stable for weeks (Bostock et al., 1991).

These results have given rise to the idea that the hippocampus contains a map-like representation of the animal's current environment, and that the firing of place cells in the CA1 and CA3 regions signal the animal's moment-to-moment location within the environment. This map is interesting because it is the best example in the brain of a complex internal representation, a true cognitive map. It differs in several ways from the classical sensory maps found, for example, in the visual or somatosensory systems. Unlike sensory maps, the map of space is not topographic because neighboring cells in the hippocampus do not represent neighboring regions in the environment. Moreover, the firing of place cells can persist after salient sensory cues are removed and even in the dark. Thus, although the activity of a place cell can be modulated by sensory input, in contrast to neurons in sensory system, activity is not dominated by such sensory input (Muller, 1996).

If hippocampal neurons encode an internal representation of space that is used to solve memory problems, how is this spatial map altered when LTP is interfered with genetically? To address this issue, we examined the positional firing properties of pyramidal neurons in the hippocampus of mice expressing the Ca-MKII-Asp286 transgene (Rotenberg et al., 1996). The experimental arrangement for studying place cells is shown in FIG. 6. A mouse is fitted with a recording electrode implanted in the hippocampus. Action potential firing from a single hippocampal neuron can be reliably recorded from the electrode for a period of several weeks. The mouse is placed in a cylindrical arena and allowed to explore for 16 minutes while the animal's location and the firing of the hippocampal neuron are simultaneously recorded. As shown in FIG. 6b, the firing rate of the neuron when the mouse is at each location in the cylinder can be plotted. These studies show that different cells have fields in different parts of the apparatus and that place fields are found with about equal density everywhere in the apparatus—reinforcing the idea that the place cells are elements of a map (Muller et al., 1987).

Sequential recordings of place cells from wild-type mice in a familiar environment show, that their fields are stable (FIG. 7). Firing fields also form in CaMKII-Asp286 transgenic mice, indicating that LTP in the 5-10 Hz range is not required for hippocampal pyramidal cells to transform sensory information into spatial information. However, the place cells of CaMKII-Asp286 transgenic mice have several deficits. First, the firing fields are less well-defined, appearing fuzzier, with the boundaries between high and low firing rate regions less distinct. Second, place cell firing rates in the transgenic mice are reduced. This effect could be a direct consequence of the abnormal generation of LTD instead of LTP in response to stimulation in the 5-10 Hz range. Third, the place cells in transgenic mice are unstable. When a place cell is recorded from a wild-type mouse, and the mouse is then removed from the recording environment for a period of time and then retested, the place cells firing field remains remarkably stable (FIG. 7). Thus, when the animal is repeatedly exposed to the same environment, as in a spatial problem-solving paradigm, information gained about that environment remains stable. However, when a similar experiment is performed on a CaMKII-Asp286 mouse, the place field is unstable and in a different location during different sessions (FIG. 7).

Which defect accounts for the deficits in spatial memory? By themselves, the less precise firing fields and the lower firing rates of place cells in CaMKII-Asp286 transgenic mice might account for spatial memory deficits by providing the animal with a less precise representation of its environment. Nevertheless, given hundreds of thousands of place cells, it is not clear that the map of the environment would be so degraded as to be unable to support normal navigation. However, a deficit in the stability of place cells would severely impair an animal's ability to learn spatial tasks—information gained on a given training session would be lost, and on a subsequent training session it would be as if the animal was presented with the task for the first time. If the place cells are the building blocks of a cognitive map, the instability of place cells would suggest that the map itself is unstable and therefore not suitable for the efficient calculation of navigational paths. In fact, the deficit at the neuronal level is very similar to the memory deficits seen in human patients with medial temporal lobe lesions. A classic example is patient H. M., for whom explicit information on each session of a multi-session learning test is like the first: he does not remember that the experiment took place previously, or even recognize the psychologists that administered the test.

In a parallel set of studies, Wilson and colleagues (1996) investigated the positional firing properties of CA1 pyramidal cells in mice with a CA1-specific knockout of the NMDA R1 subunit. These cells had stable firing fields, but the fields were larger than those in wild-type mice and, instead of having a single peak, the firing fields had multiple peaks. Furthermore, CA1 place cells with firing fields that overlapped did not tend to fire together in time (in significant temporal firing covariance). Thus, up to now, the properties of place cells have been examined in two types of mice with genetically altered LTP in the CA3-CA1 Schaffer collateral pathway. The results indicate that LTP is not required for the transformation of afferent information in place fields. Rather, LTP is needed for the fine-tuning of higher-order place field properties such as stability and synchronous firing. It is these features of place fields that seem to be necessary for spatial memory.

Overall view

The study of explicit memory storage has clearly benefited from the use of new technologies to produce genetically modified mice. First by using the CaMKIIα promoter, it has been possible to drive transgene expression in the medial temporal system and, in particular, in the neurons of the hippocampus. Second, by combining the CaMKIIα promoter with Cre recombinase, it has become possible to restrict expression to the CA1 region of the hippocampus and to delete genes in this region. Third, by combining the CaMKIIα promoter and the tetracycline-responsive tTA transcription factor, it has become possible to run transgenes off and on in limited groups of neurons in the brain. Finally, the analysis of the firing properties of place cells in the genetically modified mice adds a new dimension to our understanding of the cellular and molecular basis of memory. For example, a change in a single amino acid causes CaMKII, an enzyme important in $Ca^{2+}$ signal transduction, to become constitutively active. This elevation in the activity of CaMKIIα leads to a deficit in the LTP response to 5-10 Hz stimulation, presumably by reducing the ability to store information at synapses between cells that signal the spatial location of an animal. This loss of storage capacity in the spatial map may destabilize the positional firing patterns of place cells and cause the severe deficit in performance on spatial memory tasks in CaMKII-Asp186 transgene mice.

The combination of new genetic techniques with analysis of synaptic function in vitro and of neuronal firing patterns in vivo provides a powerful set of tools for the study of mammalian behavior—from the level of a single molecule to memory in the whole animal. However, as the complexity of the circuitry of the medial temporal lobe system indicates (FIG. 2), in studying explicit memory storage we are only at the foothills of a great mountain range. The next step is to advance these methodologies further. One needs to be able to evaluate the contribution to memory storage of each of the major regions of the hippocampus (FIG. 2). Do these regions store different types of information or do they process the same type of information, but differ in their role in memory per se? Are some regions specialized in encoding, consolidation or storage, while others are specialized in retrieval?

Answers to these questions will require still further generation of genetically modified mice using promoters to restrict expression to the various individual regions of the medial temporal lobe. In addition, attempts are underway to extend the tTA system so as to make it more useful in furthering the genetic analysis of behavior. For example, it might be possible to produce graded changes in the level of transgene expression by administering lower levels of doxycycline to the animals. Also, Bujard's group (Gossen et al., 1995) has generated a mutant of the tTA molecule that displays a reversed response to doxycycline. This reversed tTA allows one to keep expression of a transgene off during development, then rapidly turn it on by administering doxycycline to the adult mouse (Kistner et al., 1996 and authors' unpublished observations) The use of such an inducible system combined with the Cre recombinase should provide a way for inducibly knocking genes out in the brain. Other systems for regulating gene expression and gene deletion are also being explored (Feil et al., 1996; No et al., 1996). With appropriate promoters, these technologies should prove generally useful for the selective genetic modification of precisely defined neuronal circuits controlling behavior. Moreover, this approach should allow one to explore not only the individual genes but also the genetic pathways important for LTP.

References For Example 5

Squire, L R, Zola, S M: "Memory, memory impairment, and the medial temporal lobe," Cold Spring Harbor Symp. 1993 61: 183-185;

Carew, T J: "Molecular enhancement of memory formation," Neuron 1996, 16: 5-8;

Martin, K C, Kandel, E R: "Cell adhesion molecules, CREB, and the formation of new synaptic connections," Neuron 1996, 17: 567-570;

Tully, T, Bolwig, G, Christensen, J, Connolly, J, DelVecchio, M, DeZazzo, J, Dubnau, J, Jones, G, Pinto, S, Regulski, M et al., "A return to genetic dissection of memory in Drosophila," Cold Spring Harbor Symp. 1996, 61: 207-218;

Scoville, W B, Milner, B: "Loss of recent memory after bilateral hippocampal lesions,: J. Neurol. Neurosurg. Psychiatry 1957, 20: 11-21;

Burwell, R D, Suzuki, W A, Insausti, R, Amaral, D G: "Some observations on the perirhinal and parahippocampal cortices in the rat, monkey and human brains," In Perception, Memory and Emotion: Frontiers in Neuroscience, Edited by Ono, T, McNaughton, B L, Molotchnikoff, S, Rolls, E T, Nishigo, H. Pergamon Press: Elsevier Science Ltd. 1996;

Bliss, T V, Lomo, T: "Long-lasting potentiation of synaptic transmission in the dentate area of the anaesthetized rabbit following stimulation of the perforant path," J. Physiol 1973, 232: 331-356;

Bliss et al., "A synaptic model of memory: long term potentiation in the hippocampus," Nature 1993, 361: 31-39;

Morris, R G et al., "Place navigation impaired in rats with hippocampal lesions," Nature 1982, 297:681-683;

O'Keefe et al., "The hippocampus as a spatial map. Preliminary evidence from unit activity in the freely-moving rat," Brain Res. 1971, 34: 171-175;

Silva, A J et al., "Deficient hippocampal long-term potentialtion in alpha-calcium-calmodulin kinase II mutant mice," Science 1992, 257: 201-206;

Silva, A J et al., "Impaired spatial learning in alpha-calcium-calmodulin kinase II mutant mice," Science 1992, 257: 206-211;

Grant, S G et al., "Impaired long-term potentialtion, spatial learning, and hippocampal development in fyn mutant mice" [see comments], Science 1992, 258: 1903-1910;

Mayford, M et al., "The 3'-untranslated region of CaMKIIα is a cis-acting signal for the localization and translation of mRNA in dendrites," Proc Natl. Acad. Sci. USA 1996, 93: 13250-13255;

Kojima, N et al., "Rescuing impairment of long-term potentiation in fyn-deficient mice by introducing Fyn transgene," Proc. Natl. Acad. Sci USA 1997, 34: 4761-4765;

Mayford, M et al., "Control of memory formation through regulated expression of CaMKIIα transgene, "Science 1996, 274: 1678-1683;

Tsien, J Z et al., "Subregion- and cell type-restricted gene knockout in mouse brain," Cell 1996, 87: 1317-1326;

Gu, H et al., "Deletion of a DNA polymerase beta gene segment in T cells using cells using type-specific gene targeting," Science 1994, 265: 103-106;

Lakso, M et al., "Targeted oncogene activation by site-specific recombination in transgenic mice," Proc. Natl. Acad. Sci USA 1992, 89: 6232-6236;

Abremski, K et al., "Bacteriophage P1 site-specific recombination. Purification and properties of the Cre recombinase protein," J. Biol. Chem. 1984, 259: 1509-1514;

Sauer, B et al., "Site-specific DNA recombination in mammalian cells by the Cre recombinase of bacteriophage P1," Proc. Natl. Acad. Sci USA 85: 5166-5170;

Tsien, J Z et al., "The essential role of hippocampal CA1 NMDA receptor-dependent synaptic plasticity in spatial memory," Cell 1996, 87: 1327-1338;

Huang, Y Y et al., "A genetic test of the effects of mutations in PKA on mossy fiber LTP and its relation to spatial and contextual learning," Cell 1995, 83: 1211-1222;

Gossen, M et al., "Tight control of gene expression in mammalian cells by tetracycline-responsive promoters," Proc. Natl. Acad. Sci. USA 1992, 89: 5547-5551;

Furth, P A et al., "Temporal control of gene expression in transgenic mice by a tetracycline-responsive promoter," Proc. Natl. Acad. Sci. USA 1994, 91: 9302-9306;

Malinow, R et al., "Inhibition of postsynaptice PKC or CaMKIIα blocks induction but not expression of LTP," Science 1989, 254: 862-866;

Malenka, R C et al., "An essential role for postsynaptice calmodulin and protein kinase activity on long-term potentiation," Nature 1989, 340: 554-557;

Miller, S G et al., "Regulation of brain type II $Ca^{2+}$/Calmodulin-dependent protein kinase by autophosphorylation: A $Ca^{2+}$-triggered molecular switch, Cell 1986, 44: 861-870;

Lisman, J E, "The CaMKIIα hypothesis for the storage of synaptic memory," Trends Neurosci 1994, 17: 406-412;

Schworer, C M et al., "$Ca^{2+}$/calmodulin-dependent protein kinase II. Identification of a regulatory autophosphorylation site adjacent to the inhibitory and calmodulin-binding domains," J. Biol. Chem. 1988, 263: 13486-13489;

Miller, S A et al., Sequences of autophosphorylation sites in neuronal type II CaM Kinase that control $Ca^{2+}$-independent activity," Neuron 1988, 1: 593-604;

Thiel, G et al., "$Ca^{2+}$/calmodulin-dependent protein kinase II: identification of threonine-286 as the autophosphorylation site in the alpha subunit associated with the generation of $Ca^{2+}$-independent activity," Proc. Natl. Acad. Sci. USA 1988, 85: 6331-6341;

Lau, L L et al., "Distinct autophosphorylation sites sequentially produce autonomy and inhibition of the multifunctional $Ca^{2+}$/calmodulin-dependent protein kinase," J. Neurosci. 1989, 9: 2020-2032;

Fong, Y L et al., "Studies of the regulatory mechanism of $Ca^{2+}$/calmodulin-dependent protein kinase II. Mutation of threonine 286 alanine and aspartate," J. Biol. Chem. 1989, 264: 16759-16763;

Waldmann, R et al., "Mutifunctional $Ca^{2+}$/calmodulin-dependent protein kinase made $Ca^{2+}$ independent for functional studies," Biochemistry 1990, 29: 1679-1684;

Mayford, M et al., "CaMKIIα regulates the frequency-response function of hippocampal synapses for the production of both LTD and LTP," Cell 1995, 81: 891-904;

Bach, M E et al., "Impairment of spatial but not contextual memory in CaMKIIα mutant mice with a selective loss of hippocampal LTP in the range of the theta frequency," Cell 1995, 81: 905-915;

Staubli, U et al., "Stable hippocampal long-term potentiation elicited by 'theta' pattern stimulation," Brain Res. 1987, 435: 227-234;

Huerta, P T et al., "Bidirectional synaptic plasticity induced by a single burst during cholinergic theta oscillation in CA1 in vitro," Neuron 1995, 15: 1053-1063;

Bostock, E et al., "Experience-dependent modifications of hippocampal place cell firing," Hippocampus 1991, 1: 193-205;

Muller, R U, "A quarter of a century of place cells," Neuron 1996, 17: 813-822;

Rotenberg, A et al., "Mice expressing activated CaMKII lack low frequency LTP and do not form stable place cells in the CA1 region of the hippocampus," Cell 1996, 87:1351-1361;

Muller, R U et al., "Spatial firing patterns of hippocampal complex-spike cells in a fixed environment," J. Neurosci. 1987, 7: 1935-1950;

McHugh, T J et al., "Impaired hippocampal representation of space in CA1-specific NMDAR1 knockout mice," Cell 1996, 87: 1339-1349;

Gossen, M et al., "Transcriptional activation by tetracyclines in mammalian cells," Science 1995, 268: 1766-1769;

Kistner, A et al., "Doxycycline-mediated quatitative and tissue-specific control of gene expression in transgenic mice," Proc. Natl. Acad. Sci. USA 1996, 93: 10933-10938;

Feil, R et al., "Ligand-activated site-specific recombination in mice," Proc. Natl. Acad. Sci. USA 1996 93: 10887-10889.

No, D et al., "Ecdysone-inducible gene expression in mammalian cells and transgenic mice," Proc. Natl. Acad. Sci. USA 1996, 93: 3346-3351.

Figure Descriptions for Example 5. Figures may be Found in Mayford et al., Current Biology, 1997, pR580-R589.

FIG. 1. A comparison-of the medial temporal lobe system in rodents, primates, and humans. At the top is shown the lateral surface of the rat brain, the ventral surface of the monkey brain and the medial surface of the human brain. Below each of these views of the brain is an unfolded two-dimensional map of the entorhinal cortex the perirhinal cortex and the parahippocampal postrhinal cortices. As these comparisons illustrate, rodents, primates and humans have an organization of their medial temporal lobe structures that is largely conserved among mammals (Burwell et al., 1996). Abbreviations: R, rostral; C, caudal; D, dorsal; V, ventral.

FIG. 2. The flow of information in the medial temporal memory system in primates (Burwell et al., 1996). This extended view of the medial temporal lobe system emphasizes the importance of the direct projects from layers II and III of the entorhinal cortex (EC) to the CA3, CA1 and subicular regions.

FIG. 3. Regional specificity of transgene expression with the CaMKIIα promoter (Mayford et al., 1996). Regional distribution of the CaMKII-Asp286 transgene mRNA when expressed under the control of the CaMKIIα promoter alone (a) or in combination with the tTA system (b). In (a), areas CA1, CA2 and CA3 and dentate gyrus (DG) in the hippocampus, and in neocortex (Ctx), striatum (Str), Amygdala (Amy), and subiculum (Sub). In (b), expression is found only in CA1 and dentate gyrus in the hippocampus, and in striatum and amygdala.

FIG. 4. Regional specificity of gene knockout with the CaMKIIα promoter in combination with Cre-loxP system. (a) strategy used to obtain CA1-restricted gene knockout. Two independent lines of transgenic mice are generated: mouse 1 carries the CaMKIIα promoter fused to the Cre transgene; in mouse 2, the gene of interest is flanked by two loxP sequences. The transgene is introduced into the mouse with the loxP-flanked gene through mating. In mice carrying both genetic modifications (mouse 1+2), the loxP-flanked sequence is deleted only in the CA1 neurons. (b,c) Pattern of recombination in a 'reporter' mouse carrying the CaMKIIα promoter-Cre transgene and a lacZ gene that is interrupted by a stop sequence flanked by two loxP sequences. In this reporter mouse, recombination by Cre removes the stop sequence that prevents lacZ from being expressed. (b) Saggital section of a 28 day old mouse brain showing blue staining (X-gal) in CA1 pyramidal cells in the hippocampus that indicates recombination in these cells (I. M. M., M. M., and E. R. K., unpublished results). (c) High-magnification view of the hippocampus.

FIG. 5. Temporal and regional expression of the CaMKII-Asp286 transgene with the tTA system. (a) Strategy used to obtain forebrain-specific transgene expression regulated by doxycycline. Mouse 1 carries the CaMKIIα promoter fused to the tTA transgene; mouse 2 carries the tetO promoter fused to the CaMKII-Asp286 transgene. The two transgenes are introduced into a single mouse through mating. (b) The memory task undertaken by the mice—the spatial version of the Barnes maze. This circular maze has 40 holes in the perimeter and a hidden escape tunnel under one of the holes. The mouse is placed in the center of the maze and motivated to escape by bright lights and an aversive buzzer. To find the tunnel, the mouse needs to remember and use the relationships among the distal cues in the environment. To achieve the learning criterion on this task, the mouse must make three or less errors across five out of six consecutive trials. Errors are defined as searching any hole that did not have a tunnel beneath it.

FIG. 6. Place cell recordings from mice (modified from Rotenberg et al., 1996). (a) The recording setup. A mouse is trained to run all over the floor of a 49 cm diameter cylinder. Recordings are simultaneously made of the spike activity of one or more pyramidal cells and of the position of the mouse's head in the environment. Tracking is done with an overhead TV camera whose signal if fed to a detector that digitizes the position of a light on the mouse's head. (b) The positional firing patterns of three place cells recorded sequentially for 16 min each from one wild-type mouse. The circles are overhead views of the cylinder, and color represents the firing rate in each small square region (pixel). The cell's firing field is the darkly colored region. When the animal's head is in this region, the cell fires approximately 10 spikes/sec. Outside the firing field, the discharge rate is virtually zero as indicated by the yellow pixels. Thus, the positional signal is extremely strong. Note that the firing fields of the example cells are in different places in the environment. If many cells were shown, it would be clear that the fields cover the surface of the cylinder.

FIG. 7. Single place cells repeatedly recorded form wild-type mice and CaMKII-Asp286 transgenic mice (Rotenberg et al., 1996). The four 16 min recording sessions in the top row for the wild-type mouse were done in two pairs. Sessions 1 and 2 were done within 3 min of each other, without removing the mouse from the cylinder. Similarly, sessions 3 and 4 were done within 2 min of each other, again with the mouse continuously present in the cylinder. Between sessions 2 and 3, however, the mouse was removed from the cylinder for about 1 h before being replaced. Note that the position of the firing field is constant at about 10:30 o'clock across all four sessions,. When the same time sequence of four recording sessions is repeated in a CaMKII-Asp286 transgenic mouse, the firing field moves from position to position between sessions. In this example, the change in field position was greater after the mouse was removed from and replaced into the apparatus than for session pairs done at 2 min intervals. Over many cells, however, the instability was about the same for session pairs separated by minutes or by an hour.

What is claimed is:

1. A recombinant nucleic acid comprising a 3.2 kb 3' untranslated region of mouse calcium calmodulin kinase II alpha subunit-encoding mRNA and mRNA encoding a protein.

2. An isolated nucleic acid which hybridizes to the 3' untranslated region of mouse calcium calmodulin kinase II alpha subunit-encoding mRNA under conditions comprising two post-hybridization washes of 15 minutes each at 42° C. in 0.2× standard sodium citrate buffer.

3. A nucleic acid which is a plasmid designated pMM281 deposited with the American Type Culture Collection under Accession No. 98581.

4. A cell comprising the nucleic acid of any of claims 1, 2 and 3.

5. The cell of claim 4, wherein the cell is a bacterial cell, an insect cell, or a mammalian cell.

* * * * *